(12) United States Patent
Koike et al.

(10) Patent No.: US 6,538,111 B1
(45) Date of Patent: *Mar. 25, 2003

(54) ANTIBODY AGAINST HUMAN INTERLEUKIN-5 RECEPTOR ALPHA CHAIN

(75) Inventors: Masamichi Koike, Tokyo (JP); Akiko Furuya, Tokyo (JP); Kazuyasu Nakamura, Tokyo (JP); Akihiro Iida, Tokyo (JP); Hideharu Anazawa, Tokyo (JP); Nobuo Hanai, Kanagawa (JP); Kiyoshi Takatsu, Tokyo (JP)

(73) Assignee: Kyowa Hakko Kogyo Co., LTD, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,122

(22) Filed: Nov. 5, 1999

Related U.S. Application Data

(62) Division of application No. 08/836,561, filed as application No. PCT/JP96/02588 on Sep. 11, 1996, now Pat. No. 6,018,032.

(30) Foreign Application Priority Data

Sep. 11, 1995 (JP) .............................................. 7-232384

(51) Int. Cl.$^7$ ........................... C07K 16/28; C12N 5/18
(52) U.S. Cl. ............................. 530/388.22; 530/387.9; 530/388.1; 530/388.15; 435/325; 435/326; 435/328; 435/331; 435/334
(58) Field of Search .......................... 530/387.9, 388.1, 530/388.15, 388.22, 389.1; 435/325, 326, 328, 331, 334

(56) References Cited

U.S. PATENT DOCUMENTS 5,453,491 A 9/1995 Takatsu et al. ............. 530/351

FOREIGN PATENT DOCUMENTS

| EP | 0 492 214 A2 | 7/1992 |
|---|---|---|
| JP | 2257891 A | 10/1990 |
| JP | 3108497 A | 5/1991 |
| JP | 6054690 A | 3/1994 |
| JP | 6078772 A | 3/1994 |
| WO | WO 93 16184 A | 8/1993 |

OTHER PUBLICATIONS

Benhar et al., 1995, *Clinical Cancer Res.* 1:1023–1029.
Koike et al., 1996, Abstract Entitled "Monoclonal Antibodies Recognizing Human Interleukin 5 Receptor Alpha Chain", *Tissue Antigens*, 48:390.
Bird et al., 1998, *Science* 242:423–426.
Cornelis et al., 1995, *EMBO J.* 14:3395–3402.
Corrigan & Kay, 1992, *Immunol. Today* 13:501–506.
Courtenay–Luck et al., 1986, *Cancer Res.* 46:6489–6493.
DeFex et al., 1995, *FASEB J.* 9:A1502.
Dent et al., 1990, *J. Exp. Med.* 172:1425–1431.
Dillman et al., 1984, *J. Clin. Oncol.* 2:881–891.
Gleich & Adolphson, 1986, *Adv. Immunol.* 39:177–229.
Hakimi et al., 1991, *J. Immunol.* 147:1352–1359.
Houghton et al., 1985, *PNAS* 82:1242–1246.
Jones et al., 1986, *Nature* 321:522–525.
Kay et al., 1991, *J. Exp. Med.* 173:775–778.
Khazaeli et al., 1988, *J. Natl. Cancer Inst.* 80:937–942.
Kikuchi et al., 1994, *J. Immunol. Meth.* 167:289–298.
Korenaga et al., 1991, *Immunol.* 72:502–507.
LoBuglio et al., 1988, *J. Natl. Cancer Inst.* 80:932–936.
LoBuglio et al., 1989, *PNAS* 86:4220–4224.
Lopez et al., 1988, *J. Exp. Med.* 167:219–236.
Mauser et al., 1993, *Am. Rev. Respir. Dis.* 148:1623–1627.
Meeker et al., 1985, *Blood* 65:1349–1363.
Migita et al., 1991, *Cell. Immunol.* 133:484–497.
Morrison et al., 1984, *PNAS* 81:6851–6855.
Murata et al., 1992, *J. Exp. Med.* 175:341–351.
Nakamura et al., 1988, *Science* 242:426–430.
M. Nishizawa, 1990, *Protein, Nuc. Acid & Enzyme* 35:2584–2597, with English translation of its Abstract.
Pimm et al., 1985, *J. Nucl. Med.* 26:1011–1023.
Rothenberg et al., 1989, *J. Immunol.* 143:2311–2316.
C.J. Sanderson, 1992, *Blood* 79:3101–3109.
Shawler et al., 1985, *J. Immunol.* 135:1530–1535.
Takaki et al., 1990, *EMBO J.* 9:4367–4374.
Takaki et al., 1991, *EMBO J.* 10:2833–2838.
Takaki et al., 1993, *J. Exp. Med.* 177:1523–1529.
Takatsu et al., 1994, *Adv. Immunol.* 57:145–190.
Tavernier et al., 1991, *Cell* 66:1175–1184.
Tavernier et al., 1992, *PNAS* 89:7041–7045.
Tominaga et al., 1991, *J. Exp. Med.* 173:429–437.
Van Oosterhout et al., 1993, *Am. Rev. Respir. Dis.* 147:548–552.
Vaux et al., 1990, *Int. Immunol.* 2:965–971.
Webber et al., 1995, *Cancer Res.* 55:318–323.
Webber et al., 1995, *Mol. Immunol.* 32:249–258.
Yamaguchi et al., 1990, *Int. Immunol.* 2:181–187.
Derwent WPI Accession No.: 90–357863.
Derwent WPI Accession No.: 92–090329.
Derwent WPI Accession No.: 92–218502.
Derwent WPI Accession No.: 91–180932.
Blankenstein et al. Eur. J. Immunol. vol. 20, pp. 2699–2705, 1990.*
Murata et al. J. Exp. Med. vol. 175, pp. 341–351, Feb. 1992.*
Bowie et al. Science, vol. 247, pp. 1306–1310, 1990.*

* cited by examiner

*Primary Examiner*—Yvonne Eyler
*Assistant Examiner*—Sarada C Prasad
(74) *Attorney, Agent, or Firm*—Pennie & Edmonds LLP

(57) ABSTRACT

The present invention provides monoclonal antibodies and humanized antibodies which react specifically with a human interleukin-5 receptor α chain. The invention also provides hybridomas and transformants which produce the antibodies, the monoclonal antibodies and humanized antibodies, a method for detecting an interleukin-5 receptor α chain immunologically by means of these antibodies, as well as a method for diagnosing and treating diseases such as chronic bronchial asthma by means of the monoclonal antibodies and humanized antibodies. The present invention is useful for diagnosis or treatment of diseases such as chronic bronchial asthma.

41 Claims, 61 Drawing Sheets

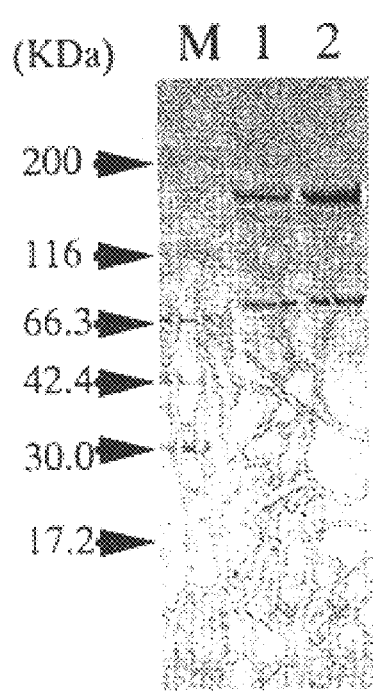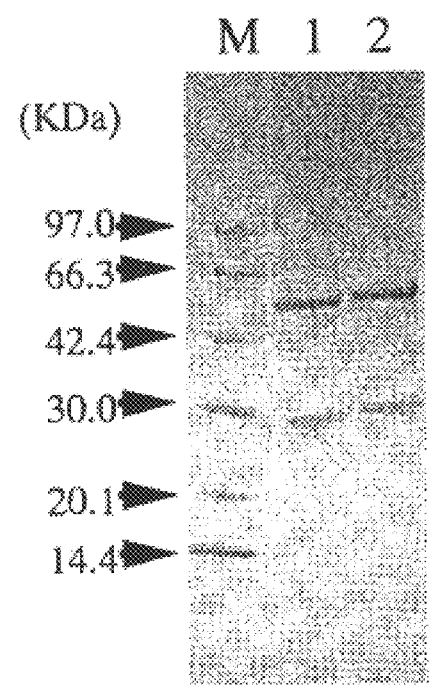
FIG.53

Dashed line: Control antibody (KM341)
Solid line: Anti-Human IL-5Rα monoclonal antibody (KM1259)

In the absence of 2-mercaptoethanol
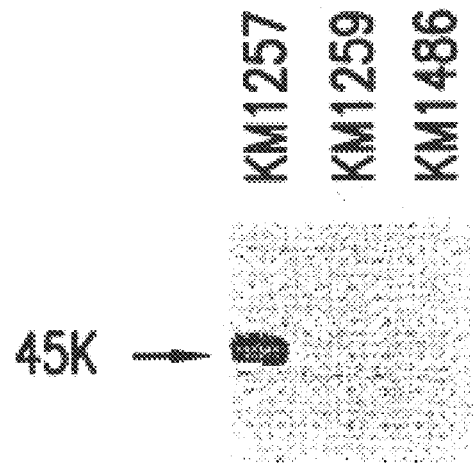
In the presence of 2-mercaptoethanol
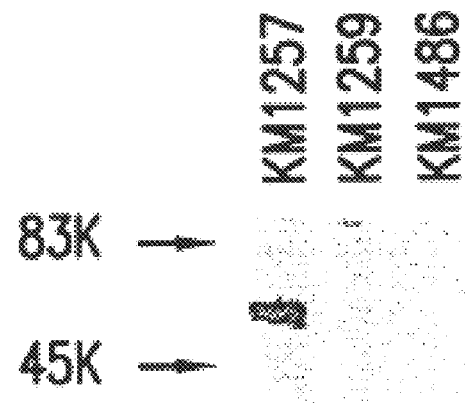
FIG.60

Immunoprecipitation of human IL-5 receptor α chain

SEQUENCE LISTING (1) GENERAL INFORMATION:

(iii) NUMBER OF SEQUENCES: 106

(2) INFORMATION FOR SEQ ID NO: 1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO: 1:

CAAAGCTTAC CATGATCATC GTGGCGCATG TA      32

(2) INFORMATION FOR SEQ ID NO: 2:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO: 2:

CAGGATCCCT ACTTACCCAC ATAAATAGGT TG      32

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 3:

CAGATATCTC ACTTCTCCCA CCTGTCA                                           27

(2) INFORMATION FOR SEQ ID NO: 4:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 4:

AGCTTCCACC ATGGAGTTTG GGCTCAGCTG GCTTTTTCTT GTCCTTGTTT TCAAAGGTGT       60

TCAGTGTGAC TTACTTCCTG ATGAAAAG                                          88

(2) INFORMATION FOR SEQ ID NO: 5:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 5:

CTTTTCATCA GGAAGTAAGT CACACTGAAC ACCTTTGAAA ACAAGGACAA GAAAAAGCCA       60

GCTGAGCCCA AACTCCATGG TGGA                                              84

(2) INFORMATION FOR SEQ ID NO: 6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 6:

AGCTTCCACC ATGGCTACAG GCTCCCGGAC GTCCCTGCTC CTGGCTTTTG G                51

(2) INFORMATION FOR SEQ ID NO: 7:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 7:

CCTGCTCTGC CTGCCCTGGC TTCAAGAGGG CAGTGCCGAC TTACTTCCTG ATGAAAAG         58

(2) INFORMATION FOR SEQ ID NO: 8:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 8:

CTTTTCATCA GGAAGTAAGT CGGCACTGCC CTCTTGAAGC CAGGGCAGGC AGAGCAGGCC          60

AAAA                                                                      64

(2) INFORMATION FOR SEQ ID NO: 9:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 9:

GCCAGGAGCA GGGACGTCCG GGAGCCTGTA GCCATGGTGG A                              41

(2) INFORMATION FOR SEQ ID NO: 10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 10:

GGCAGCGGCG GTTCCGGTGA GCCCAAATCT TGTGACAAA                                 39

(2) INFORMATION FOR SEQ ID NO: 11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 11:

CAGGATCCCC CGTCGCACTC ATTTACCCGG AGAC                                      34

(2) INFORMATION FOR SEQ ID NO: 12:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 12:

CAAAGCTTCC ACCATGGAGT TTGGGCTCAG CTGG                                      34

(2) INFORMATION FOR SEQ ID NO: 13:

(i) SEQUENCE CHARACTERISTICS:

(A) LENGTH: 39 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 13:

ACCGGAACCG CCGCTGCCCT TACCCACATA AATAGGTTG                    39

(2) INFORMATION FOR SEQ ID NO: 14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 14:

CAAAGCTTCC ACCATGGCTA CAGGCTCCCG GACG                         34

(2) INFORMATION FOR SEQ ID NO: 15:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 15:

CGATAAGCTA TGAAAACTAC AGCCTTGGAG GAAGCTTAAA TGAGCTCGAT ATCAAGGCCT    60

ACCCGGGCGC CATGCA                                            76

(2) INFORMATION FOR SEQ ID NO: 16:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 16:

CACTCAGTGT TAACTGAGGA GCAGGTGAAT TC                           32

(2) INFORMATION FOR SEQ ID NO: 17:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 17:

AGCTGAATTC ACCTGCTCCT CAGTTAACAC TGAGTGGTAC                   40

(2) INFORMATION FOR SEQ ID NO: 18:

(i) SEQUENCE CHARACTERISTICS:
        (A) LENGTH: 21 base pairs
        (B) TYPE: nucleic acid (C) STRANDEDNESS: single
        (D) TOPOLOGY: linear (ii) MOLECULE TYPE: Other (xi) SEQUENCE DESCRIPTION: SEQ ID NO: 18:

AATTCGTACG GTGGCTGCAC C                                            21

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 19:

GTGCAGCCA CCGTACG                                                  17

(2) INFORMATION FOR SEQ ID NO: 20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 20:

CTCGCGACTA GTGGGCCCGC GGCCGC                                       26

(2) INFORMATION FOR SEQ ID NO: 21:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 21:

AGCTGCGGCC GCGGGCCCAC TAGTCGCGAG GTAC                              34

(2) INFORMATION FOR SEQ ID NO: 22:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...420
        (D) OTHER INFORMATION:

(ix) FEATURE:
        (A) NAME/KEY: sig_peptide
        (B) LOCATION: 1...57
        (D) OTHER INFORMATION:

(xi) SEQUENCE DESCRIPTION: SEQ ID NO: 22:

ATG AAC TTC GGG CTC AGC TTG ATT TTC CTT GCC CTC ATT TTA AAA GGT    48
Met Asn Phe Gly Leu Ser Leu Ile Phe Leu Ala Leu Ile Leu Lys Gly

```
  1              5                    10                   15
GTC CAA TGT GAG GTG CAG TTG GTG GAG TCT GGG GGA GAC TTA GTG AAG        96
Val Gln Cys Glu Val Gln Leu Val Glu Ser Gly Gly Asp Leu Val Lys
             20                   25                  30

CCT GGA GGG TCC CTG AAA CTC TCC TGT GCA GCC TCT GGA TTC ACT TTC       144
Pro Gly Gly Ser Leu Lys Leu Ser Cys Ala Ala Ser Gly Phe Thr Phe
             35                  40                   45

AGT GAC TAT GGC ATG GCT TGG ATT CGC CAA ATT TCA GAC AAG AGG CCG       192
Ser Asp Tyr Gly Met Ala Trp Ile Arg Gln Ile Ser Asp Lys Arg Pro
    50                   55                  60

GAG TGG GTC GCA GCC ATT AGC AGT GGT GGT AGT TAC ATC CAC TTT CCA       240
Glu Trp Val Ala Ala Ile Ser Ser Gly Gly Ser Tyr Ile His Phe Pro
65                   70                  75                  80

GAC AGT TTG AAG GGG CGA TTC ACC GTC TCC AGA GAC AAT GCC AAG AAC       288
Asp Ser Leu Lys Gly Arg Phe Thr Val Ser Arg Asp Asn Ala Lys Asn
             85                  90                   95

ACC CTG TAC CTG GAA ATG AGC GGT CTG AAG TCT GAG GAC ACA GCT ATG       336
Thr Leu Tyr Leu Glu Met Ser Gly Leu Lys Ser Glu Asp Thr Ala Met
             100                 105                 110

TAT TAC TGT GCA AGA CGG GGC TTC TAT GGT AAC TAC CGG GCT ATG GAC       384
Tyr Tyr Cys Ala Arg Arg Gly Phe Tyr Gly Asn Tyr Arg Ala Met Asp
             115                 120                 125

TAC TGG GGT CAA GGA ACC TCA GTC ACC GTC TCC TCA G                     421
Tyr Trp Gly Gln Gly Thr Ser Val Thr Val Ser Ser
    130                 135                 140
```

(2) INFORMATION FOR SEQ ID NO: 23:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 23:

```
Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
             20                  25                  30

Pro Gly Gly Ser Leu Lys Leu Ser Cys Ala Ala Ser Gly Phe Thr Phe
             35                  40                  45

Ser Asp Tyr Gly Met Ala Trp Ile Arg Gln Ile Ser Asp Lys Arg Pro
    50                  55                  60

Glu Trp Val Ala Ala Ile Ser Ser Gly Gly Ser Tyr Ile His Phe Pro
65                  70                  75                  80

Asp Ser Leu Lys Gly Arg Phe Thr Val Ser Arg Asp Asn Ala Lys Asn
             85                  90                  95

Thr Leu Tyr Leu Glu Met Ser Gly Leu Lys Ser Glu Asp Thr Ala Met
             100                 105                 110

Tyr Tyr Cys Ala Arg Arg Gly Phe Tyr Gly Asn Tyr Arg Ala Met Asp
             115                 120                 125

Tyr Trp Gly Gln Gly Thr Ser Val Thr Val Ser Ser
    130                 135                 140
```

(2) INFORMATION FOR SEQ ID NO: 24:

(i) SEQUENCE CHARACTERISTICS:
    (A) LENGTH: 394 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 24:

```
ATGGAGAAAG ACACACTCCT GCTATGGGTC CTGCTTCTCT GGGTTCCAGG TTCCAGAAGT    60

GACATTGTGC TGACCCAATC TCCAGCTTCT TTGGCTGTGT CTCTAGGGCA GAGGGCCACC   120

ATCTCCTGCA GAGCCAACGA AAGTGTTGAT CATAATGGCG TCAATTTTAT GAACTGGTTC   180

CAACAGAAAC CAGGACAGTC ACCCAAGCTC CTCATCTATG CTGCATCCAA CCAAGGATCC   240

GGCGTCCCTG CCAGGTTTAG TGGCAGTGGG TCTGGGACAG ACTTCAGTCT CAACATCCAT   300

CCTATGGAGG AGGATGATGC TGCAATGTAT TTCTGTCAGC AAAGTAAGGA TGTTCCGTGG   360

ACGTTCGGTG GAGGCACCAG GTTGGAAATC AAAC                               394
```

(2) INFORMATION FOR SEQ ID NO: 25:

(i) SEQUENCE CHARACTERISTICS:
        (A) LENGTH: 131 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

```
Met Glu Lys Asp Thr Leu Leu Leu Trp Val Leu Leu Leu Trp Val Pro
 1               5                  10                  15

Gly Ser Arg Ser Asp Ile Val Leu Thr Gln Ser Pro Ala Ser Leu Ala
            20                  25                  30

Val Ser Leu Gly Gln Arg Ala Thr Ile Ser Cys Arg Ala Asn Glu Ser
        35                  40                  45

Val Asp His Asn Gly Val Asn Phe Met Asn Trp Phe Gln Gln Lys Pro
    50                  55                  60

Gly Gln Ser Pro Lys Leu Leu Ile Tyr Ala Ala Ser Asn Gln Gly Ser
65                  70                  75                  80

Gly Val Pro Ala Arg Phe Ser Gly Ser Gly Ser Gly Thr Asp Phe Ser
                85                  90                  95

Leu Asn Ile His Pro Met Glu Glu Asp Asp Ala Ala Met Tyr Phe Cys
            100                 105                 110

Gln Gln Ser Lys Asp Val Pro Trp Thr Phe Gly Gly Gly Thr Arg Leu
        115                 120                 125

Glu Ile Lys
    130
```

(2) INFORMATION FOR SEQ ID NO: 26:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

```
ATGGAATGGA GTTGGATATT TCTCTTTCTC CTGTCAGGAA CTGCAGGTGT CCACTCTGAG    60
```

| | |
|---|---|
| GTCCAGCTGC AACAGTCTGG ACCTGAGCTG GTAAAGCCTG GGGCTTCAGT GAAGATGTCC | 120 |
| TGCAAGGCTT CTGGATACAC ATTCACTAGT TATGTTATTC ACTGGGTGAA ACAGAGGCCT | 180 |
| GGTCAGGGCC TTGCGTGGAT TGGATATATT AATCCTTACA ATGATGGGAC TAAGTACAAT | 240 |
| GAGAGGTTCA AAGGCAAGGC CACACTGACT TCAGACAGAT CCTCCAGCAC AGTCTACATG | 300 |
| GAGCTCAGTA GCCTGACCTC TGAGGACTCT GCGGTCTATC TCTGTGGGAG AGAAGGAATT | 360 |
| AGGTACTATG GTCTACTGGG AGACTACTGG GGCCAAGGCA CCACTCTCAC AGTCTCCTCA | 420 |
| G | 421 |

(2) INFORMATION FOR SEQ ID NO: 27:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

```
Met Glu Trp Ser Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Ile His Trp Val Lys Gln Arg Pro Gly Gln Gly Leu
    50                  55                  60

Ala Trp Ile Gly Tyr Ile Asn Pro Tyr Asn Asp Gly Thr Lys Tyr Asn
65                  70                  75                  80

Glu Arg Phe Lys Gly Lys Ala Thr Leu Thr Ser Asp Arg Ser Ser Ser
                85                  90                  95

Thr Val Tyr Met Glu Leu Ser Ser Leu Thr Ser Glu Asp Ser Ala Val
            100                 105                 110

Tyr Leu Cys Gly Arg Glu Gly Ile Arg Tyr Tyr Gly Leu Leu Gly Asp
        115                 120                 125

Tyr Trp Gly Gln Gly Thr Thr Leu Thr Val Ser Ser
    130                 135                 140
```

(2) INFORMATION FOR SEQ ID NO: 28:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 28:

| | |
|---|---|
| ATGATGTCCT CTGCTCAGTT CCTTGGTCTC CTGTTGCTCT GTTTTCAAGA TATCAGATGT | 60 |
| GATATCCAGA TGACACAGGC TACATCCTCC CTGTCTGCCT CTCTGGGAGA CAGAGTCACC | 120 |
| ATCGGTTGCG GGACAAGTGA GGACATTATC AATTATTTAA ACTGGTATCG AAGAAACCA | 180 |
| GATGGAACTG TTGAACTCCT GATCTACCAC ACATCAAGAT TACAGTCAGG AGTCCCATCA | 240 |
| AGGTTCAGTG GCAGCGGGTC TGGAACAGAT TATTCTCTCA CCATTAGTGA CCTGGAGCAA | 300 |
| GAAGATATTG CCACTTACTT TTGCCAACAG GGTTATACGC TTCCGTACAC GGTCGGAGGG | 360 |

GGGACCAAGT TGGAAATAAA AC                                                382

(2) INFORMATION FOR SEQ ID NO: 29:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Met Met Ser Ser Ala Gln Phe Leu Gly Leu Leu Leu Cys Phe Gln
 1               5                  10                  15

Asp Ile Arg Cys Asp Ile Gln Met Thr Gln Ala Thr Ser Ser Leu Ser
            20                  25                  30

Ala Ser Leu Gly Asp Arg Val Thr Ile Gly Cys Gly Thr Ser Glu Asp
            35                  40                  45

Ile Ile Asn Tyr Leu Asn Trp Tyr Arg Lys Pro Asp Gly Thr Val
        50                  55                  60

Glu Leu Leu Ile Tyr His Thr Ser Arg Leu Gln Ser Gly Val Pro Ser
65                  70                  75                  80

Arg Phe Ser Gly Ser Gly Ser Gly Thr Asp Tyr Ser Leu Thr Ile Ser
                85                  90                  95

Asp Leu Glu Gln Glu Asp Ile Ala Thr Tyr Phe Cys Gln Gln Gly Tyr
            100                 105                 110

Thr Leu Pro Tyr Thr Val Gly Gly Gly Thr Lys Leu Glu Ile Lys
            115                 120                 125

(2) INFORMATION FOR SEQ ID NO: 30:

(i) SEQUENCE CHARACTERISTICS:
        (A) LENGTH: 412 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 30:

ATGAAATGCA GCTGGGTTAT CTTCTTCCTG ATGGCAGTGG TTACAGGGGT CAATTCAGAG    60

GTTCAGCTGC AGCAGTCTGG GGCAGAGCTT GTGAAGCCAG GGGCCTCAGT CAACTTGTCC   120

TGCACAGCTT CTGGCTTCAA CATTAAAGAC ACCTATATGC ACTGGGTGAA GCAGAGGCCT   180

GAACAGGGCC TGGAGTGGAT TGGAAGGATT GATCCTGCGA ATGGTAATAC TAAATCTGAC   240

CCGAAGTTCC AGGCCAAGGC CACTATAGCA GCAGACACAT CCTCCAACAC AGCCTACCTG   300

CAGCTCAGCA GCCTGACATC TGAGGACACT GCCGTCTATT ACTGTACTGG TGGACTACGG   360

CTACGGTTCT TTGACTATTG GGGCCAAGGC ACCACTCTCA CAGTCTCCTC AG           412

(2) INFORMATION FOR SEQ ID NO: 31:

(i) SEQUENCE CHARACTERISTICS:
        (A) LENGTH: 137 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

```
Met Lys Cys Ser Trp Val Ile Phe Phe Leu Met Ala Val Val Thr Gly
 1               5                  10                  15

Val Asn Ser Glu Val Gln Leu Gln Gln Ser Gly Ala Glu Leu Val Lys
             20                  25                  30

Pro Gly Ala Ser Val Asn Leu Ser Cys Thr Ala Ser Gly Phe Asn Ile
             35                  40                  45

Lys Asp Thr Tyr Met His Trp Val Lys Gln Arg Pro Glu Gln Gly Leu
     50                  55                  60

Glu Trp Ile Gly Arg Ile Asp Pro Ala Asn Gly Asn Thr Lys Ser Asp
 65              70                  75                  80

Pro Lys Phe Gln Ala Lys Ala Thr Ile Ala Ala Asp Thr Ser Ser Asn
             85                  90                  95

Thr Ala Tyr Leu Gln Leu Ser Ser Leu Thr Ser Glu Asp Thr Ala Val
             100                 105                 110

Tyr Tyr Cys Thr Gly Gly Leu Arg Leu Arg Phe Phe Asp Tyr Trp Gly
             115                 120                 125

Gln Gly Thr Thr Leu Thr Val Ser Ser
             130                 135
```

(2) INFORMATION FOR SEQ ID NO: 32:

(i) SEQUENCE CHARACTERISTICS:
        (A) LENGTH: 331 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 32:

```
TCCAGAGGAC AAATTGTTCT CACCCAGTCT CCAGCAATCA TGTCTGCATC TCCAGGGGAG    60
AAGGTCACCA TGACCTGCAG TGCCAGTTCA AGTGTAAGTT ACATGCACTG GTACCAGCAG   120
AAGTCAGGCA CCTCCCCCAA AGATGGATT TATGACACAT CCAAACTGGC TTCTGGAGTC   180
CCTGCTCGCT TCAGTGGCAG TGGGTCTGGG ACCTCTTACT CTCTCACAAT CAGCAGCATG   240
GAGGCTGAAG ATGCTGCCAC TTATTACTGC CAGCAGTGGA GTAGTAACCC ACCCATCACG   300
TTCGGAGGGG GGACCAAGCT GGAAATAAAA C                                  331
```

(2) INFORMATION FOR SEQ ID NO: 33:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

```
Ser Arg Gly Gln Ile Val Leu Thr Gln Ser Pro Ala Ile Met Ser Ala
 1               5                  10                  15

Ser Pro Gly Glu Lys Val Thr Met Thr Cys Ser Ala Ser Ser Ser Val
             20                  25                  30

Ser Tyr Met His Trp Tyr Gln Gln Lys Ser Gly Thr Ser Pro Lys Arg
             35                  40                  45

Trp Ile Tyr Asp Thr Ser Lys Leu Ala Ser Gly Val Pro Ala Arg Phe
     50                  55                  60

Ser Gly Ser Gly Ser Gly Thr Ser Tyr Ser Leu Thr Ile Ser Ser Met
 65              70                  75                  80
```

```
Glu Ala Glu Asp Ala Ala Thr Tyr Tyr Cys Gln Gln Trp Ser Ser Asn
            85                  90                  95

Pro Pro Ile Thr Phe Gly Gly Gly Thr Lys Leu Glu Ile Lys
            100                 105                 110
```

(2) INFORMATION FOR SEQ ID NO: 34:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

```
Asp Tyr Gly Met Ala
1               5
```

(2) INFORMATION FOR SEQ ID NO: 35:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
Ala Ile Ser Ser Gly Gly Ser Tyr Ile His Phe Pro Asp Ser Leu Lys
1               5                   10                  15
Gly
```

(2) INFORMATION FOR SEQ ID NO: 36:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
Arg Gly Phe Tyr Gly Asn Tyr Arg Ala Met Asp Tyr
1               5                   10
```

(2) INFORMATION FOR SEQ ID NO: 37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
Arg Ala Asn Glu Ser Val Asp His Asn Gly Val Asn Phe Met Asn
1               5                   10                  15
```

(2) INFORMATION FOR SEQ ID NO: 38:

(i) SEQUENCE CHARACTERISTICS:
        (A) LENGTH: 7 amino acids
        (B) TYPE: amino acid (C) STRANDEDNESS: single
        (D) TOPOLOGY: linear (ii) MOLECULE TYPE: peptide (xi) SEQUENCE DESCRIPTION: SEQ ID NO: 38:

Ala Ala Ser Asn Gln Gly Ser
1               5

(2) INFORMATION FOR SEQ ID NO: 39:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Gln Gln Ser Lys Asp Val Pro Trp Thr
1               5

(2) INFORMATION FOR SEQ ID NO: 40:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Ser Tyr Val Ile His
1               5

(2) INFORMATION FOR SEQ ID NO: 41:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Tyr Ile Asn Pro Tyr Asn Asp Gly Thr Lys Tyr Asn Glu Arg Phe Lys
1               5                   10                  15

Gly (2) INFORMATION FOR SEQ ID NO: 42:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Glu Gly Ile Arg Tyr Tyr Gly Leu Leu Gly Asp Tyr
1               5                   10

(2) INFORMATION FOR SEQ ID NO: 43:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 43:

Gly Thr Ser Glu Asp Ile Ile Asn Tyr Leu Asn
1               5                   10

(2) INFORMATION FOR SEQ ID NO: 44:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 44:

His Thr Ser Arg Leu Gln Ser
1               5

(2) INFORMATION FOR SEQ ID NO: 45:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 45:

Gln Gln Gly Tyr Thr Leu Pro Tyr Thr
1               5

(2) INFORMATION FOR SEQ ID NO: 46:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 46:

Asp Thr Tyr Met His
1               5

(2) INFORMATION FOR SEQ ID NO: 47:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 47:

Arg Ile Asp Pro Ala Asn Gly Asn Thr Lys Ser Asp Pro Lys Phe Gln
1               5                   10                  15

Ala (2) INFORMATION FOR SEQ ID NO: 48:

(i) SEQUENCE CHARACTERISTICS:
　　　　(A) LENGTH: 9 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO: 48:

Gly Leu Arg Leu Arg Phe Phe Asp Tyr
1               5

(2) INFORMATION FOR SEQ ID NO: 49:

(i) SEQUENCE CHARACTERISTICS:
　　　　(A) LENGTH: 10 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO: 49:

Ser Ala Ser Ser Ser Val Ser Tyr Met His
1               5                   10

(2) INFORMATION FOR SEQ ID NO: 50:

(i) SEQUENCE CHARACTERISTICS:
　　　　(A) LENGTH: 7 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO: 50:

Asp Thr Ser Lys Leu Ala Ser
1               5

(2) INFORMATION FOR SEQ ID NO: 51:

(i) SEQUENCE CHARACTERISTICS:
　　　　(A) LENGTH: 10 amino acids
　　　　(B) TYPE: amino acid
　　　　(C) STRANDEDNESS: single
　　　　(D) TOPOLOGY: linear (ii) MOLECULE TYPE: peptide (xi) SEQUENCE DESCRIPTION: SEQ ID NO: 51:

Gln Gln Trp Ser Ser Asn Pro Pro Ile Thr
1               5                   10

(2) INFORMATION FOR SEQ ID NO: 52:

(i) SEQUENCE CHARACTERISTICS:
　　　　(A) LENGTH: 39 base pairs
　　　　(B) TYPE: nucleic acid
　　　　(C) STRANDEDNESS: single
　　　　(D) TOPOLOGY: linear (ii) MOLECULE TYPE: Other (xi) SEQUENCE DESCRIPTION: SEQ ID NO: 52:

GCACCACTCT CACAGTCTCC TCAGCCAGTA CTAAGGGCC                    39

(2) INFORMATION FOR SEQ ID NO: 53:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 53:

CTTAGTACTG GCTGAGGAGA CTGTGAGAGT G                                        31

(2) INFORMATION FOR SEQ ID NO: 54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 54:

GACCAAGTTG GAAATAAAAC                                                        20

(2) INFORMATION FOR SEQ ID NO: 55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 55:

GTACGTTTTA TTTCCAACTT G                                                   21

(2) INFORMATION FOR SEQ ID NO: 56:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 56:

CAGGAAACAG CTATGACGCG GCCGCCACCA TGGAATGGAG TTGGATATTT CTCTTTCTCC      60

TGTCAGGAAC TGCAGGTGTC CACTCTGAGG TCCAGCT                               97

(2) INFORMATION FOR SEQ ID NO: 57:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 57:

GAATGTGTAT CCAGAAGCCT TGCAGGAAAC CTTCACTGAA GCCCCAGGCT TCTTCACCTC      60

AGCTCCAGAC TGCACCAGCT GGACCTCAGA GTGGAC                                96

(2) INFORMATION FOR SEQ ID NO: 58:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 58:

```
AGGCTTCTGG ATACACATTC ACTAGTTATG TTATTCACTG GGTGCGACAG GCCCCTGGTC    60

AGGGCCTTGA GTGGATGGGA TATATTAATC CTTACA                              96
```

(2) INFORMATION FOR SEQ ID NO: 59:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 59:

```
TGTAGGCTGT GCTCGTGGAC GTGTCTGCAG TGATTGTGAC TCTGCCTTTG AACCTCTCAT    60

TGTACTTAGT CCCATCATTG TAAGGATTAA TATATCCC                            98
```

(2) INFORMATION FOR SEQ ID NO: 60:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 60:

```
GTCCACGAGC ACAGCCTACA TGGAGCTCAG TTCGCTGAGA TCTGAGGACA CGGCGGTGTA    60

TTACTGTGCG AGAGAAGGAA TTAGGTACTA TGGTCT                              96
```

(2) INFORMATION FOR SEQ ID NO: 61:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 61:

```
GTTTTCCCAG TCACGACGGG CCCTTGGTGG AGGCTGAGGA GACTGTGACC AGGGTGCCTT    60

GGCCCCAGTA GTCTCCCAGT AGACCATAGT ACCTAATTCC                         100
```

(2) INFORMATION FOR SEQ ID NO: 62:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 62:

| | |
|---|---|
| ATGGAATGGA GTTGGATATT TCTCTTTCTC CTGTCAGGAA CTGCAGGTGT CCACTCTGAG | 60 |
| GTCCAGCTGG TGCAGTCTGG AGCTGAGGTG AAGAAGCCTG GGGCTTCAGT GAAGGTTTCC | 120 |
| TGCAAGGCTT CTGGATACAC ATTCACTAGT TATGTTATTC ACTGGGTGCG ACAGGCCCCT | 180 |
| GGTCAGGGCC TTGAGTGGAT GGGATATATT AATCCTTACA ATGATGGGAC TAAGTACAAT | 240 |
| GAGAGGTTCA AAGGCAGAGT CACAATCACT GCAGACACGT CCACGAGCAC AGCCTACATG | 300 |
| GAGCTCAGTT CGCTGAGATC TGAGGACACG GCGGTGTATT ACTGTGCGAG AGAAGGAATT | 360 |
| AGGTACTATG GTCTACTGGG AGACTACTGG GGCCAAGGCA CCCTGGTCAC AGTCTCCTCA | 420 |
| G | 421 |

(2) INFORMATION FOR SEQ ID NO: 63:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

```
Met Glu Trp Ser Trp Ile Phe Leu Phe Leu Leu Ser Gly Thr Ala Gly
 1               5                  10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Ile His Trp Val Arg Gln Ala Pro Gly Gln Gly Leu
    50                  55                  60

Glu Trp Met Gly Tyr Ile Asn Pro Tyr Asn Asp Gly Thr Lys Tyr Asn
65                  70                  75                  80

Glu Arg Phe Lys Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Gly Ile Arg Tyr Tyr Gly Leu Leu Gly Asp
        115                 120                 125

Tyr Trp Gly Gln Gly Thr Leu Val Thr Val Ser Ser
    130                 135                 140
```

(2) INFORMATION FOR SEQ ID NO: 64:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 64:

| | |
|---|---|
| CAGGAAACAG CTATGACGAA TTCCACCATG ATGTCCTCTG CTCAGTTCCT TGGTCTCCTG | 60 |
| TTGCTCTGTT TTCAAGACAT CAGATGT | 87 |

(2) INFORMATION FOR SEQ ID NO: 65:

(i) SEQUENCE CHARACTERISTICS:

(A) LENGTH: 83 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 65:

GATGGTGACT CTGTCTCCTA CAGAGGCAGA CAGGGAGGAT GGAGACTGTG TCATCTGGAT    60

ATCACATCTG ATGTCTTGAA AAC    83

(2) INFORMATION FOR SEQ ID NO: 66:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 66:

TAGGAGACAG AGTCACCATC ACTTGCGGGA CAAGTGAGGA CATTATCAAT TATTTAAACT    60

GGTATCAACA GAAACCAGGG AAAGCCCCTA AG    92

(2) INFORMATION FOR SEQ ID NO: 67:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 67:

TTCCAGACCC GCTGCCACTG AACCTTGATG GGACTCCTGA CTGTAATCTT GATGTGTGGT    60

AGATCAGGAG CTTAGGGGCT TTCCCTGGTT    90

(2) INFORMATION FOR SEQ ID NO: 68:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 68:

CAGTGGCAGC GGGTCTGGAA CAGATTTCAC TCTCACCATT AGTAGTCTGC AACCTGAAGA    60

TTTTGCCACT TACTACTGCC AACAGGGT    88

(2) INFORMATION FOR SEQ ID NO: 69:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 69:

GTTTTCCCAG TCACGACCGT ACGTTTTATT TCCACCTTGG TCCCTTGGCC GAACGTGTAC    60

```
GGAAGCGTAT AACCCTGTTG GCAGTAGTAA G                                    91
```

(2) INFORMATION FOR SEQ ID NO: 70:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 70:

```
ATGATGTCCT CTGCTCAGTT CCTTGGTCTC CTGTTGCTCT GTTTTCAAGA TATCAGATGT     60
GATATCCAGA TGACACAGTC TCCATCCTCC CTGTCTGCCT CTGTAGGAGA CAGAGTCACC    120
ATCACTTGCG GGACAAGTGA GGACATTATC AATTATTTAA ACTGGTATCA ACAGAAACCA    180
GGGAAAGCCC CTAAGCTCCT GATCTACCAC ACATCAAGAT ACAGTCAGG AGTCCCATCA     240
AGGTTCAGTG GCAGCGGGTC TGGAACAGAT TTCACTCTCA CCATTAGTAG TCTGCAACCT    300
GAAGATTTTG CCACTTACTA CTGCCAACAG GGTTATACGC TTCCGTACAC GTTCGGCCAA    360
GGGACCAAGG TGGAAATAAA AC                                             382
```

(2) INFORMATION FOR SEQ ID NO: 71:

(i) SEQUENCE CHARACTERISTICS:
        (A) LENGTH: 127 amino acids
        (B) TYPE: amino acid
        (C) STRANDEDNESS: single
        (D) TOPOLOGY: linear (xi) SEQUENCE DESCRIPTION: SEQ ID NO: 71:

```
Met Met Ser Ser Ala Gln Phe Leu Gly Leu Leu Leu Cys Phe Gln
 1               5                  10                  15
Asp Ile Arg Cys Asp Ile Gln Met Thr Gln Ser Pro Ser Ser Leu Ser
                20                  25                  30
Ala Ser Val Gly Asp Arg Val Thr Ile Thr Cys Gly Thr Ser Glu Asp
                35                  40                  45
Ile Ile Asn Tyr Leu Asn Trp Tyr Gln Gln Lys Pro Gly Lys Ala Pro
    50                  55                  60
Lys Leu Leu Ile Tyr His Thr Ser Arg Leu Gln Ser Gly Val Pro Ser
65                  70                  75                  80
Arg Phe Ser Gly Ser Gly Ser Gly Thr Asp Phe Thr Leu Thr Ile Ser
                85                  90                  95
Ser Leu Gln Pro Glu Asp Phe Ala Thr Tyr Tyr Cys Gln Gln Gly Tyr
                100                 105                 110
Thr Leu Pro Tyr Thr Phe Gly Gln Gly Thr Lys Val Glu Ile Lys
            115                 120                 125
```

(2) INFORMATION FOR SEQ ID NO: 72:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (xi) SEQUENCE DESCRIPTION: SEQ ID NO: 72:

```
GTCCACGAGC ACAGCCTACA TGGAGCTCAG TTCGCTGAGA TCTGAGGACA CGGCGGTGTA     60
TCTCTGTGGG AGAGAAGGAA TTAGGTACTA TGGTCT                              96
```

(2) INFORMATION FOR SEQ ID NO: 73:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (xi) SEQUENCE DESCRIPTION: SEQ ID NO: 73:

```
ATGGAATGGA GTTGGATATT TCTCTTTCTC CTGTCAGGAA CTGCAGGTGT CCACTCTGAG      60

GTCCAGCTGG TGCAGTCTGG AGCTGAGGTG AAGAAGCCTG GGGCTTCAGT GAAGGTTTCC     120

TGCAAGGCTT CTGGATACAC ATTCACTAGT TATGTTATTC ACTGGGTGCG ACAGGCCCCT     180

GGTCAGGGCC TTGAGTGGAT GGGATATATT AATCCTTACA ATGATGGGAC TAAGTACAAT     240

GAGAGGTTCA AGGCAGAGT CACAATCACT GCAGACACGT CCACGAGCAC AGCCTACATG     300

GAGCTCAGTT CGCTGAGATC TGAGGACACG GCGGTGTATC TCTGTGGGAG AGAAGGAATT     360

AGGTACTATG GTCTACTGGG AGACTACTGG GGCCAAGGCA CCCTGGTCAC AGTCTCCTCA     420

G                                                                    421
```

(2) INFORMATION FOR SEQ ID NO: 74:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

```
Met Glu Trp Ser Trp Ile Phe Leu Phe Leu Leu Ser Gly Thr Ala Gly
 1               5                  10                  15

Val His Ser Glu Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Ser Tyr Val Ile His Trp Val Arg Gln Ala Pro Gly Gln Gly Leu
        50                  55                  60

Glu Trp Met Gly Tyr Ile Asn Pro Tyr Asn Asp Gly Thr Lys Tyr Asn
65                  70                  75                  80

Glu Arg Phe Lys Gly Arg Val Thr Ile Thr Ala Asp Thr Ser Thr Ser
                85                  90                  95

Thr Ala Tyr Met Glu Leu Ser Ser Leu Arg Ser Glu Asp Thr Ala Val
            100                 105                 110

Tyr Leu Cys Gly Arg Glu Gly Ile Arg Tyr Tyr Gly Leu Leu Gly Asp
        115                 120                 125

Tyr Trp Gly Gln Gly Thr Leu Val Thr Val Ser Ser
    130                 135                 140
```

(2) INFORMATION FOR SEQ ID NO: 75:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (xi) SEQUENCE DESCRIPTION: SEQ ID NO: 75:

```
AGGCTTCTGG ATACACATTC ACTAGTTATG TTATTCACTG GGTGCGACAG GCCCCTGGTC      60
```

AGGGCCTTGC GTGGATGGGA TATATTAATC CTTACA 96

(2) INFORMATION FOR SEQ ID NO: 76:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (xi) SEQUENCE DESCRIPTION: SEQ ID NO: 76:

TGTAGGCTGT GCTCGTGGAC CTGTCTGCAG TGATTGTGAC TCTGCCTTTG AACCTCTCAT 60

TGTACTTAGT CCCATCATTG TAAGGATTAA TATATCCC 98

(2) INFORMATION FOR SEQ ID NO: 77:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (xi) SEQUENCE DESCRIPTION: SEQ ID NO: 77:

ATGGAATGGA GTTGGATATT TCTCTTTCTC CTGTCAGGAA CTGCAGGTGT CCACTCTGAG 60

GTCCAGCTGG TGCAGTCTGG AGCTGAGGTG AAGAAGCCTG GGCTTCAGT GAAGGTTTCC 120

TGCAAGGCTT CTGGATACAC ATTCACTAGT TATGTTATTC ACTGGGTGCG ACAGGCCCCT 180

GGTCAGGGCC TTGCGTGGAT GGGATATATT AATCCTTACA ATGATGGGAC TAAGTACAAT 240

GAGAGGTTCA AAGGCAGAGT CACAATCACT GCAGACAGGT CCACGAGCAC AGCCTACATG 300

GAGCTCAGTT CGCTGAGATC TGAGGACACG GCGGTGTATC TCTGTGGGAG AGAAGGAATT 360

AGGTACTATG GTCTACTGGG AGACTACTGG GGCCAAGGCA CCCTGGTCAC AGTCTCCTCA 420

G 421

(2) INFORMATION FOR SEQ ID NO: 78:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 78:

Met Glu Trp Ser Trp Ile Phe Leu Phe Leu Leu Ser Gly Thr Ala Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Ile His Trp Val Arg Gln Ala Pro Gly Gln Gly Leu
    50                  55                  60

Ala Trp Met Gly Tyr Ile Asn Pro Tyr Asn Asp Gly Thr Lys Tyr Asn
65                  70                  75                  80

Glu Arg Phe Lys Gly Arg Val Thr Ile Thr Ala Asp Arg Ser Thr Ser
                85                  90                  95

Thr Ala Tyr Met Glu Leu Ser Ser Leu Arg Ser Glu Asp Thr Ala Val
            100                 105                 110

```
Tyr Leu Cys Gly Arg Glu Gly Ile Arg Tyr Tyr Gly Leu Leu Gly Asp
        115                 120                 125

Tyr Trp Gly Gln Gly Thr Leu Val Thr Val Ser Ser
130                 135                 140

(2) INFORMATION FOR SEQ ID NO: 79:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 79:

AGGCTTCTGG ATACACATTC ACTAGTTATG TTATTCACTG GGTGCGACAG AGGCCTGGTC      60

AGGGCCTTGC GTGGATGGGA TATATTAATC CTTACA                               96

(2) INFORMATION FOR SEQ ID NO: 80:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 80:

TGTAGACTGT GCTCGTGGAC CTGTCTGAAG TGATTGTGAC TTTGCCTTTG AACCTCTCAT      60

TGTACTTAGT CCCATCATTG TAAGGATTAA TATATCCC                             98

(2) INFORMATION FOR SEQ ID NO: 81:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 81:

GTCCACGAGC ACAGTCTACA TGGAGCTCAG TTCGCTGAGA TCTGAGGACA CGGCGGTGTA      60

TCTCTGTGGG AGAGAAGGAA TTAGGTACTA TGGTCT                               96

(2) INFORMATION FOR SEQ ID NO: 82:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 82:

ATGGAATGGA GTTGGATATT TCTCTTTCTC CTGTCAGGAA CTGCAGGTGT CCACTCTGAG      60

GTCCAGCTGG TGCAGTCTGG AGCTGAGGTG AAGAAGCCTG GGCTTCAGT  GAAGGTTTCC    120

TGCAAGGCTT CTGGATACAC ATTCACTAGT TATGTTATTC ACTGGGTGCG ACAGAGGCCT    180

GGTCAGGGCC TTGCGTGGAT GGGATATATT AATCCTTACA ATGATGGGAC TAAGTACAAT    240

GAGAGGTTCA AAGGCAAAGT CACAATCACT TCAGACAGGT CCACGAGCAC AGTCTACATG    300
```

GAGCTCAGTT CGCTGAGATC TGAGGACACG GCGGTGTATC TCTGTGGGAG AGAAGGAATT    360

AGGTACTATG GTCTACTGGG AGACTACTGG GGCCAAGGCA CCCTGGTCAC AGTCTCCTCA    420

G    421

(2) INFORMATION FOR SEQ ID NO: 83:

(i) SEQUENCE CHARACTERISTICS:
        (A) LENGTH: 140 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Met Glu Trp Ser Trp Ile Phe Leu Phe Leu Leu Ser Gly Thr Ala Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Tyr Val Ile His Trp Val Arg Gln Arg Pro Gly Gln Gly Leu
    50                  55                  60

Ala Trp Met Gly Tyr Ile Asn Pro Tyr Asn Asp Gly Thr Lys Tyr Asn
65                  70                  75                  80

Glu Arg Phe Lys Gly Lys Val Thr Ile Thr Ser Asp Arg Ser Thr Ser
                85                  90                  95

Thr Val Tyr Met Glu Leu Ser Ser Leu Arg Ser Glu Asp Thr Ala Val
            100                 105                 110

Tyr Leu Cys Gly Arg Glu Gly Ile Arg Tyr Tyr Gly Leu Leu Gly Asp
        115                 120                 125

Tyr Trp Gly Gln Gly Thr Leu Val Thr Val Ser Ser
    130                 135                 140

(2) INFORMATION FOR SEQ ID NO: 84:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 84:

TAGGAGACAG AGTCACCATC ACTTGCGGGA CAAGTGAGGA CATTATCAAT TATTTAAACT    60

GGTATCGGCA GAAACCAGGG AAAGCCCCTG AA    92

(2) INFORMATION FOR SEQ ID NO: 85:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 85:

TTCCAGACCC GCTGCCACTG AACCTTGATG GGACTCCTGA CTGTAATCTT GATGTGTGGT    60

```
AGATCAGGAG TTCAGGGGCT TTCCCTGGTT                                              90
```

(2) INFORMATION FOR SEQ ID NO: 86:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 86:

```
GTTTTCCCAG TCACGACCGT ACGTTTTATT TCCACCTTGG TCCCTTGGCC GACCGTGTAC            60

GGAAGCGTAT AACCCTGTTG GCAGTAGTAA G                                          91
```

(2) INFORMATION FOR SEQ ID NO: 87:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 87:

```
ATGATGTCCT CTGCTCAGTT CCTTGGTCTC CTGTTGCTCT GTTTTCAAGA TATCAGATGT            60

GATATCCAGA TGACACAGTC TCCATCCTCC CTGTCTGCCT CTGTAGGAGA CAGAGTCACC           120

ATCACTTGCG GGACAAGTGA GGACATTATC AATTATTTAA ACTGGTATCG GCAGAAACCA           180

GGGAAAGCCC CTGAACTCCT GATCTACCAC ACATCAAGAT TACAGTCAGG AGTCCCATCA           240

AGGTTCAGTG GCAGCGGGTC TGGAACAGAT TTCACTCTCA CCATTAGTAG TCTGCAACCT           300

GAAGATTTTG CCACTTACTA CTGCCAACAG GGTTATACGC TTCCGTACAC GGTCGGCCAA           360

GGGACCAAGG TGGAAATAAA AC                                                    382
```

(2) INFORMATION FOR SEQ ID NO: 88:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

```
Met Met Ser Ser Ala Gln Phe Leu Gly Leu Leu Leu Leu Cys Phe Gln
 1               5                  10                  15

Asp Ile Arg Cys Asp Ile Gln Met Thr Gln Ser Pro Ser Ser Leu Ser
                20                  25                  30

Ala Ser Val Gly Asp Arg Val Thr Ile Thr Cys Gly Thr Ser Glu Asp
            35                  40                  45

Ile Ile Asn Tyr Leu Asn Trp Tyr Arg Gln Lys Pro Gly Lys Ala Pro
        50                  55                  60

Glu Leu Leu Ile Tyr His Thr Ser Arg Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gly Tyr
               100                 105                 110
```

```
        Thr Leu Pro Tyr Thr Val Gly Gln Gly Thr Lys Val Glu Ile Lys
            115                 120                 125
```

(2) INFORMATION FOR SEQ ID NO: 89:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 89:

```
TAGGAGACAG AGTCACCATC GGTTGCGGGA CAAGTGAGGA CATTATCAAT TATTTAAACT      60

GGTATCGGCA GAAACCAGGG AAAGCCCCTG AA                                   92
```

(2) INFORMATION FOR SEQ ID NO: 90:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 90:

```
CAGTGGCAGC GGGTCTGGAA CAGATTTCAC TCTCACCATT AGTGACCTGC AACCTGAAGA      60

TTTTGCCACT TACTACTGCC AACAGGGT                                        88
```

(2) INFORMATION FOR SEQ ID NO: 91:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 91:

```
ATGATGTCCT CTGCTCAGTT CCTTGGTCTC CTGTTGCTCT GTTTTCAAGA TATCAGATGT      60

GATATCCAGA TGACACAGTC TCCATCCTCC CTGTCTGCCT CTGTAGGAGA CAGAGTCACC     120

ATCGGTTGCG GGACAAGTGA GGACATTATC AATTATTTAA ACTGGTATCG GCAGAAACCA     180

GGGAAAGCCC CTGAACTCCT GATCTACCAC ACATCAAGAT ACAGTCAGG AGTCCCATCA     240

AGGTTCAGTG GCAGCGGGTC TGGAACAGAT TTCACTCTCA CCATTAGTGA CCTGCAACCT     300

GAAGATTTTG CCACTTACTA CTGCCAACAG GGTTATACGC TTCCGTACAC GGTCGGCCAA     360

GGGACCAAGG TGGAAATAAA AC                                             382
```

(2) INFORMATION FOR SEQ ID NO: 92:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

```
Met Met Ser Ser Ala Gln Phe Leu Gly Leu Leu Leu Leu Cys Phe Gln
```

```
      1               5                   10                  15
Asp Ile Arg Cys Asp Ile Gln Met Thr Gln Ser Pro Ser Ser Leu Ser
                 20                  25                  30
Ala Ser Val Gly Asp Arg Val Thr Ile Gly Cys Gly Thr Ser Glu Asp
             35                  40                  45
Ile Ile Asn Tyr Leu Asn Trp Tyr Arg Gln Lys Pro Gly Lys Ala Pro
         50                  55                  60
Glu Leu Leu Ile Tyr His Thr Ser Arg Leu Gln Ser Gly Val Pro Ser
 65                  70                  75                  80
Arg Phe Ser Gly Ser Gly Ser Gly Thr Asp Phe Thr Leu Thr Ile Ser
                 85                  90                  95
Asp Leu Gln Pro Glu Asp Phe Ala Thr Tyr Tyr Cys Gln Gln Gly Tyr
             100                 105                 110
Thr Leu Pro Tyr Thr Val Gly Gln Gly Thr Lys Val Glu Ile Lys
         115                 120                 125
```

(2) INFORMATION FOR SEQ ID NO: 93:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 93:

```
GATGGTGACT CTGTCTCCTA CAGAGGCAGA CAGGGAGGAT GTAGCCTGTG TCATCTGGAT    60

ATCACATCTG ATGTCTTGAA AAC                                           83
```

(2) INFORMATION FOR SEQ ID NO: 94:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 94:

```
TAGGAGACAG AGTCACCATC GGTTGCGGGA CAAGTGAGGA CATTATCAAT TATTTAAACT    60

GGTATCGGAA GAAACCAGGG AAAGCCCCTG AA                                 92
```

(2) INFORMATION FOR SEQ ID NO: 95:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 95:

```
CAGTGGCAGC GGGTCTGGAA CAGATTTCAC TCTCACCATT AGTGACCTGC AACCTGAAGA    60

TTTTGCCACT TACTTTTGCC AACAGGGT                                      88
```

(2) INFORMATION FOR SEQ ID NO: 96:

(i) SEQUENCE CHARACTERISTICS:
        (A) LENGTH: 91 base pairs

```
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 96:

GTTTTCCCAG TCACGACCGT ACGTTTTATT TCCACCTTGG TCCCTTGGCC GACCGTGTAC      60

GGAAGCGTAT AACCCTGTTG GCAAAAGTAA G                                    91

(2) INFORMATION FOR SEQ ID NO: 97:

(i) SEQUENCE CHARACTERISTICS:
        (A) LENGTH: 382 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 97:

ATGATGTCCT CTGCTCAGTT CCTTGGTCTC CTGTTGCTCT GTTTTCAAGA TATCAGATGT      60

GATATCCAGA TGACACAGGC TACATCCTCC CTGTCTGCCT CTGTAGGAGA CAGAGTCACC     120

ATCGGTTGCG GGACAAGTGA GGACATTATC AATTATTTAA ACTGGTATCG GAAGAAACCA     180

GGGAAAGCCC CTGAACTCCT GATCTACCAC ACATCAAGAT TACAGTCAGG AGTCCCATCA     240

AGGTTCAGTG GCAGCGGGTC TGGAACAGAT TTCACTCTCA CCATTAGTGA CCTGCAACCT     300

GAAGATTTTG CCACTTACTT TTGCCAACAG GGTTATACGC TTCCGTACAC GGTCGGCCAA     360

GGGACCAAGG TGGAAATAAA AC                                             382

(2) INFORMATION FOR SEQ ID NO: 98:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

Met Met Ser Ser Ala Gln Phe Leu Gly Leu Leu Leu Cys Phe Gln
 1               5                  10                  15

Asp Ile Arg Cys Asp Ile Gln Met Thr Gln Ala Thr Ser Ser Leu Ser
            20                  25                  30

Ala Ser Val Gly Asp Arg Val Thr Ile Gly Cys Gly Thr Ser Glu Asp
            35                  40                  45

Ile Ile Asn Tyr Leu Asn Trp Tyr Arg Lys Lys Pro Gly Lys Ala Pro
        50                  55                  60

Glu Leu Leu Ile Tyr His Thr Ser Arg Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Asp Leu Gln Pro Glu Asp Phe Ala Thr Tyr Phe Cys Gln Gln Gly Tyr
            100                 105                 110

Thr Leu Pro Tyr Thr Val Gly Gln Gly Thr Lys Val Glu Ile Lys
            115                 120                 125

(2) INFORMATION FOR SEQ ID NO: 99:
```

(i) SEQUENCE CHARACTERISTICS:
            (A) LENGTH: 92 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 99:

TAGGAGACAG AGTCACCATC GGTTGCGGGA CAAGTGAGGA CATTATCAAT TATTTAAACT      60

GGTATCGGAA GAAACCAGGG AAAGCCGTTG AA                                   92

(2) INFORMATION FOR SEQ ID NO: 100:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 100:

TTCCAGACCC GCTGCCACTG AACCTTGATG GGACTCCTGA CTGTAATCTT GATGTGTGGT      60

AGATCAGGAG TTCAACGGCT TTCCCTGGTT                                      90

(2) INFORMATION FOR SEQ ID NO: 101:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 101:

CAGTGGCAGC GGGTCTGGAA CAGATTATAC TCTCACCATT AGTGACCTGC AACCTGAAGA      60

TTTTGCCACT TACTTTTGCC AACAGGGT                                        88

(2) INFORMATION FOR SEQ ID NO: 102:

(i) SEQUENCE CHARACTERISTICS:
            (A) LENGTH: 382 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO: 102:

ATGATGTCCT CTGCTCAGTT CCTTGGTCTC CTGTTGCTCT GTTTTCAAGA TATCAGATGT      60

GATATCCAGA TGACACAGGC TACATCCTCC CTGTCTGCCT CTGTAGGAGA CAGAGTCACC     120

ATCGGTTGCG GGACAAGTGA GGACATTATC AATTATTTAA ACTGGTATCG GAAGAAACCA     180

GGGAAAGCCG TTGAACTCCT GATCTACCAC ACATCAAGAT TACAGTCAGG AGTCCCATCA     240

AGGTTCAGTG GCAGCGGGTC TGGAACAGAT TATACTCTCA CCATTAGTGA CCTGCAACCT     300

GAAGATTTTG CCACTTACTT TTGCCAACAG GGTTATACGC TTCCGTACAC GGTCGGCCAA     360

GGGACCAAGG TGGAAATAAA AC                                             382

(2) INFORMATION FOR SEQ ID NO: 103:

(i) SEQUENCE CHARACTERISTICS:

```
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 103:

Met Met Ser Ser Ala Gln Phe Leu Gly Leu Leu Leu Leu Cys Phe Gln
 1               5                  10                  15

Asp Ile Arg Cys Asp Ile Gln Met Thr Gln Ala Thr Ser Ser Leu Ser
            20                  25                  30

Ala Ser Val Gly Asp Arg Val Thr Ile Gly Cys Gly Thr Ser Glu Asp
            35                  40                  45

Ile Ile Asn Tyr Leu Asn Trp Tyr Arg Lys Lys Pro Gly Lys Ala Val
 50                  55                  60

Glu Leu Leu Ile Tyr His Thr Ser Arg Leu Gln Ser Gly Val Pro Ser
 65                  70                  75                  80

Arg Phe Ser Gly Ser Gly Ser Gly Thr Asp Tyr Thr Leu Thr Ile Ser
                85                  90                  95

Asp Leu Gln Pro Glu Asp Phe Ala Thr Tyr Phe Cys Gln Gln Gly Tyr
                100                 105                 110

Thr Leu Pro Tyr Thr Val Gly Gln Gly Thr Lys Val Glu Ile Lys
            115                 120                 125

(2) INFORMATION FOR SEQ ID NO: 104:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 104:

GCTTCCACCA AGGGCCCATC CGTCT                                              25

(2) INFORMATION FOR SEQ ID NO: 105:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO: 105:

AAGGATCCTG GCACTCATTT ACCCAGAGAC                                         30

(2) INFORMATION FOR SEQ ID NO: 106:

(i) SEQUENCE CHARACTERISTICS:
        (A) LENGTH: 313 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 106:

Asp Leu Leu Pro Asp Glu Lys Ile Ser Leu Leu Pro Pro Val Asn Phe
 1               5                  10                  15
```

-continued

```
Thr Ile Lys Val Thr Gly Leu Ala Gln Val Leu Leu Gln Trp Lys Pro
            20              25              30

Asn Pro Asp Gln Glu Gln Arg Asn Val Asn Leu Glu Tyr Gln Val Lys
            35              40              45

Ile Asn Ala Pro Lys Glu Asp Asp Tyr Glu Thr Arg Ile Thr Glu Ser
    50              55              60

Lys Cys Val Thr Ile Leu His Lys Gly Phe Ser Ala Ser Val Arg Thr
65              70              75              80

Ile Leu Gln Asn Asp His Ser Leu Leu Ala Ser Ser Trp Ala Ser Ala
            85              90              95

Glu Leu His Ala Pro Pro Gly Ser Pro Gly Thr Ser Val Val Asn Leu
            100             105             110

Thr Cys Thr Thr Asn Thr Thr Glu Asp Asn Tyr Ser Arg Leu Arg Ser
            115             120             125

Tyr Gln Val Ser Leu His Cys Thr Trp Leu Val Gly Thr Asp Ala Pro
        130             135             140

Glu Asp Thr Gln Tyr Phe Leu Tyr Tyr Arg Tyr Gly Ser Trp Thr Glu
145             150             155             160

Glu Cys Gln Glu Tyr Ser Lys Asp Thr Leu Gly Arg Asn Ile Ala Cys
                165             170             175

Trp Phe Pro Arg Thr Phe Ile Leu Ser Lys Gly Arg Asp Trp Leu Ala
            180             185             190

Val Leu Val Asn Gly Ser Ser Lys His Ser Ala Ile Arg Pro Phe Asp
            195             200             205

Gln Leu Phe Ala Leu His Ala Ile Asp Gln Ile Asn Pro Pro Leu Asn
        210             215             220

Val Thr Ala Glu Ile Glu Gly Thr Arg Leu Ser Ile Gln Trp Glu Lys
225             230             235             240

Pro Val Ser Ala Phe Pro Ile His Cys Phe Asp Tyr Glu Val Lys Ile
                245             250             255

His Asn Thr Arg Asn Gly Tyr Leu Gln Ile Glu Lys Leu Met Thr Asn
            260             265             270

Ala Phe Ile Ser Ile Ile Asp Asp Leu Ser Lys Tyr Asp Val Gln Val
        275             280             285

Arg Ala Ala Val Ser Ser Met Cys Arg Glu Ala Gly Leu Trp Ser Glu
    290             295             300

Trp Ser Gln Pro Ile Tyr Val Gly Lys
305             310
```

ANTIBODY AGAINST HUMAN INTERLEUKIN-5 RECEPTOR ALPHA CHAIN

This is a division of application No. 08/836,561, filed May 9, 1997 now U.S. Pat. No. 6,018,032, which is a 371 of PCT/JP96/02588 filed Sep. 11, 1996.

FIELD OF THE INVENTION

The present invention relates to monoclonal antibodies and humanized antibodies which bind specifically to a human interleukin-5 receptor α chain and which are therefore useful for diagnosis or treatment of diseases such as chronic bronchial asthma. The invention also relates to hybridomas and transformants which produce the antibodies, a method for detecting an interleukin-5 receptor α chain immunologically by means of the monoclonal antibodies and humanized antibodies, as well as a method for diagnosing and treating diseases such as chronic bronchial asthma by means of the monoclonal antibodies and humanized antibodies.

BACKGROUND OF THE INVENTION

Interleukin-5 (hereinafter referred to a "IL-5") is a kind of lymphokine which is secreted by T cells, mast cells and other cells. Murine IL-5 is known to act as a differentiation and growth factor for B cells and eosinophils. Human IL-5 is known to act mainly as a differentiation and growth factor for eosinophils (Advances in Immunology, 57, 145 (1994); Blood, 79, 3101 (1992)). IL-5 exhibits its action through a specific receptor (IL-5 receptor) which is expressed on the surface of a cell such as eosinophil. It has been shown that human and murine IL-5 receptors (hereinafter referred to as "IL-5Rs") are both composed of two different kinds of proteins, an α chain (hereinafter referred to as "IL-5R α") and a β chain (hereinafter referred to as "IL-5R β"). In addition, it is known that the binding of IL-5 to IL-5R is via IL-5R α and that IL-5R β alone can not bind to IL-5 (EMBO J., 9, 4367 (1990); ibid., 10, 2833 (1991); J. Exp. Med., 177, 1523 (1993); ibid., 175, 341 (1992); Cell, 66, 1175 (1991), Proc. Natl. Acad. Sci., 89, 7041 (1992)). Furthermore, IL-5R β is known to be a component of receptors for interleukin-3 (hereinafter referred to as "IL-3"), granulocyte macrophage colony-stimulating factor and others (hereinafter referred to as "GM-CSF") (Proc. Natl. Acad. Sci., 87.9655 (1990); Cell, 66, 1165 (1991)).

Eosinophils are known to increase in allergic diseases represented by chronic bronchial asthma. Significant infiltration of eosinophils is observed in airways of a patient with chronic bronchial asthma. Eosinophil contains a cytotoxic granular proteins whose deposit is observed in airway tissues of a patient with chronic bronchial asthma or at lesion sites of a patient with atopic dermatitis. These facts suggest that eosinophil plays an important role in the pathogenesis of allergic disorders such as chronic bronchial asthma, atopic dermatitis and the like (Adv. Immunol., 39, 177 (1986); Immunol. Today, 13, 501 (1992)). Hence, studying the kinetics of eosinophils is useful for clinical diagnosis. On the other hand, human IL-5 acts specifically on eosinophils, so IL-5R is believed to be expressed specifically in eosinophils and can therefore be used as a marker specific to human eosinophils. Furthermore, IL-5β is a receptor for cytokines such as IL-3, GM-CSF and others, so IL-5R α is believed to be a marker specific to eosinophils. Hence, eosinophils can be detected specifically by immunocyte staining using an anti-human IL-5R α chain antibody (hereinafter referred to as "anti-hIL-5Rα antibody"). However, no anti-hIL-5R α antibody is presently known that is capable of specific detection of eosinophils.

Significant eosinophilia was observed in IL-5 transgenic mice (J. Exp. Med., 172, 1425 (1990); ibid. 173, 429 (1991); Int. Immunol., 2, 965 (1990)). Eosinophil infiltration in tissues was suppressed by the administration of an anti-IL-5 antibody in animal models of asthma (Am. Rev. Resir. 147, 548 (1993); ibid., 148, 1623 (1993)). These phenomena indicate that IL-5 actually plays an important role in eosinophilia and the infiltration of eosinophils in vivo. It is also reported that IL-5 is expressed in airway mucosal tissues of a human patient with chronic bronchial asthma and at lesion sites of a patient with atopic dermatitis (J. Clin. Invest., 87, 1541 (1991); J. Exp. Med., 173, 775 (1991)). Further investigations demonstrate that IL-5 exhibits in vitro viability-enhancing action on human eosinophils (J. Immunol., 143, 2311 (1989)) and that IL-5 is an eosinophil-selective activator (J. Exp. Med.,167, 219 (1988)).

Hence, antibodies that bind to IL-5R and which can inhibit the biological activity of IL-5 are expected to inhibit the activity of eosinophil, thus being useful in the treatment of allergic diseases such as chronic bronchial asthma. Anti-mouse IL-5R α antibodies which can inhibit the biological activity of IL-5 were produced by using as an antigen those IL-5-dependent cells which express a large number of murine IL-5R on their surfaces (Kokai (Japanese published unexamined patent application) No. 108497/91; Int. Immunol., 2, 181 (1990)). However, in the case of humans, no cells are known which express a large number of IL-5R and the expression of IL-5R is reported to be very low in eosinophils (Cell. Immunol., 133, 484 (1991)). Hence, anti-human IL-5R α antibodies having comparable functions to anti-mouse IL-5R α antibodies are difficult to produce by methods similar to those for producing the latter. An antibody designated as "α16" is disclosed as an antibody against human IL-5R α in EMBO J., 14, 3395 (1995) but this antibody does not have any neutralization activity for IL-5R α.

Human IL-5R α gene was obtained by preparing a cDNA library from human eosinophil (J. Exp. Med., 175, 341 (1992)) or a human promyelocytic cell HL-60 (Cell, 66, 1175 (1991); Kokai No. 78772/94) and screening the library using as a probe an oligo DNA which had been synthesized on the basis of cDNA of murine IL-5R α or a partial amino acid sequence of murine IL-5R α (Kokai No. 54690/94, EMBO J., 9, 4367 (1990)). The transfer of the cDNA into a host cell resulted in the creation of a cell having hIL-5R α expressed on its surface but the expression level of hIL-5R in this cell was very low ($\leq 10^4$ molecules) (J. Exp. Med., 177, 1523 (1993)). Hence, if one attempts to produce anti-hIL-5R α antibodies by using this cell as an immunogen, he will find that the relative amount of hIL-5R α is very small, compared with those of proteins from a host cell and that the absolute protein amount of hIL-5R α is also very small. In addition, approximately 80% homology at an amino acid level is observed between murine IL-5R α and human IL-5R α and murine IL-5 can bind to human IL-5R with high affinity (J. Exp. Med.,175, 341 (1992)). These facts suggest that human IL-5R α has a lower immunogenicity for mice or rats which are commonly used as animals to be immunized. In fact, almost all of our attempts to prepare anti-hIL-5R α antibodies using hIL-5R α-expressing cells as an immunogen resulted in a failure.

In the cloning of IL-5R cDNA from a cDNA library of human eosinophil, cDNA encoding soluble human IL-5R α (hereinafter referred to as "shIL-5R α") has been obtained which corresponds to the N-terminal amino acid sequence (1-313) of IL-5R α which is defective in the transmembrane region and onwards (J. Exp. Med.,175, 341 (1992)). When shIL-5R α is used as an immunogen to produce an anti-hIL-5R α antibody, the shIL-5R α should have the same three dimensional conformation as that of IL-5R α expressed on the cell surface and it should be one secreted and produced by a eukaryotic host cell in order to obtain an anti-hIL-5R α antibody which can inhibit the biological activity of IL-5. In addition, it has been found that the production efficiency of a protein varies significantly depending on the signal peptide (Protein, Nucleic Acid and Enzyme, 35, 2584 (1990)), so it is necessary to select an appropriate signal peptide for secretion and production of the protein.

As mentioned above, it has been found that mRNA which is believed to encode only shIL-5R α is expressed in eosinophils. It has been confirmed that murine IL-5R is expressed not only in eosinophils but also in B cells and that mRNA which is believed to encode only an extracellular region of IL-5R α (hereinafter referred to as "smIL-5R α") is expressed in those cells as well as in the case of humans. In addition, it has been reported that smIL-5R α was detected in blood of mice transplanted with IL-5R expressing murine chronic B cell leukemia cell line (BCL1) or model mice of human autoimmune diseases (J. Immunol. Method, 167, 289 (1994)). These suggest the possibility that the increase in the number of IL-5R expressing cells and their activation may be reflected in the amount of smIL-5R α secreted in blood. Human IL-5R is believed to be expressed in eosinophils in a limited amount and the increase in the number of eosinophils and their activation may be potentially reflected in the amount of shIL-5R α in blood. Hence, the quantitative determination of shIL-5R α is expected to be useful in clinical diagnosis.

Any isolated monoclonal antibody which binds specifically to human IL-5R α is believed to be useful in the diagnosis and treatment of allergic diseases. However, it should be noted that if a non-human animal-derived monoclonal antibody is administered to a human, it is generally recognized as a foreign matter such that an antibody against the non-human animal-derived monoclonal antibody is produced in the human body, a reaction with the administered non-human animal-derived monoclonal antibody occurs to cause a side effect (J. Clin. Oncol., 2, 881 (1984); Blood, 65, 1349 (1985); J. Natl. Cancer Inst., 80, 932 (1988); Proc. Natl. Acad. Sci., 82, 1242 (1985)), premature clearance of the non-human animal-derived monoclonal antibody occurs (J. Nucl. Med.,26, 1011 (1985); Blood, 65, 1349 (1985); J. Natl. Cancer Inst., 80, 937 (1988)), or therapeutic effect of the monoclonal antibody is reduced (J. Immunol.,135, 1530 (1985); Cancer Res., 46, 6489 (1986)).

In order to solve these problems, attempts have been made to convert non-human animal-derived monoclonal antibodies to human chimeric antibodies or human CDR-grafted antibodies (reconstituted human antibodies) by gene recombinant techniques. A human chimeric antibody is an antibody of which the variable region (hereinafter referred to as "V region") is derived from a non-human animal antibody and the constant region (hereinafter referred to as "C region") is derived from a human antibody (Proc. Natl. Acad. Sci., 81, 6851 (1984)). It has been reported that when a human chimeric antibody is administered to a human, antibodies are hardly produced against the non-human animal-derived monoclonal antibody and a half-life in blood is increased by a factor of 6 (Proc. Natl. Acad. Sci.,86, 4220 (1989)). A human CDR-grafted antibody is a human antibody of which the CDR (complementarity determining region) is replaced with the CDR of a non-human animal-derived antibody (Nature, 321, 522 (1986)). It has been reported with experiments on monkeys that a human CDR-grafted antibody has a lower immunogenicity, with the half-life in blood being increased by a factor of 4–5 compared with a mouse antibody (J. Immunol.,147, 1352 (1991)). However, there is no report about a humanized antibody against hIL-5R α.

When a humanized antibody which binds specifically to human IL-5R α is administered to a human, it is expected to cause no production of an antibody against a non-human animal-derived monoclonal antibody, thereby reducing the side effect and prolonging the half-life in blood, which eventually leads to a high therapeutic effect against allergic diseases such as chronic bronchial asthma, atopic dermatitis and the like.

As a result of the recent progresses in protein and genetic engineering, smaller antibody molecules such as single chain antibodies (Science, 242, 423 (1988)) and disulfide stabilized antibodies (Molecular Immunology, 32, 249 (1995)) are being prepared. Since single chain antibodies and disulfide stabilized antibodies have smaller molecular weights than monoclonal antibodies and humanized antibodies, they are effective in transition into tissues and clearance from blood and their application to the imaging technology and the preparation of complexes with toxins are being underway to provide some promise in therapeutic efficacy (Cancer Research, 55, 318 (1995)). If a single chain antibody or a disulfide stabilized antibody which binds specifically to a human IL-5R α chain is produced, high diagnostic and therapeutic effects against allergic diseases and the like are anticipated. However, there is no report about a single chain antibody and a disulfide stabilized antibody against a human IL-5R α chain.

SUMMARY OF THE INVENTION

The inventors found that antibodies to a hIL-5R α chain which recognizes an epitope at 1–313 positions of the N-terminal amino acid sequence of the human IL-5R α chain which corresponds to an extracellular region defective in the transmembrane region and onwards react specifically with a human interleukin-5 receptor a chain upon immunocyte staining and inhibit the biological activity of interleukin-5. These antibodies can be used to diagnose and treat the aforementioned allergic diseases.

Hence, the present invention provides antibodies which react specifically with a human IL-5R α chain. The antibodies of the present invention include monoclonal antibodies, humanized antibodies, single chain antibodies, disulfide stabilized antibodies and the like. The antibodies of the present invention may be of any kinds, provided that they react specifically with a hIL-5R α chain. Those produced by the method explained below are preferred. Briefly, hIL-5R α protein is prepared as an antigen and applied to immunize animals such as mice, rats, hamsters, rabbits and the like used to prepare hybridomas, thereby inducing to plasma cells having an antigen specificity. The plasma cells are fused with myeloma cells to prepare hybridomas which can produce monoclonal antibodies, and the hybridomas are cultured to obtain the desired anti-IL-5R α monoclonal antibodies. Any monoclonal antibody can be used so long as it recognizes an epitope at 1–313 positions from the N-terminal amino acid of a human IL-5R α chain and reacts specifically with the human IL-5R α chain upon immunocyte staining. Alternatively, any monoclonal antibody can be used so long as it recognizes an epitope at 1–313 positions from the N-terminal amino acid of the human IL-5R α chain and inhibits the biological activity of human IL-5. The former monoclonal antibodies are exemplified by monoclonal antibody KM1257 produced by hybridoma KM1257 (FERM BP-5133). The latter monoclonal antibodies are exemplified by KM1259 produced by hybridoma KM1259 (FERM BP-5134) and KM1486 produced by hybridoma KM1486 (FERM BP-5651).

The monoclonal antibodies of the present invention react immunologically with a human IL-5R α chain, a cell having a human IL-5R α chain expressed on the surface, human eosinophil and the like. The monoclonal antibodies of the present invention react immunologically with a soluble human IL-5R α chain. Hence, the present invention also provides a method for immunologically detecting and determining a human IL-5R α chain, a, cell having a human IL-5R α chain expressed on the surface, human eosinophil and a soluble human IL-5R α chain. The results of the detection and determination can be used in the diagnosis and treatment of allergic diseases such as chronic bronchial asthma, atopic dermatitis and the like.

The present invention also provides humanized antibodies that have lesser side effects with a prolonged half-life than the monoclonal antibodies and which inhibit the biological activity of IL-5 in a more desired way as therapeutics. The term "humanized antibody" of the present invention is the general term for human chimeric antibodies and human CDR-grafted antibodies.

The term "human chimeric antibody" means an antibody consisting of a variable region in a heavy chain (hereinafter referred to as "VH") and a variable region in a light chain (hereinafter referred to as "VL") of a non-human animal antibody, as well as a constant region in a heavy chain (hereinafter referred to as "CH") and a constant region in a light chain (hereinafter referred to as "CL") of a human antibody. The term "human CDR-grafted antibody" means an antibody in which CDR sequences of VH and VL of a human antibody are replaced with CDR sequences of VH and VL of a non-human animal antibody, respectively. An anti-hIL-5R α chain human chimeric antibody which inhibits the biological activity of IL-5 can be expressed and produced by a process comprising the steps of obtaining cDNAs encoding VH and VL from a hybridoma producing an antibody which can inhibit the biological activity of IL-5, inserting the respective cDNAs into a vector for expression in animal cells which contains a gene encoding human antibody CH and human antibody CL to thereby construct a human chimeric antibody expression vector and transfecting the expression vector into an animal cell. The human chimeric antibody and human CDR-grafted antibody of the present invention may be in any immunoglobulin (Ig) classes and are preferably in a class of IgG. In addition, any C region of IgG subclasses of immunoglobulin such as IgG1, IgG2, IgG3 and IgG4 can be used.

Examples of the human chimeric antibody of the present invention include an antibody of which the VH contains the amino acid sequence of SEQ ID NO: 27, CH is human antibody IgG1, VL contains the amino acid sequence of SEQ ID NO: 29, and CL is human antibody κ. A specific example is an antibody designated as "KM1399". A specific example of the human chimeric antibody of which the CH is human antibody IgG4 is an antibody designated as "KM7399". KM1399 can be produced, for example, by transformant KM1399 (FERM BP-5650). KM7399 can be produced, for example, by transformant KM7399 (FERM BP-5649).

The anti-hIL-5R α chain human CDR-grafted antibody which inhibits the biological activity of IL-5 can be expressed and produced by a process comprising the steps of constructing cDNAs encoding a V region in which CDR sequences of VH and VL of any human antibody are replaced with CDR sequences of VH and VL, respectively, of a non-human animal antibody which can inhibit the biological activity of IL-5, inserting the respective cDNAs into a vector for expression in animal cells which contains a gene encoding human antibody CH and human antibody CL to thereby construct a human CDR-grafted antibody expression vector, and transfecting the expression vector into an animal cell. Examples of the human CDR-grafted antibody of the present invention include an antibody of which the VH contains the amino acid sequence of SEQ ID NO: 83, CH is human antibody IgG1, VL contains the amino acid sequence of SEQ ID NO: 71, and CL is human antibody κ. A specific example is an antibody designated as "KM8399". A specific example of the human CDR-grafted antibody of which the CH is human antibody IgG4 is an antibody designated as "KM9399". KM8399 can be produced, for example, by transformant KM8399 (FERM BP-5648). KM9399 can be produced, for example, by transformant KM9399 (FERM BP-5647).

The humanized antibody of the present invention reacts immunologically with a human IL-5R α chain, a cell having a human IL-5R α chain expressed on the surface, human eosinophil and the like. Hence, the humanized antibody of the present invention can be used in the diagnosis and treatment of allergic diseases such as chronic bronchial asthma, atopic dermatitis and the like.

In addition, the present invention provides single chain antibodies (single chain Fv; hereinafter referred to as "scFv") and disulfide stabilized antibodies (disulfide stabilized Fv; hereinafter referred to as "dsFv") which exhibit an ability to bind to a human IL-5R α chain.

The term "single chain antibody (scFv)" means a polypeptide represented by formula VH-L-VL or VL-L-VH in which a single chain of VH and a single chain of VL are linked by an appropriate peptide linker (hereinafter referred to as "L"). Any anti-human IL-5R α chain monoclonal antibodies or human CDR-grafted antibodies can be used as VH and VL in the scFv of the present invention.

The term "disulfide stabilized antibody (dsFv)" means an antibody prepared by binding through a disulfide bond two polypeptides in which each one of the amino acid residues in VH and VL is replaced with cysteine residues. The amino acid residues to be replaced with cysteine residues can be selected on the basis of a presumed steric structure of an antibody in accordance with the method described by Reiter et al. (Protein Engineering,7, 697 (1994)). Either a mouse anti-human IL-5R α chain monoclonal antibodies or a human CDR-grafted antibodies can be used as VH or VL in the disulfide stabilized antibody of the present invention.

The single chain antibody which has an ability to bind to a human EL-5R α chain can be expressed and produced by a process comprising the steps of obtaining cDNA encoding VH and VL from a hybridoma which produces an antibody reactive with the human IL-5R α chain, constructing a single chain antibody expression vector, and transfecting the expression vector into an E. coli, yeast or animal cell. Examples of the monoclonal antibody-derived single chain antibody of the present invention include an antibody of which the VH contains the amino acid sequence of SEQ ID NO: 27 and VL contains the amino acid sequence of SEQ ID NO: 29. Examples of the human CDR-grafted antibody-derived single chain antibody of the present invention include an antibody of which the VH contains the amino acid sequence of SEQ ID NO: 83 and VL contains the amino acid sequence of SEQ ID NO: 71.

The disulfide stabilized antibody which has an ability to bind to a human IL-5R α chain can be expressed and produced by a process comprising the steps of obtaining cDNA encoding VH and VL from a hybridoma which produces an antibody reactive with the human IL-5R α chain, inserting the cDNA into an appropriate expression vector, and transfecting the expression vector into an *E. coli*, yeast or animal cell. Examples of the monoclonal antibody-derived single chain antibody of the present invention include an antibody of which the VH contains the amino acid sequence of SEQ ID NO: 27 and VL contains the amino acid sequence of SEQ ID NO: 29. Examples of the human CDR-grafted antibody-derived disulfide stabilized antibody of the present invention include an antibody of which the VH contains the amino acid sequence of SEQ ID NO: 83 and VL contains the amino acid sequence of SEQ ID NO: 71.

A method for producing an anti-human IL-5R α chain monoclonal antibody which reacts specifically with a human IL-5R α chain or which inhibits the biological activity of human IL-5, and a method for producing an anti-human IL-5R α chain humanized antibody, an anti-human IL-5R α chain single chain antibody and an anti-human IL-5R α chain disulfide stabilized antibody all of which inhibit the biological activity of human IL-5, as well as a method for detecting and determining a human interleukin-5 receptor α chain by means of said antibodies will now be explained in detail.

DETAILED DESCRIPTION OF THE INVENTION

1. Production of Anti-hIL-5R α Monoclonal Antibody (1) Preparation of Antigen

A cell having hIL-5R α expressed on the cell surface or a cell membrane fraction thereof, or an hIL-5R α-expressing cell CTLL-2 (h5 R) or a cell membrane fraction thereof can be used as an antigen for producing an anti-hIL-5R α monoclonal antibody. CTLL-2 (h5 R) is an hIL-5R α-expressing cell which was created by inserting a cDNA encoding a full length sequence of a pre-cloned hIL-5Rα (J. Exp. Med., 175, 341 (1992)) into an expression vector for animal cells such as pCAGGS (Gene,108, 193 (1991)) and transfecting the expression vector into murine T cell line CTLL-2.

For expression in a prokaryotic host cell such as *E. coli*, a full length or partial fragment of cDNA encoding hIL-5R α can be inserted into an expression vector such as commercially available pGEX (Pharmacia), pET system (Novagen), pMKex1 to be described in section (11) of Example 1 below or the like and the full length hIL-5R α sequence or a partial fragment thereof can be expressed either as such or as a fusion protein. After disruption of the cell, the protein expressed by *E. coli* can be purified by SDS-polyacrylamide electrophoresis, affinity chromatography based on the nature of the fusion protein, or the like.

In the method of expressing the full length IL-5R α sequence or a partial fragment thereof either as such or as a fusion protein, eukaryotic host cells such as insect cells, mammalian cells and the like can be used.

In the case of using a mammalian cell, a full length or a partial fragment of cDNA encoding hIL-5R α is inserted into a vector such as pAGE107 (Cytotechnology, 3, 133 (1990)), pAGE103 (J. Biochem.,101, 1307 (1987)), pAGE210 to be described in section (1) of Example 1 below or the like to thereby construct an expression vector for the protein. In order to express efficiently the full length hIL-5R α sequence encoded by the cDNA or a partial fragment thereof either as such or as a fused protein, the nucleotide sequence encoding a signal peptide in the cDNA is preferably replaced by the nucleotide sequence encoding a signal peptide of a protein which can be expressed at a high level in a eukaryotic host cell. Known signal peptides of proteins including those of human growth hormone, anti-ganglioside GD3 chimeric antibody KM871 (Kokai No. 304989/93) and the like are preferably used.

The thus constructed expression vector can be transfected into host cells by a known method such as electroporation (Kokai No. 257891/90; Cytotechnology, 3, 133 (1990)), lipofectin method (Proc. Natl. Acad. Sci., 84, 7413 (1987)) or the like. The cultivation of the cells in an appropriate medium can result in the production of the full length hIL-5R α sequence or a partial fragment thereof either as such or as a fusion protein in the cells or the culture supernatant. A serum-free medium is preferably used because it can facilitate the purification of the partial fragment or fusion protein of hIL-5R α produced in the culture supernatant.

In the case of using an insect cell, a full length or a partial fragment of cDNA encoding hIL-5R α is inserted using a Baculo Gold Starter Kit (Pharmingen) to prepare a recombinant baculovirus and insect cells of Sf9, Sf21 (Pharmingen) or the like are infected with the recombinant virus such that the full length hIL-5R α sequence or a partial fragment thereof is produced either as such or as a fusion protein in the cells or the culture supernatant (Bio/Technology, 6, 47 (1988)).

The full length hIL-5R α sequence or a partial fragment or fusion protein thereof produced by the animal or insect cells can be purified from the culture supernatant or the like by a known method of protein purification such as salting-out, affinity chromatography, ion-exchange chromatography or the like and can be used as an antigen. Particularly in the case where the hIL-5R α is produced as a fusion protein with a constant region of immunoglobulin, it is preferably purified using an affinity column having fixed thereto protein A which has specific affinity for the constant region of immunoglobulin.

(2) Immunization of animal and preparation of antibody-producing cells

Any animal such as mice, rats, hamsters, rabbits and the like can be used as animals to be immunized, provided that they can be used to prepare hybridomas. An embodiment in which mice or rats are used will be explained herein. Mice and rats of 3–20 weeks old are immunized with shIL-5R α or CTLL-2 which have hIL-5R α expressed on the surface (J. Exp. Med., 177, 1523 (1993)) as an antigen and antibody-producing cells are collected from the spleens, lymph nodes and peripheral blood of the animals. Immunization is performed by administering the animals with the antigen together with an appropriate adjuvant such as complete Freund's adjuvant or a combination of aluminum hydroxide gel and pertussis vaccine either subcutaneously, intravenously or intraperitoneally. The antigen is administered 5–10 times at intervals of 1–2 weeks after the first administration. Blood is collected from the ophthal venous plexus at day 3–7 after each administration and the serum is examined for a reactivity with the antigen by enzyme immunoassay ("Enzyme Immunoassay (ELISA)", published by Igakushoin, 1976).

A mouse or rat whose serum shows a satisfactory antibody titer to shIL-5R α or the cells which have hIL-5R α expressed on the surface, which are used for immunization, can be used as a source of antibody-producing cells.

In order to perform fusion of a spleen cell with a myeloma cell, the spleen is removed from the immunized mouse at day 3–7 after the final administration of the antigenic substance and spleen cells are collected. The spleen is sliced in an MEM medium (Nissui Pharmaceuticals) and dispersed with a pair of tweezers. After centrifugation (1,200 rpm, 5 min), the supernatant is removed. The precipitate is treated with a Tris-ammonium chloride buffer (pH 7.65) for 1–2 minutes to remove erythrocytes and washed with MEM medium 3 times to prepare splenocytes for use in cell fusion.

(3) Preparation of Myeloma Cells

An established cell line from a mouse or a rat is used as a myeloma cell. Examples include myeloma cell lines P3-X63Ag8-U1 (P3-U1) (Curr. Topics Microbiol. Immunol., 81, 1 (1978); Europ. J. Immunol., 6, 511 (1976)), SP2/0-Ag14 (SP-2) (Nature, 276, 269 (1978)), P3-X63-Ag8653 (653) (J. Immunol., 123, 1548 (1979)) and P3-X63-Ag8 (X63) (Nature,256, 495 (1975)) which are derived from 8-azaguanine-tolerant mice (BALB/c). These cell lines can be subcultured in 8-azaguanine medium which is RPMI-1640 medium supplemented with glutamine (1.5 mM), 2-mercaptoethanol ($5 \times 10^5$ M), gentamicin (10 µg/ml) and fetal calf serum (FCS) (CSL, 10%) (hereinafter referred to as "normal medium"), which is further supplemented with 8-azaguanine (15 µg/ml). They should be subcultured in a normal medium 3–4 days before cell fusion to ensure a cell count of at least $2 \times 10^7$ cells on the day of cell fusion.

(4) Cell Fusion

The antibody-producing cells described in 1 (2) and the myeloma cells described in 1 (3) are washed thoroughly with MEM medium or PBS (1.83 g of disodium phosphate, 0.21 g of monopotassium phosphate, 7.65 g of sodium chloride, 1 L of distilled water, pH 7.2). These cells are mixed such that a cell count ratio of the antibody-producing cells to the myeloma cells is 5–10:1. After centrifugation (1,200 rpm, 5 min), the supernatant is removed. The precipitated cells are dispersed and a mixed solution composed of ethylene glycol-1000 (PEG-1000)(2 g), MEM (2 ml) and dimethyl sulfoxide (DMSO) (0.7 ml) is then added to the cells in an amount of 0.2–1 ml/$10^8$ antibody-producing cells while stirring. An MEM medium (1–2 ml) is added several times at intervals of 1–2 minutes and an additional MEM medium is then added such that the total volume is 50 ml. After centrifugation (900 rpm, 5 min), the supernatant is removed. The cells are dispersed gently and then suspended gently in 100 ml of a HAT medium (a normal medium supplemented with $10^{-4}$ M hypoxanthine, $1.5 \times 10^{-5}$ M thymidine and $4 \times 10^{-7}$ M aminopterin) by suction and blowoff with a pipette.

The cell suspension is dispensed in a 96-well culture plate in an amount of 100 µl/well and cultured in a 5% $CO_2$ incubator at 37° C. for 7–14 days.

After the cultivation, an aliquot of the culture supernatant is examined by enzyme immunoassay to be described in 1 (5) to select a well that is reactive specifically with a recombinant protein such as a fusion protein with shIL-5R α or hIL-5R α described in 1 (1). Subsequently, cloning by limiting dilution is repeated twice. An aminopterin-free HAT medium is used in the first cloning and a normal medium in the second cloning. A cell exhibiting a high antibody titer stably is selected as a hybridoma cell line which produces a mouse or rat anti-hIL-5R α monoclonal antibody.

(5) Selection of Mouse or Rat Anti-human IL-5R α Monoclonal Antibody

A mouse or rat anti-hIL-5R α monoclonal antibody-producing hybridoma is selected in accordance with a method as described in Antibodies, A Laboratory Manual, Cold Spring Harbor Laboratory, Chapter 14 (1988) by the measurement method described below. By the method, the activity of an anti-hIL-5R α antibody in the culture supernatant of the transformants producing an anti-hIL-5R α humanized antibody, a single chain antibody or a disulfide stabilized antibody which are to be described below or the activities of all purified anti-hIL-5R α antibodies can be determined.

An appropriate plate is coated with shIL-5R α or a recombinant protein such as a fusion protein with hIL-5R α described in 1 (1). The plate is reacted with a primary antibody which is the hybridoma culture supernatant or the purified antibody to be obtained in 1 (6) and reacted with a secondary antibody which is an anti-mouse immunoglobulin antibody or an anti-rat immunoglobulin antibody which is labeled with biotin, an enzyme, a chemiluminescent substance or a radioactive compound. Subsequently, a reaction is performed in accordance with the specific kind of the label, whereby a hybridoma that is reactive specifically with hIL-5R α is selected as a hybridoma producing a mouse anti-hIL-5R α monoclonal antibody.

If the culture supernatant of the transformants producing an anti-hIL-5R α humanized antibody, a single chain antibody or a disulfide stabilized antibody, or an antibody purified therefrom is reacted as a primary antibody, an anti-human immunoglobulin antibody labeled with biotin, an enzyme, a chemiluminescent substance or a radioactive compound is used as a secondary antibody and a reaction is performed in accordance with the specific kind of the label for detection.

An appropriate plate is coated with shIL-5R α or a recombinant protein such as a fusion protein with a recombinant protein hIL-5R α described in 1 (1). Any one of the hybridoma culture supernatant, the culture supernatant of the transformants producing an anti-hIL-5R α humanized antibody, a single chain antibody or a disulfide stabilized antibody, or an antibody purified therefrom is mixed and reacted with human IL-5 labeled with biotin, an enzyme, a chemiluminescent substance or a radioactive compound. Subsequently, a reaction is performed in accordance with the specific kind of the label so as to determine an activity in inhibiting the binding of human IL-5 to human IL-5R α. This method is used to screen hybridomas for selection of one having a high inhibitory activity against human IL-5.

(6) Production of Mouse or Rat Monoclonal Antibody

A 8–10 week-old mouse or nude mouse is treated with pristane. More specifically, the mouse is administered intraperitoneally with pristane (2,6,10,14- tetramethylpentadecane, 0.5 ml) and bred for 2 weeks. The mouse is administered intraperitoneally with the mouse or rat anti-hIL-5R α monoclonal antibody-producing hybridoma cell lines (as obtained in 1 (3)) in an amount of $2 \times 10^7$–$5 \times 10^6$ cells/mouse. The hybridoma caused ascites tumor after 10–21 days administration. The ascites is collected from the mouse and centrifuged (3,000 rpm, 5 min) to remove a solid portion. The precipitate is salted out and applied to a column for a caprylic acid precipitation, or a DEAE-Sepharose column, a protein A-column or a Cellulofine GSL2000 column (Biochemical Industry) to collect IgG or IgM fractions. These fractions are used as a purified monoclonal antibody.

The subclass of the antibody is determined using a mouse or rat monoclonal antibody typing kit. The mass of the protein is calculated by a Lowry method or from the absorbance at 280 nm.

2. Production of Anti-human IL-5R α Humanized Antibody (1) Construction of Humanized Antibody Expression Vector In order to produce a humanized antibody from a non-human animal antibody, a humanized antibody expression vector is prepared. The humanized antibody expression vector is a vector for expression in animal cells into which a gene encoding CH and CL, C regions of a human antibody, have been transfected. Such an expression vector is constructed by inserting two genes, one encoding CH of a human antibody and the other encoding CL of a human antibody, into an expression vector for animal cells. Any C regions of a human antibody such as Cγ1 and Cγ4 of a human antibody H chain, Cκ of a human antibody L chain and the like can be used. A chromosomal DNA consisting of an exon(s) and an intron(s) or cDNA can be used as a gene encoding a C region of a human antibody. Any expression vectors can be used as expression vectors for animal cells, provided that they can incorporate and express a gene encoding a C region of a human antibody. Examples are pAGE107 (Cytotechnology, 3, 133 (1990)), pAGE103 (J. Biochem., 101, 1307 (1987)), pHSG274 (Gene, 27, 223 (1984)), pKCR (Proc. Natl. Acad. Sci., 78, 1527 (1981)) and pSG1 βd2–4 (Cytotechnology, 4. 173 (1990)). A promoter and an enhancer to be used in preparation of an expression vector for animal cells are exemplified by an SV40 early promoter and enhancer (J. Biochem.,101, 1307 (1987)), a Moloney mouse leukemia virus LTR promoter and enhancer (Biochem. Biophys. Res. Commun., 149, 960 (1987)), an immunoglobulin H chain promoter (Cell, 41, 479 (1985)) and enhancer (Cell, 33, 717 (1983)), and the like.

The humanized antibody expression vector may be either of a type in which a gene encoding an antibody H chain and a gene encoding an antibody L chain exist on separate vectors or of a type in which both genes exist on the same vector (tandem type). In terms of ease of construction of a humanized antibody expression vector, easiness of introduction into animal cells, balance between the expression amounts of antibody H and L chains in the animal cells and for other reasons, a tandem type of humanized antibody expression vector is more preferred (J. Immunol. Methods, 167, 271 (1994)).

(2) Preparation of cDNA Encoding VH and VL of Non-human Animal Antibody cDNA encoding VH and VL of a non-human animal antibody such as a mouse anti-human IL-5R α chain monoclonal antibody is obtained, for example, as follows:

mRNA is extracted from an anti-human IL-5R α chain monoclonal antibody-producing cell such as a mouse anti-human EL-5R α chain antibody-producing hybridoma and used to synthesize cDNA. The synthesized cDNA is inserted into a vector such as a phage or a plasmid to prepare a cDNA library. From the library, with a portion in a V or C region of a non-human animal antibody such as a mouse antibody being used as a probe, a recombinant phage or plasmid which contains cDNA encoding VH and a recombinant phage or plasmid which contains cDNA encoding VL are isolated separately. The full nucleotide sequences of VH and VL of an antibody of interest which exist on the recombinant phage or plasmid are determined and the full amino acid sequences of the VH and VL are deduced from the nucleotide sequences.

(3) Construction of Human Chimeric Antibody Expression Vector

A human chimeric antibody expression vector can be constructed by inserting cDNA encoding VH and VL of a non-human animal antibody in a region upstream of the gene encoding CH and CL of the human antibody on the humanized antibody expression vector which has been constructed in 2 (1). For example, a restriction enzyme recognition site for cloning of cDNA encoding VH and VL of a non-human animal antibody is created preliminarily in a region upstream of a gene encoding CH and CL of the human antibody on a chimeric antibody expression vector. At the cloning site, cDNA encoding a V region of a non-human animal antibody is inserted through a synthetic DNA (see below) to prepare a human chimeric antibody expression vector. The synthetic DNA consists of a nucleotide sequence at the 3' end of a V region of the non-human animal and a nucleotide sequence at the 5' end of a C region of the human antibody and are prepared by a DNA synthesizer such that it has appropriate restriction enzyme sites at both ends.

(4) Identification of CDR Sequences of Non-human Animal Antibody

VH and VL which form an antigen-binding site of an antibody consist of 3 complementarity determining regions (CDRs) having a wide variety of sequences which link the VH and VL to 4 framework regions (hereinafter referred to as R regions") having relatively conserved sequences (Sequences of Proteins of Immunological Interest, US Dept. Health and Human Services, 1991). The amino acid sequence of the respective CDR (CDR sequence) can be identified by comparison with the amino acid sequences of V regions of known antibodies (Sequences of Proteins of Immunological Interest, US Dept. Health and Human Services, 1991).

(5) Construction of cDNA Encoding V Region of Human CDR-grafted Antibody cDNA encoding VH and VL of a human CDR-grafted antibody can be obtained as follows:

In the first step, for each of VH and VL, the amino acid sequence of FR in a V region of a human antibody to which CDR in a V region of a non-human animal antibody of interest is to be grafted is selected. Any amino acid sequences of FRs in V regions derived from human antibodies can be used as the amino acid sequences of FRs in V regions of human antibodies. For example, the amino acid sequences of FRs in V regions of human antibodies recorded in Protein Data Bank and amino acid sequences common to subgroups of FRs in V regions of human antibodies (Sequences of Proteins of Immunological Interest, US Dept. Health and Human Services, 1991) can be used. In order to produce a human CDR-grafted antibody having an excellent activity, an amino acid sequence having high homology with the amino acid sequence of a V region of a non-human animal antibody of interest is desired. In the second step, a DNA sequence encoding the selected amino acid sequence of FR in a V region of a human antibody is ligated to a DNA sequence encoding the amino acid sequence of CDR in a V region of a non-human animal antibody and a DNA sequence encoding the amino acid sequences of VH and VL is designed. In order to obtain a DNA sequence designed to construct a CDR-grafted antibody variable region gene, several synthetic DNAs are designed for each strand such that the full DNA sequence is covered. Using the synthetic DNAs, polymerase chain reaction (hereinafter referred to as CR") is performed. For each strand, preferably 6 synthetic DNAs are designed in view of the reaction efficiency of PCR and the lengths of DNAs which can be synthesized. After the reaction, amplified fragments are subdloned into appropriate vectors and their nucleotide sequences are determined, thereby obtaining a plasmid which contains cDNA encoding the amino acid sequence of a V region of each strand of a human CDR-grafted antibody of interest. Alternatively, cDNA encoding the amino acid sequence of a V region of each strand of a human CDR-grafted antibody of interest may be constructed by synthesizing the full sequences of sense and antisense strands using synthetic DNAs consisting of about 100 bases and subjecting them to annealing and ligation.

(6) Modification of the Amino Acid Sequence of V Region of Human CDR-grafted Antibody It is known that if a human CDR-grafted antibody is prepared by simply grafting only CDR in a V region of a non-human animal antibody of interest between FRs in a V region of a human antibody, its activity is lower than that of the original non-human animal antibody (BIO/TECHNOLOGY, 9,266 (1991)). Hence, among the amino acid sequences of FR in a V region of a human antibody, an amino acid residue which takes part in direct binding to an antigen, an amino acid residue which interacts with an amino acid residue in CDR, or an amino acid residue which may take part in the maintenance of the steric structure of an antibody is modified to an amino acid residue that is found in the original non-human animal antibody such that the activity of the human CDR-grafted antibody is increased. For efficient identification of the amino acid residue, the steric structure of an antibody is constructed and analyzed by X-ray crystallography, computer-modeling or the like. However, no method for producing a human CDR-grafted antibody which can be applied to any antibodies has yet been established and, therefore, various attempts must currently be made on a case-by-case basis.

The modification of the selected amino acid sequence of FR in a V region of a human antibody can be accomplished using various primers for mutation by PCR described in 2 (5). Amplified fragments obtained by the PCR are subcloned into appropriate vectors and their nucleotide sequences are determined, thereby obtaining a vector containing cDNA into which a mutation of interest has been introduced (hereinafter referred to as "amino acid sequence-replaced vector").

Alternatively, the modification of an amino acid sequence in a narrow region may be accomplished by a PCR-mutagenesis method using primers for mutation consisting of 20–35 bases. More specifically, a sense mutation primer and an antisense mutation primer which consist of 20–35 bases and which contain DNA sequences encoding the amino acid residue to be modified are synthesized and used to perform 2-step PCR using as a template a plasmid which contains cDNA encoding the amino acid sequence of a V region which is to be modified. The finally amplified fragments are subcloned into appropriate vectors and their nucleotide sequences are determined, thereby obtaining an amino acid sequence-modified vector containing cDNA into which a mutation of interest has been introduced.

(7) Construction of Human CDR-grafted Antibody Expression Vector

A human CDR-grafted antibody expression vector can be constructed by inserting the cDNA encoding VH and VL of the human CDR-grafted antibody obtained in 2 (5) and 2 (6) in a region upstream of the gene encoding CH and CL of the human antibody in the humanized antibody expression vector described in 2 (1). For example, if recognition sites for appropriate enzymes are introduced at the ends of the 5' and 3' terminal synthetic DNAs during PCR for construction of cDNA encoding the amino acid sequences of VH and VL of the human CDR-grafted antibody, the cDNA can be inserted in a region upstream of a gene encoding a C region of a desired human antibody such that it is expressed in an appropriate form.

(8) Transient Expression of Humanized Antibodies and Evaluation of Their Activities In order to evaluate the activities of a wide variety of humanized antibodies efficiently, the human chimeric antibody expression vector described in 2 (3), and the human CDR-grafted antibody expression vector described in 2 (7) or their modified vectors may be transfected into COS-7 cells (ATCC CRL1651) and humanized antibodies expressed transiently (Methods in Nucleic Acids Res., CRC Press, p.283, 1991), followed by determination of their activities.

Examples of the method for transfecting the expression vector into a COS-7 cell include a DEAE-dextran method (Methods in Nucleic Acids Res., CRC Press, p.283, 1991), a lipofection method (Proc. Natl. Acad. Sci., 84, 7413 (1987)) and the like.

After transfection of the vector, the activities of the humanized antibodies in the culture supernatant can be determined by the enzyme immunoassay (ELISA) described in 1 (5) and the like.

(9) Stable Expression of Humanized Antibodies and Evaluation of Their Activities Transformants which produce a humanized antibody stably can be obtained by transfecting into appropriate host cells the human chimeric antibody expression vector described in 2 (3) and the human CDR-grafted antibody expression vector described in 2 (7).

Examples of the method for transfecting the expression vector into host cells include electroporation (Kokai No. 257891/90, Cytotechnology, 3, 133 (1990)) and the like.

Any cells can be used as host cells into which the humanized antibody expression vector is to be transfected, provided that they can express a humanized antibody. Examples are mouse SP2/0-Ag14 cell (ATCC CRL1581), mouse P3X63-Ag8.653 cell (ATCC CRL1580), CHO cells which are detective in dihydrofolate reductase gene (hereinafter referred to as "DHFR gene") (Proc. Natl. Acad. Sci.,77, 4216 (1980)) and rat YB2/3HL.P2.G11.16Ag.20 cell (ATCC CRL1662, hereinafter referred to as "YB2/0 cell").

After transfection of the vector, transformants which express a humanized antibody stably are selected in accordance with the method disclosed in Kokai No. 257891/90, using an RPMI1640 medium containing G418 and FCS. The humanized antibody can be produced and accumulated in a culture medium by culturing the selected transformants in a medium. The activity of the humanized antibody in the culture medium is determined by the method described in 1 (5) or the like. The production of the humanized antibody by the transformants can be increased by the method described in Kokai No. 257891/90, utilizing a DHFR gene-amplification system or the like.

The humanized antibody can be purified from the culture supernatant of the transformants by using a protein A column (Antibodies, A Laboratory Manual, Cold Spring Harbor, Chapter 8, 1988). Any other conventional methods for protein purification can be used. For example, the humanized antibody can be purified by a combination of gel filtration, ion-exchange chromatography, ultrafiltration and the like. The molecular weight of the H chain or L chain of the purified humanized antibody or the antibody molecule as a whole is determined by polyacrylamide gel electrophoresis (SDS-PAGE) (Nature, 227, 680, (1970)), western blotting (Antibodies, A Laboratory Manual, Cold Spring Harbor Laboratory, Chapter 12, 1988) and the like.

The reactivity of the purified humanized antibody and the inhibition activity of the humanized antibody against IL-5 can be determined by the method described in 1 (5).

(10) Method of Use of Humanized Antibody

The humanized antibody of the present invention can bind specifically to a human IL-5R α chain, thereby inhibiting the biological activity of IL-5. Hence, the humanized antibody of the present invention is expected to inhibit the function of eosinophils which are controlled in differentiation and growth by IL-5. Accordingly, the humanized antibody of the present invention will be useful in the treatment of diseases where eosinophils are associated with their pathogenesis. Since almost all portions of the humanized antibody of the present invention are derived from the amino acid sequence of a human antibody, it is expected not only to exhibit no immunogenicity in the human body but also to maintain its effect for a long period of time. The humanized antibody of the present invention can be used either alone or in combination with at least one pharmaceutically acceptable adjuvant. For example, the humanized antibody is dissolved in physiological saline or an aqueous solution of glucose, lactose, mannitol or the like to prepare a pharmaceutical composition. Alternatively, the humanized antibody is lyophilized by a conventional method and sodium chloride is added to prepare an injection in a powder form. If necessary, the present pharmaceutical composition may contain any additive that is well known in the field of pharmaceutical preparations such as a pharmaceutically acceptable salt and the like.

The present pharmaceutical composition can be administered to mammals including human at a dose of 0.1–20 mg/kg/day of the humanized antibody, which may vary depending on the age and conditions of the patient and the like. The administration is given once a day (single dose or continuous administration), 1–3 times a week or once every 2–3 weeks by intravenous injection.

3. Production of Anti-human IL-5R α Single Chain Antibody (1) Construction of Single Chain Antibody Expression Vector A vector for expression of a single chain antibody of a non-human animal antibody or a single chain antibody of a human CDR-grafted antibody can be constructed by inserting into a single chain antibody expression vector the cDNAs encoding VH and VL of a non-human animal antibody or a human CDR-grafted antibody which are described in 2 (2), 2 (5) and 2 (6). Any expression vectors can be used as single chain antibody expression vectors, provided that they can incorporate and express the cDNAs encoding VH and VL of a non-human animal antibody or a human CDR-grafted antibody. Examples are pAGE107 (Cytotechnology, 3, 133 (1990)), pAGE103 (J. Biochem., 101, 1307 (1987)), pHSG274 (Gene, 27, 223 (1984)), pKCR (Proc. Natl. Acad. Sci., 78, 1527 (1981)) and pSG1 βd2–4 (Cytotechnology, 4. 173 (1990)). A host for use in expressing a single chain antibody can be selected from among *E. coli*, yeast and animal cells and the like. In this case, an expression vector which is compatible with the specific host should be selected. The single chain antibody can be secreted out of the cell and transported into the periplasm region or retained within the cell by inserting a cDNA encoding an appropriate signal peptide into the expression vector.

A single chain antibody expression vector into which the cDNA encoding a single chain antibody of interest has been inserted can be constructed by inserting the cDNA encoding a single chain antibody consisting of VH-L-VL or VL-L-VH (where L is a peptide linker) into the selected expression vector in a region downstream of an appropriate promoter and a signal peptide.

The cDNA encoding a single chain antibody can be obtained by linking a VH encoding cDNA to a VL encoding cDNA through a synthetic DNA encoding a peptide linker having recognition sites for appropriate restriction enzymes at both the ends. It is important to optimize the linker peptide such that its addition does not interfere with the binding of VH and VL to an antigen. For example, the linker described by Pantoliano et al. (Biochemistry, 30, 10117 (1991)) and its modified versions may be used.

(2) Expression of Single Chain Antibody and Evaluation of its Activity

A transformant which produces a single chain antibody of interest can be obtained by transfecting the single chain antibody expression vector constructed in 3 (1) into an appropriate host cell by electroporation (Kokai No. 257891/90; Cytotechnology, 3, 133 (1990)) or the like. After transfection of the expression vector, the activity of the single chain antibody in the culture supernatant can be determined by the method described in 1 (5) or the like.

The collection and purification of the single chain antibody of the present invention can be accomplished by a combination of known techniques. For example, if the single chain antibody is secreted in a medium, it can be concentrated by ultrafiltration and its collection and purification can be then performed by antigen affinity chromatography or ion-exchange chromatography or gel filtration. If the single chain antibody is transported into the periplasm region of the host cell, it can be concentrated by ultrafiltration following the application of an osmotic shock and its collection and purification can be then performed by antigen affinity chromatography or ion-exchange chromatography or gel filtration. If the single chain antibody is insoluble and exists as a granule (i.e., inclusion body), its collection and purification can be performed by lysis of the cell, repeated centrifugation and washing for isolation of the granule, solubilization with guanidine-HCl, an operation for returning the structure of the single chain antibody to an active structure and the subsequent purification of an active molecule.

The activity of the purified single chain antibody can be determined by the method described in 1 (5) or the like.

(3) Method of Using Single Chain Antibody

The single chain antibody of the present invention can bind specifically to a human IL-5R α chain, and inhibit the biological activity of IL-5. Hence, the single chain antibody of the present invention is expected to inhibit the function of eosinophils which are controlled in differentiation and growth by IL-5. Accordingly, the single chain antibody of the present invention will be useful in the treatment of diseases in which eosinophils are associated with the pathogenesis. The single chain antibody of the present invention can be used either alone or in combination with at least one pharmaceutically acceptable adjuvant. For example, the single chain antibody is dissolved in physiological saline or an aqueous solution of glucose, lactose, mannitol or the like to prepare a pharmaceutical composition. Alternatively, the single chain antibody is lyophilized by a conventional method and sodium chloride is added to prepare an injection in a powder form. If necessary, the present pharmaceutical composition may contain any additive that is well known in the field of pharmaceutical preparations such as a pharmaceutically acceptable salt and the like.

The present pharmaceutical composition can be administered to mammals, including humans, at a dose of 0.1–20 mg/kg/day of the signal chain antibody, which may vary depending on the age and condition of the patient and the like. The administration is given once a day (single dose or continuous administration), 1–3 times a week or once every 2–3 weeks by intravenous injection.

4. Production of Anti-human IL-5R α Disulfide Stabilized Antibody (1) Production of Disulfide Stabilized Antibody A disulfide stabilized antibody can be produced by a process comprising the steps of providing cDNAs encoding VH and VL of a non-human animal antibody or cDNAs encoding VH and VL of a human CDR-grafted antibody, modifying the DNA sequence which corresponds to a one-amino acid residue at an appropriate position in the respective cDNA with a DNA sequence corresponding to a cysteine residue, expressing the modified cDNAs and purifying the resultant peptide and then forming a disulfide bond. The modification of an amino acid residue to a cysteine residue can be performed by a mutagenesis method using PCR described in 2 (5).

A disulfide stabilized antibody H chain expression vector and a disulfide stabilized antibody L chain expression vector can be constructed by inserting the resulting cDNAs encoding the modified VH and modified VL into appropriate expression vectors. Any expression vectors can be used as disulfide stabilized antibody expression vectors, provided that they can incorporate and express cDNAs encoding a modified VH and a modified VL. For example, pAGE107 (Cytotechnology, 3, 133 (1990)), pAGE103 (J. Biochem., 101, 1307 (1987)), pHSG274 (Gene, 27, 223 (1984)), pKCR (Proc. Natl. Acad. Sci., 78, 1527 (1981)), pSG1 βd2–4 (Cytotechnology, 4. 173 (1990)) and the like can be used. A host used to express a disulfide stabilized antibody L chain expression vector and a disulfide stabilized antibody H chain expression vector for formation of a disulfide stabilized antibody can be selected from among E. coli, yeast and animal cells, and the like. In this case, an expression vector which is compatible with the specific host should be selected. The disulfide stabilized antibody can be secreted out of the cell and transported into the periplasm region or retained within the cell by inserting a cDNA encoding an appropriate signal peptide into the expression vector.

(2) Expression of Disulfide Stabilized Antibody and Evaluation of its Activity

A transformant which produces a disulfide stabilized antibody H chain or a disulfide stabilized antibody L chain of interest can be obtained by transfecting into a host cell the disulfide stabilized antibody H chain expression vector or the disulfide stabilized antibody L chain expression vector that were constructed in 4 (1) by electroporation (Kokai No. 257891/90; Cytotechnology, 3, 133 (1990)) or the like. After introduction of the expression vector, the expression of the disulfide stabilized antibody H chain or disulfide stabilized antibody L chain in the culture supernatant or the like can be confirmed by the method described in 1 (5).

The collection and purification of the disulfide stabilized antibody H chain or disulfide stabilized antibody L chain can be accomplished by combinations of known techniques. For example, if the disulfide stabilized antibody H chain or disulfide stabilized antibody L chain is secreted in a medium, they can be concentrated by ultrafiltration and their collection and purification can be then performed by various types of chromatography or gel filtration. If the disulfide stabilized antibody H chain or disulfide stabilized antibody L chain is transported into the periplasm region of the host cell, they can be concentrated by ultrafiltration after the application of an osmotic shock to the cell and their collection and purification can be then performed by various types of chromatography or gel filtration. If the disulfide stabilized antibody H chain or disulfide stabilized antibody L chain is insoluble and exists as a granule (i.e., inclusion body), their collection and purification can be performed by lysis of the cells, repeated centrifugation and washing for isolation of the granule, solubilization with guanidine-HCl and subsequent performance of various types of chromatography or gel filtration.

The purified disulfide stabilized antibody H chain and disulfide stabilized antibody L chain are mixed and subjected to a refolding procedure for deriving an active structure (Molecular Immunology, 32, 249 (1995)), thereby forming a disulfide bond. Subsequently, the active disulfide stabilized antibody can be purified by antigen affinity chromatography or ion-exchange chromatography or gel filtration. The activity of the disulfide stabilized antibody can be determined by the method described in 1 (5) or the like.

(3) Method of Use of Disulfide Stabilized Antibody

The disulfide stabilized antibody of the present invention can bind specifically to a human IL-5R α chain, thereby inhibiting the biological activity of IL-5. Hence, the disulfide stabilized antibody of the present invention is expected to inhibit the function of eosinophils which are controlled in differentiation and growth by IL-5. Accordingly, the disulfide stabilized antibody of the present invention will be useful in the treatment of diseases in which eosinophils are associated with the pathogenesis. The disulfide stabilized antibody of the present invention can be used either alone or in combination with at least one pharmaceutically acceptable adjuvant. For example, the single chain antibody or disulfide stabilized antibody is dissolved in physiological saline or an aqueous solution of glucose, lactose, mannitol or the like to prepare a pharmaceutical composition. Alternatively, the disulfide stabilized antibody is lyophilized by a conventional method and sodium chloride is added to prepare an injection in a powder form. If necessary, the present pharmaceutical composition may contain any additive that is well known in the field of pharmaceutical preparations such as a pharmaceutically acceptable salt and the like.

The present pharmaceutical composition can be administered to mammals, including humans, at a dose of 0.1–20 mg/kg/day of the disulfide stabilized antibody, which may vary depending on the age and condition of the patient and the like. The administration is given once a day (single dose or continuous administration), 1–3 times a week or once every 2–3 weeks by intravenous injection.

5. Method for Detection and Determination of Human Interleukin-5 Receptor α Chain Using Anti-human IL-5R α Antibody (1) Immunocyte Staining Using Anti-human IL-5R α Antibody When immunocytes are suspended cells, they are used as such in the following treatment. When immunocytes are adherent cells, they are detached with trypsin in EDTA and then used in the following treatment. The immunocytes are suspended in an immunocyte stain buffer (PBS containing 1% BAS, 0.02% EDTA and 0.05% sodium azide) or the like and dispensed in an amount of $1 \times 10^5$–$2 \times 10^6$ cells. The culture supernatant of the anti-human IL-5R α monoclonal antibody-producing hybridoma obtained in 1 (4), the culture supernatant of the anti-human IL-5R α humanized antibody transformant obtained in 2 (9) or the purified antibody obtained in 1 (6) or 2 (9), or the product obtained by labeling the purified antibody with an appropriate labeling substance (e.g., biotin) by a known method (KOUSOKOUTAIHOU (Methods for Enzymes and Antibodies), published by Gakusai Kikaku, 1985) and diluting the labeled antibody with an immunocyte stain buffer or a 10% animal serum-containing immunocyte stain buffer to a concentration of 0.1–50 μg/ml is dispensed in an amount of 20–500 μl and reacted on ice for 30 minutes. When the culture supernatant of the mouse anti-human IL-5R α monoclonal antibody-producing hybridoma obtained in 1 (4), the anti-human IL-5R α humanized antibody transformant obtained in 2 (9) or the purified antibody obtained in 1 (6) or 2 (9) has been reacted, the cells are washed with an immunocyte stain buffer after completion of the reaction and an immunocyte stain buffer containing about 0.1–50 μg/ml of an anti-mouse immunoglobulin antibody, anti-rat immunoglobulin antibody or anti-human immunoglobulin antibody which have been labeled with a fluorochrome such as FITC or phycoerythrin is dispensed in an amount of 50–500 μl, followed by reaction on ice for 30 minutes in the dark. When the biotin-labeled monoclonal antibody has been reacted, streptoavidin labeled with a fluorochrome such as FITC or phycoerythrin is dispensed in an amount of 50–500 μl and reaction is performed on ice for 30 minutes in the dark. When the monoclonal antibody labeled with a fluorochrome such as FITC or phycoerythrin has been reacted, an immunocyte stain buffer containing about 0.1–50 μg/ml of the monoclonal antibody is dispensed in an amount of 50–500 μl and reaction is performed on ice for 30 minutes in the dark. In each of these cases, the reaction mixture is washed thoroughly with an immunocyte stain buffer after the reaction and subjected to an analysis with a cell sorter.

(2) Test for Inhibition of Growth of Human IL-5-Dependent Cells Using Anti-human IL-5R α Antibody In order to show the biological inhibition activity of the obtained anti-human IL-5R α antibody, the effect on the growth of human IL-5-dependent cells is examined using human IL-5 dependent cells. Examples of the evaluation method include incorporation of tritium-labeled thymidine into cells, color development methods using cell counting kits and the like. A color development method used in the present invention will now be explained.

CTLL-2 (h5R) cells ($1 \times 10^4$) are suspended in a normal medium (50 μl) and dispensed in a 96-well culture plate. To the plate are added 25 μl of a solution of the purified antibody (0.01–50 μg/ml) obtained in 1 (6) or 2 (9) and a normal medium containing 0.4–40 ng/ml of human IL-5 and the mixture is cultured in a 5% $CO_2$ incubator at 37° C. for 24–72 hours. Subsequently, a cell counting kit solution is added at 10 μl/well and the cultivation is continued in a 5% $CO_2$ incubator at 37° C. for 4 hours. After completion of the cultivation, the absorbance at 450 nm is determined with a microwell plate reader Emax (Molecular Device) and the CTLL-2 (h5R) cell growth-inhibiting activity of the respective antibody is calculated.

(3) Suppression of Survival of Human Eosinophils by Anti-human IL-5R α Antibody

Human polymorphonuclear leukocyte fractions which contain eosinophils are prepared from human peripheral blood with a commercially available corpuscle separation medium such as a polymorphprep (Nikomed) or a percoll (Pharmacia). The fractions are suspended in a normal medium and the resulting cells are dispensed in a 96, 48 or 24-well culture plate in an amount of $1 \times 10^6$–$1 \times 10^7$ cells/well, followed by addition of human IL-5 to a final concentration of 0.001–10 ng/ml. The culture supematant of the anti-human IL-5R α monoclonal antibody-producing hybridoma obtained in 1 (4) or the culture supernatant of the anti-human IL-5R α humanized antibody transformant obtained in 2 (9) or the purified antibody obtained in 1 (6) or 2 (9) is added and the mixture is cultured in a 5% $CO_2$ incubator at 37° C. for 2–5 days. After completion of the cultivation, a cell sample is prepared from each well and stained by May-Grunwald-Giemsa staining method (SENSHOKUHOU NO SUBETE (Techniques for Staining, published by Ishiyaku Shuppan Cor., Ltd., 1988) or the like and the percentage of eosinophils is determined. The absence or presence of the activity of the monoclonal antibody in suppressing the viability enhancement of IL-5-dependent human eosinophils is confirmed by comparing the percentage of eosinophils in the absence of the anti-human IL-5R α antibody with that in the presence of the anti-human IL-5R α antibody.

(4) Determination of shIL-5R α Using Monoclonal Antibody

A plate is coated with 0.1–50 μg/ml of the purified antibody obtained in 1 (6) or 2 (9) as a primary antibody. The coated plate is reacted with 0.1–10,000 ng/ml of the purified shIL-5R α obtained in 1 (1) or a sample such as human serum. The plate is washed thoroughly and then reacted with a secondary antibody which is an anti-human IL-5R α antibody recognizing an epitope other than that recognized by the anti-human WL-5R α antibody which was selected for use as the primary antibody from the purified antibodies obtained in 1 (6) or 2 (9). The secondary antibody was labeled with biotin, an enzyme, a chemiluminescent substance, a radioactive compound or the like prior to the reaction. Subsequently, a reaction is performed in accordance with the label. A calibration curve is constructed on the basis of the reactivity with the purified shIL-5R and the concentration of shIL-5R in the sample is calculated.

(5) Detection of shIL-5R α by Western Blotting

The purified shML-5R α obtained in 1 (1) is subjected to SDS polyacrylamide electrophoresis (SDS-PAGE) and then blotted on a polyvinylidene difluoride membrane (hereinafter referred to as "PVDF membrane", Millipore). The PVDF membrane is immersed in PBS supplemented with 1–10% bovine serum albumin (BSA) and left to stand at 4° C. overnight for blocking, followed by thorough washing with PBS containing 0.05% Tween. The PVDF membrane is immersed in the culture supernatant of the hybridoma obtained in 1 (5) or a solution of the purified antibody obtained in 1 (6) at room temperature for 2 hours and washed thoroughly with PBS containing 0.05% Tween. The PVDF membrane is immersed in a solution of an anti-mouse immunoglobulin antibody or anti-rat immunoglobulin antibody as a secondary antibody at room temperature for 1 hour and washed thoroughly with PBS containing 0.05% Tween. The secondary antibody was labeled preliminarily with biotin, an enzyme, a chemiluminescent substance, a radioactive compound or the like. After removing the washing solution completely, a reaction is performed in accordance with the label on the secondary antibody and a check is made for the reactivity with a protein which agrees in the molecular weight to the purified shrL-5R α.

(6) Immunoprecipitation of shIL-5R α

An anti-mouse immunoglobulin antibody or anti-rat immunoglobulin antibody is diluted 10–1000 fold with PBS or other buffer. The dilutions are dispensed in a 96-well ELISA plastic plate at 50–200 μl/well and left to stand at 4° C. overnight or at room temperature for at least 2 hours, whereby they are adsorbed on the plate. The plate is washed with PBS. PBS containing 1–10% BSA and the like is dispensed in the plate at 300 μl/well and left to stand at 4° C. overnight or at room temperature for at least 30 minutes to achieve blocking. The plate is washed with PBS. The culture supernatant of the hybridoma obtained in 1 (5) or a solution of the purified antibody obtained in 1 (6) (0.01–50 μg/ml) is added at 50–200 μl/well and left to stand at 4° C. overnight, thereby adsorbing the antibody on the plate. After the plate is washed, the shIL-5R α obtained in 1 (1) is diluted with PBS or the like containing 1% BSA to a concentration of 0.1–100 μg/ml and the dilutions are dispensed at 50–200 μl/well, followed by reaction at 4° C. overnight. After the plate is washed with PBS or the like containing 0.05% Tween, a 1×–5× sample buffer for SDS-PAGE is dispensed at 50–200 μl/well and shaken at room temperature for at least 30 minutes. After optional dilution with PBS, the solution is added to each lane in an amount of 5–25 μl and subjected to SDS-PAGE, followed by blotting on a PVDF membrane or the like by a conventional method. The PVDF membrane is subjected to western blotting as described in 5 (5), thereby detecting shIL-5R α.

BRIEF DESCRIPTION OF THE DRAWINGS

FIG. 53 shows SDS-PAGE (on 4–15% gradient gel) electrophoresis patterns of anti-human IL-5R α chain human chimeric antibody KM7399 of a human antibody IgG4 subclass and human IL-5R α chain human CDR-grafted antibody KM9399 of a human antibody IgG4 subclass. The left of the Figure shows the pattern of electrophoresis under non-reducing conditions and the right of the Figure under reducing conditions. On the left-hand side, M is a lane of high molecular weight markers, 1 is a lane of KM9399 and 2 is a lane of KM7399. On the right-hand side, M is a lane of low molecular weight markers, 1 is a lane of KM9399 and 2 is a lane of KM7399.

FIG. 60 shows the results of detection of shIL-5R α by Western blotting using anti-human IL-5R α monoclonal antibodies KM1257, KM1259 and KM1486.

EXAMPLES

Example 1

1. Preparation of Antigens (1) Construction Expression Vector for Animal Cell pAGE210

Expression vector for animal cell, pAGE210, was constructed as described below using expression vectors for animal cell pAGE207 (Kokai No. 46841/94) and pAGE148 (Kokai No. 205694/94).

Three μg of plasmid pAGE207 or pAGE148 was dissolved in 30 μl of a buffer containing 10 mM Tris-HCl (pH 7.5), 10 mM magnesium chloride, 50 mM sodium chloride and 1 mM dithiothreitol (hereinafter referred to as "DTT"). To the resultant mixture, 10 units each of ClaI and KpnI (both manufactured by Takara Shuzo; unless otherwise indicated, the restriction enzymes used herein below are those manufactured by Takara Shuzo) were added and reacted at 37° C. for 4 hours. After the reaction mixture was subjected to agarose gel electrophoresis, about 0.5 μg of a 4.7 kb DNA fragment containing the SV40 early promoter and enhancer (hereinafter referred to as "$P_{SE}$"), a hygromycin resistance gene and an ampicillin resistance gene was recovered from pAGE207 and about 0.5 μg of a 4.3 kb DNA fragment containing a dihydrofolate reductase (hereinafter referred to as "dhfr") gene was recovered from pAGE148.

Figure 1:
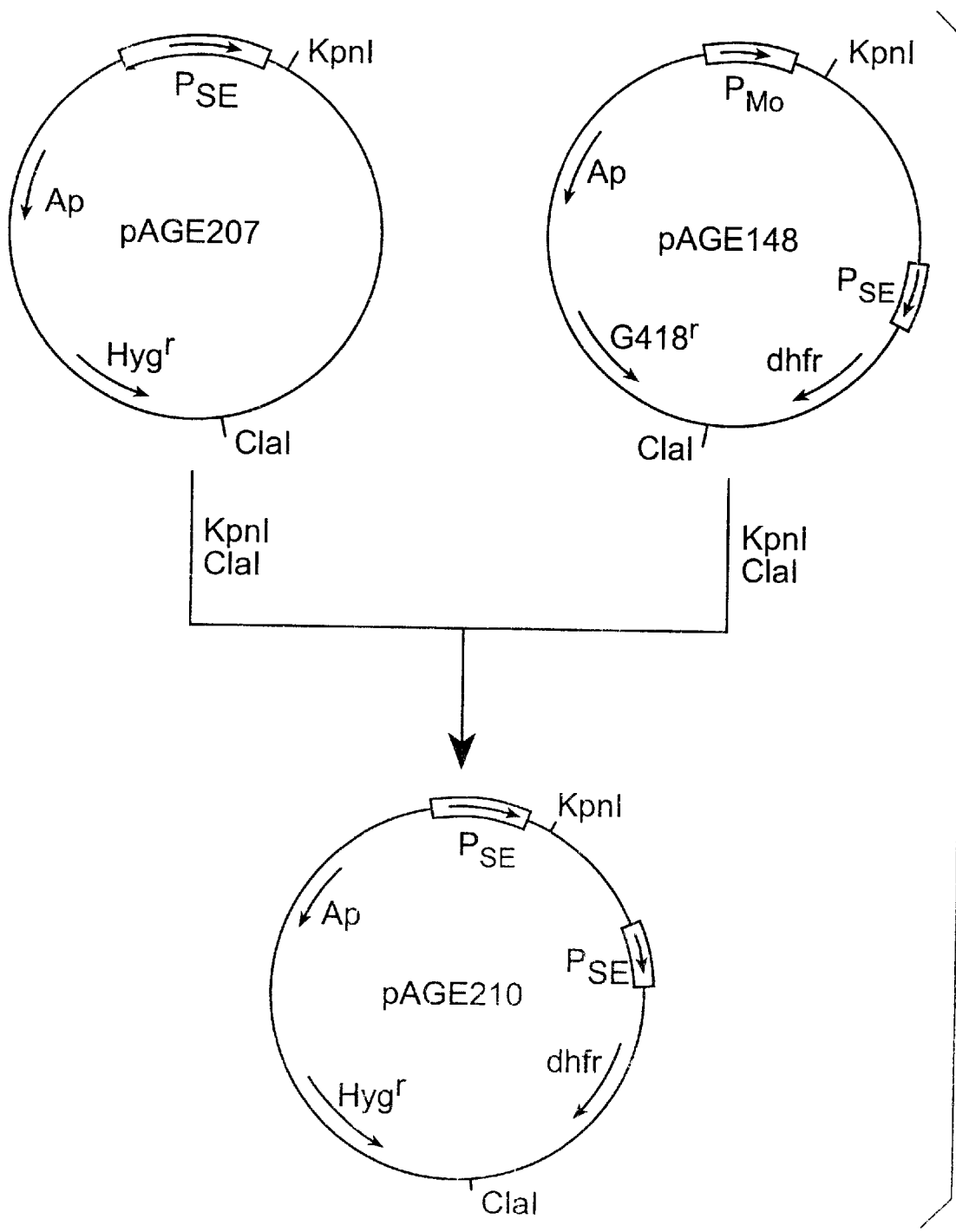
FIG. 1 shows steps for constructing plasmid pAGE210.

The ClaI-KpnI fragment obtained from pAGE207 (50 ng) and the KpnI-ClaI fragment obtained from pAGE148 (50 ng) were dissolved in 20 μl of T4DNA ligase buffer [a buffer containing 66 mM Tris-HCl (pH 7.5), 6.6 mM magnesium chloride, 10 mM DTT and 0.1 mM adenosine triphosphate (hereinafter referred to as "ATP"]. To the resultant mixture, 200 units of T4DNA ligase (Takara Shuzo) was added and ligation was performed at 12° C. for 16 hours. Using the prepared recombinant plasmid DNA, E. coli strain JM109 was transformed to thereby obtain plasmid pAGE210 shown in FIG. 1.

(2) Making shIL-5R α cDNA into a Cassette for the Construction of an shIL-5R α Expression Vector In order to construct an shIL-5R α expression vector, the modification of the 5' and 3' non-translational region of shIL-5R α cDNA and the introduction of a restriction enzyme recognition sequence were carried out using the PCR method [Maniatis et al. (eds.), Molecular Cloning, 14.2, Cold Spring Harbor Laboratory, 1989] according to the procedures described below.

Figure 2:
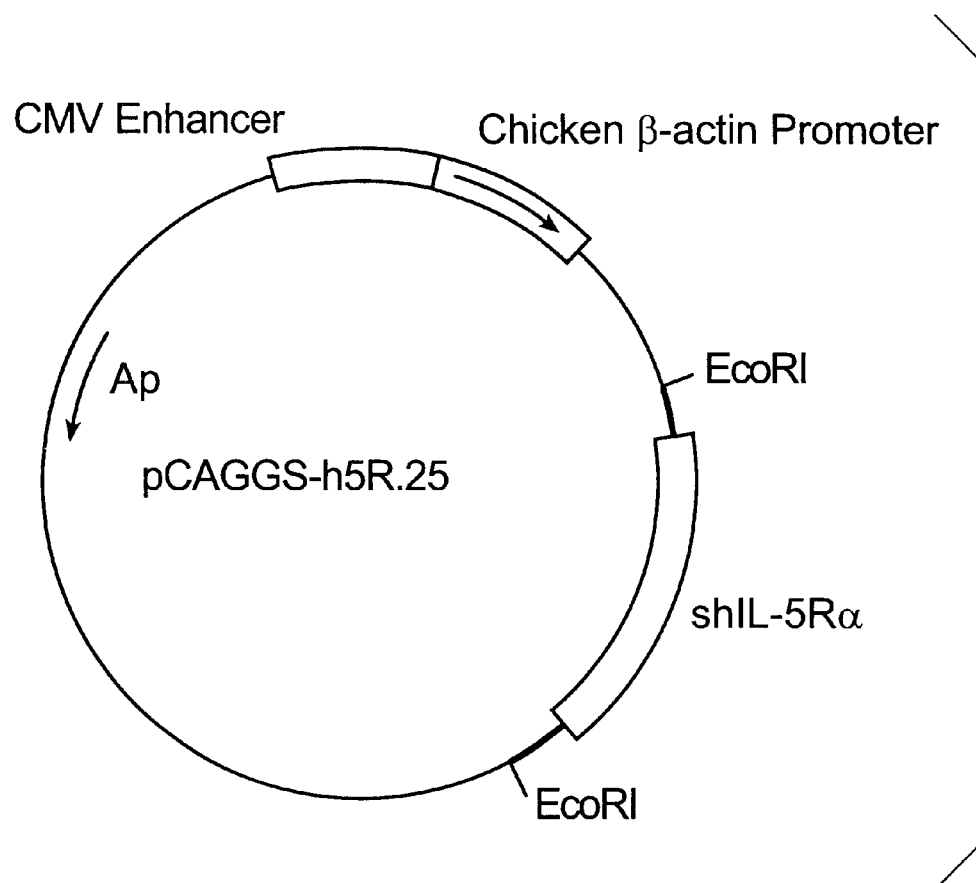
FIG. 2 shows the restriction map of plasmid pCAGGS-h5R.25.

Plasmid pCAGGS-h5R.25 is obtained by inserting shIL-5R α cDNA into the known plasmid pCAGGS [Gene, 108, 193 (1991)] as shown in FIG. 2 [J. Exp. Med., 175, 341 (1992)]. Three μg of this pCAGGS-h5R.25 were added to 30 μl of a buffer containing 50 mM Tris-HCl (pH 7.5), 10 mM magnesium chloride, 100 mM sodium chloride and 1 mM DTT. Then, 10 units of EcoRI were added thereto, and reacted at 37° C. for 4 hours. After the reaction mixture was subjected to agarose gel electrophoresis, about 0.3 μg of a 1.4 kb DNA fragment containing shIL-5R α cDNA was recovered.

Then, 1 ng of the DNA fragment obtained above was dissolved in 50 μl of PCR buffer [a buffer containing 50 mM potassium chloride, 10 mM Tris-HCl (pH 8.3), 1.5 mM magnesium chloride, 0.2 mM deoxyadenosine triphosphate (hereinafter referred to as "dATP"), 0.2 mM deoxyguanosine triphosphate (hereinafter referred to as "dGTP"), 0.2 mM deoxycytosine triphosphate (hereinafter referred to as "dCTP") and 0.2 mM deoxythymidine triphosphate (hereinafter referred to as "dTTP")]. To the resultant mixture, 50 pmol each of a synthetic DNA having the base sequence shown in SEQ ID NO: 1 and a synthetic DNA having the base sequence shown in SEQ ID NO: 2 [both synthesized with an automatic DNA synthesizer; Model 380A (Applied Biosystems Co., Ltd.)] and 1.6 units of Vent DNA polymerase (New England BioLabs, Inc.) were added and PCR was performed through 30 cycles under a series of conditions of 94° C. for 1 minute, 55° C. for 2 minutes and 72° C. for 3 minutes using a Perkin Elmer DNA thermal cycler (this was also used for the other PCR reactions). After the completion of the reaction, 2 μl of a buffer containing 100 mM Tris-HCl (pH 7.5), 100 mM magnesium chloride, 500 mM sodium chloride and 10 mM DTT, 8 μl of distilled water, and 10 units of HindIII were added to 10 μl of the reaction mixture and reacted at 37° C. for 4 hours. Then, DNA fragments were recovered from the reaction mixture by ethanol precipitation [Maniatis et al. (eds.), Molecular Cloning, E. 10, Cold Spring Harbor Laboratory, 1989] and redissolved in 20 μl of a buffer containing 20 mM Tris-HCl (pH 8.5), 10 mM magnesium chloride, 10 mM potassium chloride and 1 mM DTT. To the resultant mixture, 10 units of BamHI were added and reacted at 37° C. for 4 hours. After the reaction mixture was subjected to agarose gel electrophoresis, about 0.3 μg of a 1.0 kb DNA fragment was recovered.

In a separate step, 3 μg of plasmid pUC19 (Pharmacia Biotech) was dissolved in 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. Thereafter, DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT. To the resultant mixture, 10 units of BamHI were added and reacted at 37° C. for 4 hours. After the reaction mixture was subjected to agarose gel electrophoresis, about 0.5 μg of the HindIII/BamHI fragment from pUC19 was recovered.

One hundred ng of the HindIII/BamHI fragment from pUC19 and 50 ng of shLL-5R α cDNA fragment were dissolved in 20 μl of T4DNA ligase buffer, to which 200 units of T4DNA ligase were added. Then, ligation was performed at 12° C. for 16 hours. Using the recombinant plasmid DNA thus prepared, E. coli strain JM109 was transformed to thereby obtain plasmid pAI234 shown in FIG. 3.

(3) Construction of a Human Soluble IL-5R α Expression Vector

An shIL-5R α expression vector, pAI230, was constructed as described below by ligating the HindIII-BamHI fragment from pAGE210 obtained in subsection (1) of Example 1 to the shIL-5R α cDNA-containing HindIII-BanmHI fragment from pAI234 obtained in subsection (2) of Example 1.

Briefly, 3 μg of pAGE210 was added to 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT, to which 10 units of BamHI were added and reacted at 37° C. for 4 hours. After the reaction mixture was subjected to agarose gel electrophoresis, about 0.5 μg of a 9.0 kb DNA fragment was recovered.

Three μg of pAI234 were added to 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT, to which 10 units of BamHI was added and reacted at 37° C. for 4 hours. After the reaction mixture was subjected to agarose gel electrophoresis, about 0.3 μg of a 1.0 kb DNA fragment was recovered.

Figure 4:
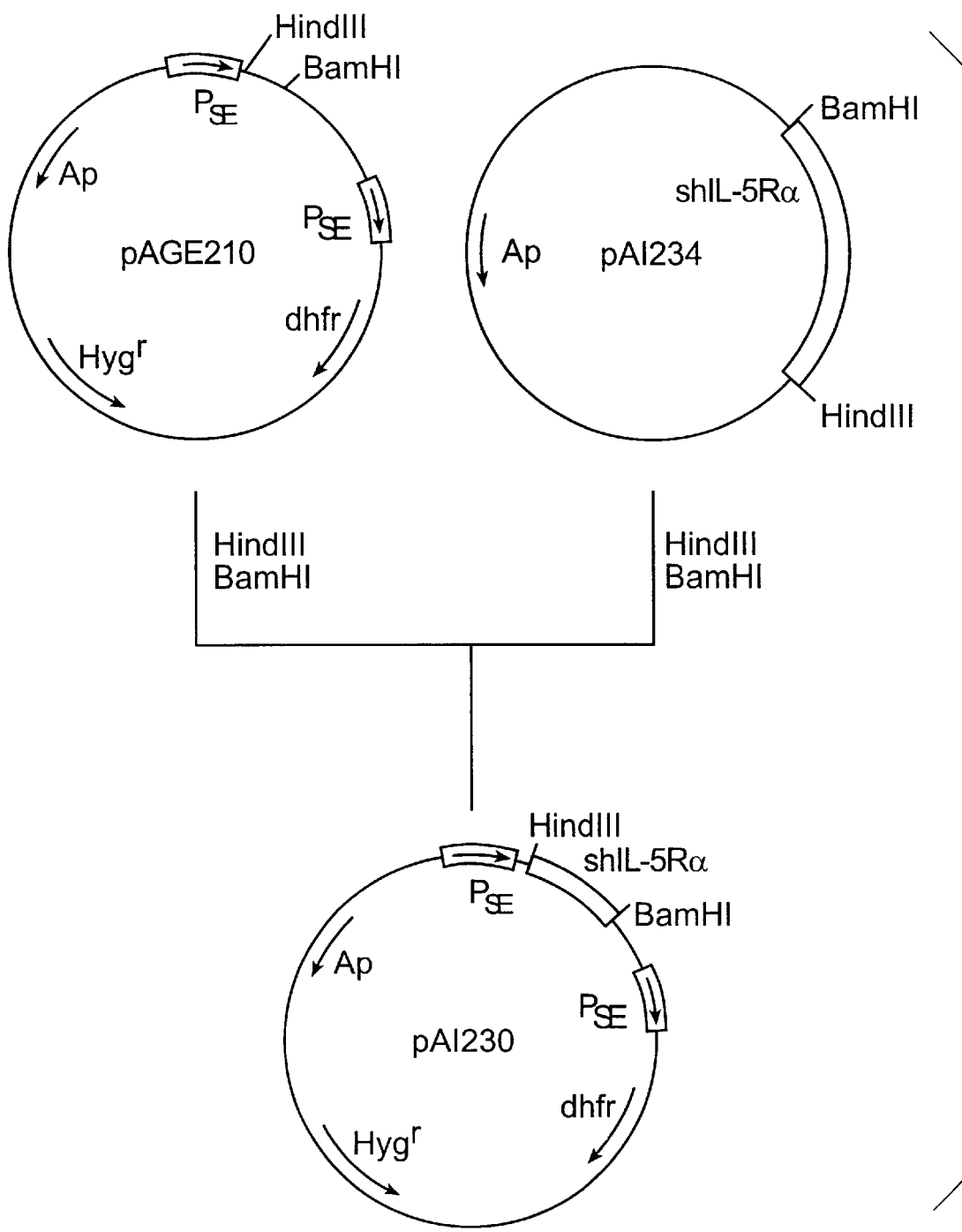
FIG. 4 shows steps for constructing plasmid pAI230.

Subsequently, 300 ng of the HindIII-BamHI fragment from pAGE210 and 50 ng of the HindIII-BamHI fragment from pAI234 were dissolved in 20 μl of T4DNA ligase buffer, to which 200 units of T4DNA ligase were added. Then, ligation was performed at 12° C. for 16 hours. Using the recombinant plasmid DNA thus prepared, E. coli strain JM109 was transformed to thereby obtain plasmid pAI230 shown in FIG. 4.

(4) Modification of the Signal Sequence

In order to produce shIL-5R α efficiently in animal cells, the signal sequence of the cDNA coding for shIL-5R α was modified according to the procedures described below by introducing an EcoRV recognition sequence into the cDNA at the 3' end of the signal sequence and subsequently replacing the original signal sequence with a signal sequence from a human growth hormone [Science, 205, 602 (1979)] or anti-ganglioside GD3 chimeric antibody KM871 (Kokai No. Hei 5-304989) using synthetic DNAs.

Briefly, 3 μg of plasmid pAI234 obtained in subsection (2) of Example 1 were added to 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT, to which 10 units of BamHI were added and reacted at 37° C. for 4 hours. After the reaction mixture was subjected to agarose gel electrophoresis, about 0.3 μg of a 1.0 kb DNA fragment was recovered.

In a separate step, 3 μg of plasmid pUC19 were added to 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. Then, DNA fragments were recovered from the reaction mixture by ethanol precipitation and about 0.5 μg of a HindII fragment from pUC19 was recovered.

Figure 5:
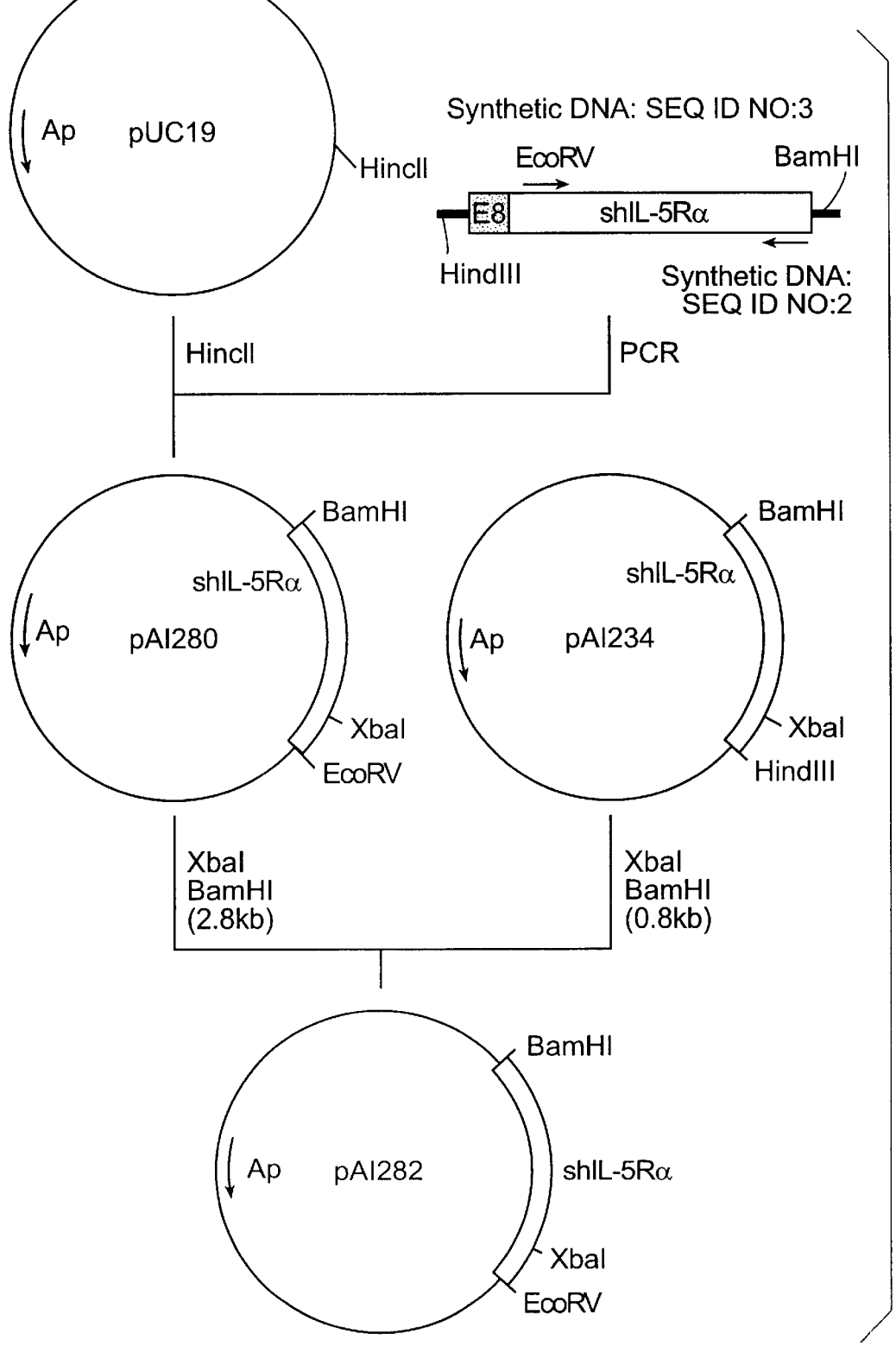
FIG. 5 shows steps for constructing plasmid pAI282.

About 1 ng of the DNA fragment obtained above was dissolved in 50 μl of PCR buffer, to which 50 pmol each of a synthetic DNA having the base sequence shown in SEQ ID NO: 2 and a synthetic DNA having the base sequence shown in SEQ ID NO: 3 and 1.6 units of vent DNA polymerase were added. Then, PCR was performed through 30 cycles under a series of conditions of 94° C. for 1 minute, 48° C. for 2 minutes and 72° C. for 3 minutes. Then, the reaction mixture was subjected to agarose gel electrophoresis, and 0.5 μg of about 0.9 kb cDNA fragment coding for a portion of hIL-5R α was recovered. Fifty ng of this DNA and 100 ng of the HindII fragment from pUC19 were dissolved in 20 μl of T4 ligase buffer, to which 200 units of T4DNA ligase were added. Then, ligation was performed at 12° C. for 16 hours. Using the recombinant plasmid DNA thus prepared, E. coli strain JM109 was transformed to thereby obtain plasmid pAI280 shown in FIG. 5. Three μg of the thus obtained plasmid pAI280 were added to 30 μl of a buffer containing 10 mM Tris-HCl (pH 7.5), 10 mM magnesium chloride, 50 mM sodium chloride and 1 mM DTT, to which 10 units of XbaI were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT, to which 10 units of BamHI were added and reacted at 37° C. for 4 hours. After the reaction mixture was subjected to agarose gel electrophoresis, about 0.8 μg of a 2.8 kb DNA fragment was recovered.

In a separate step, 3 μg of plasmid pAI234 were added to 30 μl of a buffer containing 10 mM Tris-HCl (pH 7.5), 10 mM magnesium chloride, 50 mM sodium chloride and 1 mM DTT, to which 10 units of XbaI were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT, to which 10 units of BamHI were added and reacted at 37° C. for 4 hours. After the reaction mixture was subjected to agarose gel electrophoresis, about 0.2 μg of a 0.8 kb DNA fragment was recovered.

Subsequently, 200 ng of the XbaI-BamHI from pAI280 and 50 ng of the XbaI-BamHI from pAI234 were dissolved in 20 μl of T4 ligase buffer, to which 200 units of T4DNA ligase were added. Then, ligation was performed at 12° C. for 16 hours. Using the recombinant plasmid DNA thus prepared, E. coli strain JM109 was transformed to thereby obtain plasmid pAI282 shown in FIG. 5. Three μg of this plasmid pAI282 were added to 30 μl of a buffer containing 50 mM Tris-HCl (pH 7.5), 10 mM magnesium chloride, 100 mM sodium chloride and 1 mM DTT, to which 10 units of EcoRV were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 10 mM potassium chloride and 1 mM DTT, to which 10 units of BamHI were added and reacted at 37° C. for 4 hours. After the reaction mixture was subjected to agarose gel electrophoresis, about 0.3 μg of a 0.9 kb DNA fragment was recovered.

Figure 6:
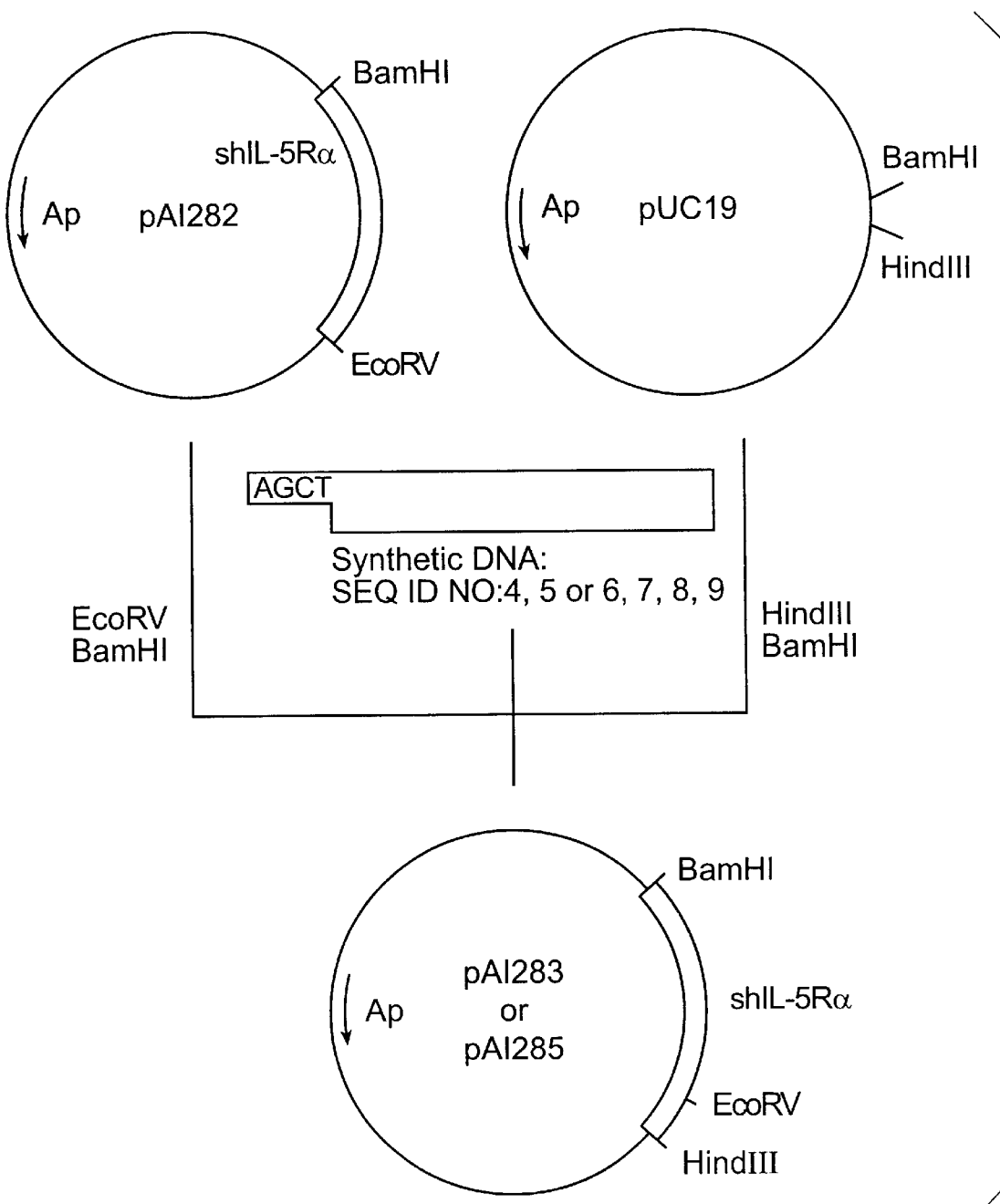
FIG. 6 shows steps for constructing plasmids pAI283 and pAI285.

One μg each of a synthetic DNA having the base sequence shown in SEQ ID NO: 4 and a synthetic DNA having the base sequence shown in SEQ ID NO: 5 were dissolved in 10 μl of distilled water. The resultant mixture was heated at 95° C. for 5 minutes and then cooled to room temperature over 30 minutes for annealing. A hundred ng of the HindII-BamHI fragment from pUC19 obtained in subsection (2) of Example 1, 50 ng of the EcoRV-BamHI fragment from pAI282, and 50 ng of the synthetic DNAs having the base sequences shown in SEQ ID NOS. 4 and 5 which had been annealed as described above were dissolved in 20 µl of T4DNA ligase buffer, to which 200 units of T4DNA ligase was added. Then, ligation was performed at 12° C. for 16 hours. Using the recombinant plasmid DNA thus prepared, E. coli strain JM109 was transformed to thereby obtain plasmid pAI283 shown in FIG. 6.

One µg each of a synthetic DNA having the base sequence shown in SEQ ID NO: 6 and a synthetic DNA having the base sequence shown in SEQ ID NO: 9 were dissolved in 10 µl of distilled water. The resultant mixture was heated at 95° C. for 5 minutes and then cooled to room temperature over 30 minutes for annealing. To this reaction mixture, 2.5 µl of a buffer containing 500 mM Tris-HCl (pH 7.6), 100 mM magnesium chloride, 50 mM DTT and 1 mM EDTA, 2.5 µl of 10 mM ATP solution, 9 µl of distilled water and 5 units of T4 polynucleotide kinase (Takara Shuzo) were added, and phosporylation was performed at 37° C. for 2 hours. Separately, 1 µg each of a synthetic DNA having the base sequence shown in SEQ ID NO: 7 and a synthetic DNA having the base sequence shown in SEQ ID NO: 8 were dissolved in 10 µl of distilled water. The resultant mixture was heated at 95° C. for 5 minutes and then cooled to room temperature over 30 minutes for annealing.

One hundred ng of the HindIII-BamHI fragment from pUC19, 50 ng of the EcoRV-BamHI fragment from pAI282, and 50 ng each of the synthetic DNAs as prepared above were dissolved in 20 µl of T4DNA ligase buffer, to which 200 units of T4DNA ligase were added. Then, ligation was performed at 12° C. for 16 hours. Using the thus prepared recombinant plasmid DNA, E. coli strain JM109 was transformed to thereby obtain plasmid pAI285 shown in FIG. 6.

(5) Construction of Signal Sequence-Modified shIL-5R α Expression Vectors

Human soluble IL-5R α expression vectors, pAI284 and pAI289, were constructed as described below by ligating the HindIII-BamHI fragment from pAGE210 obtained in subsection (1) of Example 1 to the HindIII-BamHI fragment containing human soluble IL-5R α cDNA from pAI283 or pAI285 obtained in subsection (4) of Example 1.

Briefly, 3 µg each of pAI283 and pAI285 were added separately to 30 µl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. DNA fragments were recovered from the reaction mixture by ethanol precipitation and redissolved in 30 µl of a buffer containing 20 mM Tris-HCl (pH 8.5), 10 mM magnesium chloride, 10 mM potassium chloride and 1 mM DTT, to which 10 units of BamHI were added and reacted at 37° C. for 4 hours. After the reaction mixture was subjected to agarose gel electrophoresis, about 0.3 µg of a 1.0 kb DNA fragment was recovered for each of the plasmids used.

Figure 7:
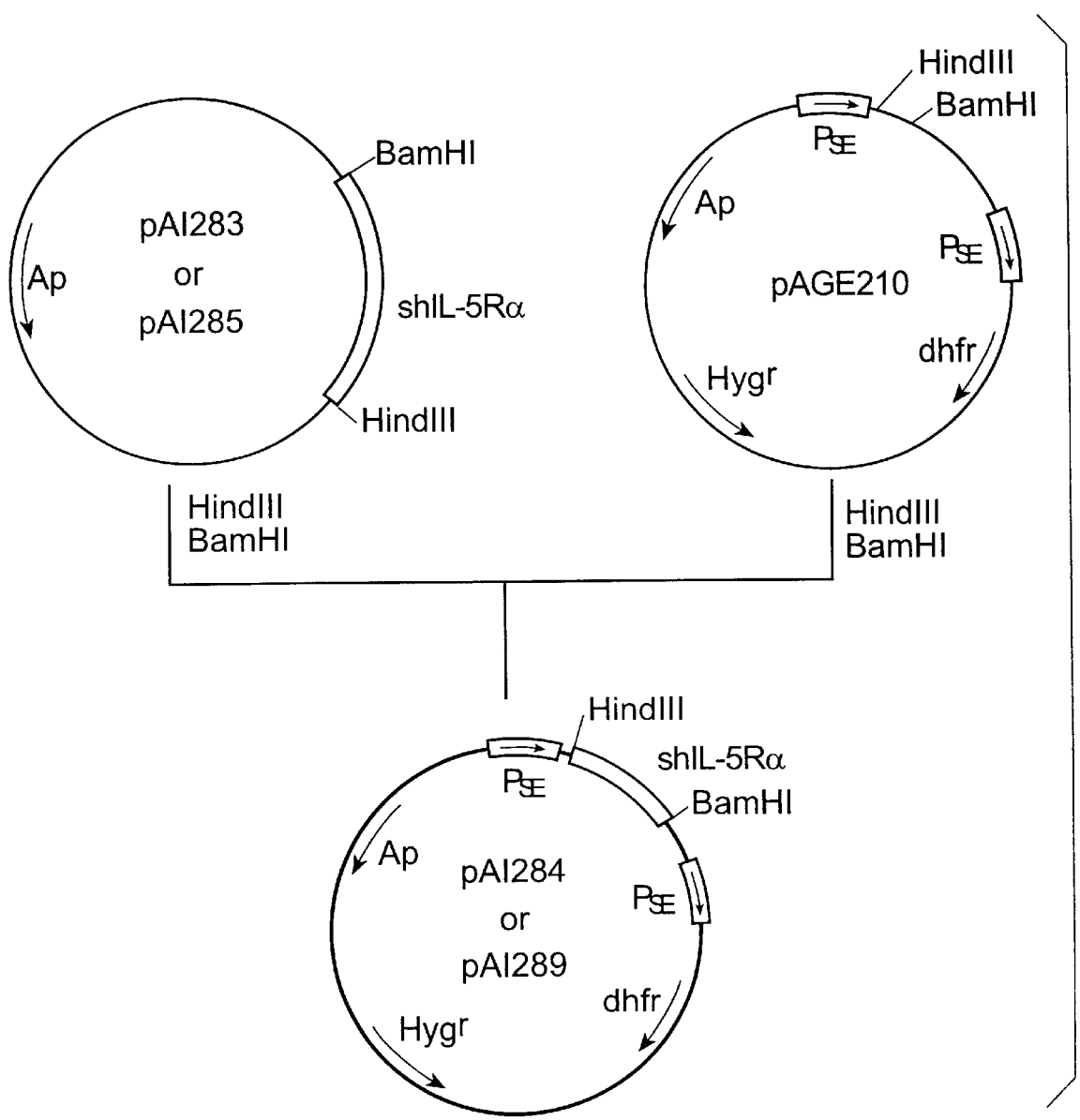
FIG. 7 shows steps for constructing plasmids pAI284 and pAI289.

Three hundred ng of the HindIII-BamHI fragment from pAGE210 and 50 ng of the HindIII-BamHI fragment from pAI283 or pAI285 were dissolved in 20 µl of T4DNA ligase buffer, to which 200 units of T4DNA ligase were added. Then, ligation was performed at 12° C. for 16 hours. Using the recombinant plasmid DNA thus prepared, E. coli strain JM109 was transformed to thereby obtain plasmids pAI284 and pAI289 shown in FIG. 7.

(6) Preparation of a Fusion Protein Composed of Human IL-5R α and Human Immunoglobulin Constant Region A fusion protein in which the extracellular region of human IL-5R α was linked to a human immunoglobulin constant region (hereinafter referred to as "Fc") through a linker having an amino acid sequence of (Gly-Ser-Gly)$_4$ (hereinafter, this fusion protein is referred to as "hIL-5R α-Fc") was prepared according to the procedures described below.

As a cDNA coding for a human immunoglobulin constant region, the portion of the human chimeric antibody H chain expression vector pChiIgHB2 (Kokai No. Hei 5-304989) which coded for the human IgG1 constant region was used. First, about 1 ng of pChiIgHB2 was dissolved in 50 µl of PCR buffer. To this solution, 50 pmol each of a synthetic DNA having the base sequence shown in SEQ ID NO: 10 and a synthetic DNA having the base sequence shown in SEQ ID NO: 11 and 1.6 units of vent DNA polymerase were added. Then, PCR was performed through 30 cycles under a series of conditions of 94° C. for 1 minute, 48° C. for 2 minutes and 72° C. for 3 minutes. After the completion of the reaction, 2.5 µl of a buffer containing 200 mM Tris-HCl (pH 8.5), 100 mM magnesium chloride, 1000 mM potassium chloride and 10 mM, 2.5 µl of distilled water, and 10 units of BamHI were added to 20 µl of the reaction mixture and reacted at 37° C. for 4 hours. After the completion of the reaction, the reaction mixture was subjected to agarose gel electrophoresis, and about 0.5 µg of a 0.7 kb DNA fragment containing a cDNA coding for the human IgG1 constant region was recovered.

About 1 ng of pAI283 obtained in subsection (4) of Example 1 was dissolved in 50 µl of PCR buffer, to which 50 pmol each of a synthetic DNA having the base sequence shown in SEQ ID NO: 12 and a synthetic DNA having the base sequence shown in SEQ ID NO: 13 and 1.6 units of vent DNA polymerase were added. Then, PCR was performed through 30 cycles under a series of conditions of 94° C. for 1 minute, 48° C. for 2 minutes and 72° C. for 3 minutes. After the completion of the reaction, 2.5 µl of a buffer containing 100 mM Tris-HCl (pH 7.5), 100 mM magnesium chloride, 500 mM sodium chloride and 10 mM DTT, 2.5 µl of distilled water, and 10 units of HindIII were added to 20 µl of the reaction mixture and reacted at 37° C. for 4 hours. After the completion of the reaction, the reaction mixture was subjected to agarose gel electrophoresis. Thereafter, about 0.5 µg of a 1.0 kb DNA fragment containing a cDNA coding for the extracellular region of hIL-5R α was recovered.

Figure 8:
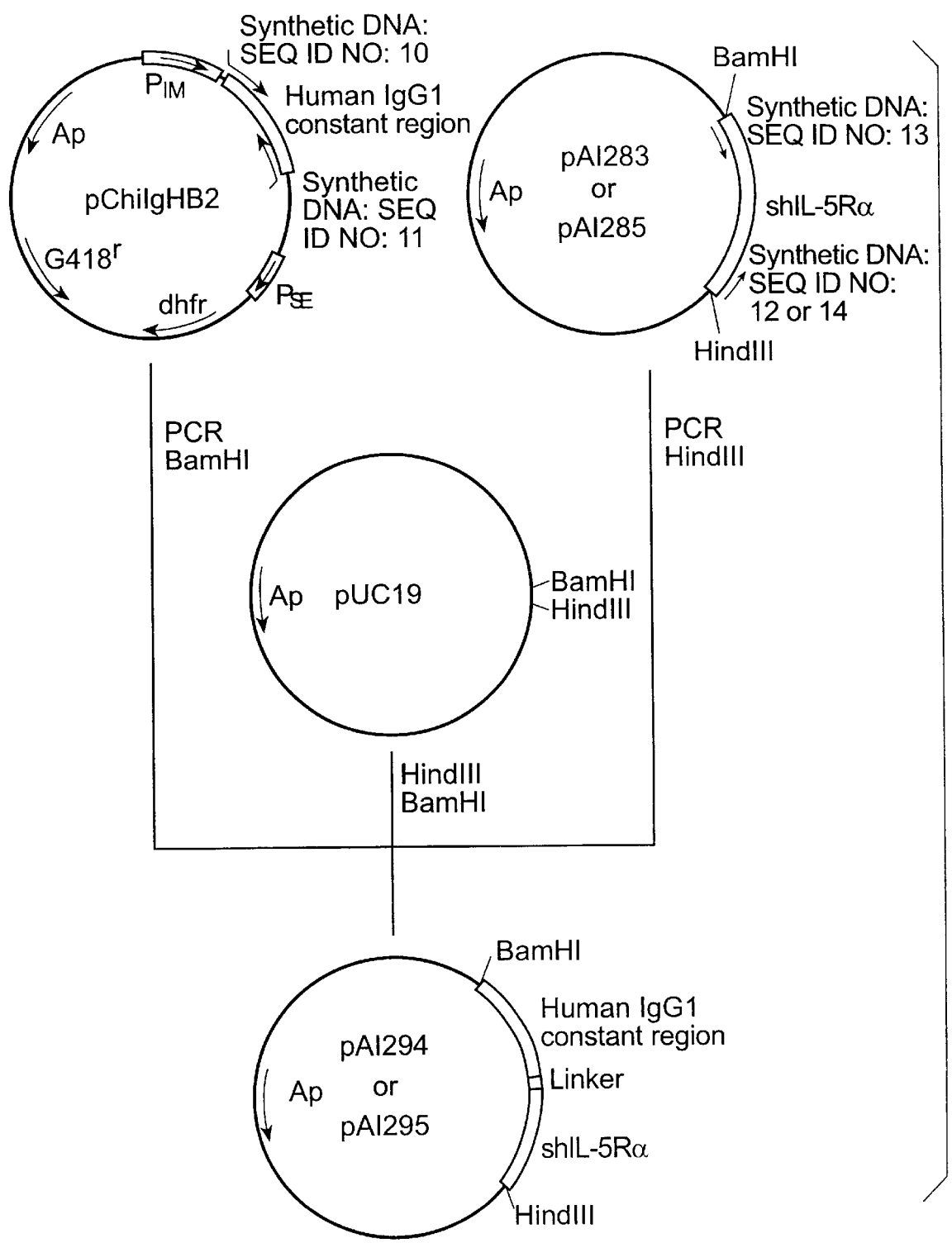
FIG. 8 shows steps for constructing plasmids pAI294 and pAI295.

Fifty ng of the 0.7 kb DNA fragment containing the cDNA coding for the human IgG1 constant region, 50 ng of the DNA fragment containing the cDNA coding for the extracellular region of hIL-5R α and 100 ng of the HindIII-BamHI fragment from pUC 19 were dissolved in 20 µl of T4DNA ligase buffer, to which 200 units of T4DNA ligase were added. Then, ligation was performed at 12° C. for 16 hours. Using the recombinant plasmid DNA thus prepared, E. coli strain JM109 was transformed to thereby obtain plasmid pAI294 shown in FIG. 8.

In a separate step, PCR reaction was conducted under conditions similar to those described above using pAI285 obtained in subsection (4) of Example 1 as a template and also using synthetic DNAs having the base sequences shown in SEQ ID NOS: 13 and 14, as primers. After the completion of the reaction, the reaction mixture was subjected to agarose gel electrophoresis. Subsequently, about 0.5 μg of a 1.0 kb DNA fragment containing the cDNA coding for the extracellular region of human IL-5R α was recovered. Fifty ng of the thus obtained DNA fragment, 50 ng of the 0.7 kb DNA fragment containing the cDNA coding for the human IgG1 constant region and 100 ng of the HindIII-BamHI fragment from pUC19 were dissolved in 20 μl of T4DNA ligase buffer, to which 200 units of T4DNA ligase were added. Then, ligation was performed at 12° C. for 16 hours. Using the recombinant plasmid DNA thus prepared, *E. coli* strain JM109 was transformed to thereby obtain plasmid pAI295 shown in FIG. 8.

(7) Construction of a Fusion Protein Expression Vector

An hIL-5R α-Fc expression vector, pAI299, was constructed as described below by ligating the HindIII-BamHI fragment from pAGE210 obtained in subsection (1) of Example 1 to the HindIII-BamHI fragment from pAI294 obtained in subsection (6) of Example 1 containing the cDNA coding for hIL-5R α-Fc.

Briefly, 3 μg of plasmid pAI294 were added to 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. DNA fragments were recovered from the reaction mixture by ethanol precipitation and redissolved in 30 μl of a buffer containing 20 mM Tris-HCl (pH 8.5), 10 mM magnesium chloride, 100 mM potassium chloride and 1 mM DTT. To the resultant mixture, 10 units of BamHI were added and reacted at 37° C. for 4 hours. After the reaction mixture was subjected to agarose gel electrophoresis, about 0.4 μg of a 1.7 kb DNA fragment containing a cDNA coding for a fusion protein composed of human IL-5R α and the human immunoglobulin constant region was recovered.

Figure 9:
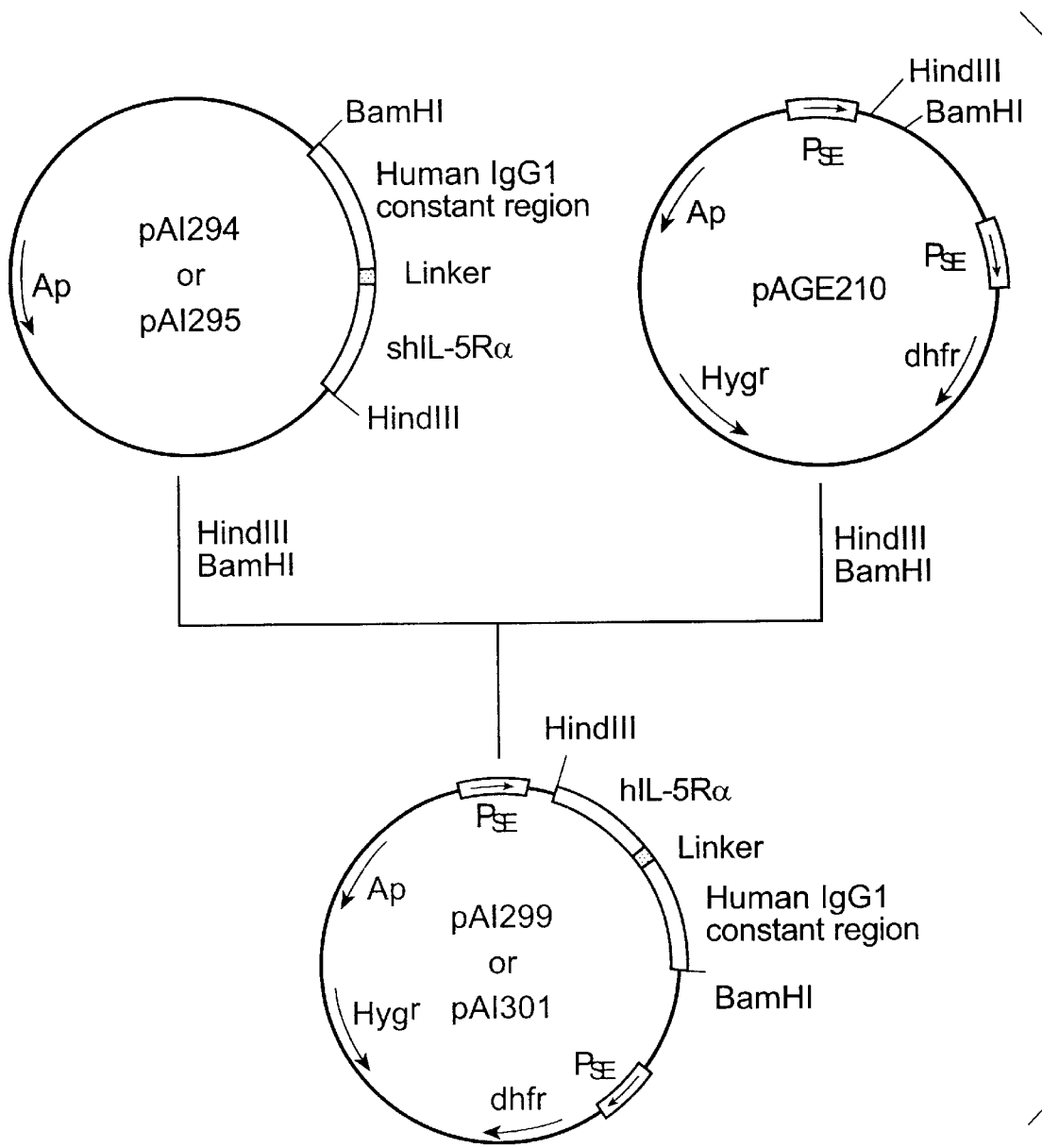
FIG. 9 shows steps for constructing plasmids pAI299 and pAI301.

One hundred ng of the HindIII-BamHI fragment from pAGE210 and 50 ng of the HindIII-BanHI fragment from pAI294 were dissolved in 20 μl of T4DNA ligase buffer, to which 200 units of T4DNA ligase were added. Then, ligation was performed at 12° C. for 16 hours. Using the recombinant plasmid DNA thus prepared, *E. coli* strain JM109 was transformed to thereby obtain plasmid pAI299 shown in FIG. 9.

Further, an hIL-5R α-Fc expression vector, pAI301, was constructed similarly by ligating the HindIII-BamHI fragment from pAGE210 to the HindIII-BamHI fragment from pAI295 obtained in subsection (6) of Example 1 containing the cDNA coding for hIL-5R α-Fc.

(8) Preparation of a Recombinant Virus for Expressing shIL-5R α in Insect Cells

For the production of a protein in insect cells, a recombinant virus inserting a gene of interest is prepared. The preparation of such a virus is performed through a process in which a cDNA coding for a gene of interest is incorporated into a special plasmid called "a transfer vector" and a subsequent process in which a wild-type virus and the transfer vector are co-transfected into insect cells to obtain a recombinant virus by homologous recombination. The processes described above were performed using BaculoGold Starter Kit (Cat. No. PM-21001K) manufactured by Pharmingen according to the manufacturer's manual.

Briefly, 3 μg of pAI285 obtained in subsection (4) of Example 1 or pAI294 obtained in subsection (6) of Example 1 were added to 30 μl of a buffer containing 10 mM Tris-HCl (pH 7.5), 10 mM magnesium chloride, 50 mM sodium chloride and 1 mM DTT, to which 10 units of HindIII were added and reacted at 37° C. for 4 hours. DNA fragments were recovered from the reaction mixture by ethanol precipitation and dissolved in 20 μl of DNA polymerase I buffer [a buffer containing 5 mM Tris-HCl (pH 7.5), 1 mM magnesium sulfate, 0.01 mM DTT, 5 μg/ml bovine serum albumin, 0.08 mM dATP, 0.08 mM dGTP, 0.08 mM dCTP and 0.08 mM dTTP]. To the resultant mixture, 5 units of *E. coli* DNA polymerase I Klenow fragment (Takara Shuzo) were added and reacted at 22° C. for 30 minutes, whereby the 5' sticky ends generated by the HindIII digestion were changed to blunt ends. Further, the reaction mixture was subjected to phenol-chloroform extraction followed by ethanol precipitation. To the precipitate, 30 μl of a buffer containing 20 mM Tris-HCl (pH 8.5), 10 mM magnesium chloride, 100 mM potassium chloride and 1 mM DTT, and 10 units of BamHI were added and reacted at 37° C. for 4 hours. The reaction mixture was subjected to agarose gel electrophoresis, and about 0.3 μg of an approx. 1.0 kb DNA fragment containing the cDNA coding for shIL-5R α and about 0.3 μg of a 1.7 kb DNA fragment containing the cDNA coding for the fusion protein composed of human IL-5 α and the human immunoglobulin constant region were recovered.

Subsequently, 3 μg of plasmid pVL1393 contained in BaculoGold Starter Kit (Pharmingen) were added to 30 μl of a buffer containing 10 mM Tris-HCl (pH 7.5), 10 mM magnesium chloride, 100 mM sodium chloride and 1 mM DTT, to which 10 units of EcoRI were added and reacted at 37° C. for 4 hours. DNA fragments were recovered from the reaction mixture by ethanol precipitation and dissolved in 20 μl of DNA polymerase I buffer, to which 5 units of *E. coli* DNA polymerase I Klenow fragment were added and reacted at 22° C. for 30 minutes, whereby the 5' sticky ends generated by the EcoRI digestion were changed to blunt ends. Further, the reaction mixture was subjected to phenol-chloroform extraction followed by ethanol precipitation. To the precipitate, 30 μl of a buffer containing 50 mM Tris-HCl (pH 7.5), 10 mM magnesium chloride, 100 mM sodium chloride and 1 mM DTT, and 10 units of BglII were added and reacted at 37° C. for 4 hours. The reaction mixture was subjected to agarose gel electrophoresis, and about 0.9 μg of an approx. 9.6 kb DNA fragment was recovered.

Figure 10:
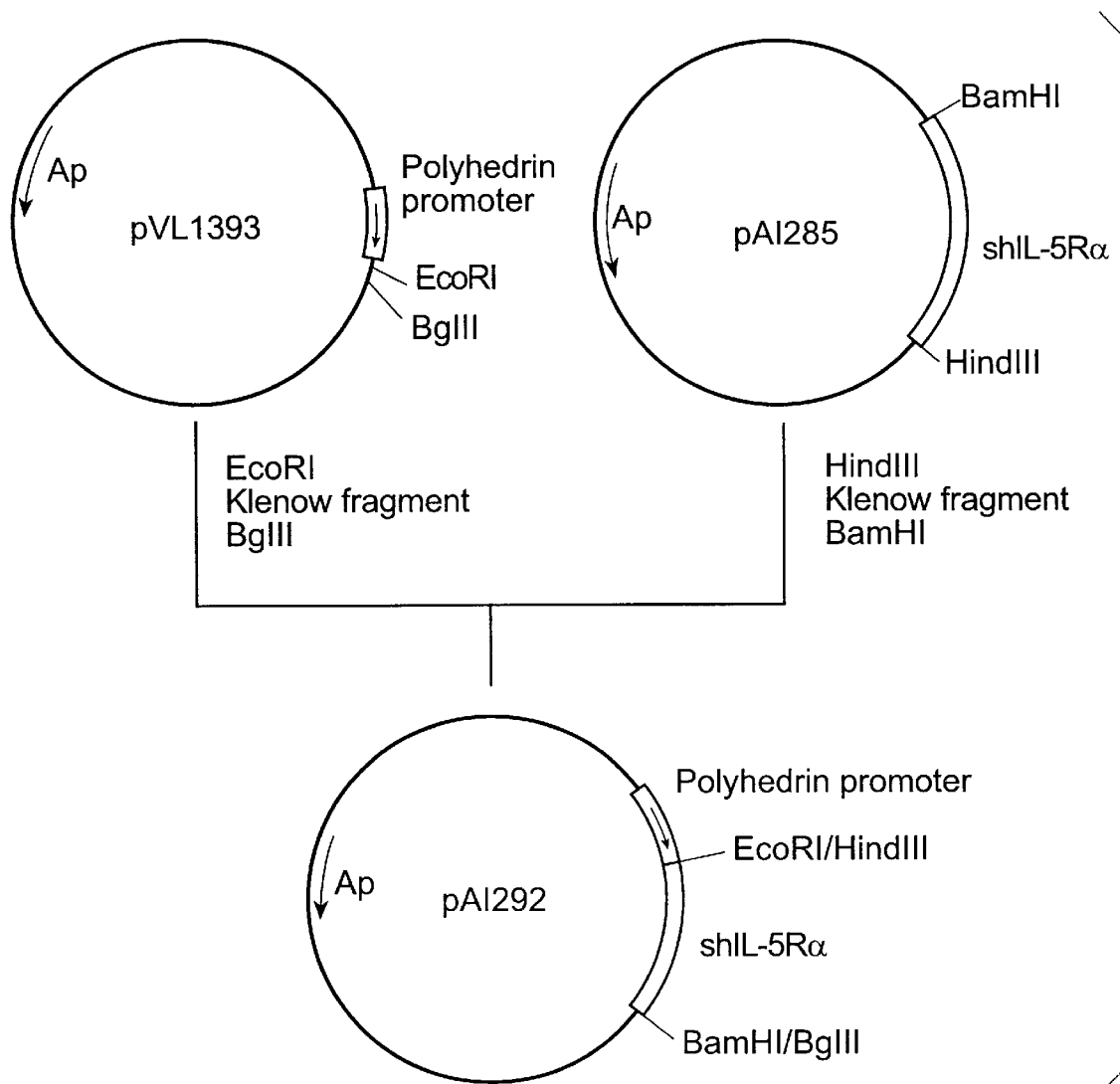
FIG. 10 shows steps for constructing plasmid pAI292.
Figure 11:
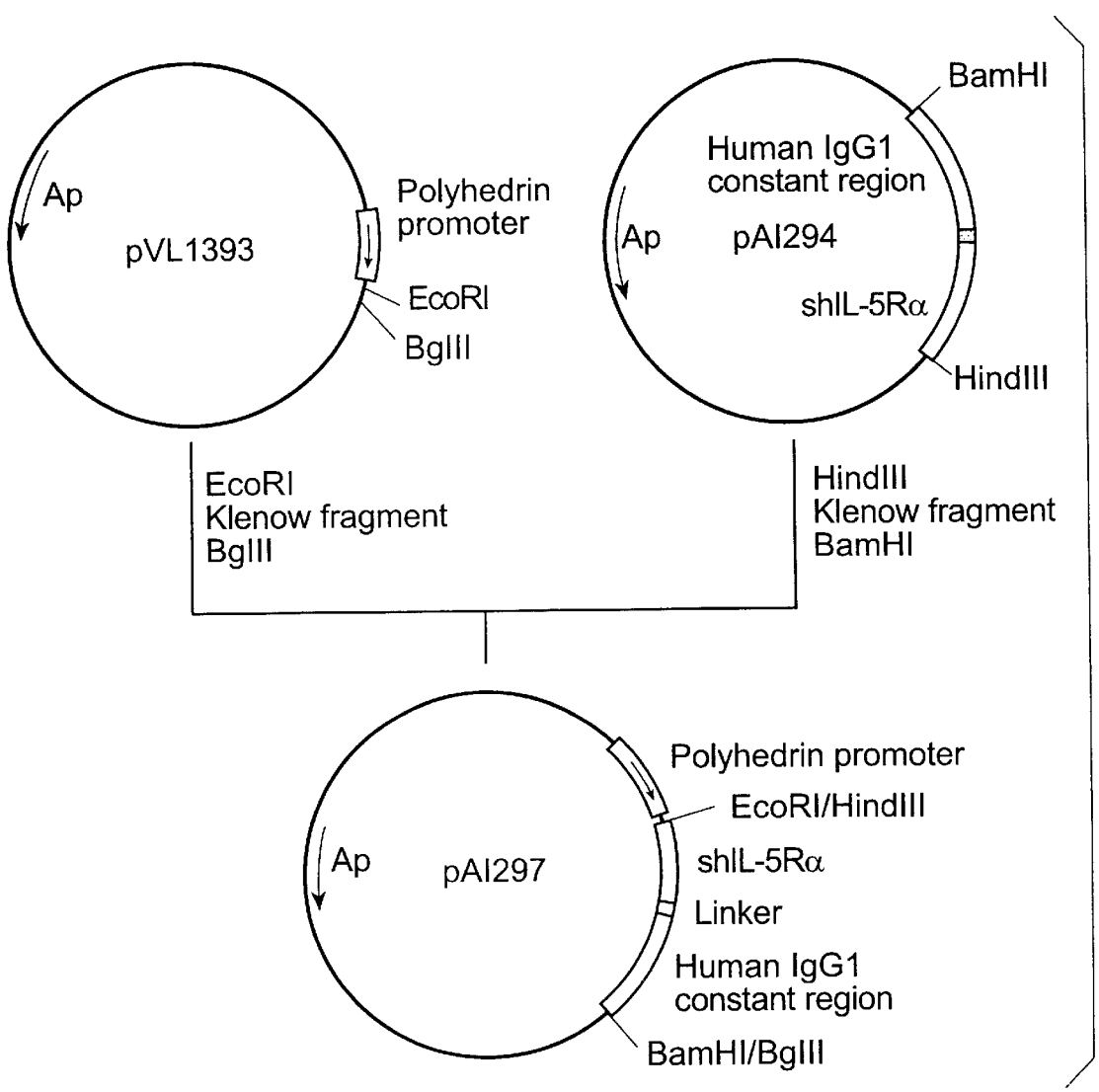
FIG. 11 shows steps for constructing plasmid pAI297.

Thereafter, 200 ng of the thus obtained EcoRI (blunt end)-BglII fragment from pVL1393 and 50 ng of the HindIII (blunt end)-BamHI fragment from pAI285 or pAI294 were dissolved in 20 μl of T4DNA ligase buffer, to which 200 units of T4DNA ligase were added. Then, ligation was performed at 12° C. for 16 hours. Using the recombinant plasmid DNA thus prepared, *E. coli* strain JM109 was transformed to thereby obtain plasmids pAI292 and pAI297 shown in FIGS. 10 and 11, respectively.

The subsequent preparation of a recombinant virus was performed as described below by transfecting into an insect cell, Sf9 (obtained from Pharmningen), cultured in TMN-FH Insect Medium (Pharmingen), a linear baculovirus DNA (BaculoGold baculovirus DNA; Pharmingen) and the prepared transfer vector DNA by the lipofectin method [TANPAKUSHITSU, KAKUSAN, KOHSO (Protein, Nucleic Acid, Enzyme), 37, 2701 (1992)].

Briefly, 1 μg of pAI292 or pAI297 and 20 ng of the linear baculovirus DNA were dissolved in 12 μl of distilled water, to which a mixture of 6 μl of lipofectin and 6 μl of distilled water were added and left at room temperature for 15 minutes. In a separate step, $1 \times 10^6$ Sf9 cells were suspended in 2 ml of Sf900-II medium (Gibco) and put in a plastic cell culture dish 35 mm in diameter. To this dish, a total volume of the above-described mixture of plasmid DNA, linear baculovirus DNA and lipofectin was added, and cells were cultured at 27° C. for 3 days. Thereafter, 1 ml of the culture supernatant containing a recombinant virus was taken. One ml of a fresh Sf900-II medium was added to the dish and cells were cultured at 27° C. for another 3 days. Then, an additional 1.5 ml of the culture supernatant containing a recombinant virus was obtained.

Subsequently, the thus obtained recombinant virus was propagated for the purpose of use in protein expression, according to the procedures described below.

Briefly, $2 \times 10^7$ Sf9 cells were suspended in 10 ml of Sf900-II medium, put in a 175 cm2 flask (Greiner) and left at room temperature for 1 hour to allow cells to adhere to the flask. Thereafter, the supernatant was removed, and 15 ml of a fresh TMN-FH Insect Medium and 1 ml of the above-obtained culture supernatant containing the recombinant virus were added to the flask. Then, cells were cultured at 27° C. for 3 days. After the cultivation, the supernatant was centrifuged at 1,500×g for 10 minutes to remove cells. Thus, a viral solution to be used for protein expression was obtained.

With respect to the thus obtained solution of the recombinant virus, the viral titer was calculated by the method described below (BaculoGold Starter Kit Manual; Pharmingen). A number ($6 \times 10^6$) of Sf9 cells were suspended in 4 ml of Sf900-II medium, put in a plastic cell culture dish 60 mm in diameter and left at room temperature for 1 hour to allow cells to adhere to the dish. After the removal of the supernatant, 400 μl of a fresh Sf900-II medium and the above-described recombinant virus solution diluted 10,000 folds with Sf900-II medium were added to the dish and left at room temperature for 1 hour. Then, the medium was removed, and 5 ml of a medium containing 1% low melting point agarose (Agarplaque Agarose; Pharmingen) (a medium obtainable by mixing 1 ml of sterilized 5% aqueous Agarplaqueplus Agarose solution and 4 ml of TMN-FH Insect Medium and keeping the mixture at 42° C.) was poured into the dish. After the dish was left at room temperature for 15 minutes, vinyl tape was wound round the dish to prevent dryness. Then, the dish was placed in an airtight plastic container and cells were cultured at 27° C. for 6 days. After 1 ml of PBS containing 0.01% Neutral Red was added to the dish and cells were cultured for an additional day, the number of plaques formed was counted. From the operations described above, it was found that each of the recombinant virus solutions contained about $1 \times 10^7$ plaque forming units(PFU)/ml of virus.

(9) Expression of shIL-5R α or hIL-5R α-Fc in Animal Cells

The introduction of a plasmid into animal cells was performed according to the method of Miyaji et al. using electroporation [Cytotechnology, 3, 133 (1990)].

Briefly, 4 μg of pAI289 obtained in subsection (5) of Example 1 or pAI301 obtained in subsection (7) of Example 1 were transfected into $4 \times 10^6$ dhfr gene-deficient CHO cells [Proc. Nati. Acad. Sci., 77, 4216 (1980)], which were then suspended in 40 ml of RPMI1640-FCS(10) [RPMI1640 medium containing 10% FCS, 1/40 volume 7.5% NaHCO3, 3% 200 mM L-glutamine solution (Gibco) and 0.5% penicillin/streptomycin solution (Gibco; containing 5000 units/ml penicillin and 5000 μg/ml streptomycin); manufactured by Nissui Pharmaceuticals] and dispensed into a 96-well microtiter plate (200 μl/well). After the cells were cultured in a $CO_2$ incubator at 37° C. for 24 hours, hygromycin (Gibco) was added to give a concentration of 0.5 mg/ml. Then, the cells were cultured for an additional 1–2 weeks. Cells were recovered from those wells which became confluent with the appearance of colonies of transformant, and suspended in RPMI1640-FCS(10) medium containing 0.5 mg/ml hygromycin and 50 nM methotrexate (hereinafter referred to as "MTX") to give a cell density of $1-2 \times 10^5$ cells/ml. The cell suspension was dispensed into a 24-well plate (2 ml/well) and the cells were cultured in a $CO_2$ incubator at 37° C. for 1–2 weeks to thereby induce 50 nM MTX resistant clones.

The thus obtained 50 nM MTX resistant clones were suspended in RPMI1640-FCS(10) medium containing 0.5 mg/ml hygromycin and 200 nM MTX to give a cell density of $1-2 \times 10^5$ cells/ml. The cell suspension was dispensed into a 24-well plate (2 ml/well) and the cells were cultured in a $CO_2$ incubator at 37° C. for 1–2 weeks to thereby induce 200 nM MTX resistant clones.

Further, the thus obtained 200 nM MTX resistant clones were suspended in RPMI1640-FCS(10) medium containing 0.5 mg/ml hygromycin and 500 nM MTX to give a cell density of $1-2 \times 10^5$ cells/ml. The cell suspension was dispensed into a 24-well plate (2 ml/well) and the cells were cultured in a $CO_2$ incubator at 37° C. for 1–2 weeks to thereby induce 500 nM MTX resistant clones.

The above transformants were suspended in a serum-free medium for CHO cells, CHO-S-SFMII medium (Gibco), to give a cell density of $1-2 \times 10^5$ cells/ml, and the cell suspension was dispensed into 225 cm2 flasks (Greiner) in an amount of 100 ml/flask. The cells were cultured in a $CO_2$ incubator at 37° C. for 5–7 days and the culture medium was recovered when confluence was attained.

The purification of hIL-5R α from the culture supernatant was performed as follows. To 1 liter of the culture medium of pAI289-derived transformant, 29.2 g of sodium chloride and 20 ml of 1 M Tris-HCl (pH 7.4) were added. Then, the pH of the resultant mixture was adjusted to 7.4 with 1 N sodium hydroxide solution. A column was packed with about 10 ml of Concanavalin A-Sepharose (Pharmacia) gel and then washed with 50 ml of a buffer containing 20 mM Tris-HCl (pH 7.4) and 0.5 M sodium chloride at a flow rate of 0.5 ml/min. After the washing, the mixture containing shIL-5R α prepared as described above was applied to the Concanavalin A-Sepharose column at a flow rate of 0.5 ml/min. Then, the column was washed with 80 ml of a buffer containing 20 mM Tris-HCl (pH 7.4) and 0.5 M sodium chloride at a flow rate of 0.5 ml/min. Thereafter, the protein adsorbed on Concanavalin A-Sepharose was eluted and, simultaneously, the eluate was fractionated into 1 ml fractions (fractions 1–30) with 15 ml of a buffer containing 20 mM Tris-HCl (pH 7.4) and 0.5 M sodium chloride and 15 ml of a buffer containing 0.5 M α-methylmannoside, 20 mM Tris-HCl (pH 7.4) and 0.5 M sodium chloride by linearly changing the α-methylmannoside concentration from 0 to 0.5 M. Further, 20 ml of a buffer containing 1 M α-methylmannoside, 20 mM Tris-HCl (pH 7.4) and 0.5 M sodium chloride were applied to the column and the eluate was fractionated into 2 ml fractions (fractions 31–40). The protein concentration of each fraction was measured using a protein concentration measurement kit (Bio-rad) and fractions 10–40 having high protein concentration were recovered. The resultant protein solution was concentrated by a factor of about 10 using Centricon-30 (Amicon), placed in a dialysis tube and dialyzed against PBS. Thus, a purified shIL-5R α (protein concentration: 4 mg/ml; 3.5 ml) was obtained.

In a separate step, hIL-5R α-Fc was obtained as follows. A column was packed with about 5 ml of Protein A-Sepharose gel and then washed with 50 ml of PBS. After the washing, 1 liter of the culture medium of the pAI301-derived transformants described above was applied to the Protein A-Sepharose column at a flow rate of 0.5 ml/min. Then, the column was washed with 50 ml of PBS. Thereafter, 20 ml of 0.1 M citrate buffer (pH 3.0) were applied to the column to thereby elute the protein adsorbed on Protein A-Sepharose and, simultaneously, fractionate the eluate into 1-ml fractions. To each of the fractions, 0.15 ml of 2M Tris-HCl (pH 9.0) was added for pH adjustment. The protein concentration of each fraction was measured using a protein concentration measurement kit (Bio-rad) and those fractions having high protein concentration were recovered. The resultant protein solution was placed in a dialysis tube and dialyzed against PBS. Thus, a purified hIL-5R α-Fc (protein concentration: 1.8 mg/ml; 5.5 ml) was obtained.

(10) Expression of shIL-5R α or hIL-5R α-Fc in Insect Cells

The expression of shIL-5R α and hIL-5R α-Fc was performed by the procedures described below according to the manual attached to BaculoGold Starter Kit (Pharmingen).

The recovery of shIL-5R α and hIL-5R α-Fc from culture mediums was performed using Concanavalin A-Sepharose and Diethylaminoethyl(DEAE)-Sepharose, or Protein A-Sepharose (all manufactured by Pharmacia Biotech), respectively. shIL-5R α was obtained as follows. Briefly, $6 \times 10^6$ Sf9 cells were suspended in 45 ml of Grace's Insect Medium (Gibco) containing 10% FCS in a 225 cm2 flask (Greiner) and cultured at 27° C. for 3–4 days. After the culture supernatant was removed, 30 ml of a fresh Grace's Insect Medium containing 10% FCS and 1 ml of a solution in which the recombinant virus derived from the transfer vector pAI292 obtained in 1(8) of Example 1 were contained at a concentration of approx. $1 \times 10^7$ PFU/ml were added. The cells were cultured at 27° C. for one additional day. Then, after the removal of the culture supernatant, 45 ml of a fresh Sf900-II medium were added and the cells were cultured for 2–3 days. After the completion of the cultivation, the culture supernatant was recovered and centrifuged at 1,500×g for 10 minutes, to thereby obtain a supernatant. To the resultant culture medium, sodium chloride was added to give a final concentration of 0.5 M. Then, 1/50 volume of 1 M Tris-HCl (pH 7.4) was added and the pH of the resultant mixture was adjusted to 7.4 with 1 N sodium hydroxide solution.

A column was packed with about 10 ml of Concanavalin A-Sepharose gel and washed with 50 ml of a buffer containing 20 mM Tris-HCl (pH 7.4) and 0.5 mM sodium chloride at a flow rate of 0.5 ml/min. After the washing, 500 ml of the shIL-5R α containing culture medium prepared as described above were applied to the Concanavalin A-Sepharose column at a flow rate of 0.5 ml/min. Then, the column was washed with 80 ml of a buffer containing 20 mM Tris-HCl (pH 7.4) and 0.5 mM sodium chloride at a flow rate of 0.5 ml/min. Thereafter, 60 ml of a buffer containing 1 M α-methylmannoside, 20 mM Tris-HCl (pH 7.4) and 0.5 M sodium chloride were applied to the column to thereby elute the protein adsorbed on Concanavalin A-Sepharose and, simultaneously, fractionate the eluate into 2-ml fractions. The protein concentration of each fraction was measured using a protein concentration measurement kit (Bio-rad). Those fractions with high protein-concentration were recovered in a total amount of 44 ml and dialyzed against 20 mM Tris-HCl (pH 7.4). Further, similar operations were performed on 900 ml of the shIL-5R α containing culture medium prepared as described above so as to recover those fractions with high protein-concentration in a total amount of 40 ml, which were dialyzed against 20 mM Tris-HCl (pH 7.4).

After the dialysis, the two protein solutions were combined and applied to a column packed with 10 ml of Diethylaminoethyl(DEAE)-Sepharose gel to have the protein adsorbed. The elution of shIL-5R α from the column was performed by linearly changing the sodium chloride concentration from 0 to 0.5 M. Thus, those fractions with high concentration of shIL-5R α were recovered in a total amount of 4 ml. This protein solution was placed in a dialysis tube and dialyzed against PBS. Thus, a purified shIL-5R α (protein concentration: 400 μg/ml; 4.5 ml) was obtained.

In a separate step, hIL-5R α-Fc was obtained as follows. Briefly, $6 \times 10^6$ Sf9 cells were suspended in 45 ml of Grace's Insect Medium (Gibco) containing 10% FCS in a 225 cm2 flask (Greiner) and cultured at 27° C. for 3–4 days. After the culture supernatant was removed, 30 ml of a fresh Grace's Insect Medium containing 10% FCS and 1 ml of a solution in which the recombinant virus derived from the transfer vector pAI297 obtained in 1(8) of Example 1 were contained at a concentration of approx. $1 \times 10^7$ PFU/ml were added. The cells were cultured further at 27° C. for one additional day. Then, after the removal of the culture supernatant, 45 ml of a fresh Sf900-II medium were added and the cells were cultured for 2–3 days. After the completion of the cultivation, the culture supernatant was recovered and centrifuged at 1,500×g for 10 minutes, to thereby obtain a supernatant.

A column was packed with about 5 ml of Protein A-Sepharose gel and washed with 50 ml of PBS. After the washing, 450 ml of the shIL-5R α-Fc containing culture medium as described above were applied to the Protein A-Sepharose column at a flow rate of 0.5 ml/min. Then, the column was washed with 50 ml of PBS. Thereafter, 20 ml of 0.1 M citrate buffer (pH 3.0)

were applied to the column to thereby elute the protein adsorbed on Protein A-Sepharose and, simultaneously, fractionate the eluate into 1-ml fractions. To each of the fractions, 0.15 ml of 2 M Tris-HCl (pH 9.0) was added for pH adjustment. The protein concentration of each fraction was measured using a protein concentration measurement kit (Bio-rad) and those fractions with high protein concentration were recovered. The thus obtained protein solution was concentrated by a factor of about 3 using Centricon-30 (Amicon), placed in a dialysis tube and dialyzed against PBS. Thus, a purified shIL-5R α-Fc (protein concentration: 0.4 mg/ml; 1.8 ml) was obtained.

(11) Expression of an shIL-5R α Partial Fragment in *E. coli*

The expression of an shIL-5R α partial fragment in *E. coli* was performed by inserting a DNA fragment containing a cDNA coding for an shIL-5R α partial fragment into *E. coli* expression vector pMKex1 to be described below so as to construct pAI263 and transform *E. coli* with pAI263.

Briefly, 3 μg of plasmid pGHA2 (Kokai No. Sho 60-221091) were added to 30 μl of a buffer containing 50 mM Tris-HCl (pH 7.5), 10 mM magnesium chloride, 100 mM sodium chloride and 1 mM DTT, to which 10 units of EcoRI were added and reacted at 37° C. for 4 hours. DNA fragments were recovered from the reaction mixture by ethanol precipitation. To these DNA fragments, 30 μl of a buffer containing 10 mM Tris-HCl (pH 7.5), 10 mM magnesium chloride, 50 mM sodium chloride and 1 mM DTT, and 10 units of ClaI were added and reacted at 37° C. for 4 hours. The reaction mixture was subjected to agarose gel electrophoresis, and about 0.3 μg of the EcoRI-ClaI fragment from pGHA2 containing the promoter region was recovered.

Three μg of plasmid pTerm2 (Kokai No. 227075/90) were added to 30 μl of a buffer containing 50 mM Tris-HCl (pH 7.5), 10 mM magnesium chloride, 100 mM sodium chloride and 1 mM DTT, to which 10 units of EcoRI were added and reacted at 37° C. for 4 hours. DNA fragments were recovered from the reaction mixture by ethanol precipitation. To these DNA fragments, 30 μl of a buffer containing 10 mM Tris-HCl (pH 8.4), 10 mM magnesium chloride, 100 mM sodium chloride and 1 mM DTT and 10 units of NsiI were added and reacted at 37° C. for 4 hours. The reaction mixture was subjected to agarose gel electrophoresis, and about 0.8 μg of the EcoRI-NsiI fragment from pTerm2 was recovered.

Fifty μg of the EcoRI/ClaI fragment from pGHA2, 100 ng of the EcoRI/NsiI fragment from pTerrn2 and 100 ng of a synthetic DNA shown in SEQ ID NO: 15 were dissolved in 20 μl of T4DNA ligase solution, to which 200 units of T4DNA ligase were added. Then, ligation was performed at 12° C. for 16 hours. Using the thus prepared recombinant plasmid DNA, *E. coli* strain JM109 was transformned to thereby obtain plasmid pMKex1 shown in FIG. 12.

Figure 3:
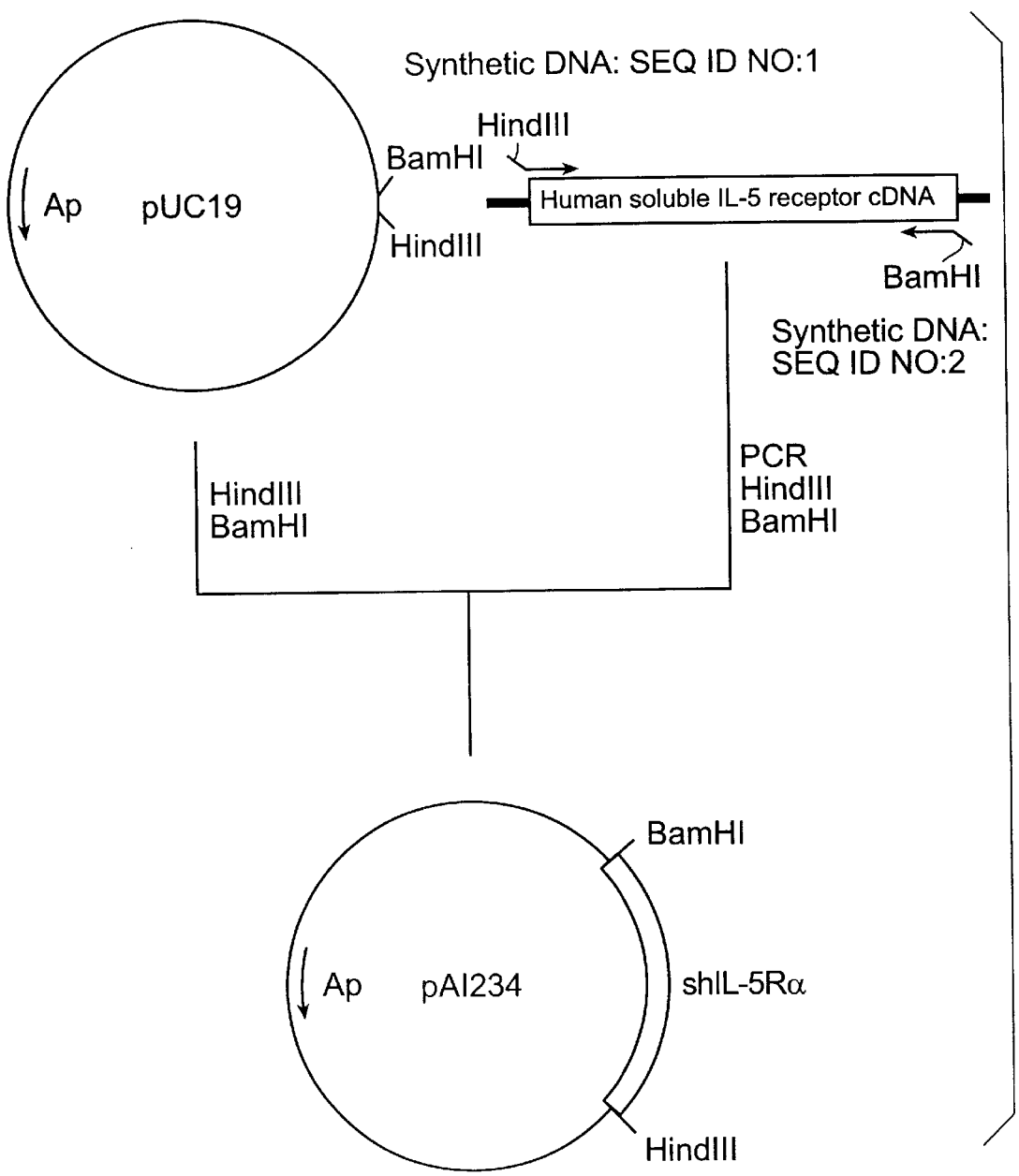
FIG. 3 shows steps for constructing plasmid pAI234.

In a separate step, 3 μg of pAI234 obtained in FIG. 3 were added to 30 μl of a buffer containing 50 mM Tris-HCl (pH 7.5), 10 mM magnesium chloride, 100 mM sodium chloride and 1 mM DTT, to which 10 units of PstI were added and reacted at 37° C. for 4 hours. DNA fragments were recovered from the reaction mixture by ethanol precipitation and dissolved in 20 μl of T4DNA polymerase I buffer [a buffer containing 33 mM Tris-HCl (pH 8.0), 66 mM potassium acetate, 10 mM magnesium acetate, 0.5 mM DTT and 0.01% BSA]. To the resultant mixture, 5 units of T4DNA polymerase I (Takara Shuzo) were added and reacted at 12° C. for 15 minutes, whereby the 5' cohesive ends generated by the PstI digestion were changed to blunt ends. The reaction mixture was subjected to phenol-chloroform extraction followed by ethanol precipitation. To the precipitate, 30 μl of a buffer containing 20 mM Tris-HCl (pH 8.5), 10 mM magnesium chloride, 100 mM potassium chloride and 1 mM DTT and 10 units of BamHI were added and reacted at 37° C. for 4 hours. The reaction mixture was subjected to agarose gel electrophoresis, and about 0.3 μg of an approx. 0.7 kb DNA fragment containing a cDNA coding for an shIL-5R α fragment was recovered.

Figure 12:
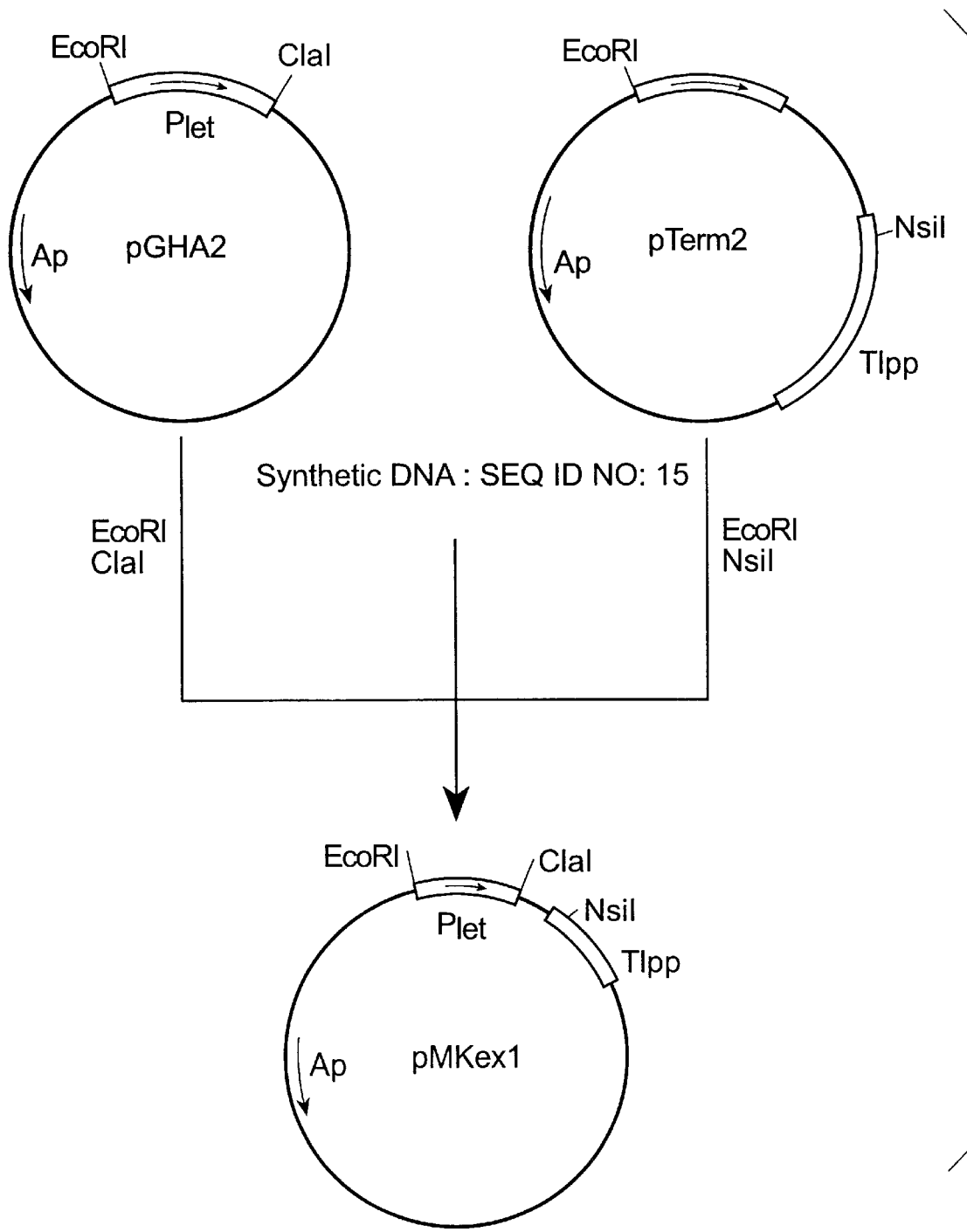
FIG. 12 shows steps for constructing plasmid pMKex 1.

Three μg of the expression vector for *E. coli*, pMKex1 obtained in FIG. 12 were dissolved in 30 μl of a buffer containing 20 mM Tris-HCl (pH 8.5), 10 mM magnesium chloride, 100 mM potassium chloride and 1 mM DTT, to which 10 units of BamHI were added and reacted at 37° C. for 4 hours. DNA fragments were recovered from the reaction mixture by ethanol precipitation and dissolved in 30 μl of a buffer containing 50 mM Tris-HCl (pH 7.5), 10 mM magnesium chloride, 100 mM sodium chloride and 1 mM DTT, to which 10 units of EcoRV were added and reacted at 37° C. for 4 hours. About 1.5 μg of DNA fragments were recovered from the reaction mixture by ethanol precipitation.

Figure 13:
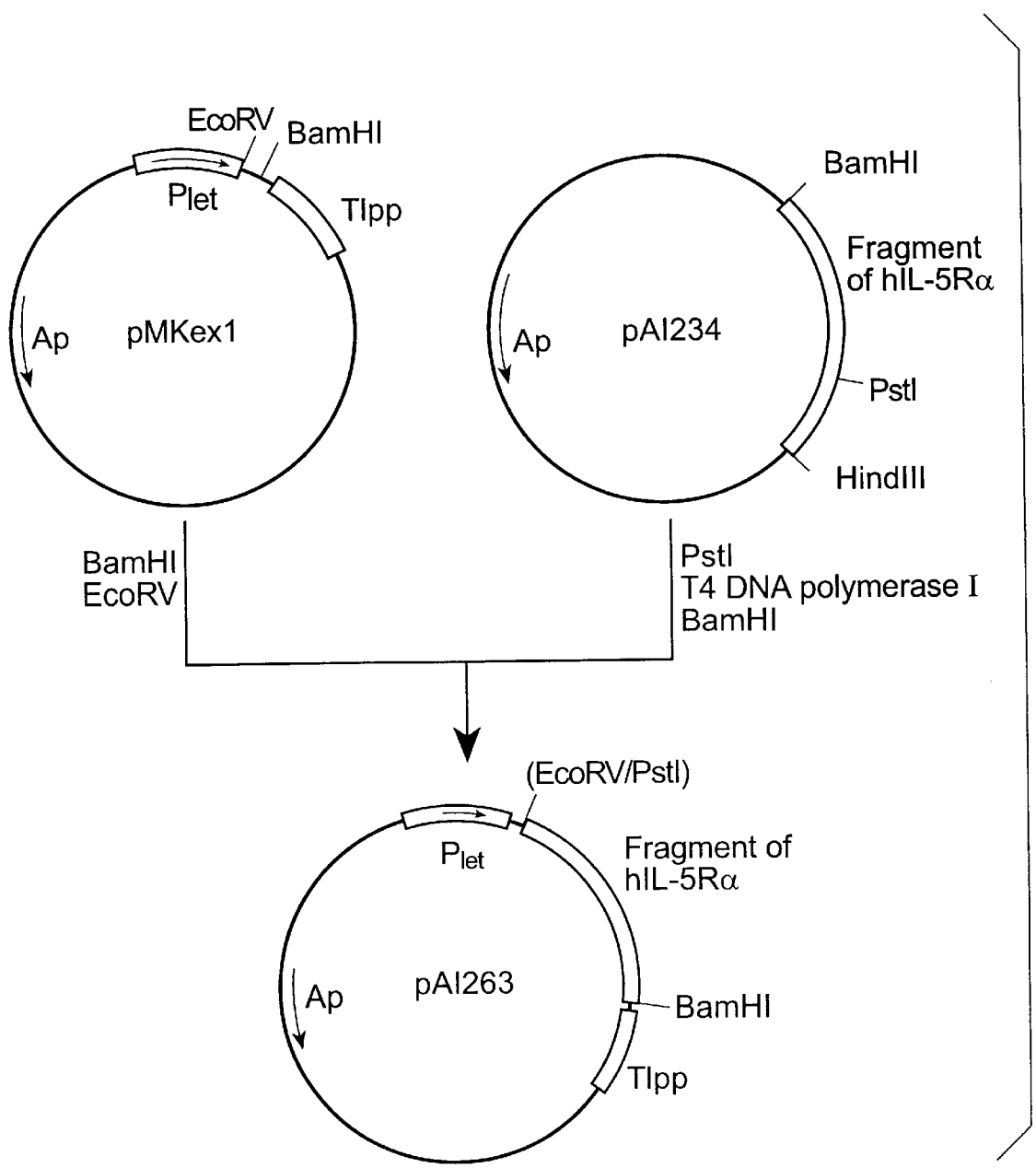
FIG. 13 shows steps for constructing plasmid pAI263.

Fifty μg of the thus obtained cDNA coding for an shIL-5R α fragment and 100 ng of the thus obtained RcoRV/BamHI fragment from pMKex1 were dissolved in 20 μl of T4DNA ligase buffer, to which 200 units of T4DNA ligase were added. Then, ligation was performed at 12° C. for 16 hours. Using the thus prepared recombinant plasmid DNA, *E. coli* strain JM109 was transformed to thereby obtain plasmid pAI263 shown in FIG. 13.

The above plasmid pAI263 was transfected into *E. coli* (Molecular Cloning, A Laboratory Manual, 2nd Edition published by Cold Spring Harbor Laboratory Press, 1989), which was cultured in 400 ml of LB medium containing 200 μg/ml of ampicillin at 37° C. for 4 hours. Then, 0.5 mM IPTG was added and the cells were cultured at 37° C. for another 2 hours. Four hundred ml of the culture medium were centrifuged at 3,000×g for 15 minutes. The precipitate containing the cells of *E. coli* was suspended in 100 ml of buffer I [10 mM Tris-HCl (pH 8.0), 1 mM EDTA, 150 mM sodium chloride]. After recentrifugation, the precipitate was suspended in 7 ml of buffer I and sonicated to disrupt cells. The resultant suspension was centrifuged at 10,000×g for 30 minutes, and the precipitate was dissolved in 500 μl of SDS-polyacrylamide gel electrophoresis sample buffer [6 mM Tris-HCl (pH 6.8), 2% SDS, 10% glycerol, 5% 2-mercaptoethanol] and subjected to polyacrylamide gel electrophoresis. Thus, a purified shIL-5R α fragment having a molecular weight of about 27 kD was obtained.

(12) Preparation of a Cell Membrane Fraction from Human IL-5R α Expressing Cells The preparation of a membrane component from the hIL-5R α gene transfected CTLL-2 cells [J. Exp. Med., 177, 1523 (1993)] or control CTLL-2 cells [ATCC TIB 214] was performed as described below.

Briefly, the cells were centrifuged (1,200 rpm, 5 min.), washed with PBS twice, and then suspended in cell disruption buffer [20 mM HEPES (pH 7.4), 1 mM EDTA, 0.5 mM PMSF, 250 mM sucrose] and disrupted with a homogenizer. After the disruption, the cells were centrifuged at 5,500 rpm for 15 minutes to remove the precipitate. The cells were further centrifuged at 35,000 rpm to recover cell membrane fractions as a precipitate.

2. Immunization of Animals and Preparation of Antibody-Producing Cells

Fifty μg of each of the antigens obtained in subsections (9), (10), (11) or (12) of section 1 of Example 1 were administered independently to 5-week old female BALB/c mice or female SD rats together with 2 mg of aluminum gel and 1×10$^9$ cells of pertussis vaccine (Chiba Prefectural Serum Research Institute). 2 weeks after the administration, 50 μg of the protein were administered once a week in total of 4 times. Blood samples were collected from the venous plexus of eyegrounds or the tail vein, and antibody titer of the serum thereof was examined by the enzyme immunoassay described below under 3. Spleens were removed 3 days after the final immunization from those mice or rats which exhibited a sufficient antibody titer. In this immunization experiment, the cell membrane fraction obtained in subsection (12) of section 1 of Example 1 was used as an antigen to immunize 13 mice and 5 rats. However, no remarkable rise in antibody titer was observed in those animals. Also, no satisfactory rise in antibody titer was observed in the 5 rats immunized with the shIL-5R α obtained in subsection (9) of section 1 of Example 1 or the 10 rats immunized with the shIL-5R α obtained in subsection (10) of section 1 of Example 1.

The spleen was cut into pieces in MEM medium (Nissui Pharmnaceuticals), loosened with tweezers and centrifuged (1,200 rpm, 5 min.). Then, the supernatant was discarded and the remainder was treated with Tris-ammonium chloride buffer (pH 7.65) for 1–2 minutes to remove erythrocytes and washed with MEM medium 3 times. The resultant splenocytes were used for cell fusion.

3. Enzyme Immunoassay

The measurement of antisera or culture supernatants of hybridoma cells derived from mice or rats immunized with the shIL-5R α obtained in subsections (9) or (10) of section 1 of Example 1 was performed according to the two methods described below using, as an antigen, the hIL-5R α-Fc obtained from a culture supernatant of insect cells as described in subsection (10) of section 1 Example 1.

(A) To a 96-well EIA plate (Greiner), hIL-5R α-Fc diluted to 1 μg/ml with PBS and a control antigen, anti-GD3 chimeric antibody KM871 having a common human Ig constant region, were dispensed separately in an amount of 50 μl/well and left at 4° C. overnight to have the proteins adsorbed. After washing, PBS containing 1% bovine serum albumin (BSA) (hereinafter, referred to as 1% BSA-PBS) was added to the plate (100 μl/well) and reacted at room temperature for 1 hour to thereby block the remaining active groups. After discarding 1% BSA-PBS, an immunized mouse or rat-derived antiserum and culture supernatant of a hybridoma were dispensed into the wells (50 μl/well) and reacted for 2 hours. After washing with Tween-PBS, peroxidase-labeled rabbit anti-mouse immunoglobulin or anti-rat immunoglobulin (DAKO) was added to the plate (50 μl/well), reacted for 1 hour and washed with Tween-PBS. Thereafter, the resultant mixture was allowed to form a color by using ABTS substrate solution [a solution obtained by dissolving 550 mg of 2,2' azinobis(3-ethylbenzothiazoline-6-sulfonic acid)diammonium salt in 1 L of 0.1 M citrate buffer (pH 4.2) and adding 1 μl/ml of hydrogen peroxide immediately before use] to measure the absorbance at OD415 mn (NJ2001; Japan Intermed).

(B) Further, for the purpose of selecting a monoclonal antibody having neutralizing activity against IL-5 with a higher probability, screening was performed for an activity to inhibit binding to an IL-5 receptor by the following procedures using a biotin-labeled human IL-5 and the shIL-5R α-Fc obtained from the insect cell culture supernatant in subsection (10) of section 1 of Example 1. The human IL-5 used for biotin labeling was prepared according to the method described in Journal of Immunological Method, 125, 233 (1989).

The biotin labeling of the human IL-5 was performed according to the protocol attached to a biotin-labeling reagent (Biotin-LC-Hydrazide) (Pierce) by the following procedures. First, 1.6 mg/ml of human IL-5 dissolved in PBS was applied to a PD10 column (Pharmacia) equilibrated with a labeling buffer (100 mM sodium acetate, 0.02% NaN3, pH 5.5) for salt exchange and 1 ml of a fraction having high protein concentration was recovered. To 0.5 ml of this human IL-5 solution, 1 ml of a labeling buffer containing 30 mM metaperiodic acid was added and reacted at room temperature for 30 minutes while shielding the light. After the completion of the reaction, the reaction mixture was applied to a PD10 column equilibrated with a labeling buffer to remove the unreacted metaperiodic acid. Thus, 1.5 ml of a fraction having high protein concentration was recovered. To this fraction, 20 μl of a labeling buffer containing 5 mM biotin-labeling reagent as described above were added and reacted at room temperature for 1 hour. After the completion of the reaction, 50 μl of reaction termination buffer (0.1 M Tris, pH 7.5) were added, and then the reaction mixture was applied to a PD10 column equilibrated with 0.05% NaN3-containing PBS to exchange salts and, simultaneously, remove unreacted reagents. The thus obtained biotin-labeled human IL-5 was stored at 4° C.

The shIL-5R α-Fc obtained from the insect cell culture supernatant in subsection (10) of section 1 of Example 1 was diluted to a concentration of 5 μg/ml with PBS, dispensed into a 96-well EIA plate (Greiner) (50 μl/well) and left at 4° C. overnight to have the protein adsorbed. After washing with PBS, PBS containing 1% bovine serum albumin (BSA) (1% BSA-PBS) was added to the plate (100 μl/well) and reacted at room temperature for 1 hour to block the remaining active groups. Then, the plate was washed with Tween-PBS. Thereafter, an antiserum derived from immunized mouse or rat and the culture supernatant of the hybridoma, and the biotin-labeled human IL-5 described above were each added to the plate in an amount of 50 μl/well and reacted at 4° C. overnight. On the next day, the plate was washed with Tween-PBS, and then 50 μl/well of peroxidase-labeled avidin (Nippon Reizo) diluted 4000 folds with 1% BSA-PBS were added and reacted at room temperature for 1 hour. After washing with Tween-PBS, 50 μl/well of ABTS substrate solution were added to allow color development and the absorbance at OD415 was measured.

With respect to the measurement of antisera and culture supernatants of hybridomas derived from those mice or rats immunized with the hIL-5R α fragment obtained in subsection (11) of section 1 of Example 1, the hIL-5R α fragment produced by E. coli in subsection (11) of section 1 of Example 1 was used as an antigen. In a manner similar to that described above, the shIL-5R α produced by E. coli and an E. coli cell protein (control antigen) were adsorbed on plates separately. Using thus prepared plates, the reactivity of culture supernatants of hybridomas and antisera of immunized mice or rats was examined.

Further, with respect to the measurement of antisera and culture supernatants of hybridomas derived from those mice or rats immunized with the cell membrane fraction from hIL-5R α expressing cells obtained in subsection (12) of section 1 of Example 1, the cell membrane fraction obtained in subsection (12) of section 1 of Example 1 was used as an antigen. In a manner similar to that described above, the cell membrane fraction from IL-5R α-expressing cells and a cell membrane fraction from control cells were adsorbed on plates separately. Using thus prepared plates, the reactivity of culture supernatants of hybridomas and antisera of immunized mice or rats was examined.

4. Preparation of Mouse Myeloma Cells

An 8-azaguanine resistant mouse myeloma cell line, P3-U1, was cultured in a normal medium and not less than $2 \times 10^7$ cells were secured and submitted for cell fusion as a parent line.

5. Preparation of Hybridomas

The mouse or rat splenocytes obtained in section 2 of Example 1 and the myeloma cells obtained in section 4 of Example 1 were mixed at a ratio of 10:1, and the mixture was centrifuged (1,200 rpm, 5 min.). Then, the supernatant was discarded and the precipitated cells were loosened sufficiently. To the resultant cells, a mixed solution composed of 2 g of polyethylene glycol-1000 (PEG-1000), 2 ml of MEM medium and 0.7 ml of DMSO was added in an amount of 0.2 to 1 ml per $10^8$ mouse splenocytes, followed by the addition of 1 to 2 ml portions of MEM medium at 1 to 2 minute interval at 37° C. Thereafter, MEM medium was added to give a total volume of 50 ml. After centrifugation (900 rpm, 5 min.), the supernatant was discarded and cells were loosened gently. Then, cells were gently suspended in 100 ml of HAT medium by suction and release with a pipette.

This cell suspension was dispensed into a 96-well culture plate (100 µl/well) and cultured in a 5% $CO_2$ incubator at 37° C. for 10–14 days. The resultant culture supernatant was examined by the enzyme immunoassay described in section 3 of Example 1, and those wells which showed specific reaction with the hIL-5R α-Fc prepared from an insect cell culture supernatant or with the shIL-5R α produced by *E. coli* were selected. Further, the medium was replaced with HT medium and a normal medium, and cloning was repeated twice. As a result, hybridoma cell lines producing an anti-human IL-5R α monoclonal antibody were established.

As a result of screening about 4000 hybridoma clones obtained from 6 mice or 8 rats immunized with the hIL-5R α fragment obtained in subsection (11) of section 1 of Example 1, an anti-human IL-5R α monoclonal antibody was obtained and designated as KM1074. Its reactivity with IL-5R α was extremely weak compared to that of anti-human IL-5R α monoclonal antibodies KM1257 and KM1259 to be described later.

In a separate step, hybridomas were obtained from 12 or 6 animals that exhibited a high antibody titer and which were selected from 15 or 20 mice immunized with the shIL-5R α obtained in subsection (9) of section 1 of Example 1 or the shIL-5R α obtained in subsection (10) of section 1 of Example 1. As a result of screening more than 10000 hybridoma clones, 81 hybridoma clones were established that produced an anti-human IL-5R α monoclonal antibody and which showed a specific reactivity with hIL-5R α expressing cells when tested by the method described later in section 1 of Example 3. Among these, the monoclonal antibody which exhibited the most strong reactivity in the immunocyte staining method described later in section 1 of Example 3 later was KM1257. Hybridoma KM1257 was deposited at the National Institute of Bioscience and Human-Technology, Agency of Industrial Science and Technology (1–3, Higashi 1-Chome, Tsukuba City, Ibaraki, Japan; hereinafter, the address is the same for this Institute) on Jun. 13, 1995 under accession number FERM BP-5133. Of those 81 clones, only six clones exhibited a strong inhibition activity against the biological activity of IL-5 which is described later in section 2 of Example 3. Among these six clones, the monoclonal antibodies which exhibited the strongest inhibition activity were KM1259 and KM1486. Hybridoma KM1259 was deposited under accession number FERM BP-5134 on Jun. 13, 1995 and hybridoma KM1486 was deposited under accession number FERM BP-5651 on Sep. 3, 1996 both at the National Institute of Bioscience and Human-Technology, Agency of Industrial Science and Technology.

Figure 14:
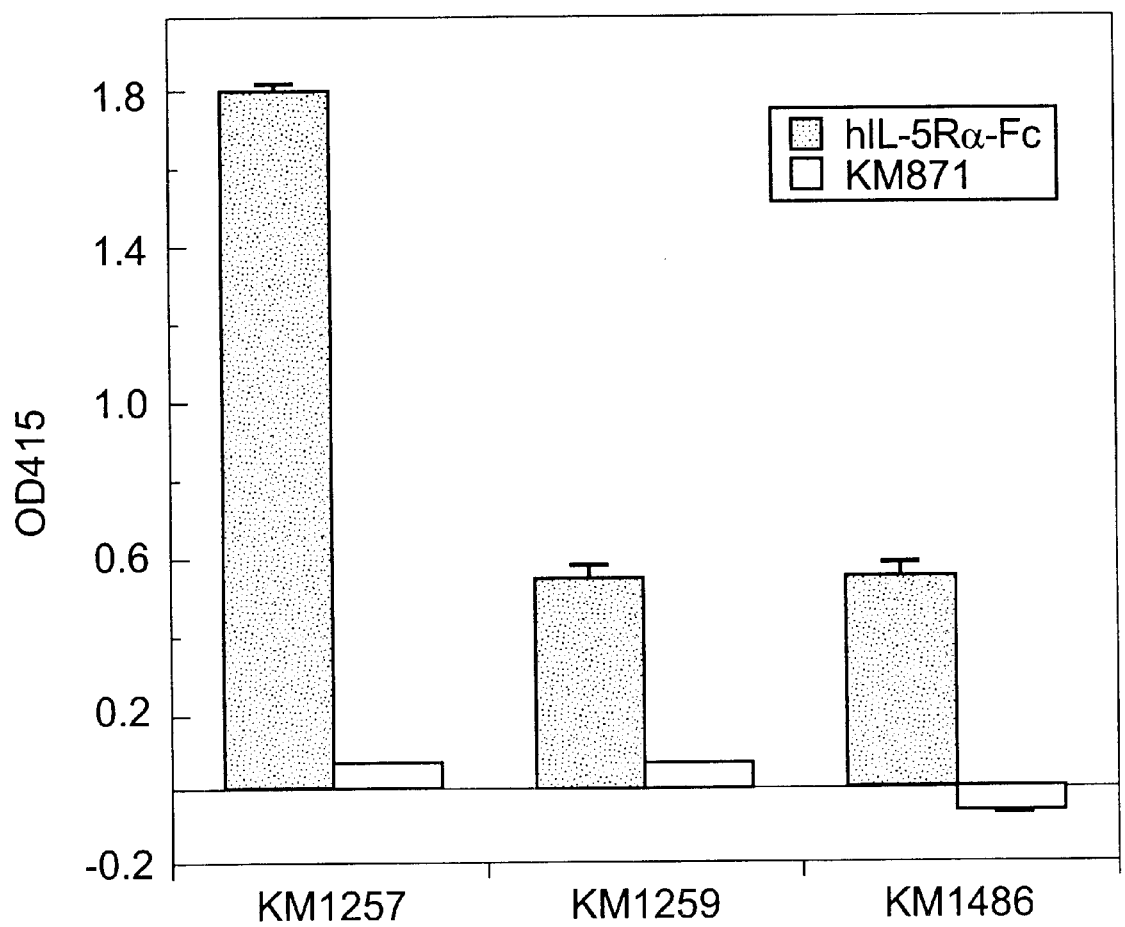
FIG. 14 shows the binding reactivities of anti-human IL-5R α monoclonal antibody KM1257 and KM1259 with a human IL-5R α-human immnunoglobulin constant region fusion protein in an enzyme immunoassay.

The reactivities of monoclonal antibodies KM1257, KM1259 and KM1486 are shown in FIG. 14. Subclass of each antibody was determined by an enzyme immunoassay using a subclass typing kit. As a result, the antibody classes of KM1257, KM1259 and KM1486 were all IgG1.

6. Purification of Monoclonal Antibodies

The hybridoma cell line obtained in 5 above was intraperitoneally administered to pristane-treated, female nude mice (Balb/c) of 8 weeks of age at a dose of $(5-20 \times 10^6$ cells/mouse). The hybridoma caused ascites tumor 10 to 21 days after the administration. From those mice in which ascites accumulated, ascites was collected (1–8 ml/mouse), centrifuged (3,000 rpm, 5 min.) to remove the solids and then purified by the caprylic acid precipitation method (Antibodies—A Laboratory Manual, Cold Spring Harbor Laboratory, 1988) to obtain purified monoclonal antibody.

Example 2

Preparation of Anti-Human IL-5R α Humanized Antibodies

1. Construction of Tandem Cassette-Type Humanized Antibody Expression Vector pKANTEX93

A tandem cassette-type humanized antibody expression vector, pKANTEX93, for expressing a humanized antibody of human antibody IgG1, κ type in animal cells and into which a cDNA coding for a humanized antibody VH and a CDNA coding for a humanized antibody VL were transfected upstream of a cDNA coding for human antibody Cγ1 and a CDNA coding for human antibody Cκ, respectively, was constructed as described below based on the plasmid pSE1UK1SEd1-3 disclosed in Kokai No. 257891/90. The humanized antibody expression vector constructed was used for the expression of human chimeric antibodies and human CDR-grafted antibodies in animal cells.

(1) Modification of the ApaI and EcoRI Restriction Sites present in Rabbit β-Globin Gene Splicing Signal and Poly (A) Signal The modification of the ApaI and EcoRI restriction sites present in rabbit β-globin gene splicing poly (A) signal of plasmid pSE1UK1SEd1-3 was performed as described below in order to enable the construction of a human chimeric antibody expression vector or a human CDR-grafted antibody (=humanized antibody) expression vector by inserting into a humanized antibody expression vector the variable region of a human chimeric antibody or a human CDR-grafted antibody in a cassette using a NotI-ApaI fragment (VH) and an EcoRI-SplI fragment (VL).

Figure 15:
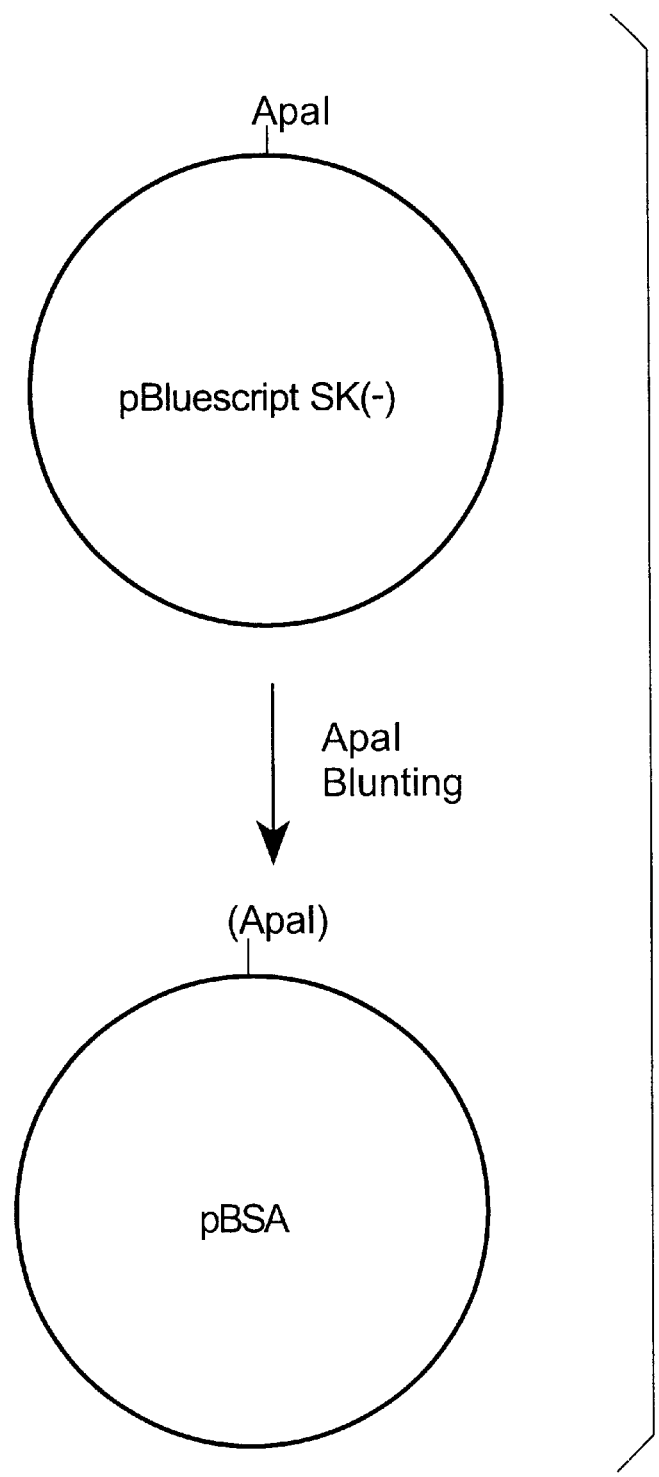
FIG. 15 shows steps for constructing plasmid pBSA.

Briefly, 3 µg of plasmid pBluescript SK(–)(Stratagene) were added to 10 µl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the 3' sticky ends generated by the ApaI digestion were blunted using DNA Blunting Kit (Takara Shuzo) and the resultant DNA fragments were ligated using DNA Ligation Kit (Takara Shuzo). Using the thus obtained recombinant plasmid DNA solution, *E. coli* HB101 was transformed to obtain plasmid pBSA shown in FIG. 15.

Figure 16:
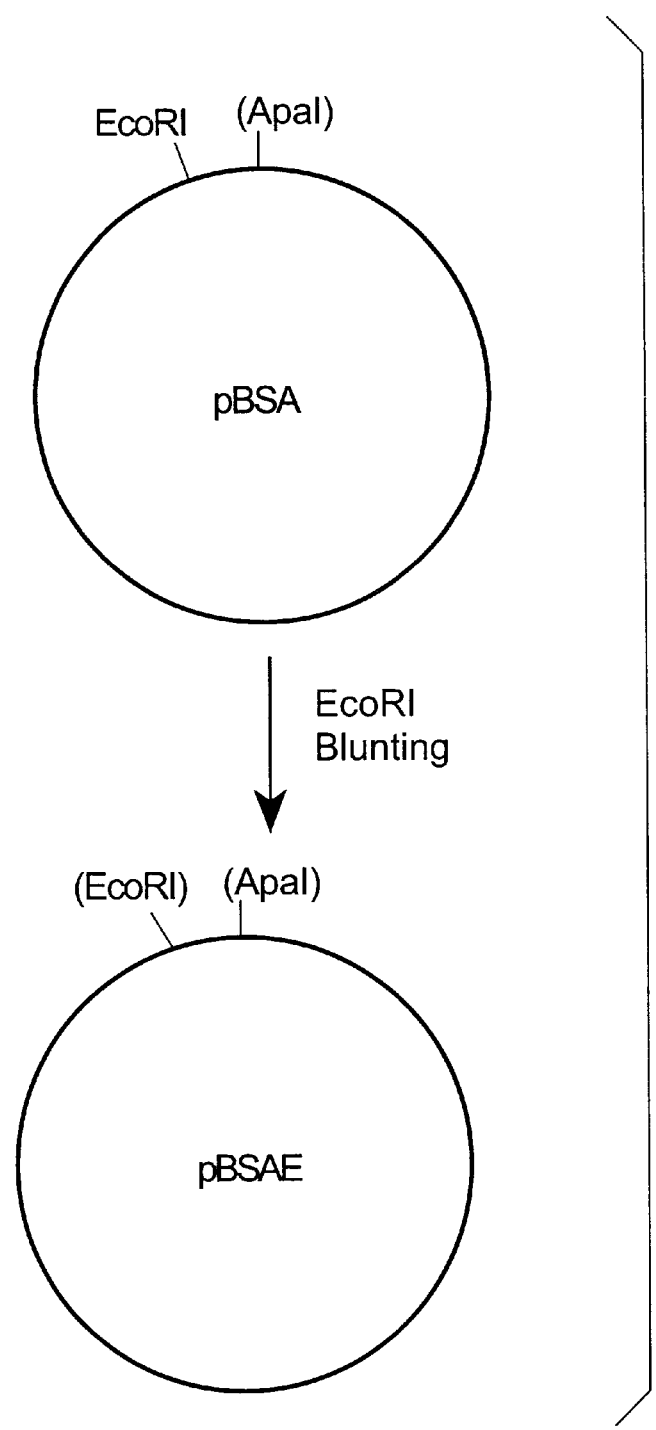
FIG. 16 shows steps for constructing plasmid pBSAE.

Further, 3 μg of the thus obtained plasmid pBSA were added to 10 μl of a buffer containing 50 mM Tris-HCl (pH 7.5), 10 mM magnesium chloride, 100 mM sodium chloride and 1 mM DTT, to which 10 units of the restriction enzyme EcoRI (Takara Shuzo) were added and reacted at 37° C. for 1 hour. The reaction mixture was ethanol-precipitated, and the 5' sticky ends generated by the EcoRI digestion were blunted using DNA Blunting Kit (Takara Shuzo) and the resultant DNA fragments were ligated using DNA Ligation Kit (Takara Shuzo). Using the thus obtained recombinant plasmid DNA solution, *E. coli* HB101 was transformed to obtain plasmid pBSAE shown in FIG. 16.

Subsequently, 3 μg of the thus obtained plasmid pBSAE were added to 10 μl of a buffer containing 10 mM Tris-HCl (pH 7.5), 10 mM magnesium chloride, 50 mM sodium chloride and 1 mM DTT, to which 10 units of the restriction enzyme HindIII (Takara Shuzo) were added and reacted at 37° C. for 1 hour. The reaction mixture was ethanol-precipitated, and the precipitate was dissolved in 20 μl of a buffer containing 10 mM Tris-HCl (pH 7.5), 10 mM magnesium chloride and 1 mM DTT. The resultant mixture was divided into two 10 μl portions. To one portion, 10 units of the restriction enzyme SacII (Toyobo) were added, and to the other portion, 10 units of the restriction enzyme KpnI (Takara Shuzo) were added. Then, both mixtures were reacted at 37° C. for 1 hour. Both reaction mixtures were subjected to agarose gel electrophoresis, and an approx. 2.96 kb HindIII-SacII fragment and an approx. 2.96 kb KpnI-HindIII fragment were recovered, each in about 0.3 μg.

Subsequently, 3 μg of plasmid pSE1UK1SEd1-3 were added to 10 μl of a buffer containing 10 mM Tris-HCl (pH 7.5), 10 mM magnesium chloride and 1 mM DTT, to which 10 units of the restriction enzyme SacII (Toyobo) and 10 units of the restriction enzyme KpnI (Takara Shuzo) were added and reacted at 37° C. for 1 hour. The reaction mixture was ethanol-precipitated, and the precipitate was dissolved in 10 μl of a buffer containing 10 mM Tris-HCl (pH 7.5), 10 mM magnesium chloride, 50 mM sodium chloride and 1 mM DTT. To the resultant mixture, 10 units of the restriction enzyme HindIII (Takara Shuzo) were added and reacted at 37° C. for 1 hour. The reaction mixture was subjected to agarose gel electrophoresis, and an approx. 2.42 kb HindIII-SacII fragment and an approx. 1.98 kb KpnI-HindIII fragment were recovered, each in about 0.2 μg.

Figure 17:
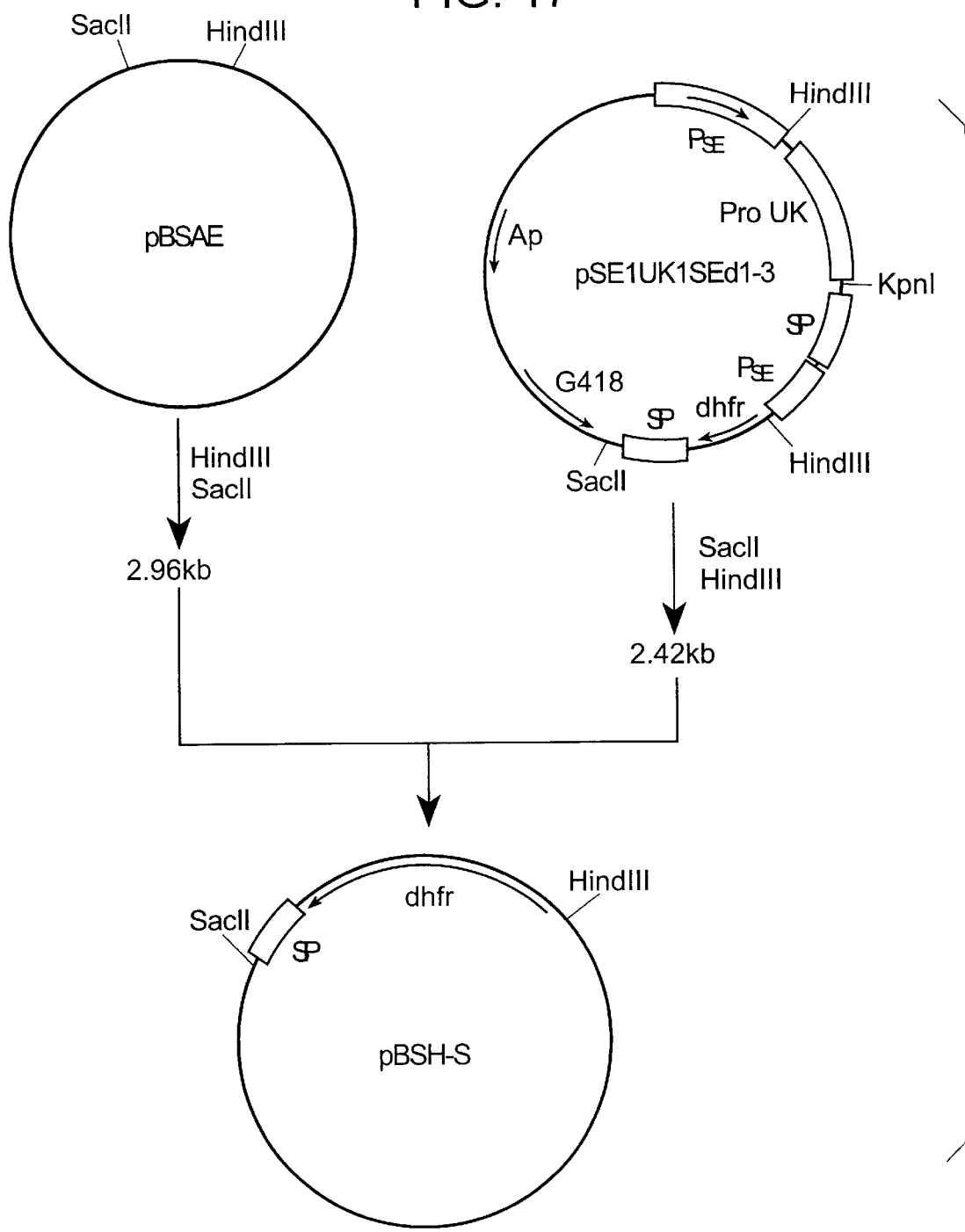
FIG. 17 shows steps for constructing plasmid pBSH-S.
Figure 18:
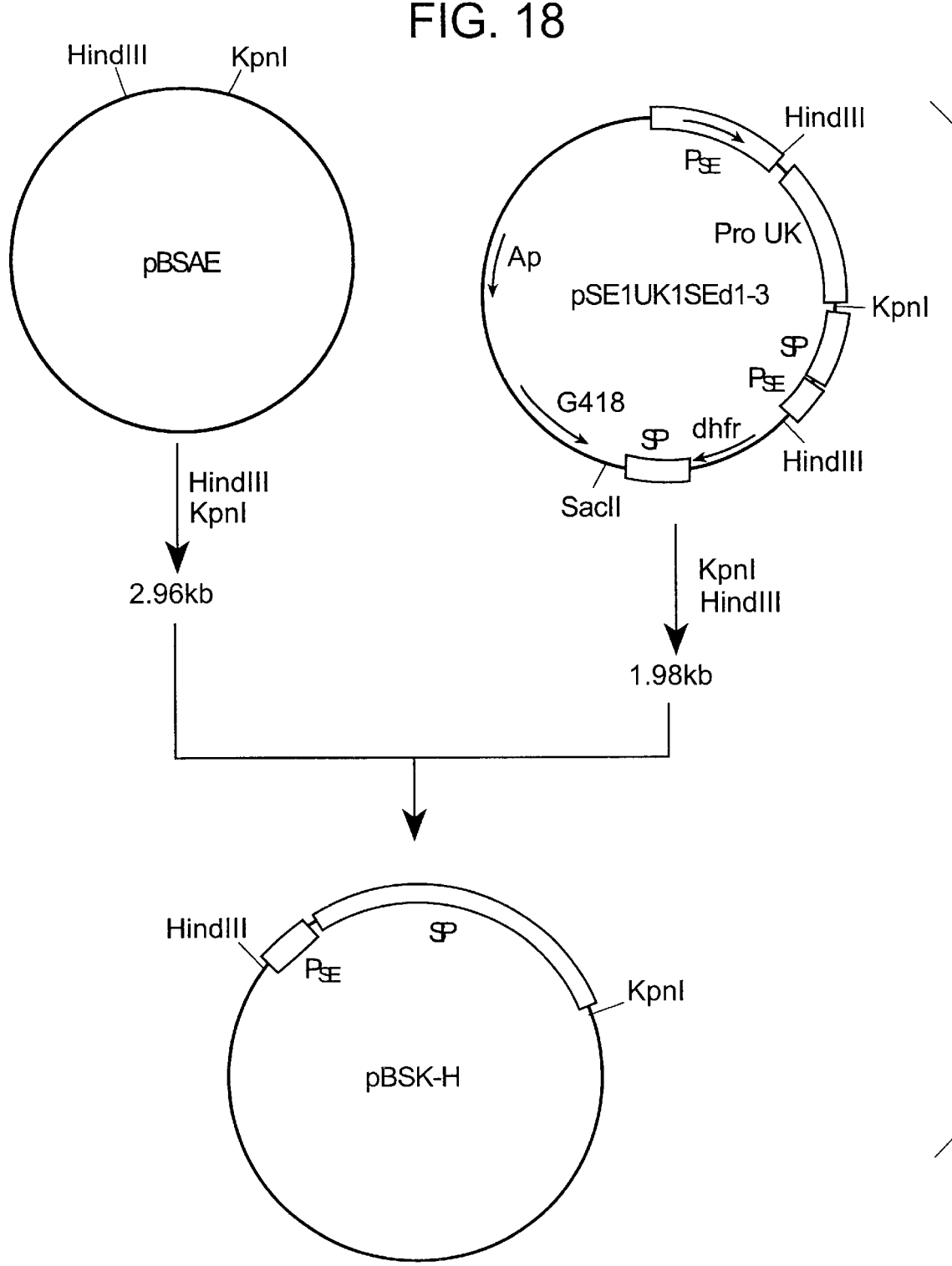
FIG. 18 shows steps for constructing plasmid pBSK-H.

Then, 0.1 μg of the HindIII-SacII fragment from plasmid pSE1UK1SEd1-3 and 0.1 μg of the HindIII-SacII fragment from pBSAE obtained above were dissolved in sterilized water to give a total volume of 20 μl and ligated using Ready-To-Go T4 DNA Ligase (Pharmacia Biotech). Using the thus obtained recombinant plasmid DNA solution, *E. coli* HB101 was transformed to obtain plasmid pBSH-S shown in FIG. 17. Also, 0.1 μg of the KpnI-HindIII fragment from plasmid pSE1UK1SEd1-3 and 0.1 μg of the KpnI-HindIII fragment from pBSAE obtained above were dissolved in sterilized water to give a total volume of 20 μl and ligated using Ready-To-Go T4 DNA Ligase (Pharmacia Biotech). Using the thus obtained recombinant plasmid DNA solution, *E. coli* HB101 was transformed to obtain plasmid pBSK-H shown in FIG. 18.

Figure 19:
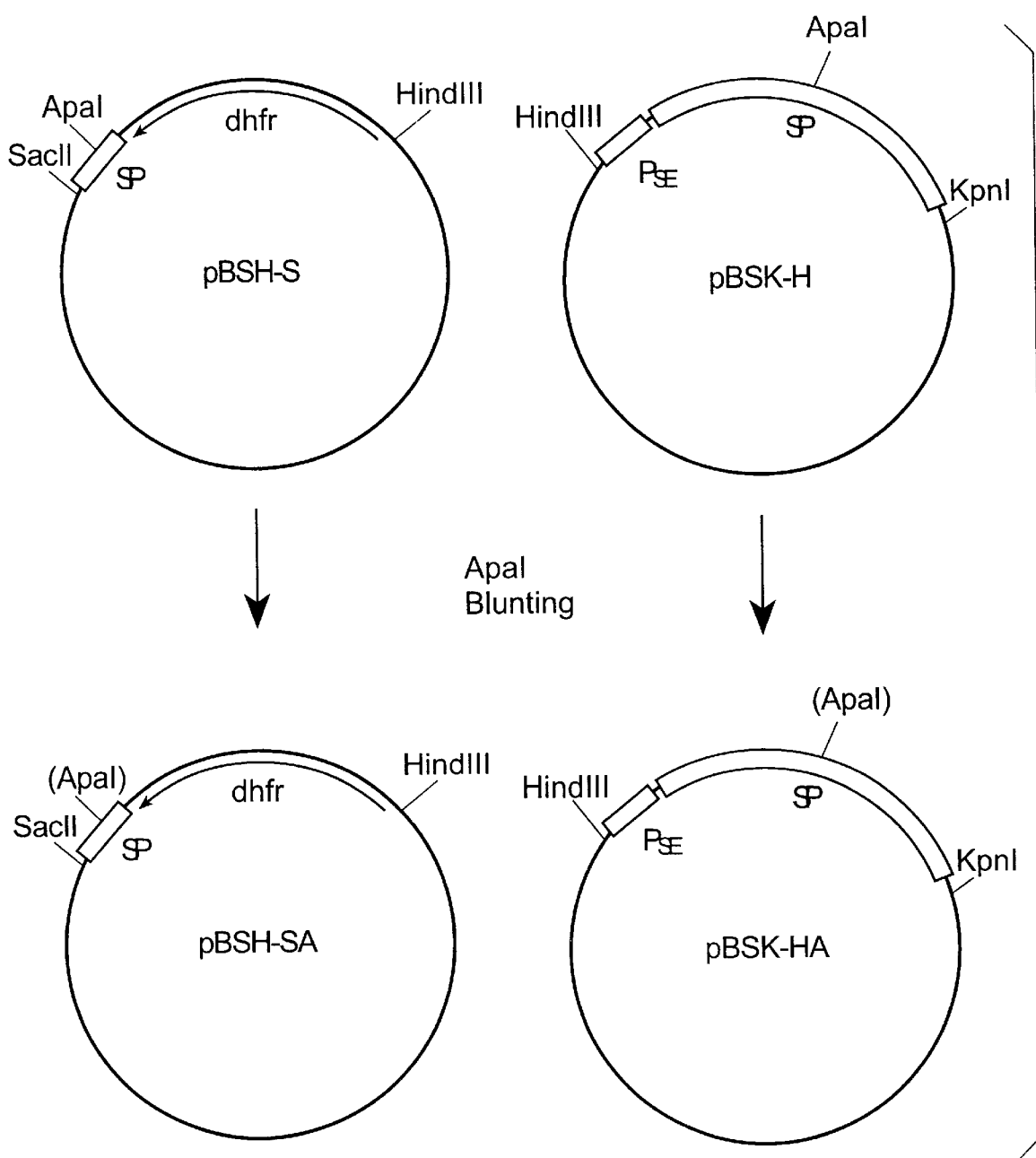
FIG. 19 shows steps for constructing plasmids pBSH-SA and pBSK-HA.

Subsequently, 3 μg each of the thus obtained plasmids pBSH-S and pBSK-H were added separately to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. Both reaction mixtures were ethanol-precipitated, and the 3' sticky ends generated by the ApaI digestion were blunted using DNA Blunting Kit (Takara Shuzo) and the resultant DNA fragments were ligated using DNA Ligation Kit (Takara Shuzo). Using each of the thus obtained recombinant plasmid DNA solutions, *E. coli* HB101 was transformed to obtain plasmid pBSH-SA and pBSK-HA shown in FIG. 19.

Figure 20:
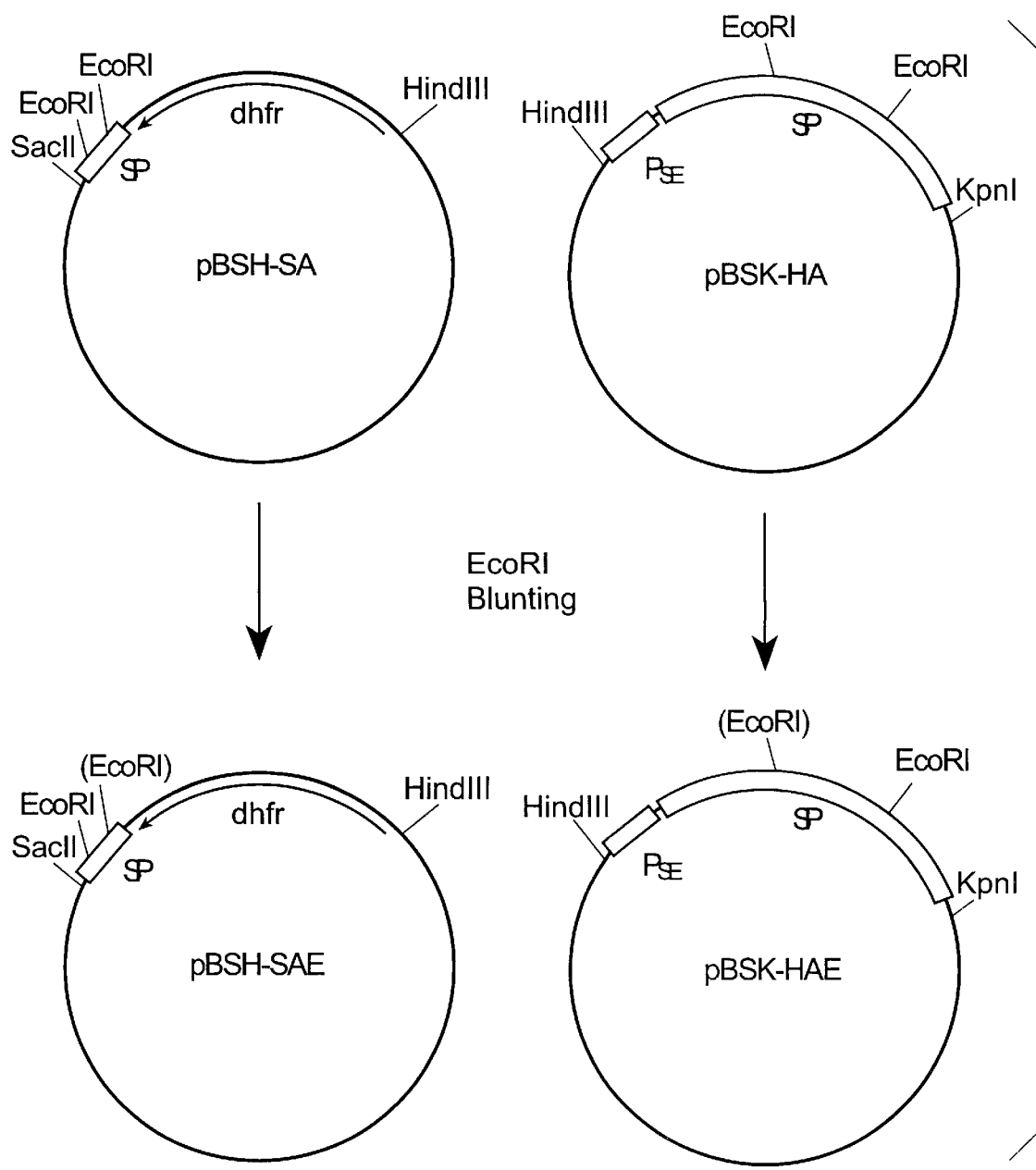
FIG. 20 shows steps for constructing plasmids pBSH-SAE and pBSK-HAE.

Subsequently, 5 μg each of the thus obtained plasmids pBSH-SA and PBSK-HA were added separately to 10 μl of a buffer containing 50 mM Tris-HCl (pH 7.5), 10 mM magnesium chloride, 100 mM sodium chloride and 1 mM DTT, to which 10 units of the restriction enzyme EcoRI (Takara Shuzo) were added and reacted at 37° C. for 10 minutes so that the plasmid was partially digested. Then, both reaction mixtures were ethanol-precipitated. After the 5' sticky ends generated by the EcoRI digestion were blunted using DNA Blunting Kit (Takara Shuzo), both reaction mixtures were subjected to agarose gel electrophoresis, and an approx. 5.38 kb fragment and an approx. 4.94 kb fragment were recovered, each in about 0.5 μg. Then, 0.1 μg each of the thus recovered fragments were dissolved separately in sterilized water to give a total volume of 20 μl and ligated using Ready-To-Go T4 DNA Ligase (Pharmacia Biotech). Using each of the thus obtained recombinant plasmid DNA solutions, *E. coli* HB101 was transformed to obtain plasmids pBSH-SAE and pBSK-HAE shown in FIG. 20.

Figure 21:
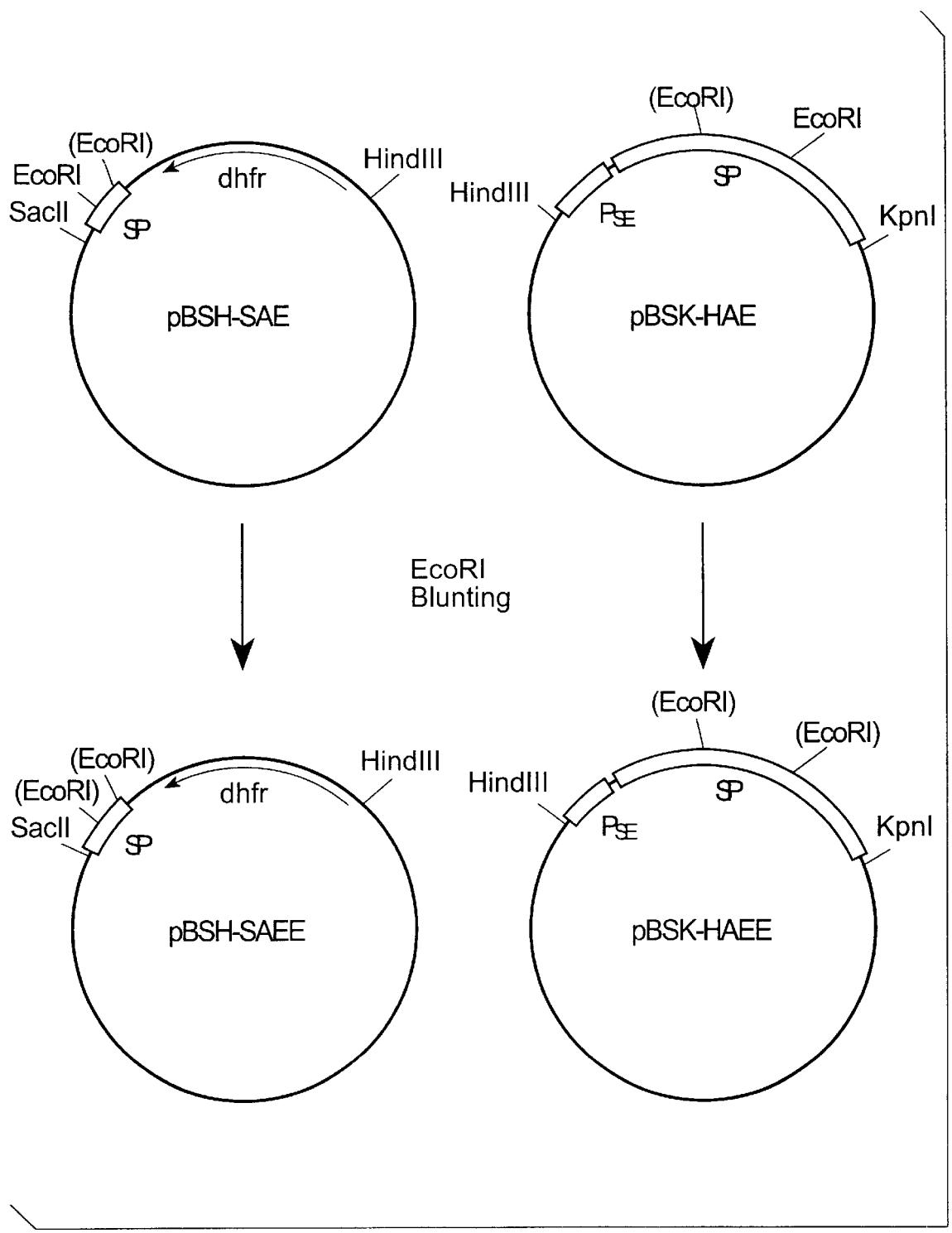
FIG. 21 shows steps for constructing plasmids pBSH-SAE and pBSK-HAEE.

Subsequently, 3 μg each of the thus obtained plasmids pBSH-SAE and pBSK-HAE were added separately to 10 μl of a buffer containing 50 mM Tris-HCl (pH 7.5), 10 mM magnesium chloride, 100 mM sodium chloride and 1 mM DTT, to which 10 units of the restriction enzyme EcoRI (Takara Shuzo) were added and reacted at 37° C. for 1 hour. Both reaction mixtures were ethanol-precipitated and the 5' sticky ends generated by the EcoRI digestion were blunted using DNA Blunting Kit (Takara Shuzo) and the resultant DNA If fragments were ligated using DNA Ligation Kit (Takara Shuzo). Using each of the thus obtained recombinant plasmid DNA solutions, *E. coli* HB101 was transformed to obtain plasmids pBSH-SAEE and pBSK-HAEE shown in FIG. 21. Ten μg each of the thus obtained plasmids were separately reacted according to the recipe attached to AutoRead Sequencing Kit (Pharmacia Biotech) and then electrophoresed with A.L.F. DNA Sequencer (Pharmacia Biotech) to thereby determine the base sequence. As a result, it was confirmed that both the ApaI and EcoRI restriction sites had been eliminated by the above-described modification.

(2) Introduction of a SalI Restriction Site into the Downstream Portion consisting of the Rabbit β-Globin Gene Splicing Signal, Rabbit β-Globin Gene Poly (A) Signal and SV40 Early Gene Poly (A) Signal In order to ensure that expression promoters for the human antibody H and L chains in a humanized antibody expression vector could be replaced with any promoters, a SalI restriction site was transfected into the downstream portion consisting of the rabbit β-globin gene splicing signal, rabbit β-globin gene poly (A) signal and SV40 early gene poly (A) signal of plasmid pSE1UK1SEd1-3 as described below.

Figure 22:
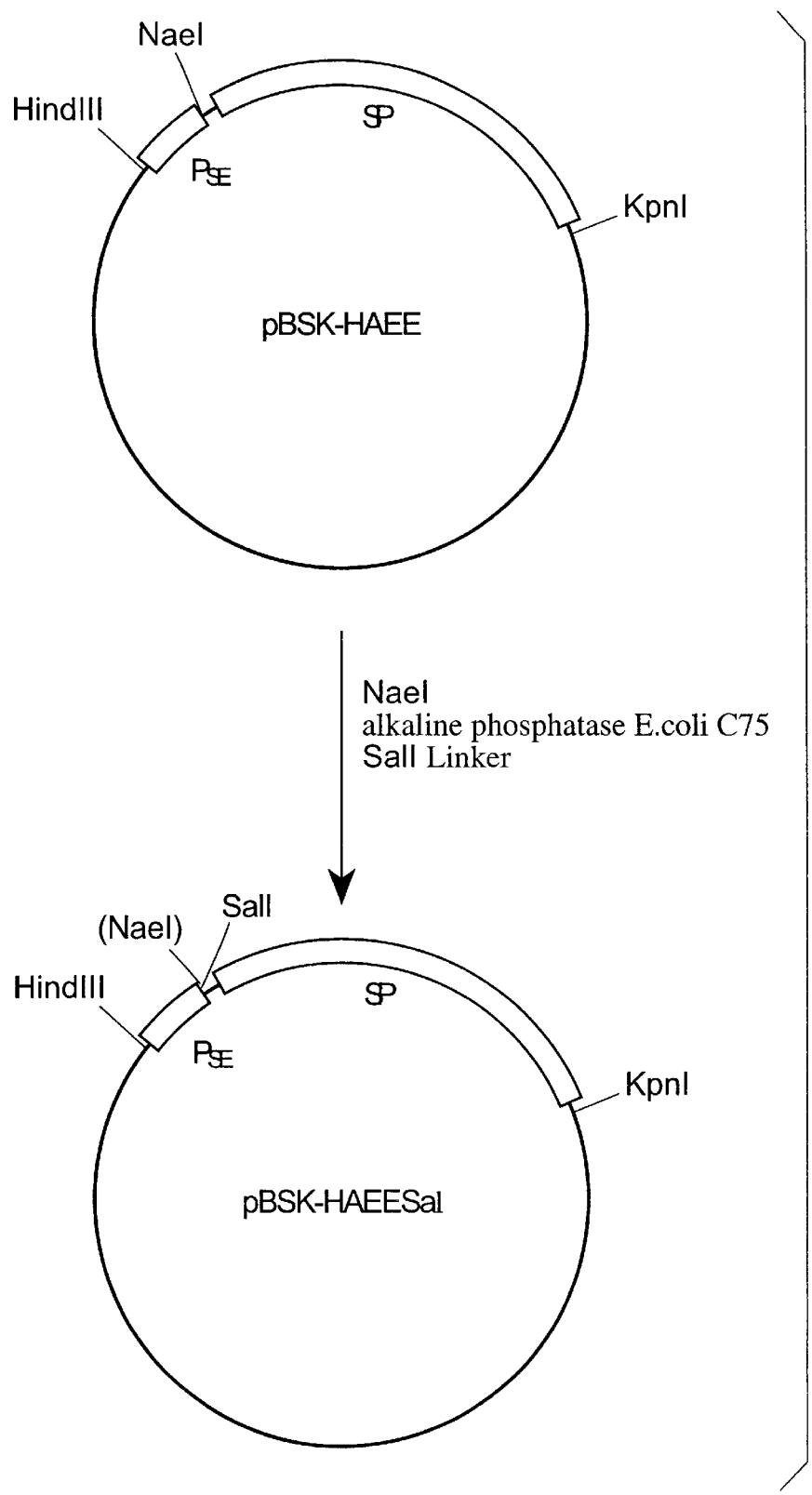
FIG. 22 shows steps for constructing plasmid pSAEad pBSK-HAEEa1.

Briefly, 3 μg of the plasmid pBSK-HAEE obtained in subsection (1) of section 1 of Example 2 were added to 10 μl of a buffer containing 10 mM Tris-HCl (pH 7.5), 10 mM magnesium chloride and 1 mM DTT, to which 10 units of the restriction enzyme NaeI (Takara Shuzo) were added and reacted at 37° C. for 1 hour. The reaction mixture was ethanol-precipitated and the precipitate was dissolved in 20 μl of a buffer containing 50 mM Tris-HCl (pH 9.0) and 1 mM magnesium chloride, to which 1 unit of alkaline phosphatase (*E. coli* C75, Takara Shuzo) was added and reacted at 37° C. for 1 hour to dephosphorylate 5' ends. Then, the reaction mixture was subjected to phenol-chloroform extraction, followed by ethanol precipitation. The precipitate was dissolved in 20 μl of a buffer containing 10 mM Tris-HCl (pH 8.0) and 1 mM ethylenediamine-tetraacetic acid disodium (hereinafter referred to as "TE buffer"). One μl of the mixture and 0.1 μg of a phosphorylated SalI linker (Takara Shuzo) were added to sterilized water to give a total volume of 20 μl, and ligated using Ready-To-Go T4 DNA Ligase (Pharmacia Biotech). Using the thus obtained recombinant plasmid DNA solution, *E. coli* HB101 was transformed to obtain plasmids pBSK-HAEESal shown in FIG. 22. Ten μg each of the thus obtained plasmid were reacted according to the recipe attached to AutoRead Sequencing Kit (Pharmacia Biotech) and then electrophoresed with A.L.F. DNA Sequencer (Pharmacia Biotech) to thereby determine the base sequence. As a result, it was confirmed that one SalI restriction site had been transfected into the downstream portion consisting of the rabbit β-globin gene splicing signal, rabbit β-globin gene poly (A) signal and SV40 early gene poly (A) signal.

(3) Modification of the ApaI Restriction Site present in the Poly (A) Signal of Herpes Simplex Virus Thymidine Kinase (hereinafter referred to as "HSVtk") Gene The modification of the ApaI restriction site present in the poly (A) signal of HSVtk gene located downstream of Tn5 kanamycin phosphotransferase gene in plasmid pSE1UK1SEd1-3 was performed as described below.

Briefly, 3 μg of the plasmid pBSA obtained in subsection (1) of section 1 of Example 2 were added to 10 μl of a buffer containing 10 mM Tris-HCl (pH 7.5), 10 mM magnesium chloride and 1 mM DTT, to which 10 units of the restriction enzyme SacII (Toyobo) were added and reacted at 37° C. for 1 hour. The reaction mixture was ethanol-precipitated and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. The reaction mixture was subjected to agarose gel electrophoresis and about 1 μg of an approx. 2.96 kb SacII-XhoI fragment was recovered.

Subsequently, 5 μg of plasmid pSE1UK1SEd1-3 were added to 10 μl of a buffer containing 10 mM Tris-HCl (pH 7.5), 10 mM magnesium chloride and 1 mM DTT, to which 10 units of the restriction enzyme SacII (Toyobo) were added and reacted at 37° C. for 1 hour. The reaction mixture was ethanol-precipitated and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. The reaction mixture was subjected to agarose gel electrophoresis and about 1 μg of an approx. 4.25 kb SacII-XhoI fragment was recovered.

Figure 23:
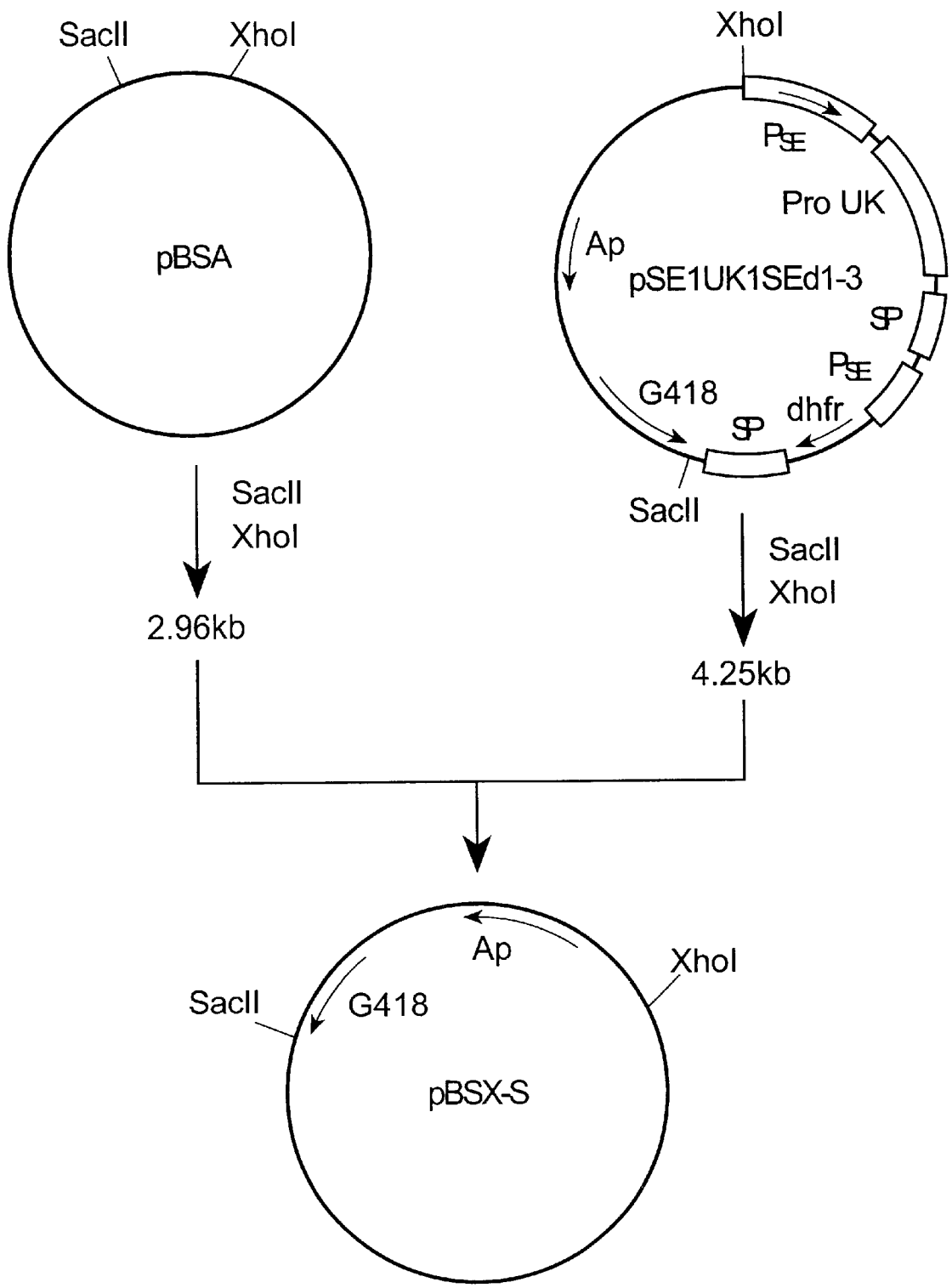
FIG. 23 shows steps for constructing plasmid pBSX-S.

Subsequently, 0.1 μg of the SacII-XhoI fragment from pBSA and the SacII-XhoI fragment from plasmid PSE1UK1SEd1-3 as obtained above were added to sterilized water to give a total volume of 20 μl, and then ligated using Ready-To-Go T4 DNA Ligase (Pharmacia Biotech). Using the thus obtained recombinant plasmid DNA solution, *E. coli* HB101 was transformed to obtain plasmid pBSX-S shown in FIG. 23.

Figure 24:
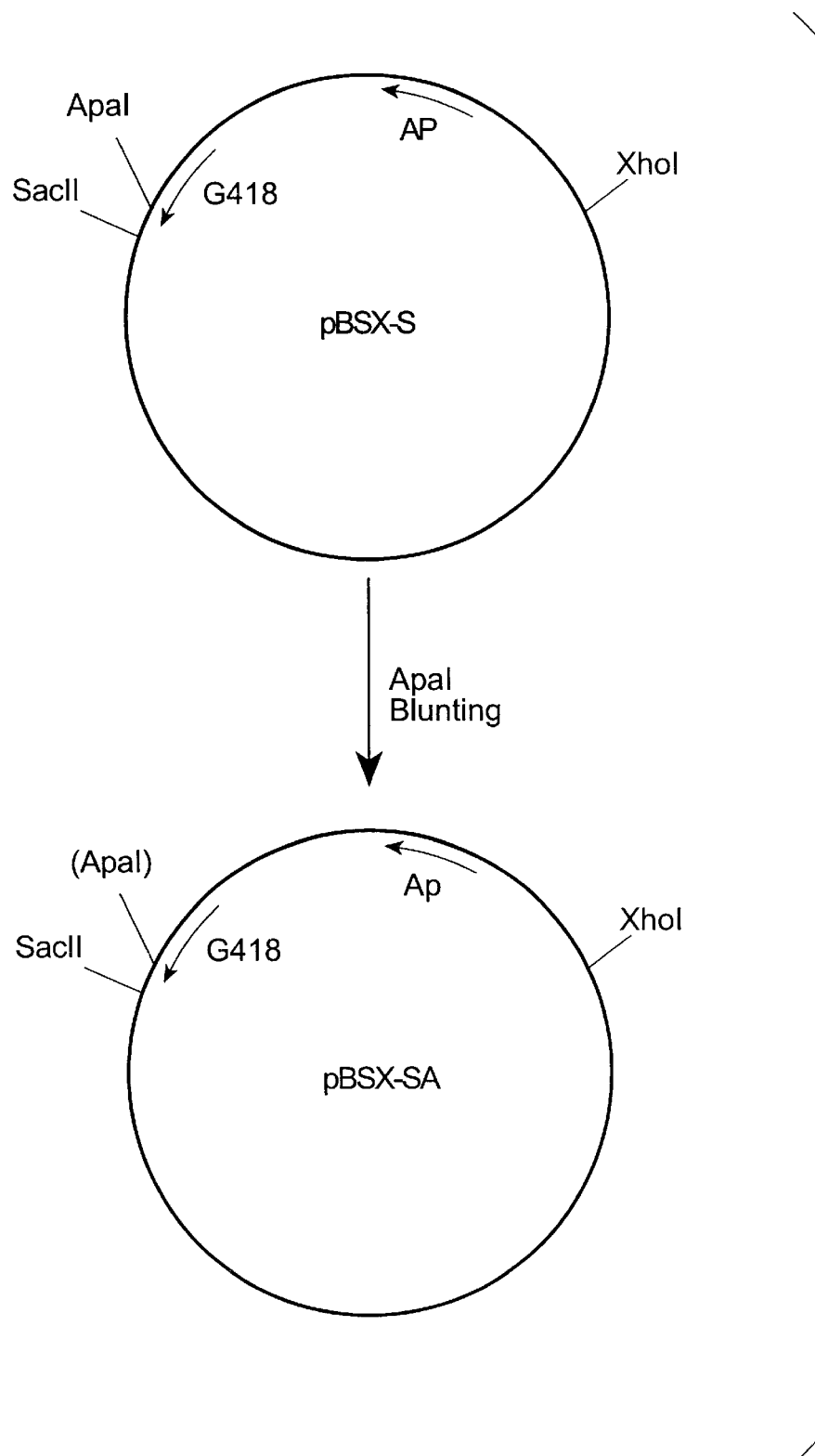
FIG. 24 shows steps for constructing plasmid pBSX-SA.

Subsequently, 3 μg of the thus obtained plasmid pBSX-X were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the 3' sticky ends generated by the ApaI digestion were blunted using DNA Blunting Kit (Takara Shuzo) and the resultant DNA fragments were ligated using DNA Ligation Kit (Takara Shuzo). Using the thus obtained recombinant plasmid DNA solution, *E. coli* HB101 was transformed to obtain plasmid pBSX-SA shown in FIG. 24. Ten μg of the thus obtained plasmid were reacted according to the recipe attached to AutoRead Sequencing Kit (Pharmacia Biotech) and then electrophoresed with A.L.F. DNA Sequencer (Pharmacia Biotech) to thereby determine the base sequence. As a result, it was confirmed that the ApaI restriction site of the HSVtk gene poly (A) signal had been eliminated.

(4) Construction of a Humanized Antibody L Chain Expression Unit

Plasmid mMohCκ having a humanized antibody L chain expression unit in which a cDNA coding for the constant region of human κ-type L-chain (Cκ) was located downstream of the promoter/enhancer of the terminal repeated sequence of Moloney mouse leukemia virus and into which a cDNA coding for VL of a human chimeric antibody or human CDR-grafted antibody could be inserted in a cassette was constructed as described below.

Figure 25:
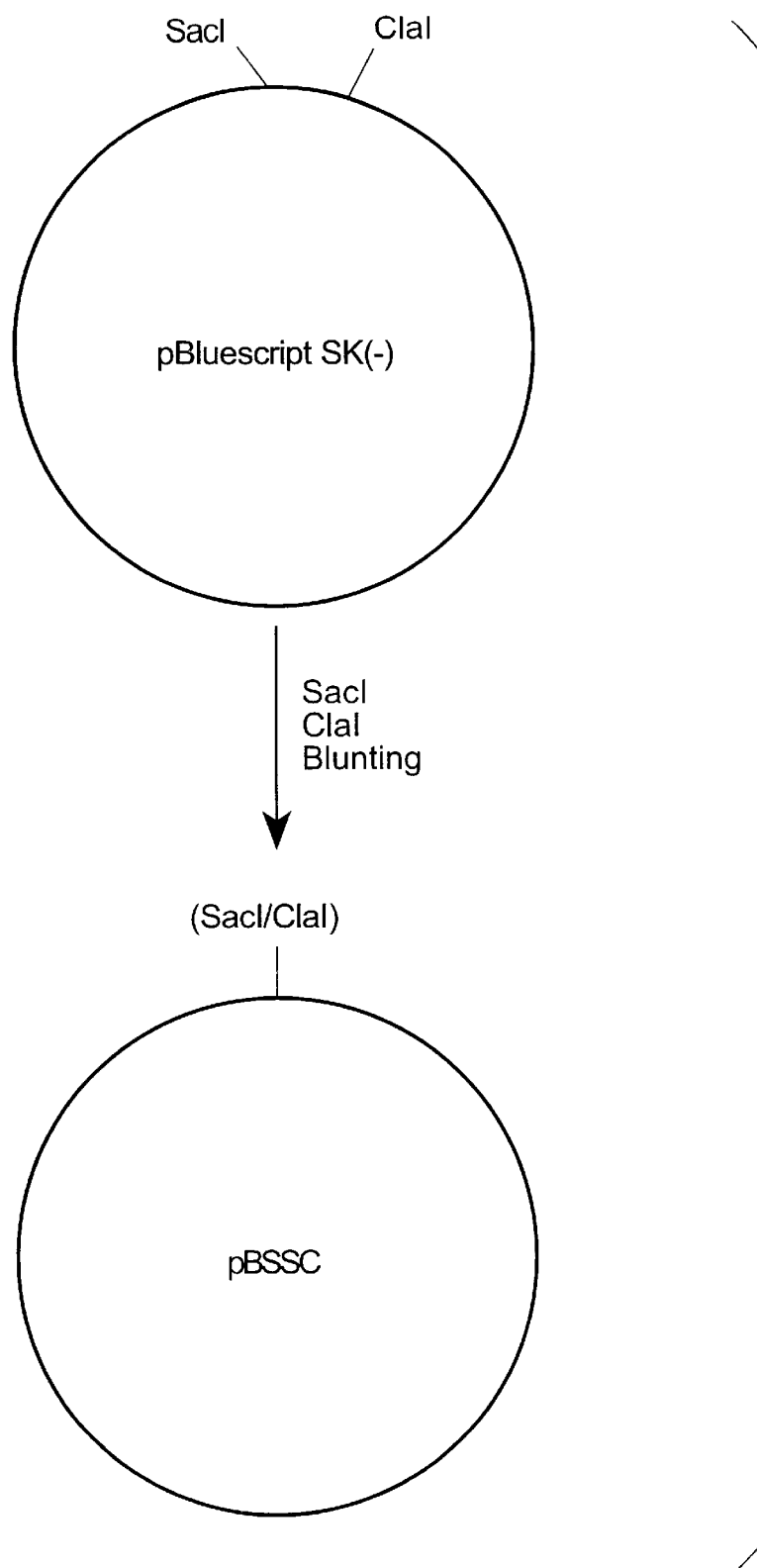
FIG. 25 shows steps for constructing plasmid pBSSC.

Briefly, 3 μg of plasmid pBluescript SK(−) (Stratagene) were added to 10 μl of a buffer containing 10 mM Tris-HCl (pH 7.5), 10 mM magnesium chloride and 1 mM DTT, to which 10 units of the restriction enzyme SacI (Takara Shuzo) were added and reacted at 37° C. for 1 hour. The reaction mixture was ethanol-precipitated, and the precipitate was added to 10 μl of a buffer containing 10 mM Tris-HCl (pH 7.5), 50 mM sodium chloride, 10 mM magnesium chloride and 1 mM DTT, to which 10 units of the restriction enzyme ClaI (Takara Shuzo) were added and reacted at 37° C. for 1 hour. The reaction mixture was ethanol-precipitated, and the sticky ends generated by the SacI and ClaI digestions were blunted using DNA Blunting Kit (Takara Shuzo). Then, the reaction mixture was subjected to agarose gel electrophoresis to thereby recover about 1 μg of an approx. 2.96 kb DNA fragment. Then, 0.1 μg of the recovered DNA fragment was added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pBSSC shown in FIG. 25.

Subsequently, 3 μg of the thus obtained plasmid pBSSC were added to 10 μl of a buffer containing 10 mM Tris-HCl (pH 7.5), 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. Then, the reaction mixture was subjected to agarose gel electrophoresis to thereby recover about 1 μg of an approx. 2.96 kb KpnI-XhoI fragment.

Subsequently, 5 μg of the plasmid pAGE147 disclosed in Kokai No. 205694/94 were added to 10 μl of a buffer containing 10 mM Tris-HCl (pH 7.5), 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. Then, the reaction mixture was subjected to agarose gel electrophoresis to thereby recover about 0.3 μg of an approx. 0.66 kb KpnI-XhoI fragment containing the promoter/enhancer of the terminal repeated sequence of Moloney mouse leukemia virus.

Figure 26:
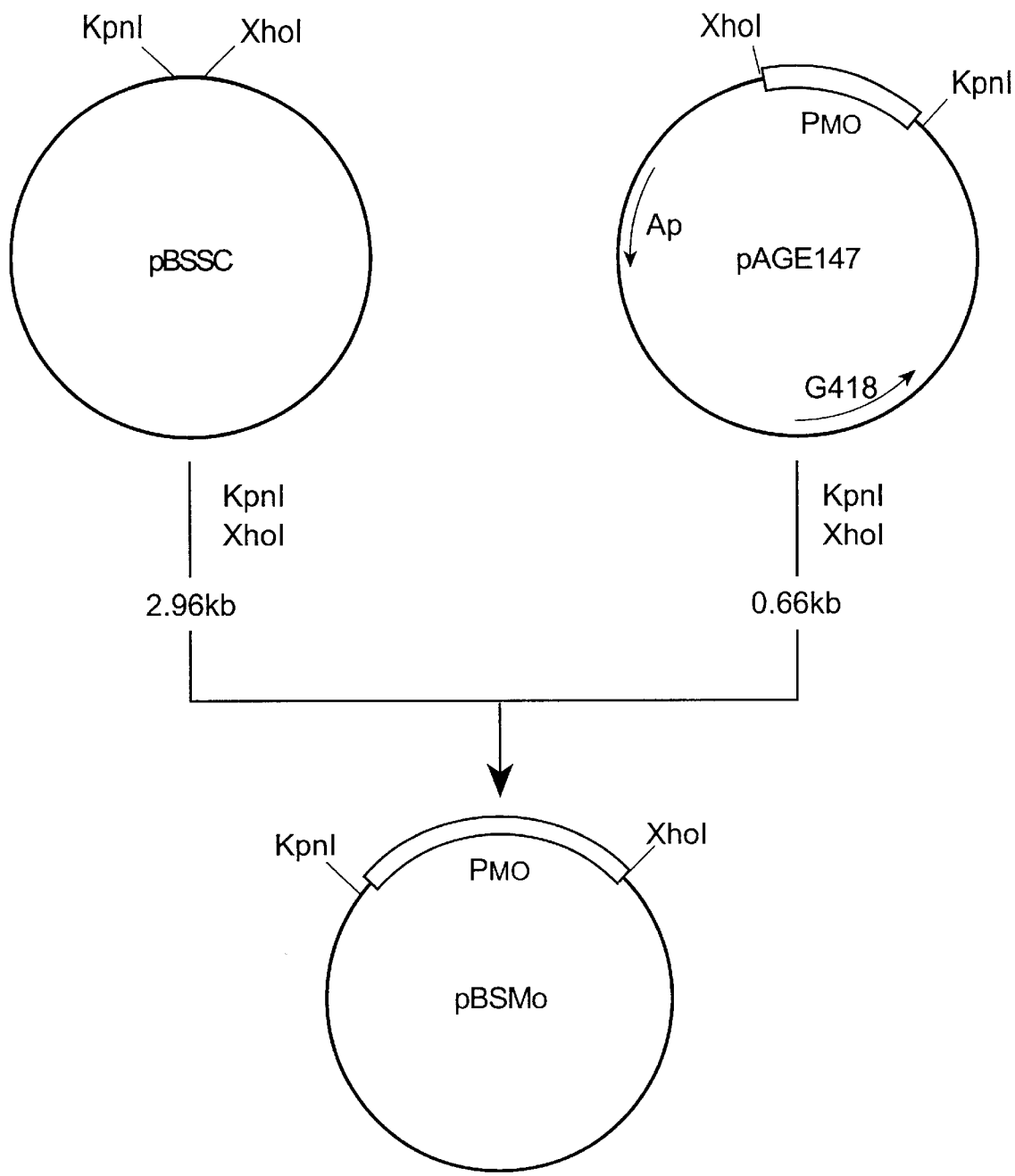
FIG. 26 shows steps for constructing plasmid pBSMo.

Subsequently, 0.1 μg of the KpnI-XhoI fragment from pBSSC and 0.1 μg of the KpnI-XhoI fragment from pAGE147 as obtained above were dissolved in sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pBSMo shown in FIG. 26.

Subsequently, 3 μg of the plasmid pBSMo obtained above were added to 10 μl of a buffer containing 10 mM Tris-HCl (pH 7.5), 10 mM magnesium chloride and 1 mM DTT, to which 10 units of the restriction enzyme KpnI (Takara Shuzo) were added further and reacted at 37° C. for 1 hour. The reaction mixture was ethanol-precipitated, and the precipitate was dissolved in 10 μl of a buffer containing 10 mM Tris-HCl (pH 7.5), 50 mM sodium chloride, 10 mM magnesium chloride and 1 mM DTT, to which 10 units of the restriction enzyme HindIII (Takara Shuzo) were added further and reacted at 37° C. for 1 hour. Then, the reaction mixture was subjected to agarose gel electrophoresis to thereby recover about 1 μg of an approx. 3.62 kb KpnI-HindIII fragment.

Figure 27:
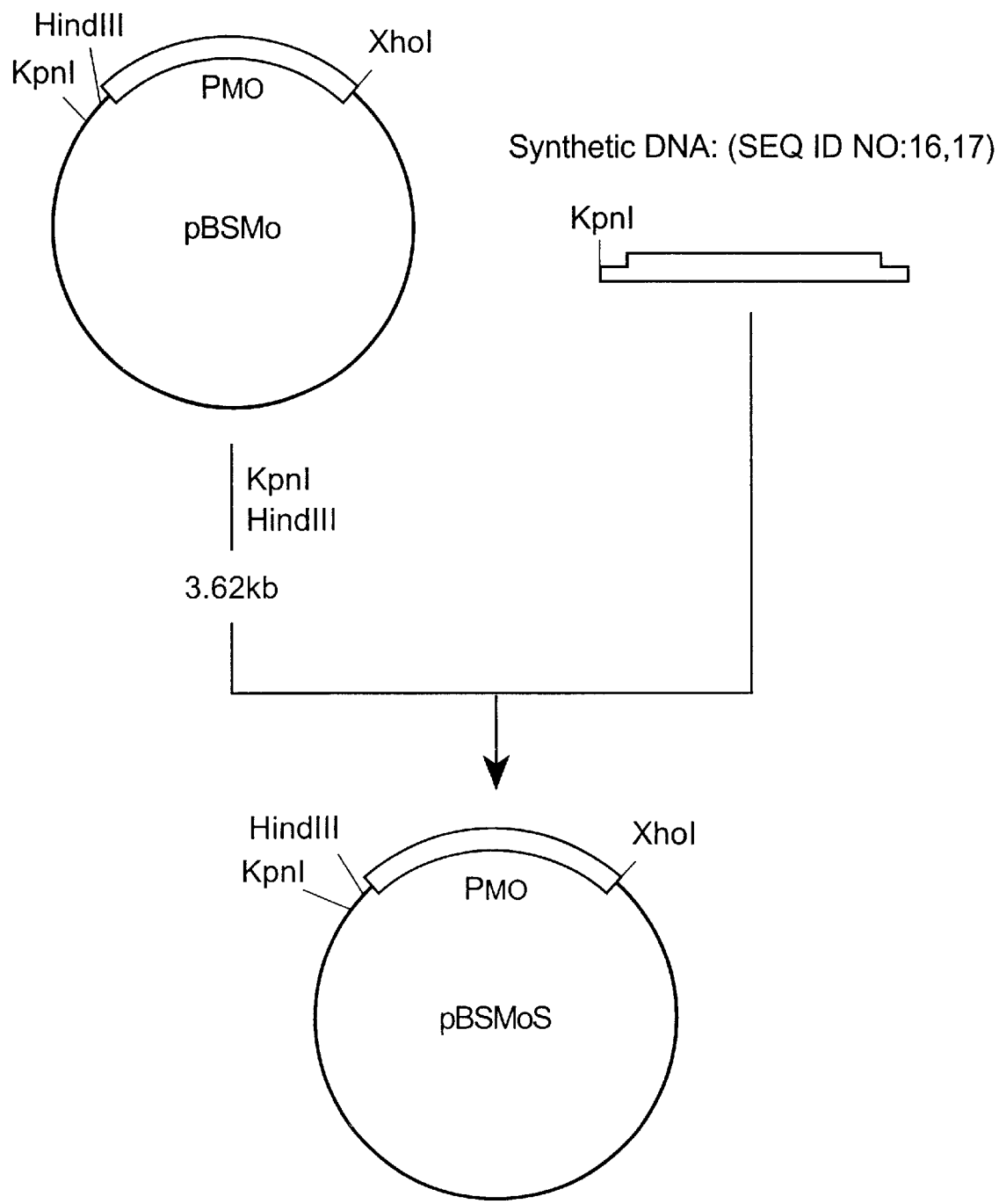
FIG. 27 shows steps for constructing plasmid pBSMoS.

Subsequently, two synthetic DNAs having the base sequences shown in SEQ ID NOS: 16 and 17, respectively, were synthesized using an automatic DNA synthesizer (380A, Applied Biosystems). Then, 0.3 μg each of the synthetic DNAs obtained were added to 15 μl of sterilized water and heated at 65° C. for 5 minutes. The reaction mixture was left at room temperature for 30 minutes. To this mixture, 2 μl of a 10× buffer [500 mM Tris-HCl (pH 7.6), 100 mM magnesium chloride, 50 mM DTT] and 2 μl of 10 mM ATP were added. Further, 10 units of T4 polynucleotide kinase (Takara Shuzo) were added and reacted at 37° C. for 30 minutes to phosphorylate the 5' ends. Then, 0.1 μg of the KpnI-HindIII fragment (3.66 kb) from plasmid pBSMo as obtained above and 0.05 μg of the phosphorylated synthetic DNAs were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pBSMoS shown in FIG. 27. Ten μg of the thus obtained plasmid were reacted according to the recipe attached to Auto-Read Sequencing Kit (Pharmacia Biotech) and then electrophoresed with A.L.F. DNA Sequencer (Pharmacia Biotech) to thereby determine the base sequence. As a result, it was confirmed that the synthetic DNAs of interest had been transfected.

Figure 28:
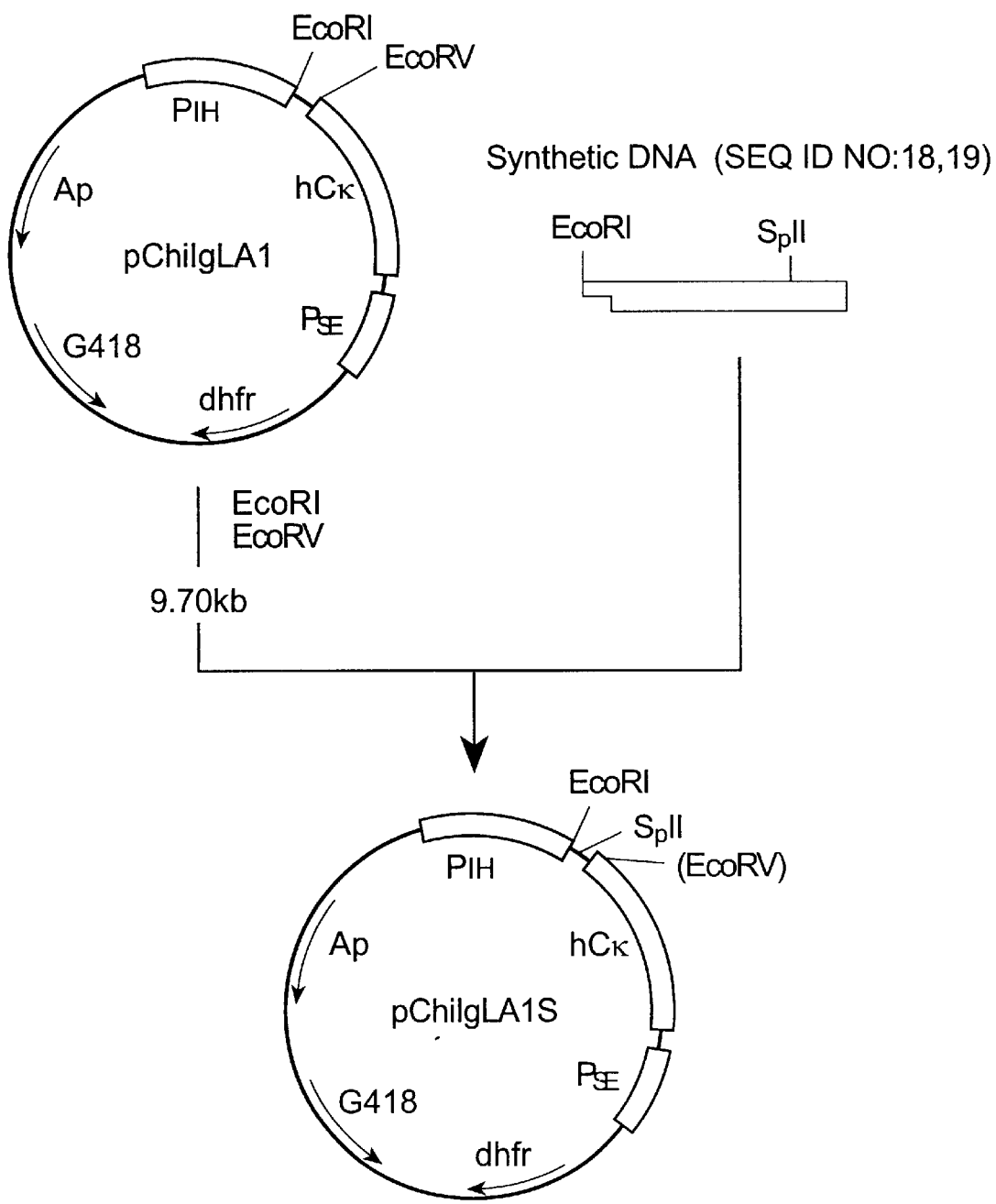
FIG. 28 shows steps for constructing plasmid pChiIgLA1S.

Subsequently, 3 μg of the plasmid pChiIgLA1 disclosed in Kokai No. 304989/93 were dissolved in 10 μl of a buffer containing 50 mM Tris-HCl (pH 7.5), 100 mM sodium chloride, 10 mM magnesium chloride and 1 mM DTT, to which 10 units each of the restriction enzymes EcoRI (Takara Shuzo) and RcoRV (Takara Shuzo) were added and reacted at 37° C. for 1 hour. The reaction mixture was subjected to agarose gel electrophoresis to thereby recover about 1 μg of an approx. 9.70 kb EcoRI-EcoRV fragment. Subsequently, two synthetic DNAs having the base sequences shown in SEQ ID NOS: 18 and 19, respectively, were synthesized using an automatic DNA synthesizer (380A, Applied Biosystems). Then, 0.3 μg each of the obtained synthetic DNAs were added to 15 μl of sterilized water and heated at 65° C. for 5 minutes. The reaction mixture was left at room temperature for 30 minutes. To this solution, 2 μl of a 10× buffer [500 mM Tris-HCl (pH 7.6), 100 mM magnesium chloride, 50 mM DTT] and 2 μl of 10 mM ATP were added. Further, 10 units of T4 polynucleotide kinase (Takara Shuzo) were added and reacted at 37° C. for 30 minutes to phosphorylate the 5' ends. Then, 0.1 μg of the EcoRI-EcoRV fragment (9.70 kb) from plasmid pChiIgLA1 as obtained above and 0.05 μg of the phosphorylated synthetic DNAs were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pChiIgLA1S shown in FIG. 28.

Subsequently, 3 μg of the plasmid pBSMoS as obtained above were dissolved in 10 μl of a buffer containing 20 mM Tris-HCl (pH 8.5), 100 mM potassium chloride, 10 mM magnesium chloride and 1 mM DTT, to which 10 units of the restriction enzyme HpaI (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme EcoRI (Takara Shuzo) were added and reacted at 37° C. for 1 hour. Then, the reaction mixture was subjected to agarose gel electrophoresis to recover about 1 μg of an approx. 3.66 kb HpaI-EcoRI fragment.

Subsequently, 10 μg of the plasmid pChiIgLA1S as obtained above were dissolved in 10 μl of a buffer containing 20 mM Tris-HCl (pH 7.9), 50 mM potassium acetate, 10 mM magnesium acetate, 1 mM DTT and 100 μg/ml BSA, to which 10 units of the restriction enzyme NlaIV (New England Biolabs) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme EcoRI (Takara Shuzo) were added and reacted at 37° C. for 1 hour. Then, the reaction mixture was subjected to agarose gel electrophoresis to recover about 0.3 μg of an approx. 0.41 kb NlaIV-EcoRI fragment.

Figure 29:
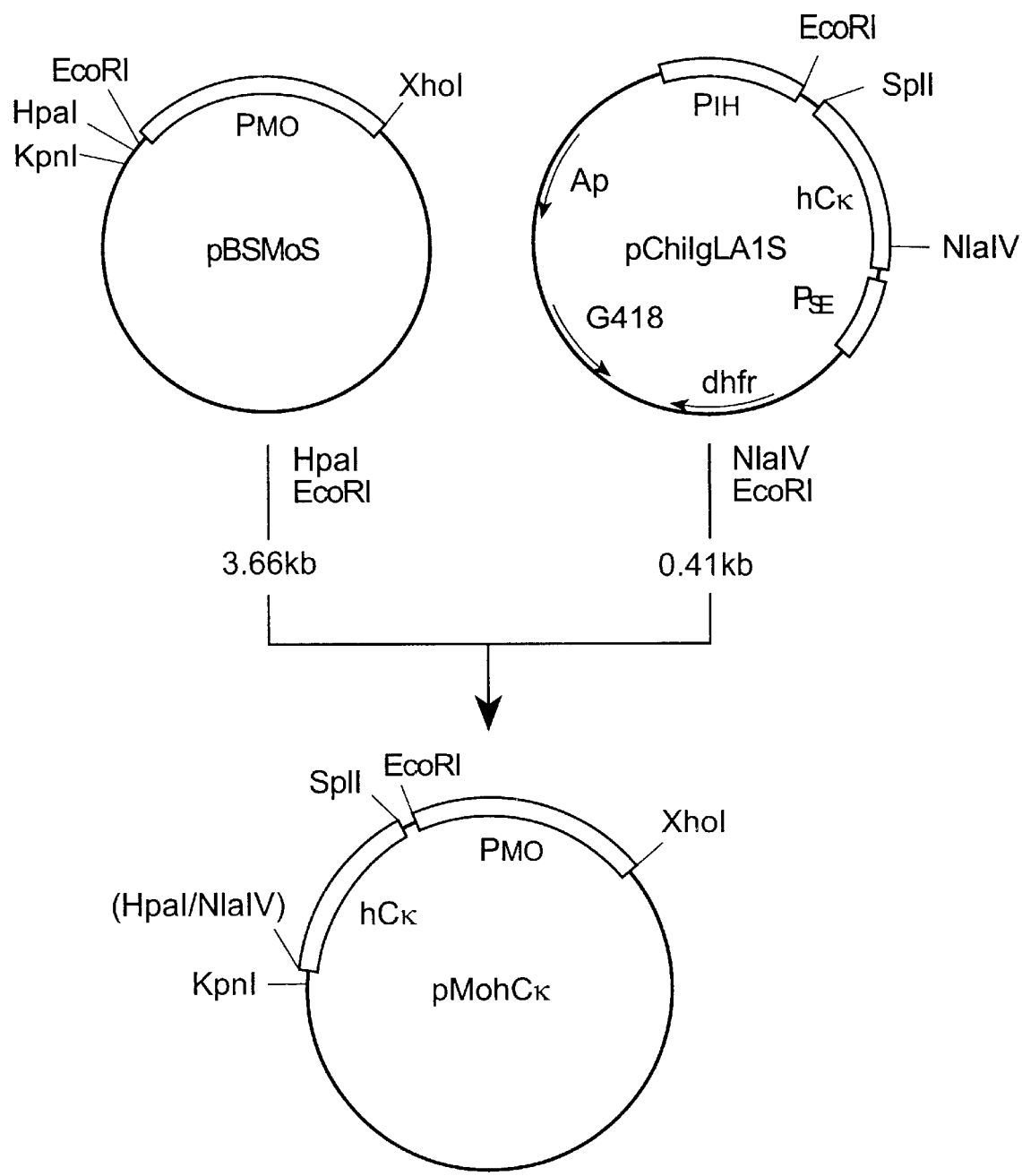
FIG. 29 shows steps for constructing plasmid pMohCκ.

Subsequently, 0.1 μg each of the HpaI-EcoRI fragment from pBSMoS and the NlaIV-EcoRI fragment from pChiIgLA1S as obtained above were added to sterilized water to give a total volume of 20 μl and ligated using Ready-To-Go T4 DNA Ligase (Pharmacia Biotech). Using the thus obtained recombinant plasmid DNA solution, *E. coli* HB101 was transformed to obtain plasmid pMohCκ shown in FIG. 29.

(5) Construction of a Humanized Antibody H Chain Expression Unit

Plasmid mMohCγ1 having a humanized antibody H chain expression unit in which a cDNA coding for the constant region of human IgG1 type H-chain (Cγ1) was located downstream of the promoter/enhancer of the terminal repeated sequence of Moloney mouse leukemia virus and into which a cDNA coding for VH of a human chimeric antibody or human CDR-grafted antibody could be inserted in a cassette was constructed as described below.

Figure 30:
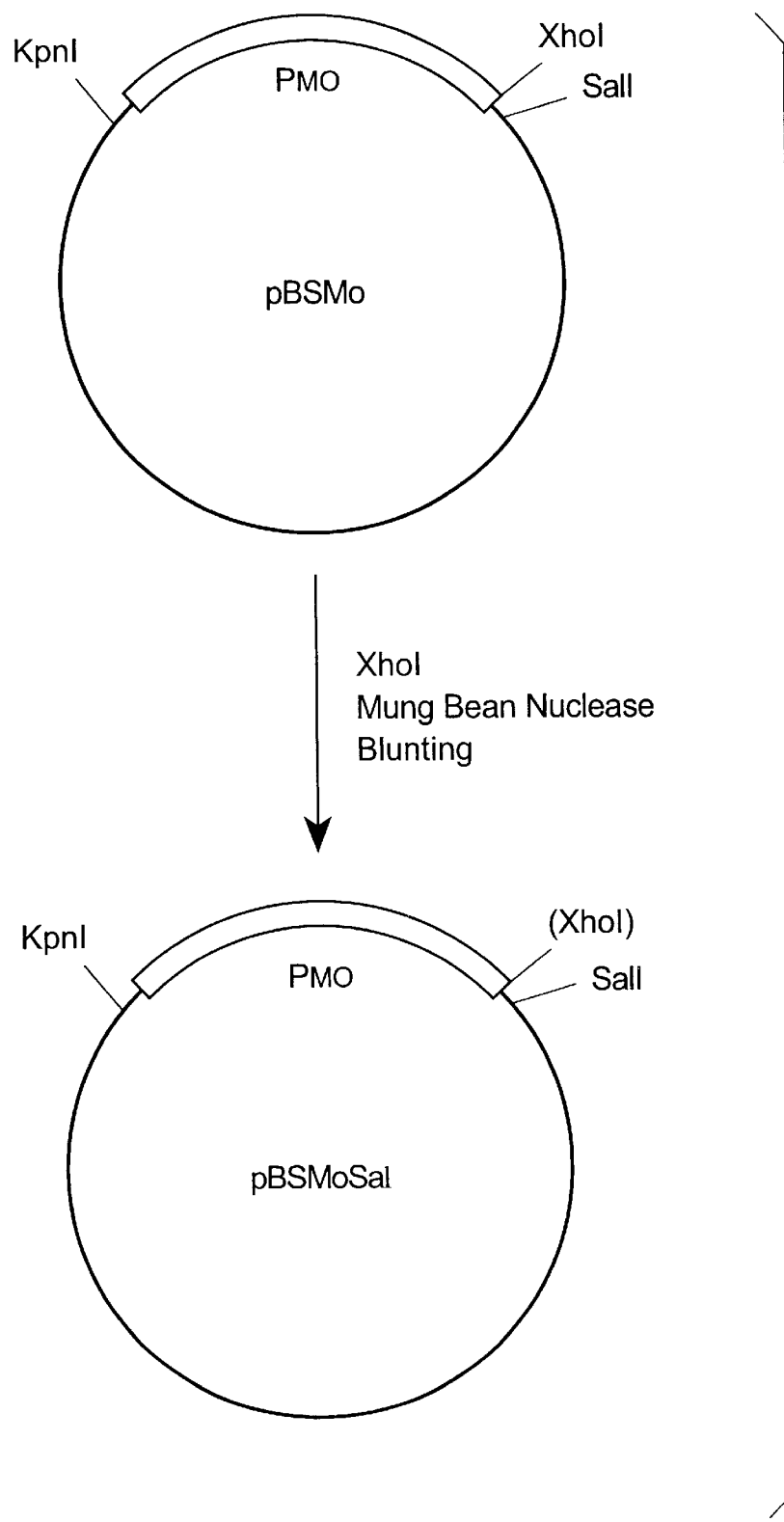
FIG. 30 shows steps for constructing plasmid pBSMoSa1.

Briefly, 3 μg of the plasmid pBSMo obtained in subsection (4) of section 1 of Example 2 were added to 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. The reaction mixture was ethanol-precipitated, and the precipitate was dissolved in 10 μl of a buffer containing 30 mM sodium acetate (pH 5.0), 100 mM sodium chloride, 1 mM zinc acetate and 10% glycerol, to which 10 units of mung bean nuclease (Takara Shuzo) were added and reacted at 37° C. for 10 minutes. The reaction mixture was subjected to phenol-chloroform extraction, followed by ethanol precipitation. Then, the sticky ends were blunted using DNA Blunting Kit (Takara Shuzo) and the resultant DNA fragments were ligated using DNA Ligation Kit (Takara Shuzo). Using the thus obtained recombinant plasmid DNA solution, *E. coli* HB101 was transformed to obtain plasmid pBSMoSal shown in FIG. 30. Ten μg of the thus obtained plasmid was reacted according to the recipe attached to AutoRead Sequencing Kit (Pharmacia Biotech) and then electrophoresed with A.L.F. DNA Sequencer (Pharmacia Biotech) to thereby determine the base sequence. As a result, it was confirmed that the XhoI restriction site located upstream of the promoter/enhancer of the terminal repeated sequence of Moloney mouse leukemia virus had been eliminated.

Figure 31:
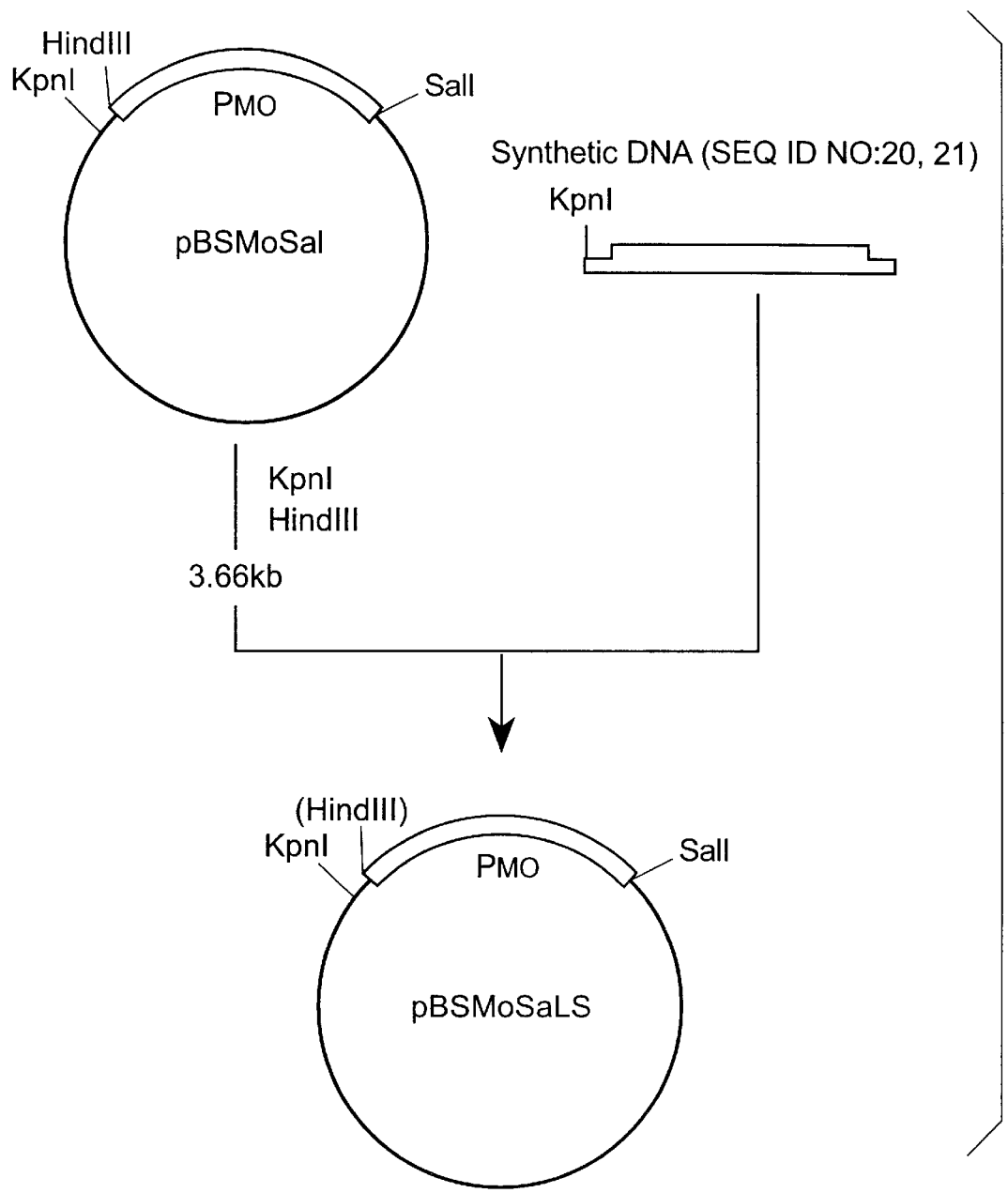
FIG. 31 shows steps for constructing plasmid pBSMoSa1S.

Subsequently, 3 μg of the plasmid pBSMosal as obtained above were added to 10 μl of a buffer containing 10 mM Tris-HCl (pH 7.5), 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 10 mM Tris-HCl (pH 7.5), 50 mM sodium chloride, 10 mM magnesium chloride and 1 mM DTT, to which 10 units of the restriction enzyme HindIII (Takara Shuzo) were added and reacted at 37° C. for 1 hour. Then, the reaction mixture was subjected to agarose gel electrophoresis to thereby recover about 1 μg of an approx. 3.66 kb KpnI-HindIII fragment. Subsequently, two synthetic DNAs having the base sequences shown in SEQ ID NOS: 20 and 21, respectively, were synthesized using an automatic DNA synthesizer (380A, Applied Biosystems). Then, 0.3 μg each of the obtained synthetic DNAs were added to 15 μl of sterilized water and heated at 65° C. for 5 minutes. The reaction mixture was left at room temperature for 30 minutes. To this solution, 2 μl of a 10× buffer [500 mM Tris-HCl (pH 7.6), 100 mM magnesium chloride, 50 mM DTT] and 2 μl of 10 mM ATP were added. Further, 10 units of T4 polynucleotide kinase (Takara Shuzo) were added and reacted at 37° C. for 30 minutes to phosphorylate the 5' ends. Then, 0.1 μg of the KpnI-HindIII fragment (3.66 kb) from plasmid pBSMoSal as obtained above and 0.05 μg of the phosphorylated synthetic DNAs were added to sterilized water to give a total volume of 20 μl and ligated using Ready-To-Go T4 DNA Ligase (Pharmacia Biotech). Using the thus obtained recombinant plasmid DNA solution, *E. coli* HB101 was transformed to obtain plasmid pBSMoSalS shown in FIG. 31. Ten μg of the thus obtained plasmid were reacted according to the recipe attached to AutoRead Sequencing Kit (Pharmacia Biotech) and then electrophoresed with A.L.F. DNA Sequencer (Pharmacia Biotech) to thereby determine the base sequence. As a result, it was confirmed that the synthetic DNAs of interest had been transfected.

Subsequently, 10 μg of the plasmid pChiIgHB2 disclosed in Kokai No. 304989/93 were dissolved in 10 μl of a buffer containing 50 mM Tris-HCl (pH 7.5), 100 mM sodium chloride, 10 mM magnesium chloride and 1 mM DTT, to which 10 units of the restriction enzyme Eco52I (Toyobo) were added and reacted at 37° C. for 1 hour. The reaction mixture was ethanol-precipitated, and the precipitate was dissolved in 10 μl of a buffer containing 30 mM sodium acetate (pH 5.0), 100 mM sodium chloride, 1 mM zinc acetate and 10% glycerol, to which 10 units of mung bean nuclease (Takara Shuzo) were added and reacted at 37° C. for 10 minutes. The reaction mixture was subjected to phenol-chloroform extraction, followed by ethanol precipitation. Then, the sticky ends were blunted using DNA Blunting Kit (Takara Shuzo). After ethanol precipitation, the precipitate was dissolved in 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was subjected to agarose gel electrophoresis to thereby recover about 0.7 μg of an approx. 0.99 kb ApaI-blunt end fragment.

Subsequently, 3 μg of plasmid pBluescript SK(−) (Stratagene) were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the precipitate was added to 10 μl of a buffer containing 33 mM Tris-HCl (pH 7.9), 10 mM magnesium acetate, 66 mM potassium acetate, 0.5 mM DTT and 10 μg/ml BSA, to which 10 units of the restriction enzyme SmaI (Takara Shuzo) were added and reacted at 30° C. for 1 hour. The reaction mixture was subjected to agarose gel electrophoresis to thereby recover about 1 μg of an approx. 3.0 kb ApaI-SmaI fragment.

Figure 32:
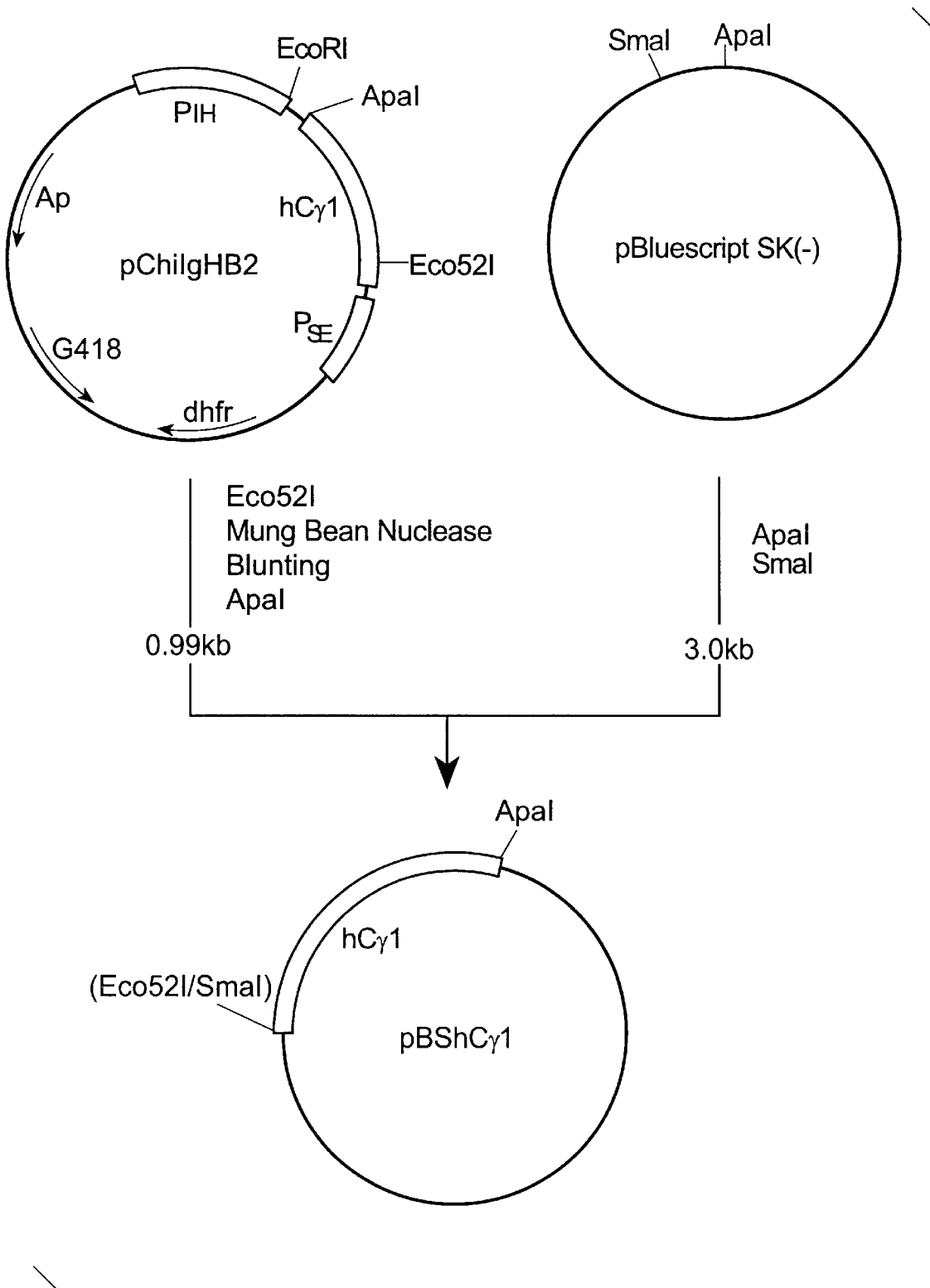
FIG. 32 shows steps for constructing plasmid pBShCγ1.

Subsequently, 0.1 μg of the ApaI-blunt end fragment from plasmid pChiIgHB2 as obtained above and 0.1 μg of the ApaI-SmaI fragment from pBluescript SK(-) were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pBShCγ1 shown in FIG. 32.

Subsequently, 5 μg of the plasmid pBShCγ1 as obtained above were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the precipitate was dissolved in 10 μl of a buffer containing 10 mM Tris-HCl (pH 7.5), 50 mM sodium chloride, 10 mM magnesium chloride and 1 mM DTT, to which 10 units of the restriction enzyme SpeI (Takara Shuzo) were added and reacted at 37° C. for 1 hour. Then, the reaction mixture was subjected to agarose gel electrophoresis to thereby recover about 1 μg of an approx. 1.0 kb ApaI-SpeI fragment.

Subsequently, 3 μg of the plasmid pBSMoSalS as obtained above were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the precipitate was dissolved in 10 μl of a buffer containing 10 mM Tris-HCl (pH 7.5), 50 mM sodium chloride, 10 mM magnesium chloride and 1 mM DTT, to which 10 units of the restriction enzyme SpeI (Takara Shuzo) were added and reacted at 37° C. for 1 hour. Then, the reaction mixture was subjected to agarose gel electrophoresis to thereby recover about 1 μg of an approx. 3.66 kb ApaI-SpeI fragment.

Figure 33:
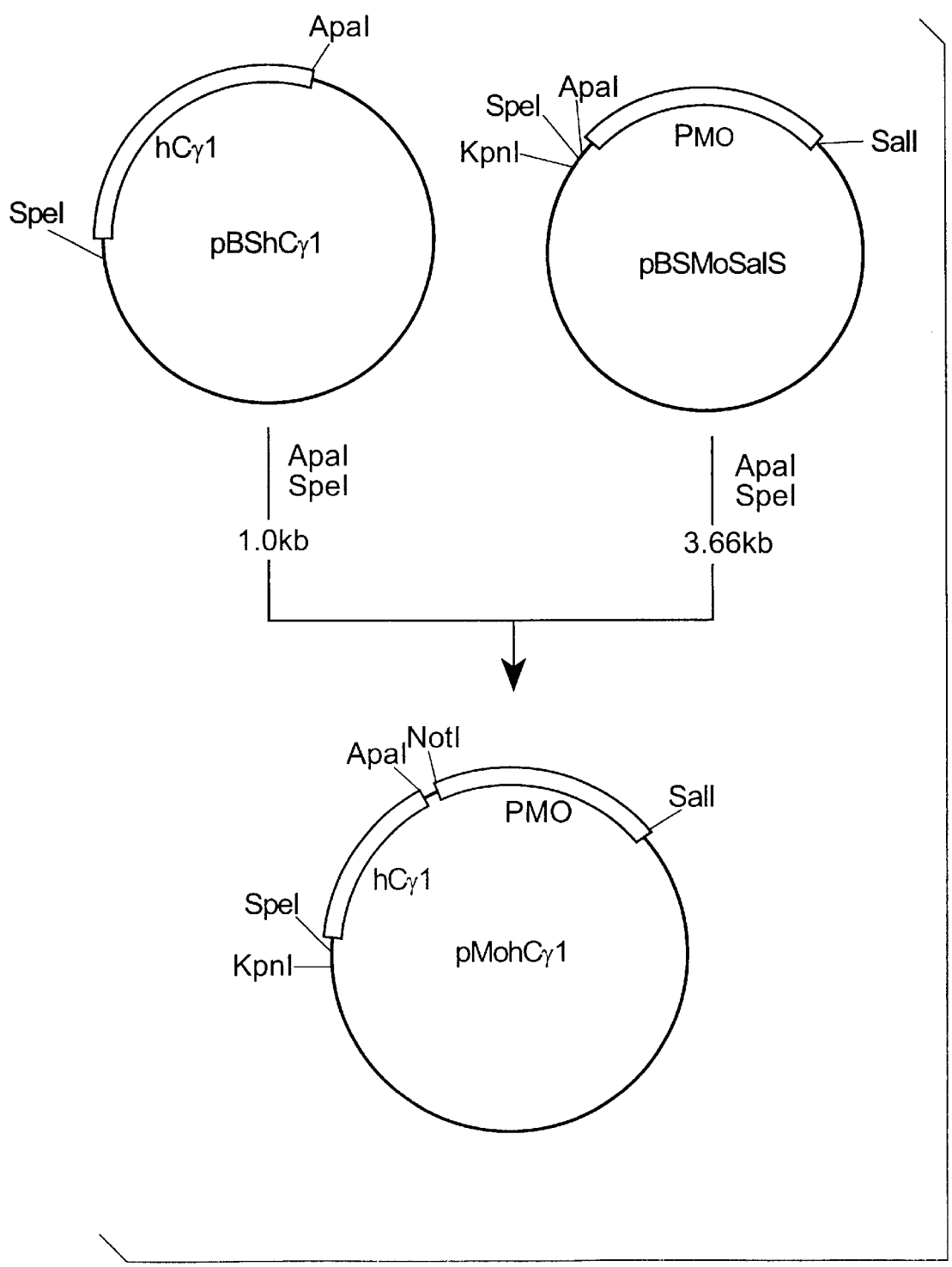
FIG. 33 shows steps for constructing plasmid pMohCγ1.

Subsequently, 0.1 μg each of the ApaI-SpeI fragment from pBShCγ1 and the ApaI-SpeI fragment from pBSMoSalS as obtained above were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pMohCγ1 shown in FIG. 33.

(6) Construction of Tandem Cassette-Type Humanized Antibody Expression Vector pKANTEX93

A tandem cassette-type humanized antibody expression vector, pKANTEX93, was constructed as follows using the various plasmids obtained in subsections (1)–(5) of section 1 of Example 2.

Briefly, 3 μg of the plasmid pBSH-SAEE obtained in subsection (1) of section 1 of Example 2 were added to 10 μl of a buffer containing 10 mM Tris-HCl (pH 7.5), 50 mM sodium chloride, 10 mM magnesium chloride and 1 mM DTT, to which 10 units of the restriction enzyme HindIII (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme SalI (Takara Shuzo) were added and reacted at 37° C. for 1 hour. Then, the reaction mixture was subjected to agarose gel electrophoresis to thereby recover about 1 μg of an approx. 5.42 kb HindIII-SalI fragment.

Subsequently, 5 μg of the plasmid pBSK-HAEE obtained in subsection (1) of section 1 of Example 2 were added to 10 μl of a buffer containing 10 mM Tris-HCl (pH 7.5), 50 mM sodium chloride, 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 10 mM Tris-HCl (pH 7.5), 50 mM sodium chloride, 10 mM magnesium chloride and 1 mM DTT, to which 10 units of the restriction enzyme HindIII (Takara Shuzo) were added and reacted at 37° C. for 1 hour. Then, the reaction mixture was subjected to agarose gel electrophoresis to thereby recover about 0.8 μg of an approx. 1.98 kb KpnI-HindIII fragment containing rabbit β-globin gene splicing poly (A) signal, SV40 early gene poly (A) signal and SV40 early gene promoter.

Subsequently, 5 μg of the plasmid pMohCγ1 obtained in subsection (5) of section 1 of Example 2 were added to 10 μl of a buffer containing 10 mM Tris-20 HCl (pH 7.5), 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme SalI (Takara Shuzo) were added and reacted at 37° C. for 1 hour. Then, the reaction mixture was subjected to agarose gel electrophoresis to thereby recover about 0.8 μg of an approx. 1.66 kb KpnI-SalI fragment containing the humanized antibody H chain expression unit.

Figure 34:
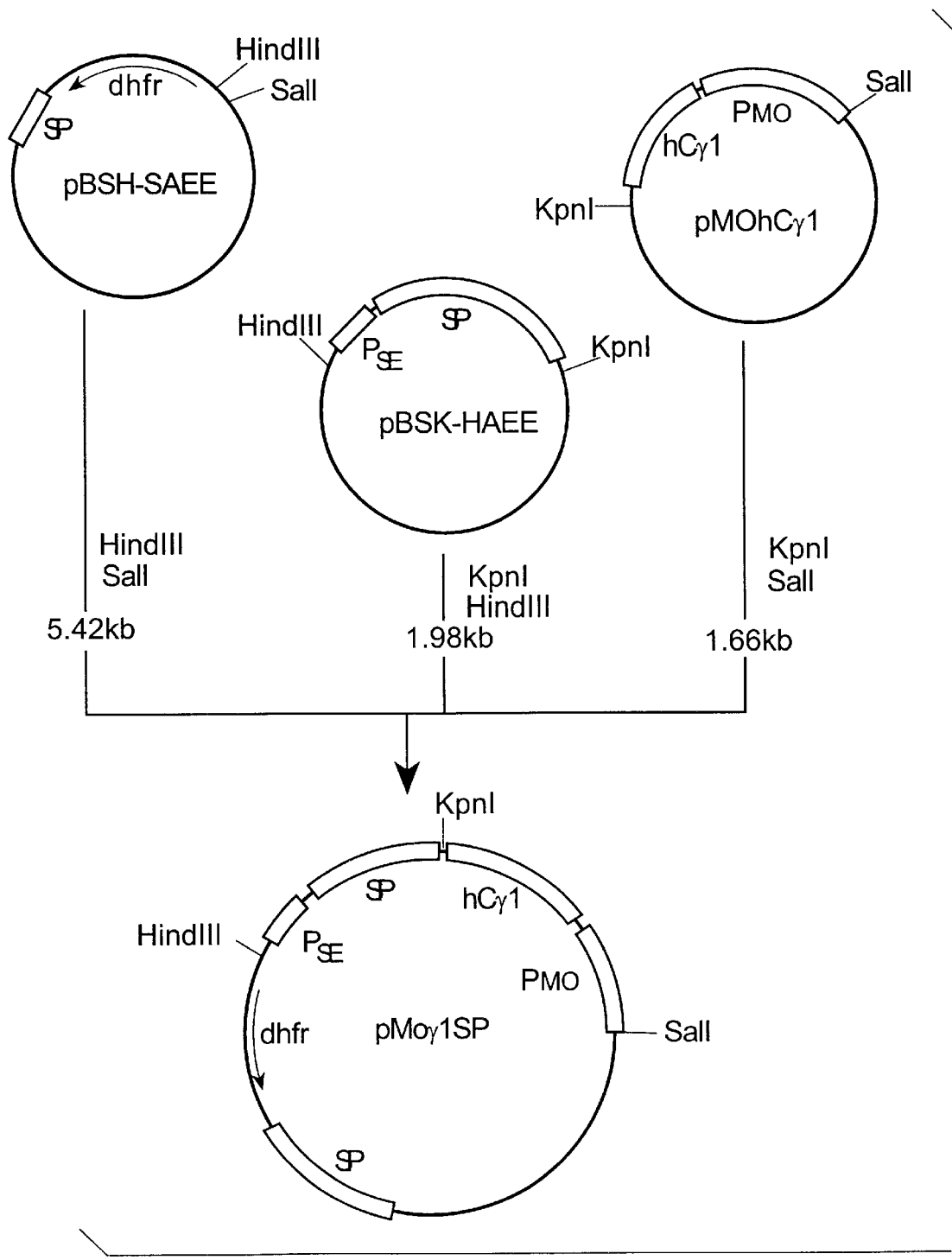
FIG. 34 shows steps for constructing plasmid pMoγ1SP.

Subsequently, 0.1 μg each of the HindIII-SalI fragment from pBSH-SAEE, the KpnI-HindIII fragment from pBSK-HAEE and the KpnI-SalI fragment from pMohCγ1 as obtained above were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pMoγ1SP shown in FIG. 34.

Subsequently, 3 μg of the thus obtained plasmid pMoγ1SP were added to 10 μl of a buffer containing 50 mM Tris-HCl (pH 7.5), 100 mM sodium chloride, 10 mM magnesium chloride and 1 mM DTT, to which 10 units each of the restriction enzymes SalI (Takara Shuzo) and XhoI were added and reacted at 37° C. for 1 hour. The reaction mixture was subjected to agarose gel electrophoresis to thereby recover about 1 μg of an approx. 9.06 kb SalI-XhoI fragment.

Subsequently, 5 μg of the plasmid pBSK-HAEESal obtained in subsection (2) of section 1 of Example 2 were added to 10 μl of a buffer containing 10 mM Tris-HCl (pH 7.5), 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme SalI (Takara Shuzo) were added and reacted at 37° C. for 1 hour. Then, the reaction mixture was subjected to agarose gel electrophoresis to thereby recover about 0.7 μg of an approx. 1.37 kb KpnI-SalI fragment containing rabbit β-globin gene splicing signal, rabbit β-globin gene splicing signal poly (A) signal and SV40 early gene poly (A) signal.

Subsequently, 5 μg of the plasmid pMohCκ obtained in subsection (4) of section 1 of Example 2 were added to 10 μl of a buffer containing 10 mM Tris-HCl (pH 7.5), 10 mM magnesium chloride and 1 mM DTT, to which 10 units of the restriction enzyme KpnI (Takara Shuzo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. Then, the reaction mixture was subjected to agarose gel electrophoresis to thereby recover about 0.7 μg of an approx. 1.06 kb KpnI-XhoI fragment containing the humanized antibody L chain expression unit.

Figure 35:
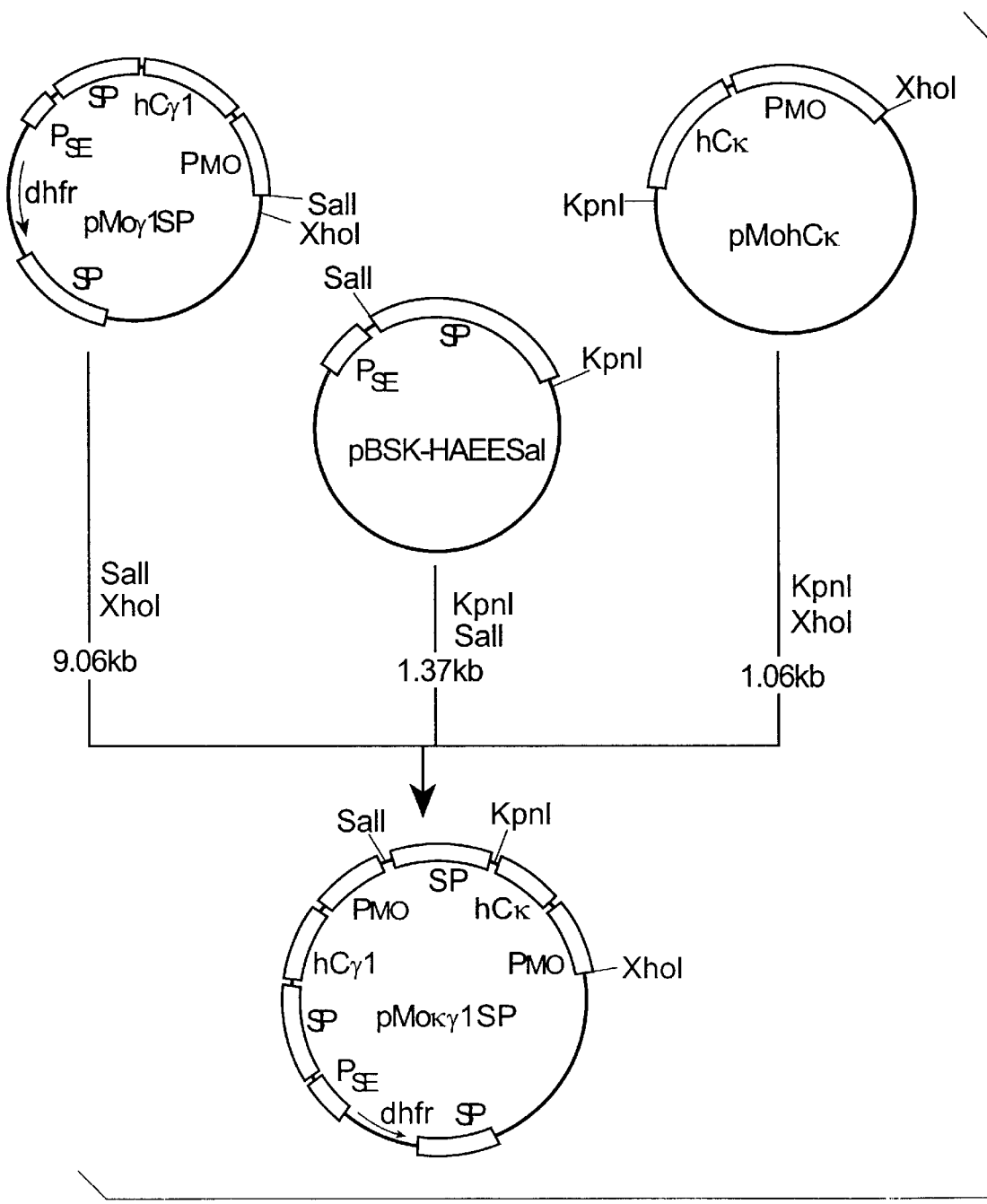
FIG. 35 shows steps for constructing plasmid pMoκγ1SP.

Subsequently, 0.1 μg each of the SalI-XhoI fragment from pMoγ1SP, the KpnI-SalI fragment from pBSK-HAEESal and the KpnI-XhoI fragment from pMohCκ as obtained above were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pMOκγ1SP shown in FIG. 35.

Subsequently, 3 μg of the thus obtained plasmid PMOκγ1SP were dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. The reaction mixture was ethanol-precipitated, and the precipitate was added to 10 μl of a buffer containing 10 mM Tris-HCl (pH 7.5), 10 mM magnesium chloride and 1 mM DTT, to which 10 units of the restriction enzyme SacII (Toyobo) were added and reacted at 37° C. for 10 minutes so that the DNA fragments were partially digested. Then, the reaction mixture was subjected to agarose gel electrophoresis to thereby recover about 0.2 μg of an approx. 8.49 kb SacII-XhoI fragment.

Subsequently, 3 μg of plasmid pBSX-SA obtained in subsection (3) of section 1 of Example 2 were added to 10 μl of a buffer containing 10 mM Tris-HCl (pH 7.5), 10 mM magnesium chloride and 1 mM DTT, to which 10 units of the restriction enzyme SacII (Toyobo) were added and reacted at 37° C. for 1 hour. The reaction mixture was ethanol-precipitated, and the precipitate was dissolved in 10 μl of a buffer containing 50 mM Tris-HCl (pH 7.5), 100 mM sodium chloride, 10 mM magnesium chloride and 1 mM DTT, to which 10 units of the restriction enzyme XhoI (Takara Shuzo) were added and reacted at 37° C. for 1 hour. Then, the reaction mixture was subjected to agarose gel electrophoresis to thereby recover about 1 μg of an approx. 4.25 kb SacII-XhoI fragment.

Figure 36:
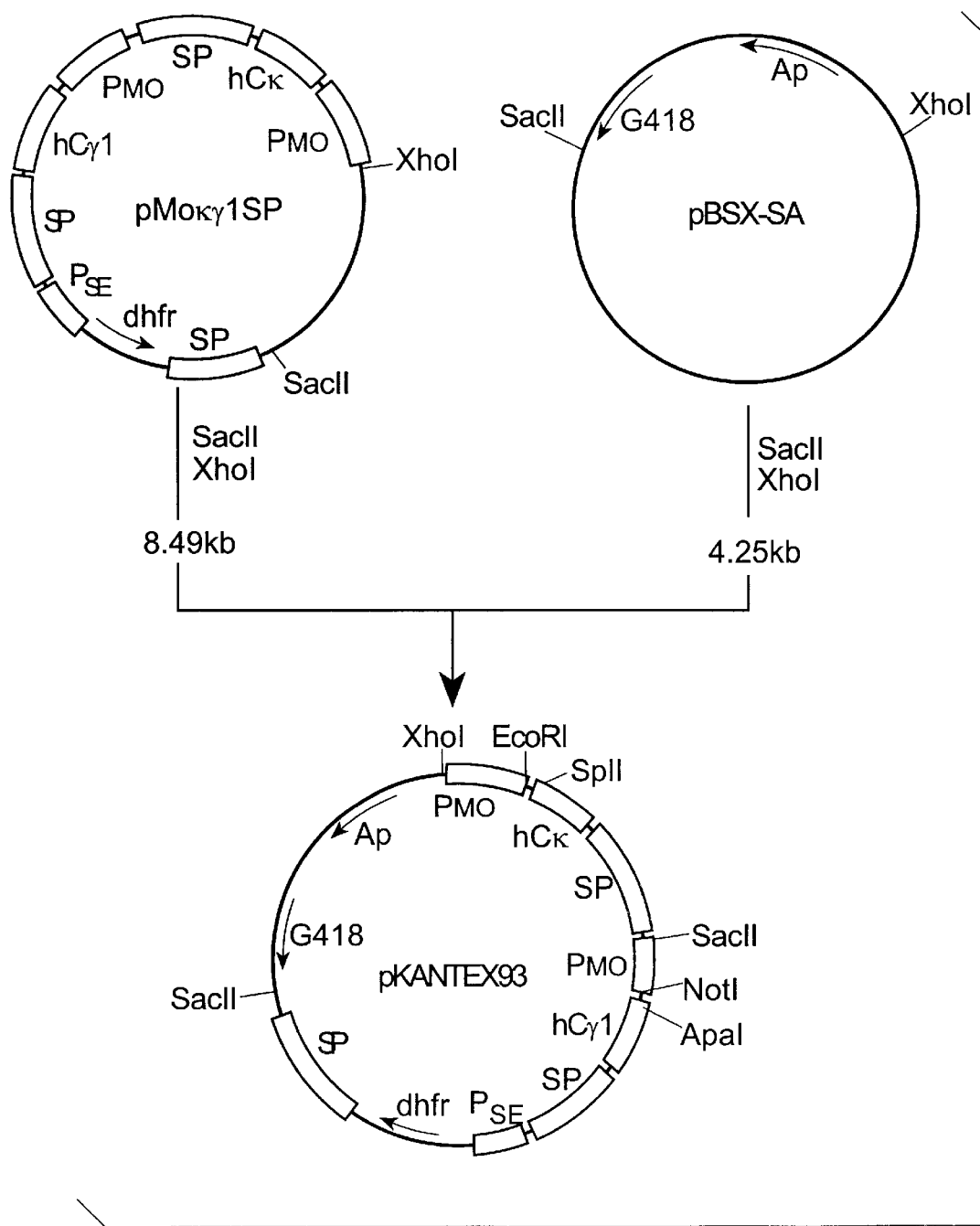
FIG. 36 shows steps for constructing plasmid pKANTEX93.

Subsequently, 0.1 μg each of the SacII-XhoI fragment from pMOκγ1SP and the SacII-XhoI fragment from pBSX-SA as obtained above were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to obtain plasmid pKANTEX93 shown in FIG. 36.

2. Isolation and Analysis of the cDNAs Coding for Anti-Human IL-5R α Monoclonal Antibodies (1) Isolation of mRNA from Anti-Human IL-5R α Monoclonal Antibody-Producing Hybridomas Using Fast Track, an mRNA extraction kit manufactured by Invitrogen, mRNA was isolated from $1 \times 10^8$ cells each of mouse anti-human IL-5R α monoclonal antibodies KM 1257, KM1259 and KM 1486 producing hybridoma cell lines (corresponding to hybridomas FERM BP-5133, FERM BP-5134 and FERM BP-5651, respectively) in accordance with the instructions attached to the kit.

(2) Preparation of H and L Chain cDNA Libraries from Mouse Anti-Human IL-5R α Monoclonal Antibody-Producing Hybridomas Using cDNA Synthesis Kit (Pharmacia Biotech) and according to the instructions attached to the kit, a cDNA having an EcoRI adapter at both ends was synthesized separately from 5 μg each of the mRNAs obtained from KM1257, KM1259 and KM1486 in subsection (1) of section 2 of Example 2. About 6 μg of each cDNA were dissolved in 10 μl of sterilized water and subjected to agarose gel electrophoresis, to thereby recover about 0.1 μg each of an approx. 1.5 kb cDNA fragment corresponding to the cDNA encoding for the H chain of IgG type antibody and an approx. 1.0 kb fragment corresponding to the L chain of immunoglobulins. Then, 0.1 μg of the approx. 1.5 kb cDNA fragment or the approx. 1.0 kb cDNA fragment and 1 μg of Lamda ZAPII vector (as treated with calf intestine alkaline phosphatase after cleavage with EcoRI; Stratagene) were dissolved in 11.5 μl of T4 ligase buffer, to which 175 units of T4 DNA ligase were added and incubated at 12° C. for 24 hours, followed by incubation at room temperature for another 2 hours. Using 4 μl of each reaction mixture, cDNAs were packed into a λ phage using Giga Pack Gold (Stratagene) by conventional methods (Molecular Cloning, 2.95, Cold Spring Harbor Laboratory, 1989). The resultant A phages were infected to E. coli strain XL1-Blue [Biotechniques, 5,376 (1987)] in Giga Pack Gold by conventional methods (Molecular Cloning, 2.95–107, Cold Spring Harbor Laboratory, 1989) to obtain about 4000 phage clones for each of the H chain cDNA library and the L chain cDNA library of KM1257, KM1259 and KM1486.

(3) Cloning of the cDNAs Coding for the H and L Chains of Anti-Human IL-5R α Monoclonal Antibody-Producing Hybridomas The recombinant phages prepared in subsection (2) of section 2 of Example 2 was fixed on a nitrocellulose filter by conventional methods (Molecular Cloning, 2.12, Cold Spring Harbor Laboratory, 1989). The cDNA coding for the C region of mouse Ig the H chain was a fragment from mouse Cγ1 cDNA [Cell, 18, 559 (1979)] and the L chain was a fragment from mouse Cκ cDNA [Cell, 22, 197 (1980)] were labeled using ECL direct nucleic acid labeling and detection systems (Amersham). Using those labeled cDNA as probes, recombinant phages were screened. Subsequently, according to the instructions attached to Lamda ZAPII vector (Stratagene), the phage clones were replaced with plasmid pBluescriptSK(-). Finally, the following plasmids were obtained: recombinant plasmid pKM1257H comprising a cDNA coding for the H chain of KM1257 and recombinant plasmid pKM1257L comprising a cDNA coding for the L chain of KM1257; recombinant plasmid pKM1259H comprising a cDNA coding for the H chain of KM1259 and recombinant plasmid pKM1259L comprising a cDNA coding for the L chain of KM1259; and recombinant plasmid pKM1486H comprising a cDNA coding for the H chain of KM1486 and recombinant plasmid pKM1486L comprising a cDNA coding for the L chain of KM1486.

(4) Determination of the Base Sequences for the V Regions of the cDNAs Coding for the H and L Chains of Anti-Human IL-5R α Monoclonal Antibodies The base sequence for the V region of each of the cDNAs coding for the H and L chains of mouse anti-human IL-5R α monoclonal antibodies as obtained in subsection (3) of section 2 of Example 2 was analyzed by reacting 10 μg of the resultant plasmid according to the recipe attached to AutoRead Sequencing Kit (Pharmacia Biotech) and then electrophoresed with A.L.F. DNA Sequencer (Pharmacia Biotech). From the base sequence thus determined for each of the cDNAs, amino acid sequences for the V regions of the L and H chains of KM1257, KM1259 and KM1486 were determined. SEQ ID NOS: 22 & 23 show the base sequence and amino acid sequence of the V region of the H chain of KM1257; SEQ ID NOS:24 & 25 show those of the L chain of KM1257; SEQ ID NOS: 26 & 27 show those of the H chain of KM1259; SEQ ID NOS:28 & 29 show those of the L chain of KM1259; SEQ ID NOS:30 & 31 show those of the H chain of KM1486; and SEQ ID NOS:32 & 33 show those of the L chain of KM1486.

(5) Identification of CDR sequences for the H and L Chains of Anti-Human IL-5R α Monoclonal Antibodies CDR sequence for each H chain and those for each L chain were identified from the amino acid sequences for the V regions of the H and L chains of each mouse anti-human IL-5R α as monoclonal antibody determined in subsection (4) of section 2 of Example 2 by comparing the above amino acid sequences with the V region amino acid sequences for known antibodies (Sequences of Proteins of Immunological Interest, US Dept. Health and Human Services, 1991). SEQ ID NOS: 34, 35 and 36 show the amino acid sequences for CDR1, CDR2 and CDR3, respectively, of the H chain of KM1257. SEQ ID NOS: 37, 38 and 39 show the amino acid sequences for CDR1, CDR2 and CDR3, respectively, of the L chain of KM1257. SEQ ID NOS: 40, 41 and 42 show the amino acid sequences for CDR1, CDR2 and CDR3, respectively, of the H chain of KM1259. SEQ ID NOS: 43, 44 and 45 show the amino acid sequences for CDR1, CDR2 and CDR3, respectively, of the L chain of KM1259. SEQ ID NOS: 46, 47 and 48 show the amino acid sequences for CDR1, CDR2 and CDR3, respectively, of the H chain of KM1486. SEQ ID NOS: 49, 50 and 51 show the amino acid sequences for CDR1, CDR2 and CDR3, respectively, of the L chain of KM1486.

3. Preparation of Anti-Human EL-5R α Human Chimeric Antibody

An anti-human IL-5R α human chimeric antibody derived from the anti-human IL-5R α monoclonal antibody KM1259 having an activity to inhibit the biological activity of human IL-5 was prepared as described below.

(1) Construction of Expression Vector pKANTEX 1259 for Anti-Human IL-5R α Human Chimeric Antibody An expression vector, pKANTEX1259, for an anti-human IL-5R α human chimeric antibody was constructed as follows using the humanized antibody expression vector pKANTEX93 constructed in section 1 of Example 2 and the plasmids pKM1259H and pKM1259L obtained in section 2 of Example 2.

Briefly, 3 μg of the humanized antibody expression vector pKANTEX93 were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the precipitate was added to 10 μl of a buffer containing 50 mM Tris-HCl (pH 7.5), 100 mM sodium chloride, 10 mM magnesium chloride, 1 mM DTT, 100 μg/ml BSA and 0.01% Triton X-100, to which 10 units of the restriction enzyme NotI (Takara Shuzo) were added and reacted at 37° C. for 1 hour. The reaction mixture was subjected to agarose gel electrophoresis to thereby recover about 1 μg of an approx. 12.75 kb ApaI-NotI fragment. Subsequently, 5 μg of plasmid pKM1259H was added to 10 μl of a buffer containing 10 mM Tris-HCl (pH 7.5), 10 mM magnesium chloride and 1 mM DTT, to which 10 units of the restriction enzyme BanI (Toyobo) were added and reacted at 37° C. for 1 hour. The reaction mixture was ethanol-precipitated, and the precipitate was added to 10 μl of a buffer containing 50 mM Tris-HCl (pH 7.5), 100 mM sodium chloride, 10 mM magnesium chloride, 1 mM DTT, 100 μg/ml BSA and 0.01% Triton X-100, to which 10 units of the restriction enzyme NotI (Takara Shuzo) were added and reacted at 37° C. for 1 hour. The reaction mixture was subjected to agarose gel electrophoresis to thereby recover about 0.5 μg of an approx. 0.41 kb BanI-NotI fragment.

Subsequently, two synthetic DNAs having the base sequences shown in SEQ ID NOS: 52 and 53, respectively, were synthesized with an automatic DNA synthesizer (380A, Applied Biosystems). Then, 0.3 μg each of the obtained synthetic DNAs were added to 15 μl of sterilized water and heated at 65° C. for 5 minutes. After the reaction mixture was left at room temperature for 30 minutes, 2 μl of a 10× buffer [500 mM Tris-HCl (pH 7.6), 100 mM magnesium chloride, 50 mM DTT] and 2 μl of 10 mM ATP were added. Further, 10 units of T4 polynucleotide kinase were added and reacted at 37° C. for 30 minutes to thereby phosphorylate the 5' ends.

Figure 37:
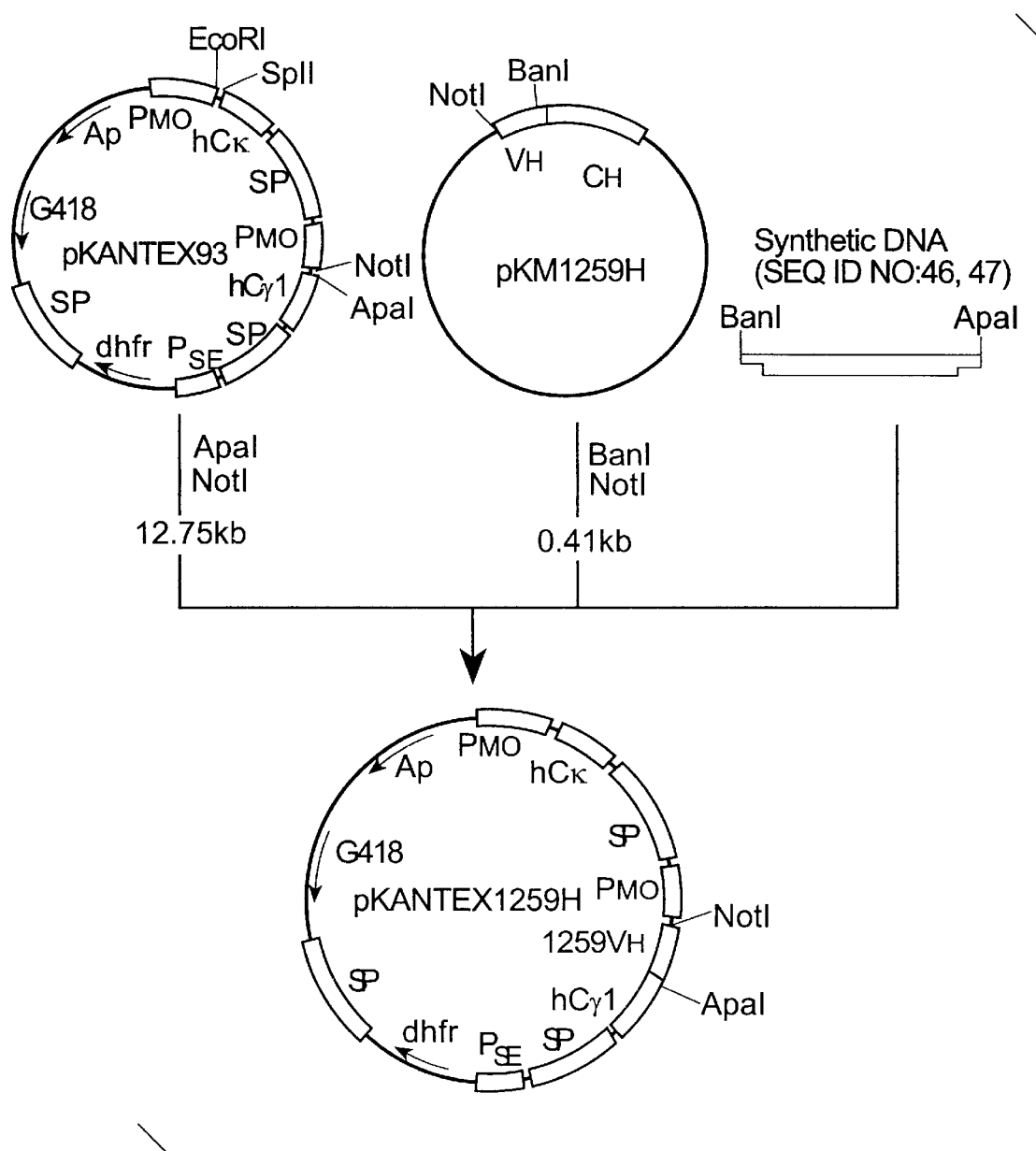
FIG. 37 shows steps for constructing plasmid pKANTEX1259H.

Then, 0.1 μg of the ApaI-NotI fragment from the humanized antibody expression vector pKANTEX93, 0.1 μg of the BanI-NotI fragment from plasmid pKM1259H and 0.05 μg of the phosphorylated synthetic DNAs as obtained above were added to sterilized water to give a total volume of 20 μl and ligated using Ready-To-Go T4 DNA Ligase (Pharmacia Biotech). Using the thus obtained recombinant plasmid DNA solution, *E. coli* HB101 was transformed to obtain plasmid pKANTEX1259H shown in FIG. 37.

Subsequently, 3 μg of the thus obtained plasmid pKANTEX1259H were added to 10 μl of a buffer containing 50 mM Tris-HCl (pH 7.5), 100 mM sodium chloride, 10 mM magnesium chloride, 1 mM DTT and 100 μg/ml BSA, to which 10 units each of the restriction enzymes EcoRI (Takara Shuzo) and SplI (Takara Shuzo) were added and reacted at 37° C. for 1 hour. The reaction mixture was subjected to agarose gel electrophoresis to thereby recover about 1 μg of an approx. 13.20 kb EcoRI-SplI fragment.

Subsequently, 5 μg of plasmid pKM1259L were added to 10 μl of a buffer containing 10 mM Tris-HCl (pH 7.5), 50 mM sodium chloride, 10 mM magnesium chloride and 1 mM DTT, to which 10 units of the restriction enzyme AvaII (Takara Shuzo) were added and reacted at 37° C. for 1 hour. The reaction mixture was ethanol-precipitated, and the precipitate was added to 10 μl of a buffer containing 50 mM Tris-HCl (pH 7.5), 100 mM sodium chloride, 10 mM magnesium chloride and 1 mM DTT, to which 10 units of the restriction enzyme EcoRI (Takara Shuzo) were added and reacted at 37° C. for 1 hour. The reaction mixture was subjected to agarose gel electrophoresis to thereby recover about 0.5 μg of an approx. 0.38 kb AvaII-EcoRI fragment.

Subsequently, two synthetic DNAs having the base sequences shown in SEQ ID NOS: 54 and 55, respectively, were synthesized with an automatic DNA synthesizer (380A, Applied Biosystems). Then, 0.3 μg each of the obtained synthetic DNAs were added to 15 μl of sterilized water and heated at 65° C. for 5 minutes. After the reaction mixture was left at room temperature for 30 minutes, 2 μl of a 10× buffer [500 mM Tris-HCl (pH 7.6), 100 mM magnesium chloride, 50 mM DTT] and 2 μl of 10 mM ATP were added. Further, 10 units of T4 polynucleotide kinase were added and reacted at 37° C. for 30 minutes to thereby phosphorylate the 5' ends.

Figure 38:
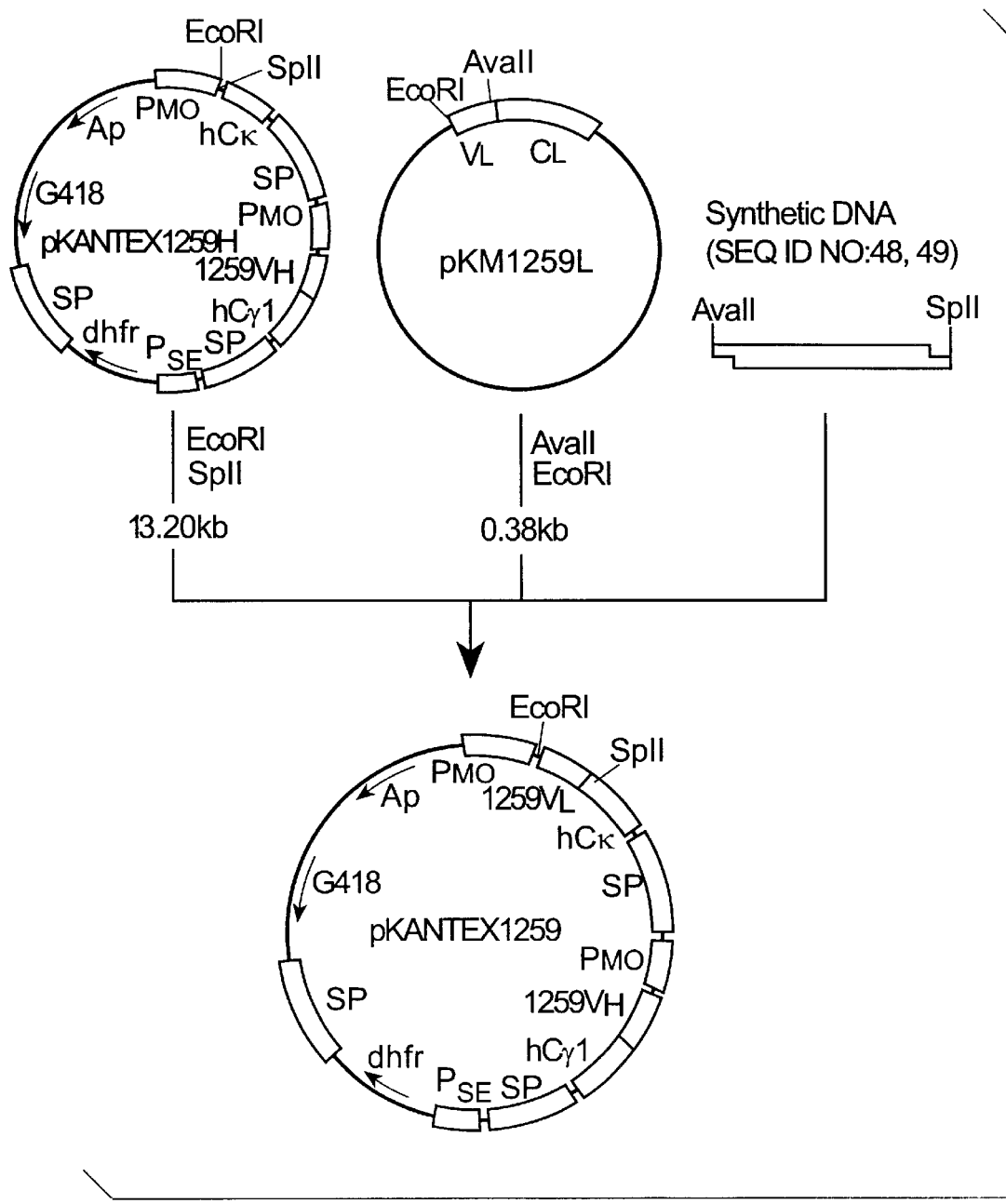
FIG. 38 shows steps for constructing plasmid pKANTEX1259.

Then, 0.1 μg of the EcoRI-SplI fragment from plasmid KANTEX1259H, 0.1 μg of the AvaII-EcoRI fragment from plasmid pKM1259L and 0.05 μg of the phosphorylated synthetic DNAs as obtained above were added to sterilized water to give a total volume of 20 μl and ligated using Ready-To-Go T4 DNA Ligase (Pharmacia Biotech). Using the thus obtained recombinant plasmid DNA solution, *E. coli* HB101 was transformed to obtain plasmid pKANTEX1259 shown in FIG. 38.

(2) Expression of Anti-Human IL-5 α Human Chimeric Antibody in Rat Myeloma YB2/0 Cells (ATCC CRL1581) using pKANTEX1259

The transfection of the anti-human IL-5 α human chimeric antibody expression vector pKANTEX1259 into YB2/0 cells was performed according to the method of Miyaji et al. by electroporation [Cytotechnology,3, 133, (1990)].

Briefly, 4 μg of the pKANTEX1259 obtained in subsection (1) of section 3 of Example 2 were transfected into 4×10⁶ YB2/0 cells. Then, RPMI1640-FCS(10) was dispensed into a 96-well microtiter plate (200 μl/well). Cells were cultured in a 5% CO₂ incubator at 37° C. for 24 hours. Then, Geneticin (hereinafter referred to as "G418"; Gibco) was added to give a concentration of 0.5 mg/ml and cells were cultured for another 1–2 weeks. The culture supernatants were recovered from those wells which had become confluent with the appearance of transformant colonies having G418 resistance. The activity of an anti-human IL-5R α human chimeric antibody in the supernatants was determined by ELISA method 1 or 2 as described below.

ELISA Method 1

The shIL-5R α-Fc obtained from the insect cell culture supernatant in subsection (10) of section 1 of Example 1 was diluted with PBS to a concentration of 5 μg/ml or less. The diluent was dispensed into a 96-well EIA plate (Greiner) (50 μl/well), which was left at 4° C. overnight to allow the protein to be adsorbed. After washing the plate, PBS containing 1% bovine serum albumin (BSA)(1% BSA-PBS) was added to the plate in an amount of 100 μl/well and reacted at room temperature for 1 hour to thereby block the remaining active groups. After discarding 1% BSA-PBS, the culture supernatants from the transformant or various purified anti-human EL-5 α antibodies at a concentration of 40 μg/ml were added to the plate in an amount of 25 μl/well. Further, the biotin-labeled human IL-5 (0.4 μg/ml) prepared in section 3 of Example 1 was added to the plate in an amount of 25 μl/well and reacted at room temperature for 4 hours. After washing with 0.05% Tween-PBS, peroxidase-labeled avidin D (Nippon Reizo) diluted 4000 folds with 1% BSA-PBS was added to the plate in an amount of 50 μl/well and reacted at room temperature for 1 hour. After washing with 0.05% Tween-PBS, an ABTS substrate solution [as prepared by dissolving 550 mg of 2,2' azinobis(3-ethylbenzothiazoline-6-sulfonic acid)diammonium in 1 L of 0.1 M citrate buffer (pH 4.2) and adding 1 μl/ml of hydrogen peroxide immediately before use] was added at 50 μl/well to allow color development. Then, the absorbance (OD) at 415 nm was measured. The absorbance value in the absence of an antibody was regarded as zero percent inhibition, and the percent inhibitions of antibodies against the biotin-labeled IL-5 were calculated by the following formula to evaluate each sample.

$$\text{Percent binding inhibition} = \frac{A - C}{100 - B - C} \times 100$$

wherein

A: OD value in the presence of an antibody

B: OD value in the absence of an antibody

C: OD value in the absence of biotin-labeled human IL-5.

ELISA Method 2

The shIL-5R α obtained from the insect cell culture supernatant in subsection (10) of section 1 of Example 1 was diluted with PBS to a concentration of 2 μg/ml or less. The diluent was dispensed into a 96-well EIA plate (Greiner) (50 μl/well), which was left at 4° C. overnight to allow the protein to be adsorbed. Alter washing the plate, PBS containing 1% bovine serum albumin (BSA)(1% BSA-PBS) was added to the plate in an amount of 100 μl/well and reacted at room temperature for 1 hour to thereby block the remaining active groups. After discarding 1% BSA-PBS, the culture supernatants from the transformant or various purified anti-human IL-5 α antibodies at a concentration of 50 μg/ml were added to the plate in an amount of 50 μl/well and reacted at room temperature for 2 hours. After washing with 0.05% Tween-PBS, peroxidase-labeled anti-human IgG antibody (American Qualex International, Inc.) diluted 500 folds with 1% BSA-PBS was added to the plate in an amount of 50 μl/well and reacted at room temperature for 1 hour. After washing with 0.05% Tween-PBS, an ABTS substrate solution [as prepared by dissolving 550 mg of 2,2' azinobis (3-ethylbenzothiazoline-6-sulfonic acid)diammonium in 1 L of 0.1 M citrate buffer (pH 4.2) and adding 1 μl/ml of hydrogen peroxide immediately before use] was added at 50 μl/well to allow color development. Then, the absorbance (OD) at 415 nm was measured.

Those transformants in which the activity of anti-human IL-5R α human chimeric antibody was observed in their culture supernatants were suspended in RPMI1640-FCS(10) medium containing 0.5 mg/ml G418 and 50 nM MTX (Sigma), and cultured in a 5% $CO_2$ incubator at 37° C. for 1–2 weeks, to thereby induce transfonmants having resistance to 50 nM MTX. When transformants became confluent in wells, the activity of anti-human IL-5R α human chimeric antibody in the supernatant was measured by either of the ELISA methods described above. Those transformants in which the activity was observed were further cultured in a manner similar to that described above, with the MTX concentration increased to 100 nM and to 200 nM. Thus, transformants which could grow in RPMI1640-FCS(10) medium containing 0.5 mg/ml G418 and 200 nM MTX and which produced an anti-human IL-5R α human chimeric antibody were obtained. The thus obtained transformants were subjected to cloning by the applications of the limiting dilution method to thereby obtain final anti-human IL-5R α human chimeric antibody-producing transformants. As a specific example of the anti-human IL-5R α human chimeric antibody-producing transformant, KM1399 (FERM BP-5650) may be given. The anti-human IL-5R α human chimeric antibody produced by this strain was designated as KM1399. The transformant KM1399 was deposited with the National Institute of Bioscience and Human-Technology, Agency of Industrial Science and Technology on Sep. 3, 1996 under accession number FERM BP-5650. The productivity of the anti-human IL-5R α human chimeric antibody KM1399 in the transformant clone KM1399 was approximately 5 $\mu g/10^6$ cells/24 hr.

Figure 39:
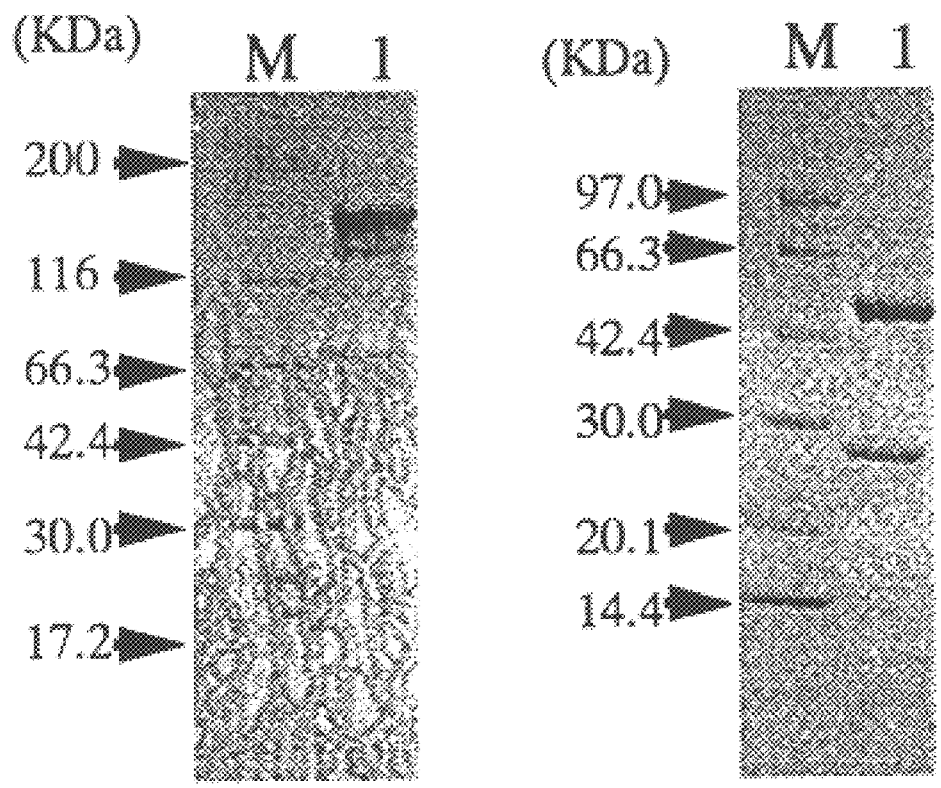
FIG. 39 shows SDS-PAGE (on 4–15% gradient gel) electrophoresis patterns of anti-human IL-5R α chain human chimeric antibody KM1399. The left of the Figure shows the pattern of electrophoresis under non-reducing conditions and the right of the Figure under reducing conditions. On the left-hand side, M is a lane of high molecular weight markers and 1 is a lane of KM1399. On the right-hand side, M is a lane of low molecular weight markers and 1 is a lane of KM1399.

(3) Purification of the Anti-Human IL-5R α Human Chimeric Antibody KM1399 from Culture Supernatant The anti-human IL-5R α human chimeric antibody KM1399 obtained in subsection (2) of section 3 of Example 2 was suspended in GIT medium (Nippon Pharmaceuticals) containing 0.5 mg/ml G418 and 200 mM MTX to give a concentration of $1-2 \times 10^5$ cells/ml, and dispensed in 200 ml portions into 175 $cm^2$ flasks (Greiner). The cells were cultured in a 5% $CO_2$ incubator at 37° C. for 5–7 days, and the culture supernatant was recovered when each flask became confluent. From about 1.0 liter of the culture supernatant, about 3 mg of purified anti-human IL-5R α human chimeric antibody KM1399 were obtained using a Procep A (Bioprocessing) column. About 4 $\mu g$ of the purified anti-human IL-5R α human chimeric antibody KM1399 were electrophoresed according to known methods [Nature, 227, 680 (1970)] to perform molecular weight analyses. The results are shown in FIG. 39. As seen from FIG. 39, the molecular weight of the antibody H chain was about 50 KDa and that of the antibody L chain about 25 KDa under reducing conditions. Thus, the expression of the H and L chains with correct molecular weights was confirmed. On the other hand, under non-reducing conditions, the molecular weight of the anti-human IL-5R α human chimeric antibody KM 1399 was about 140 KDa. Thus, the expression of a human chimeric antibody of the correct molecule weight composed of two H chains and two L chains was confirmed. Further, the N terminal amino acid sequences for the H and L chains of the purified anti-human IL-5R α human chimeric antibody KM1399 were analyzed with a protein sequencer (470A, Applied Biosystems) by the automatic Edman method. As a result, the expected correct amino acid sequences were obtained.

(4) Reactivity of the Anti-Human IL-5R α Human Chimeric Antibody KM1399 with Human IL-5R α (ELISA Method 1)

Figure 40:
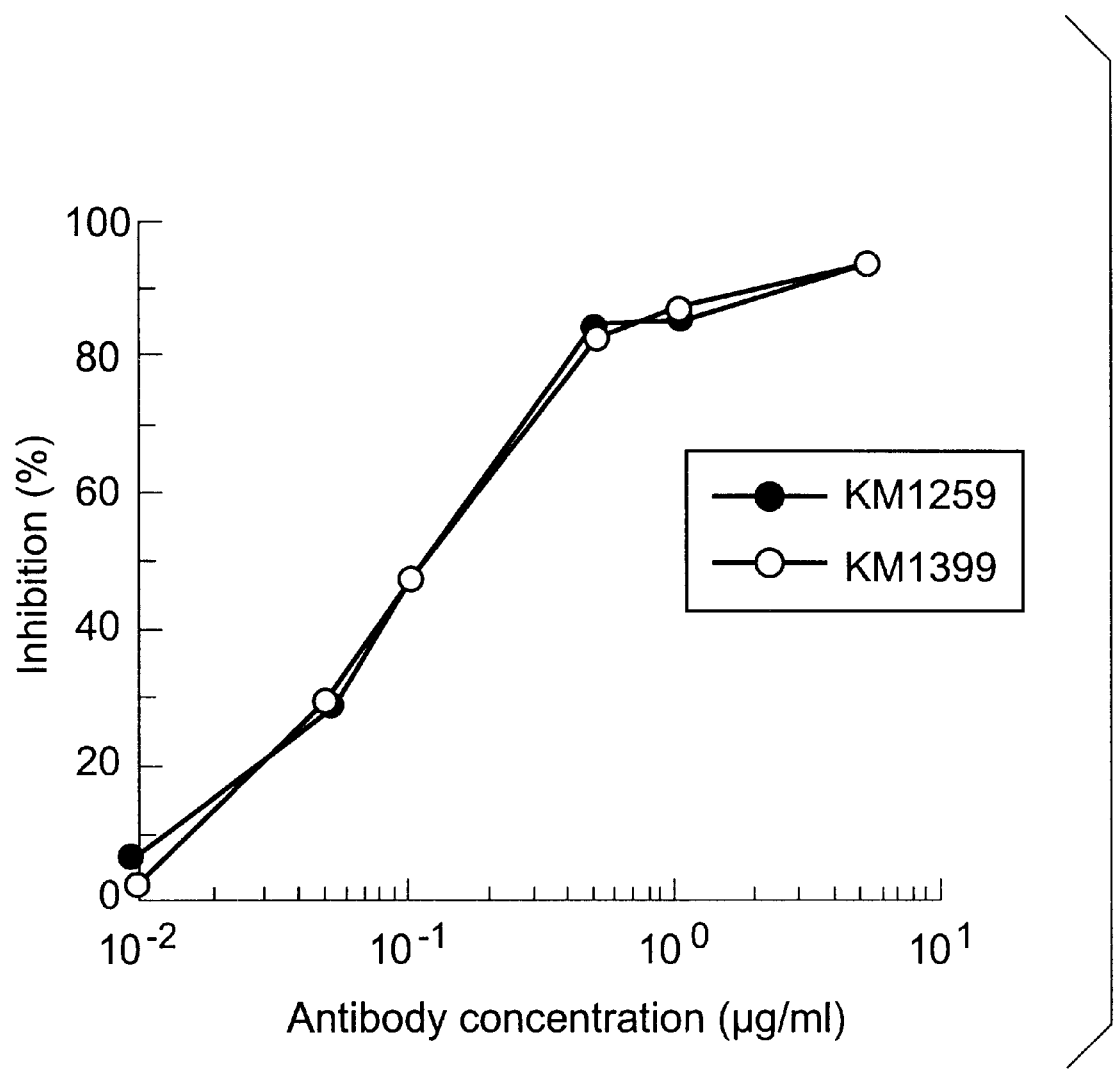
FIG. 40 shows the inhibition activities of anti-human IL-5R α chain mouse antibody KM1259 and anti-human IL-5R α chain human chimeric antibody KM1399 against binding of human IL-5 to a human IL-5 α chain. The vertical axis of the graph plots the inhibition activity and the horizontal axis, the antibody concentration. ● refers to the activity of KM1259 and ○, the activity of KM1399.

The reactivities of the anti-human IL-5R α mouse antibody KM1259 and the anti-human IL-5R α human chimeric antibody KM1399 with human IL-5R α were determined by the ELISA method 1 described in subsection (2) of section 3 of Example 2. The results are shown in FIG. 40. As seen from FIG. 40, the anti-human IL-5R α human chimeric antibody KM1399 proved to have a strong reactivity with human IL-5R α which was comparable to the reactivity of the anti-human IL-5R α mouse antibody KM1259.

4. Transient Expression of Anti-Human IL-5R α Human Chimeric Antibody in COS-7 Cells (ATCC CRL1651)

In order to evaluate the activities of various versions of the anti-human IL-5R α human CDR-grafted antibody to be described later more quickly, the transient expression of an anti-human IL-5R α human chimeric antibody in COS-7 cells was examined as follows using pKANTEX1259 and a modified vector thereof by the lipofectamine method.

(1) Construction of a improved vector of pKANTEX1259

Since the efficiency of the transient expression of a gene in animal cells depends on the number of copies of the expression vector transfected thereinto, it was assumed that a smaller expression vector would lead to a better expression efficiency. Therefore, a smaller anti-human IL-5R α human chimeric antibody expression vector, pT1259, was constructed as follows by deleting some regions of pKANTEX1259 which were believed not to influence the expression of an antibody.

Figure 41:
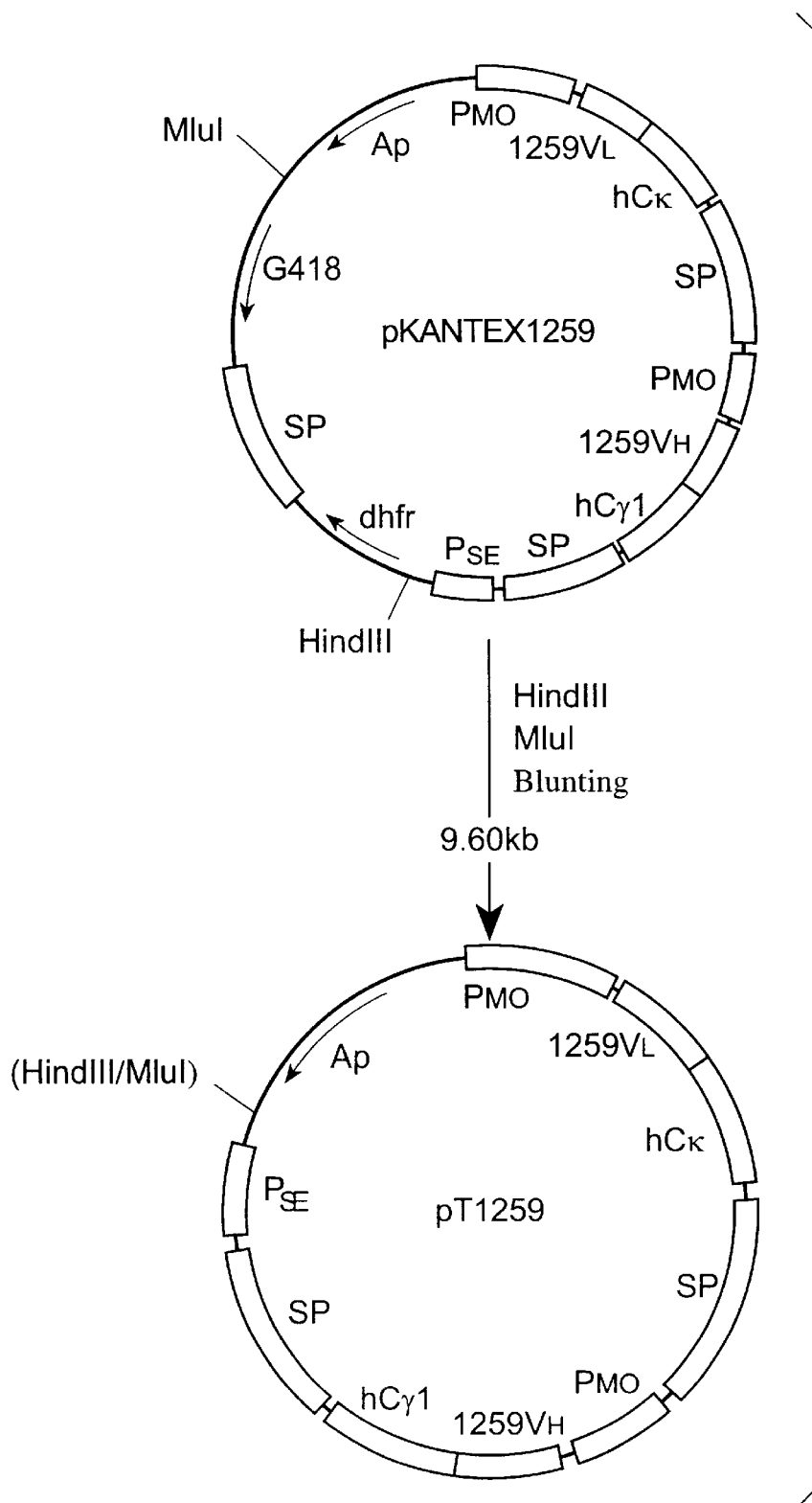
FIG. 41 shows steps for constructing plasmid pT1259.

Briefly, 3 $\mu g$ of plasmid pKANTEX 1259 were added to 10 $\mu l$ of a buffer containing 10 mM Tris-HCl (pH 7.5), 50 mM sodium chloride, 10 mM magnesium chloride and 1 mM DTT, to which 10 units of the restriction enzyme HindIII (Takara Shuzo) were added and reacted at 37° C. for 1 hour. The reaction mixture was ethanol-precipitated and the precipitate was added to 10 $\mu l$ of a buffer containing 50 mM Tris-HCl (pH 7.5), 100 mM sodium chloride, 10 mM magnesium chloride and 1 mM DTT, to which 10 units of the restriction enzyme MluI (Takara Shuzo) were added and reacted at 37° C. for 1 hour. The reaction mixture was ethanol-precipitated and the 5' sticky ends generated by the digestion with the restriction enzyme were blunted using DNA Blunting Kit (Takara Shuzo). The reaction mixture was subjected to agarose gel electrophoresis to thereby recover about 1 $\mu g$ of an approx. 9.60 kb DNA fragment. Then, 0.1 $\mu g$ of the recovered DNA fragment was added to sterilized water to give a total volume of 20 $\mu l$ and ligated using Ready-To-Go T4 DNA Ligase (Pharmacia Biotech). Using the thus obtained recombinant plasmid DNA solution, *E. coli* HB101 was transformed to thereby recover plasmid pT1259 shown in FIG. 41.

(2) Transient Expression of Anti-Human IL-5R α Human Chimeric Antibody using pT1259

Figure 42:
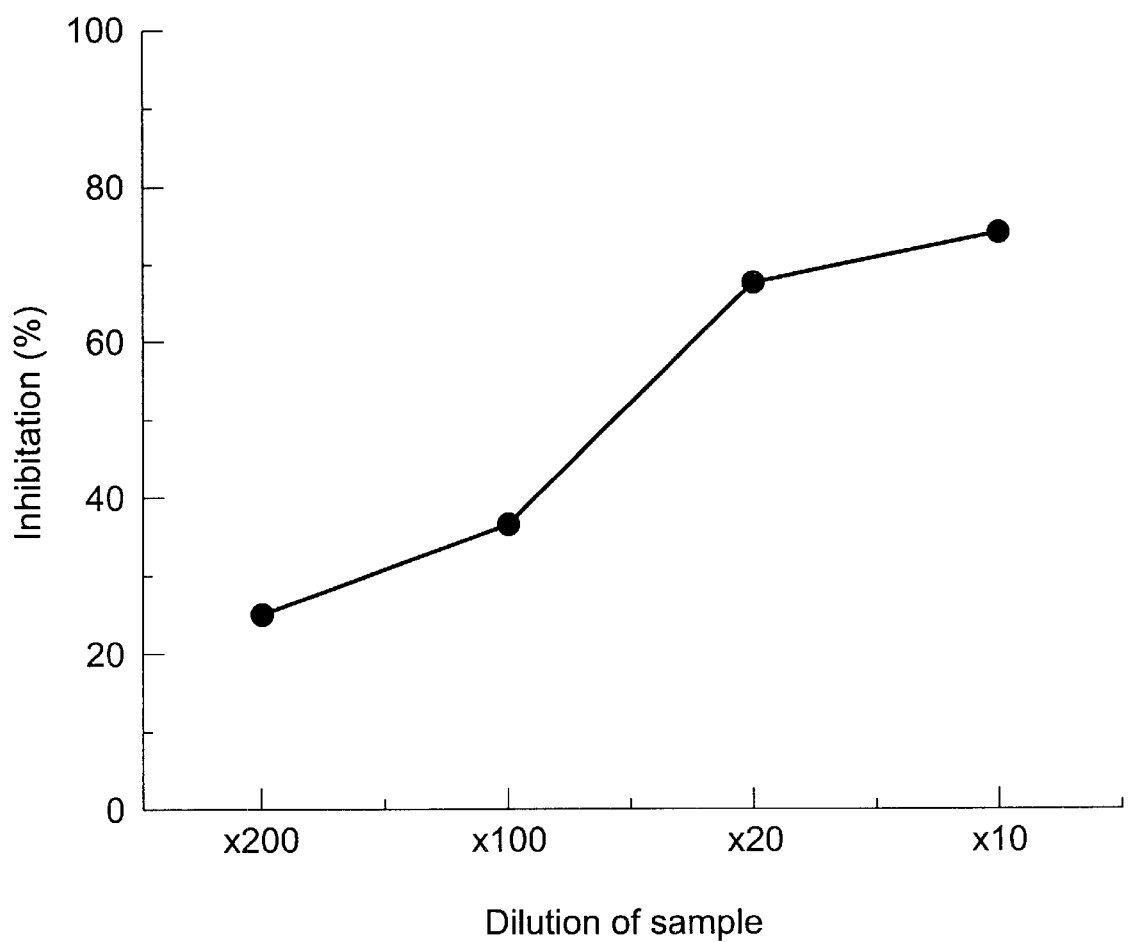
FIG. 42 shows the results of evaluation of activity on the basis of transient expression of an anti-human IL-5R α chain human chimeric antibody using plasmid pT1259. The vertical axis of the graph plots the inhibition activity against binding of human IL-5 to a human IL-5R α chain and the horizontal axis plots the dilution factor for the transient expression-culture supernatant.

COS-7 cells at a concentration of $1 \times 10^5$ cells/ml were dispersed into a 6-well plate (2 ml/well) and cultured at 37° C. overnight. To 100 $\mu l$ of OPTI-MEM (Gibco), 2 $\mu g$ of pT1259 were added, followed by addition of a solution, obtained by adding 10 $\mu l$ of lipofectamine reagent (Gibco) to 100 $\mu l$ of OPTI-MEM medium (Gibco). The resultant mixture was reacted at room temperature for 40 minutes to thereby form a DNA-liposome complex. COS-7 cells described above were washed with 2 ml of OPTI-MEM medium (Gibco)

twice, and the solution containing the DNA-liposome complex was added thereto. Then, the cells were cultured at 37° C. for 7 hours. After the removal of the cultured fluid, 2 ml of DMEM medium (Gibco) containing 10% FCS were added and the cells were cultured at 37° C. At 72 hours from the start of the cultivation, the culture supernatant was recovered, and the activity of an anti-human IL-5R α human chimeric antibody in the culture supernatant was evaluated by the ELISA method 1 described in subsection (2) of section 3 of Example 2. As shown in FIG. 42, concentration-dependent activity was observed in the culture supernatant of COS-7 cells into which pT1259 had been transfected. Thus, the expression of an anti-human IL-5R α human chimeric antibody was confirmed. From these results, it has been shown to be possible to evaluate the activities of humanized antibodies derived from various expression vectors in a transient expression system by preparing a improved small-size vector pKANTEX93, and by then transfecting the vector into COS-7 cells. Further, in order to compare correctly the activities of the various anti-human IL-5R α human CDR-grafted antibodies to be described later, the concentration of antibody formed by the transient expression in culture supernatant was determined by the ELISA method described in subsection (3) of section 4 below.

(3) Determination of the Humanized Antibody Concentration in the Transient Expression-Culture Supernatant by ELISA To a 96-well microtiter plate, a solution obtained by diluting goat anti-human IgG(γ-chain) antibody (institute of Medicine & Biology) to 400 fold with PBS was dispensed (50 μl/well) and reacted at 4° C. overnight. After the removal of the antibody solution, 100 μl/well of 1% BSA-PBS were added and reacted at 37° C. for 1 hour to thereby block the remaining active groups. After discarding 1% BSA-PBS, 50 μl/well of the transient expression-culture supernatant or the purified anti-human IL-5R α human chimeric antibody KM1399 was added and reacted at room temperature for 1 hour. After the reaction, the mixture was removed and the plate was washed with 0.05% Tween-PBS. Then, 50 μl/well of a solution obtained by diluting peroxidase-labeled mouse anti-humanK L chain antibody (Zymed) 500 folds with 1% BSA-PBS were added to the plate and reacted at room temperature for 1 hour. After washing with 0.05% Tween-PBS, 50 μl/well of ABTS substrate solution [as obtained by dissolving 550 mg of 2,2'azinobis(3-ethylbenzothiazoline-6-sulfonic acid)diammonium in 1 L of 0.1 M citrate buffer (pH 4.2) and adding 1 μl/ml of hydrogen peroxide immediately before use] were added to allow color development. Then, the absorbance at OD of 415 nm was measured.

Preparation of an Anti-Human IL-5Rα Human CDR-Grafted Antibody

An anti-human IL-5R α human CDR-grafted antibody was prepared as described below; the antibody had a comparable activity to the mouse anti-human IL-5R α monoclonal antibody KM1259 and the anti-human IL-5R α human chimeric antibody KM1399, both of which had an activity to inhibit the biological activity of human IL-5.

(1) Construction of a cDNA coding for the VH of an Anti-Human IL-5R α Human CDR-Grafted Antibody based on the Consensus Sequence for the VH of Known Human Antibodies Kabat et al. (Sequences of Proteins of Immunological Interest, US Dept. Health and Human Services, 1991) classified various known human antibody VH into subgroups 1–III (HSG I–III) based on the homology of FR sequence, and identified the consensus sequence for each subgroup. The present inventors therefore decided to design an amino acid sequence for an anti-human IL-5R α human CDR-grafted antibody VH based on those consensus sequences. First, in order to select a consensus sequence to be used as the base, the homology between the FR sequence for the VH of the mouse anti-human IL-5R α monoclonal antibody KM1259 and the FR sequence of the consensus sequence of human antibody VH of each subgroup was examined (Table 1).

TABLE 1

Homology (%) between the FR Sequence for Mouse KM1259VH and the FR Sequence of the Consensus Sequence of Human Antibody VH of Each Subgroup

| HSGI | HSGII | HSGIII |
|---|---|---|
| 72.1 | 50.6 | 55.2 |

As a result, it was confirmed that mouse KM1259VH has the highest homology to subgroup I in FR sequence. Thus, the amino acid sequence for an anti-human IL-5R α human CDR-grafted antibody VH was designed based on the consensus sequence of subgroup I, and a cDNA coding for the above amino acid sequence was constructed as described below using PCR.

Briefly, 6 synthetic DNAs having the base sequences shown in SEQ ID NOS: 56–61, respectively, were synthesized with an automatic DNA synthesizer (380A; Applied Biosystems). Each of the synthesized DNAs was added to 50 μl of a buffer containing 10 mM Tris-HCl (pH 8.3), 50 mM potassium chloride, 1.5 mM magnesium chloride, 0.001% gelatin, 200 μM dNTP, 0.5 μM M13primer RV (Takara Shuzo), 0.5 μM M13primer M4 (Takara Shuzo) and 2 units of TaKaRa Taq DNA polymerase (Takara Shuzo) to give a final concentration of 0.1 μM. Then, the resultant mixture was covered with 50 μl of mineral oil and set in a DNA thermal cycler (PJ480; Perkin Elmer). Then, PCR was performed through 30 cycles, each cycle consisting of 9° C. for 2 minutes, 55° C. for 2 minutes and 72° C. for 2 minutes. The reaction mixture was ethanol-precipitated and the precipitate was dissolved in 20 μl of TE buffer. Thereafter, the mixture was subjected to agarose gel electrophoresis to thereby recover about 0.2 μg of an approx. 0.48 kb amplified fragment.

Subsequently, 3 μg of plasmid pBluescriptSK(−) (Stratagene) were added to 10 μl of a buffer containing 33 mM Tris-HCl (pH 7.9), 10 mM magnesium acetate, 66 mM potassium acetate, 0.5 mM DTT and 100 μg/ml BSA, to which 10 units of the restriction enzyme SmaI (Takara Shuzo) were added and reacted at 30° C. for 1 hour. The reaction mixture was ethanol-precipitated, and the precipitate was added to 20 μl of a buffer containing 50 mM Tris-HCl (pH 9.0) and 1 mM magnesium chloride, to which 1 unit of alkaline phosphatase (*E. coli* C75, Takara Shuzo) was added and reacted at 37° C. for 1 hour to thereby dephosphorylate 5' ends. Then, the reaction mixture was subjected to phenol-chloroform extraction, followed by ethanol precipitation. The precipitate was dissolved in 20 μl of TE buffer.

Figure 43:
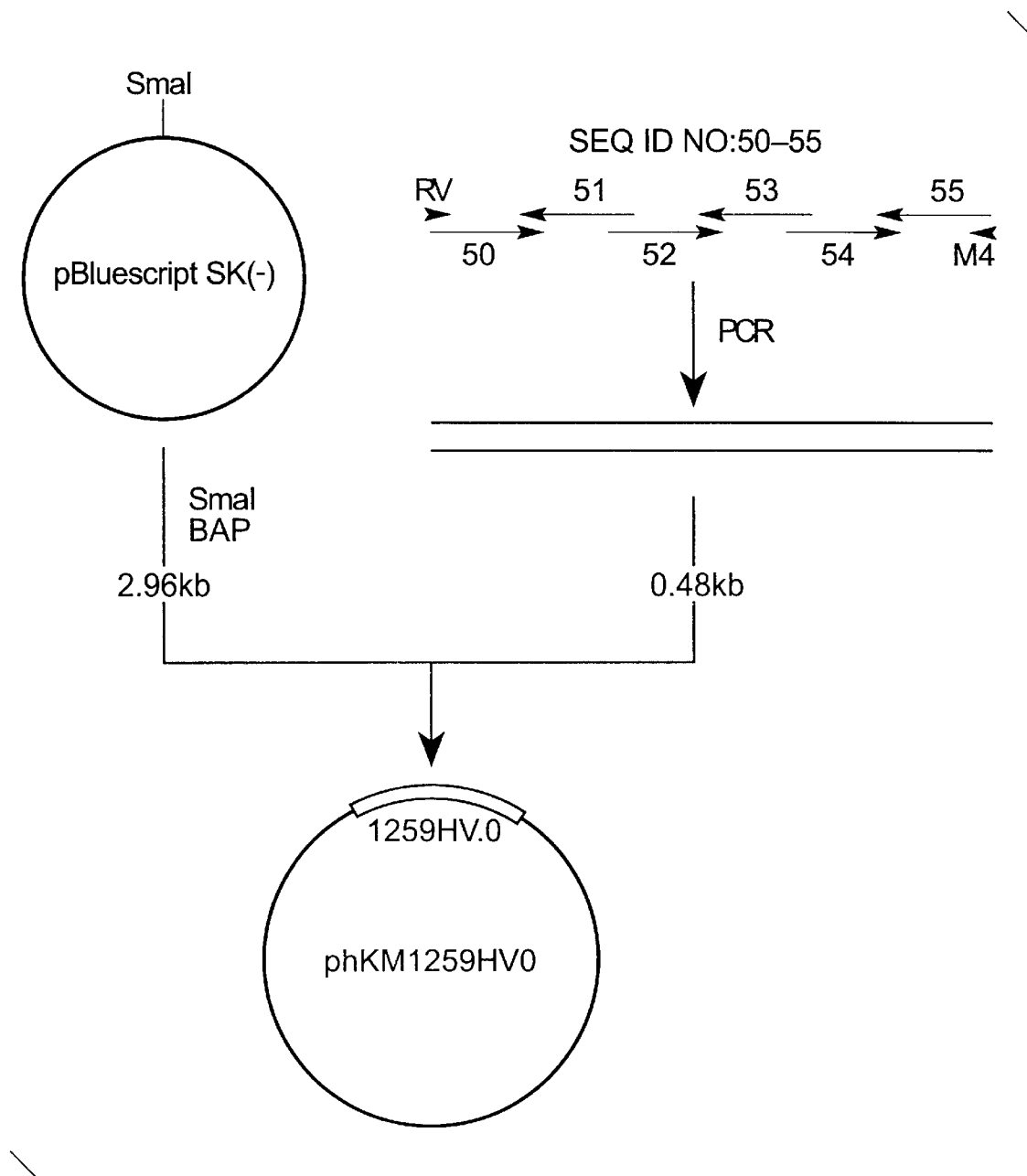
FIG. 43 shows steps for constructing plasmid phKM1259HV0.

Subsequently, 0.1 μg of the amplified fragment obtained by PCR and 0.1 μg of the SmaI fragment from pBluescriptSK(–) were added to sterilized water to give a total volume of 20 μl and ligated using Ready-To-Go T4 DNA Ligase (Pharmacia Biotech). Using the thus obtained recombinant plasmid DNA solution, E. coli HB101 was transformed. From 10 transformant clones, plasmid DNA was prepared individually and the base sequence thereof was determined. As a result, plasmid phKM1259HV0 shown in FIG. 43 comprising a cDNA coding for the amino acid sequence for an anti-human IL-5R α human CDR-grafted antibody VH of interest was obtained. The base sequence and the amino acid sequence for the anti-human IL-5R α human CDR-grafted antibody VH contained in phKM1259HV0 (hereinafter referred to as "HV.0") are shown in SEQ ID NOS: 62 and 63.

(2) Construction of a cDNA coding for the VL of an Anti-Human IL-5Rα Human CDR-Grafted Antibody based on the Consensus Sequence for the VL of Known Human Antibodies Kabat et al. classified various known human antibody VL into subgroups I–IV (HSG I–IV) based on the homology of FR sequence, and identified the consensus sequence for each subgroup. The present inventors therefore decided to design an amino acid sequence for an anti-human IL-5R α human CDR-grafted antibody VL based on those consensus sequences. First, in order to select a consensus sequence to be used as the base, the homology between the FR sequence for the VH of the mouse anti-human IL-5R α monoclonal antibody KM1259 and the FR sequence of the consensus sequence of human antibody VL of each subgroup was examined (Table 2).

TABLE 2

Homology (%) between the FR Sequence for Mouse KM1259VL and the FR Sequence of the Consensus Sequence of Human Antibody VL of Each Subgroup

| HSGI | HSGII | HSGIII | HSGIV |
|------|-------|--------|-------|
| 73.8 | 57.5  | 60.0   | 65.0  |

As a result, it was confirmed that mouse KM1259VL has the highest homology to subgroup I in FR sequence. Thus, the amino acid sequence for an anti-human IL-5R α human CDR-grafted antibody VL was designed based on the consensus sequence of subgroup I, and a cDNA coding for the above amino acid sequence was constructed as described below using PCR.

Briefly, 6 synthetic DNAs having the base sequences shown in SEQ ID NOS: 64–69, respectively, were synthesized with an automatic DNA synthesizer (380A; Applied Biosystems). Each of the synthesized DNAs was added to 50 μl of a buffer containing 10 mM Tris-HCl (pH 8.3), 50 mM potassium chloride, 1.5 mM magnesium chloride, 0.001% gelatin, 200 μM dNTP, 0.5 μM M13primer RV (Takara Shuzo), 0.5 μM M13primer M4 (Takara Shuzo) and 2 units of TaKaRa Taq DNA polymerase (Takara Shuzo) to give a final concentration of 0.1 μM. Then, the resultant mixture was covered with 50 μl of mineral oil and set in a DNA thermal cycler (PJ480; Perkin Elmer). Then, PCR was performed through 30 cycles, each cycle consisting of 94° C. for 2 minutes, 55° C. for 2 minutes and 72° C. for 2 minutes. The reaction mixture was ethanol-precipitated and the precipitate was dissolved in 20 μl of TE buffer. Thereafter, the solution was subjected to agarose gel electrophoresis to thereby recover about 0.2 μg of an approx. 0.43 kb amplified fragment.

Figure 44:
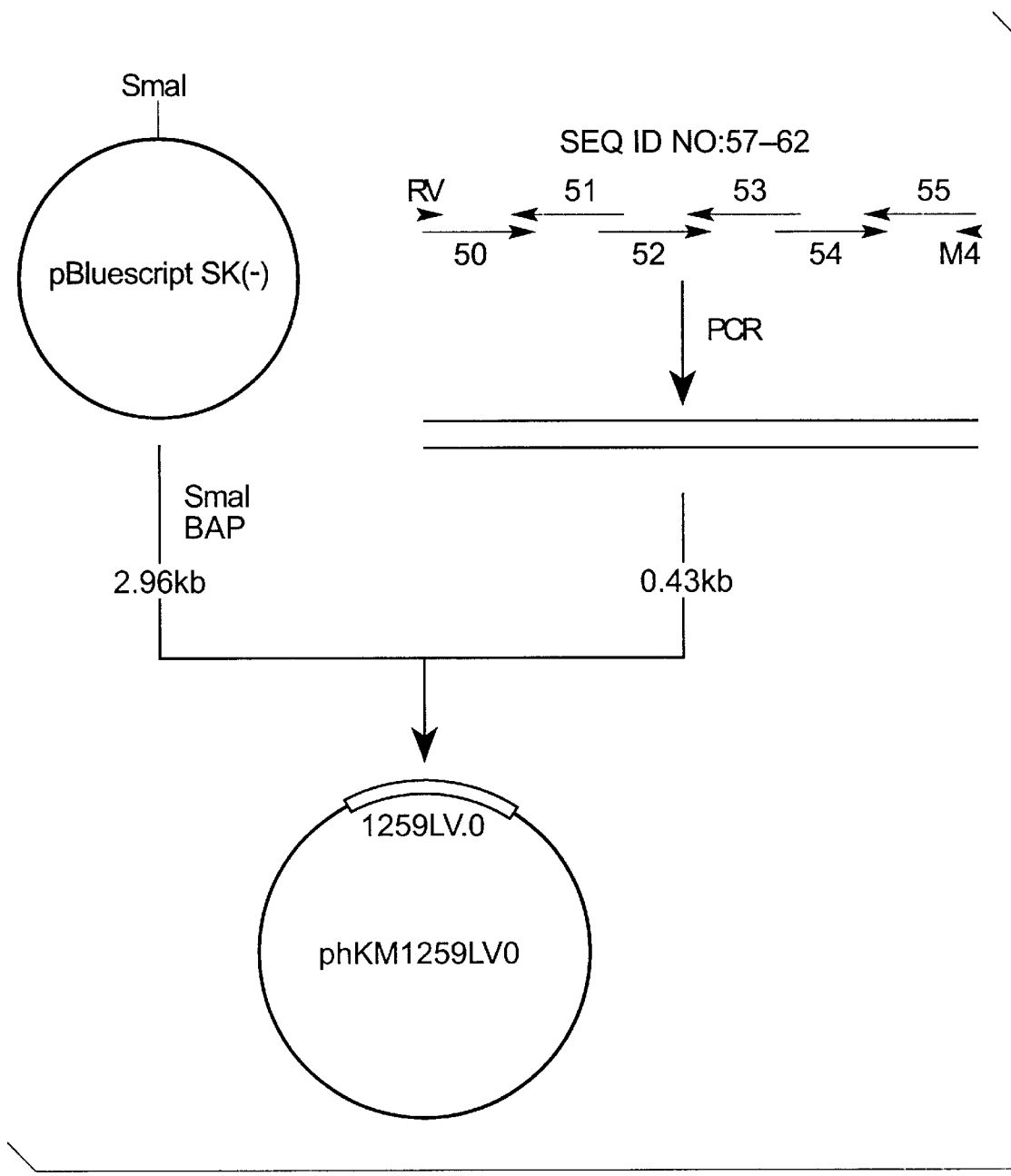
FIG. 44 shows steps for constructing plasmid phKM1259LV0.

Subsequently, 0.1 μg of the amplified fragment obtained above by PCR and 0.1 μg of the SmaI fragment from pBluescriptSK(–) obtained in subsection (1) of section 5 of Example 2 were added to sterilized water to give a total volume of 20 μl and ligated using Ready-To-Go T4 DNA Ligase (Pharmacia Biotech). Using the thus obtained recombinant plasmid DNA solution, E. coli HB101 was transformed. From 10 transformant clones, plasmid DNA was prepared individually and the base sequence thereof was determined. As a result, plasmid phKM1259LV0 shown in FIG. 44 comprising a cDNA coding for the amino acid sequence for the anti-human IL-5R α human CDR-grafted antibody VL of interest was obtained. The base sequence and the amino acid sequence for the anti-human IL-5R α human CDR-grafted antibody VL contained in phKM1259LV0 (hereinafter referred to as "LV.0") are shown in SEQ ID NOS: 70 & 71.

(3) Construction of Expression Vector for Anti-Human IL-5R α Human CDR-Grafted Antibody pKANTEX1259HV0LV0, based on the Consensus Sequence of V Regions of Known Human Antibodies An anti-human IL-5R α human CDR-grafted antibody expression vector, pKANTEX1259HV0LV0, was constructed as described below using the humanized antibody expression vector pKANTEX93 obtained in section 1 of Example 2, the plasmid phKM1259HV0 obtained in subsection (1) of section 5 of Example 2 and the plasmid phKM1259LV0 obtained in subsection (2) of section 5 of Example 2.

Briefly, 5 μg of plasmid pKMh1259HV0 were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated and the precipitate was added to 10 μl of a buffer containing 50 mM Tris-HCl (pH 7.5), 100 mM sodium chloride, 10 mM magnesium chloride, 1 mM DTT, 100 μg/ml BSA and 0.01% Triton X-100, to which 10 units of the restriction enzyme NotI (Takara Shuzo) were added and reacted at 37° C. for 1 hour. The reaction mixture was subjected to agarose gel electrophoresis to thereby recover about 0.5 μg of an approx. 0.44 kb ApaI-NotI fragment.

Figure 45:
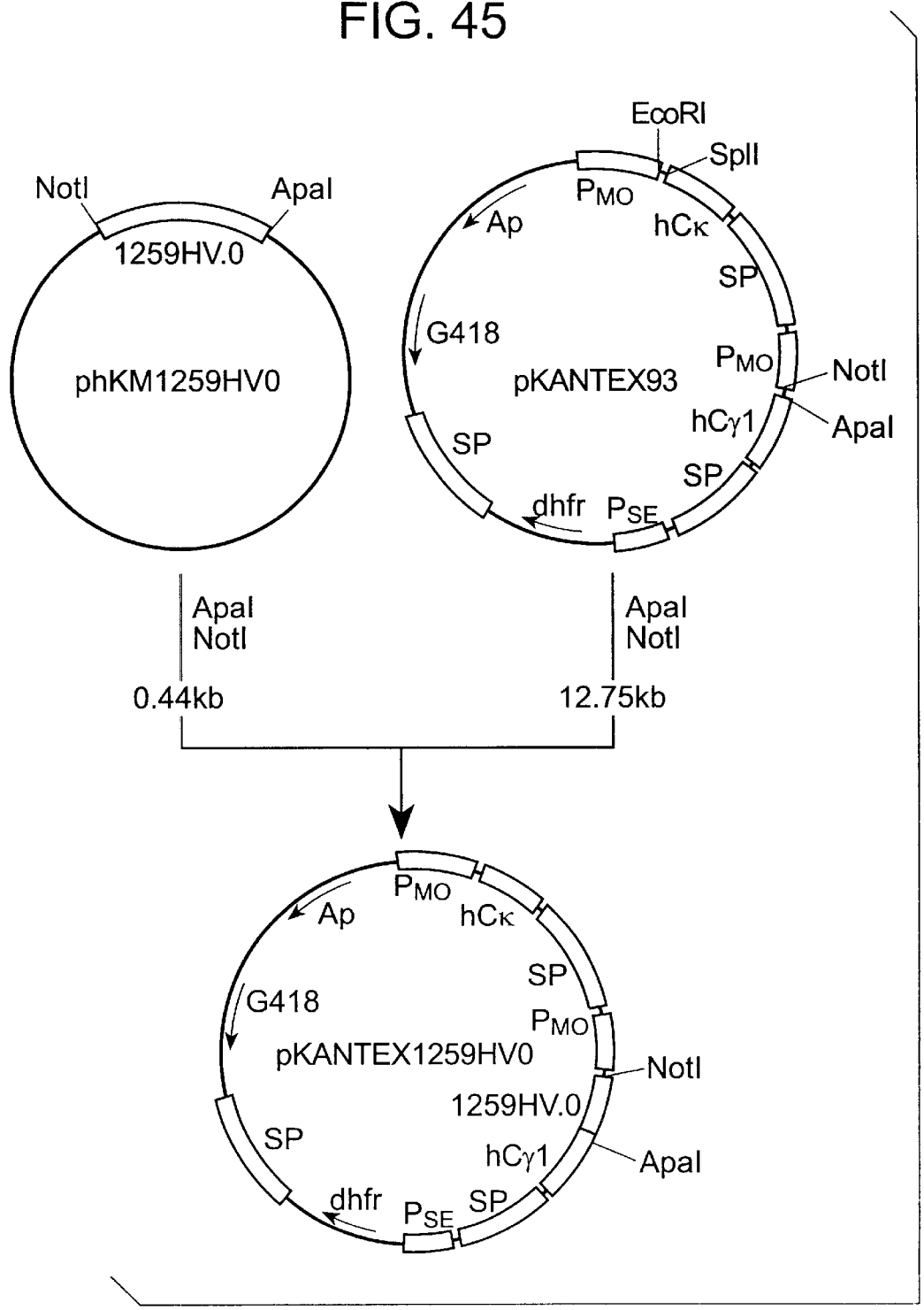
FIG. 45 shows steps for constructing plasmid pKANTEX1259HV0.

Subsequently, 0.1 μg of the ApaI-NotI fragment from the humanized antibody expression vector pKANTEX93 obtained in subsection (1) of section 3 of Example 2 and 0.1 μg of the ApaI-NotI fragment from plasmid phKM1259HV0 obtained above were added to sterilized water to give a total volume of 20 μl and ligated using Ready-To-Go T4 DNA Ligase (Pharmacia Biotech). Using the thus obtained recombinant plasmid DNA solution, E. coli HB101 was transformed to thereby obtain plasmid pKANTEX1259HV0 shown in FIG. 45.

Subsequently, 3 μg of the thus obtained plasmid pKANTEX1259HV0 were added to 10 μl of a buffer containing 50 mM Tris-HCl (pH 7.5), 100 mM sodium chloride, 10 mM magnesium chloride, 1 mM DTT and 100 μg/ml BSA, to which 10 units each of the restriction enzyme EcoRI (Takara Shuzo) and the restriction enzyme SplI (Takara Shuzo) were added and reacted at 37° C. for 1 hour. The reaction mixture was subjected to agarose gel electrophoresis to thereby recover about 1 μg of an approx. 13.20 kb EcoRI-SplI fragment.

Subsequently, 5 μg of plasmid phKM1259LV0 were added to 10 μl of a buffer containing 50 mM Tris-HCl (pH 7.5), 100 mM sodium chloride, 10 mM magnesium chloride, 1 mM DTT and 100 μg/ml BSA, to which 10 units each of the restriction enzyme EcoRI (Takara Shuzo) and the restriction enzyme SplI (Takara Shuzo) were added and reacted at 37° C. for 1 hour. The reaction mixture was subjected to agarose gel electrophoresis to thereby recover about 0.5 μg of an approx. 0.39 kb EcoRI-SplI fragment.

Figure 46:
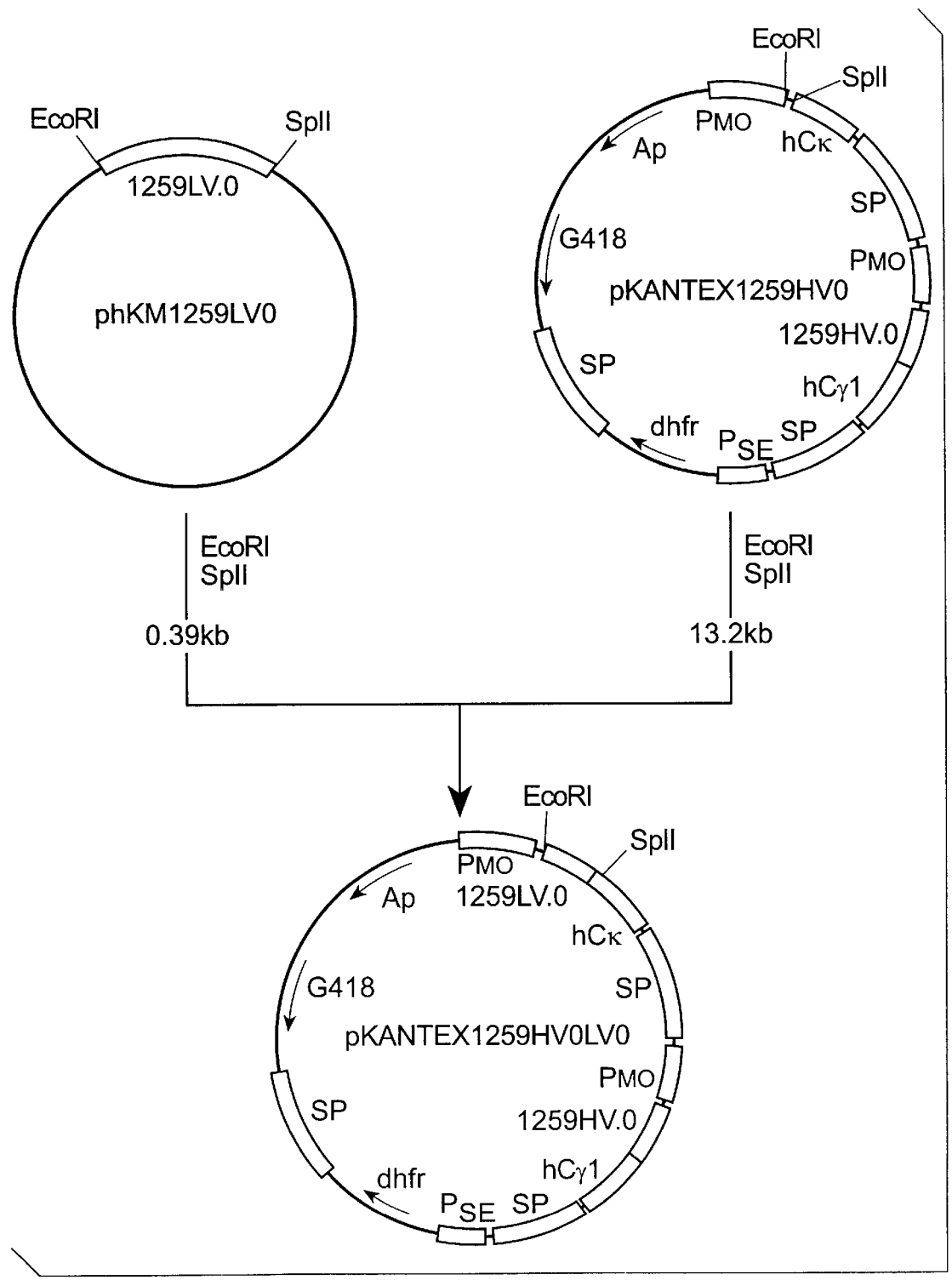
FIG. 46 shows steps for constructing plasmid pKANTEX1259HV0LV0.

Then, 0.1 μg of the EcoRI-SplI fragment from plasmid pKANTEX1259HV0 obtained above and 0.1 μg of the EcoRI-SplI fragment from plasmid phKM 1259LV0 obtained above were added to sterilized water to give a total volume of 20 μl and ligated using Ready-To-Go T4 DNA Ligase (Pharmacia Biotech). Using the thus obtained recombinant plasmid DNA solution, *E. coli* HB101 was transformed to thereby obtain plasmid pKANTEX1259HV0LV0 shown in FIG. 46.

(4) Expression of an Anti-Human IL-5R α Human CDR-Grafted Antibody based on the Consensus Sequence of Known Human Antibody V Regions in Rat Myeloma YB2/0 Cells (ATCC CRL1581) using pKANTEX1259HV0LV0

The expression of an anti-human IL-5R α human CDR-grafted antibody based on the consensus sequence of known human antibody V regions in rat myeloma YB2/0 cells (ATCC CRL1581) was performed using pKANTEX1259HV0LV0 according to the method described in subsection (2) of section 3 of Example 2.

As a result, KM8397 was obtained as a transformant producing an anti-human IL-5R α human CDR-grafted antibody based on the consensus sequence of known human antibody V regions. The anti-human IL-5R α human CDR-grafted antibody produced by the strain was designated as KM8397. The productivity of the anti-human IL-5R α human CDR-grafted antibody KM8397 in the transformant KM8397 was about 4 μg/$10^6$ cells/24 hr.

Figure 47:
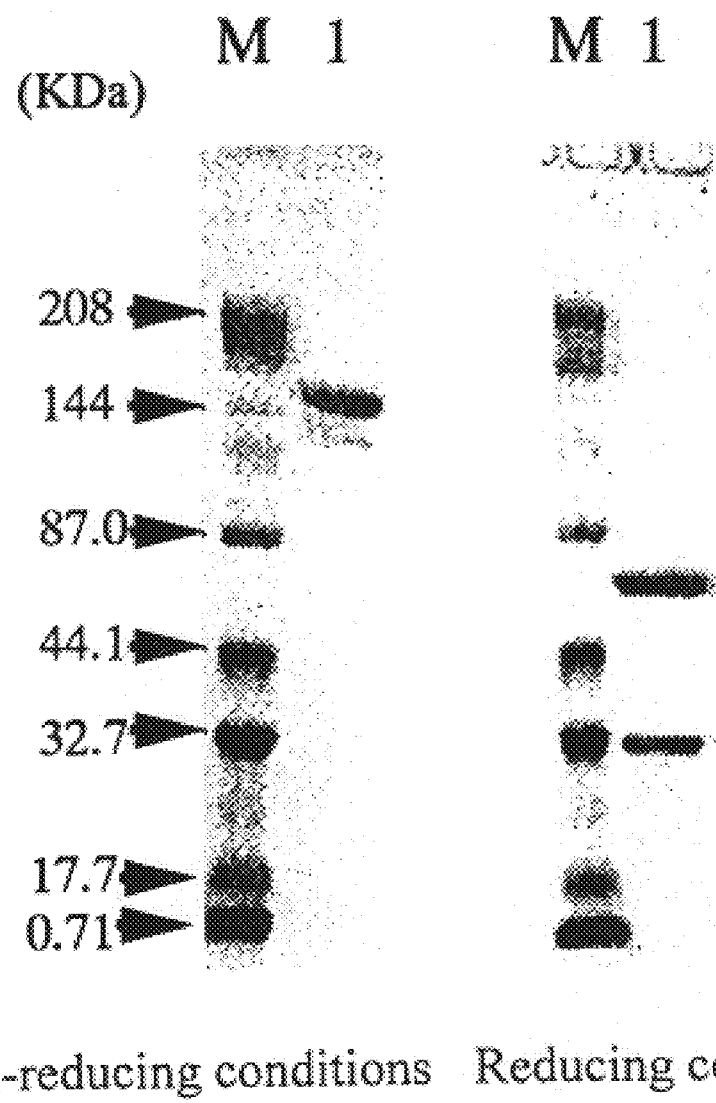
FIG. 47 shows SDS-PAGE (on 4–15% gradient gel) electrophoresis patterns of anti-human IL-5R α chain human CDR-grafted antibody KM8397. The left of the Figure shows the pattern of electrophoresis under non-reducing conditions and the right of the Figure under reducing conditions. M is a lane of molecular weight markers and 1 is a lane of KM8397.

(5) Purification of the Anti-Human IL-5R α Human CDR-Grafted Antibody KM8397 from Culture Supernatant The anti-human IL-5R α human CDR-grafted antibody-producing clone KM8397 obtained in subsection (4) of section 5 of Example 2 was cultured according to the method described in subsection (3) of section 3 of Example 2 and purified to thereby obtain about 2 mg of KM8397. About 4 μg of the purified anti-human IL-5R α human CDR-grafted antibody KM8397 was electrophoresed according to the method described in subsection (3) of section 3 of Example 2 in order to examine its molecular weight. The results are shown in FIG. 47. As shown in FIG. 47, the molecular weight of the antibody H chain is about 50 KDa and that of the antibody L chain about 25 KDa under reducing conditions. Thus, the expression of the H and L chains with the correct molecular weights was confirmed. On the other hand, under non-reducing conditions, the molecular weight of the anti-human IL-5R α human CDR-grafted antibody KM8397 is about 140 KDa. Thus, the expression of a human CDR-grafted antibody of the correct size composed of two H chains and two L chains was confirmed. Further, the N terminal amino acid sequences for the H and L chains of the purified anti-human IL-5R α human CDR-grafted antibody KM8397 were analyzed with a protein sequencer (470A, Applied Biosystems) by the automatic Edman method. As a result, the correct amino acid sequences as expected were obtained.

(6) Reactivity of the Anti-Human IL-5R α Human CDR-Grafted Antibody KM8397 with Human IL-5R α (ELISA method 2)

Figure 48:
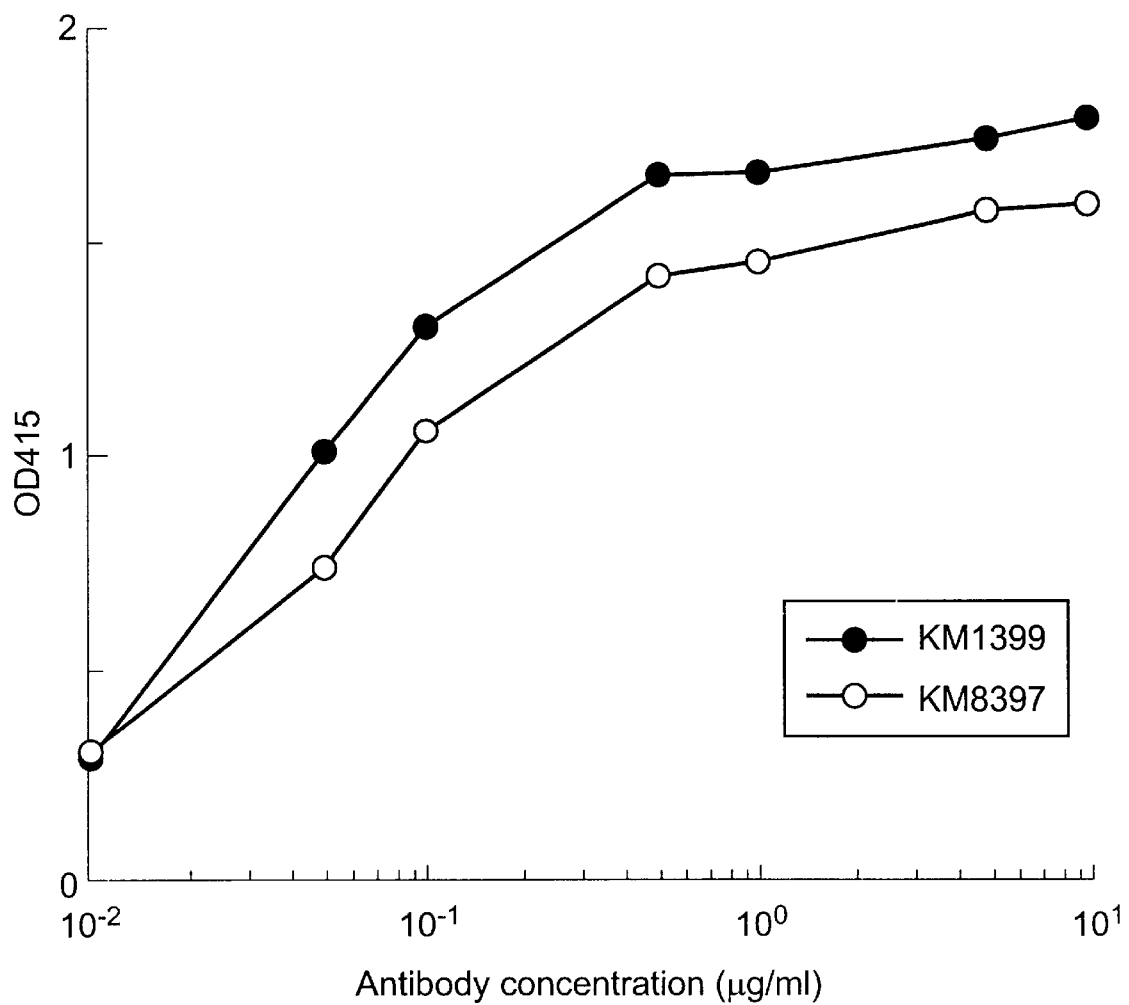
FIG. 48 shows the activities of anti-human IL-5R α chain human chimeric antibody KM1399 and anti-human IL-5R α chain human CDR-grafted antibody KM8397 in binding to a human IL-5 α chain. The vertical axis of the graph plots the activity in binding to the human IL-5 α chain and the horizontal axis, an antibody concentration. ● refers to the activity of KM1399 and ○, the activity of KM8397.

The reactivities of the anti-human IL-5R α human chimeric antibody KM1399 and the anti-human IL-5R α human CDR-grafted antibody KM8397 with human IL-5R α were determined by the ELISA method 2 described in subsection (2) of section 3 of Example 2. The results are shown in FIG. 48. As shown in FIG. 48, the reactivity of the anti-human IL-5R α human CDR-grafted antibody KM8397 with human IL-5R α was shown to be about one half the reactivity of the anti-human IL-5R α human chimeric antibody KM1399.

6. Increase in Activity by Modification of the Amino Acid Sequence for the V Region of the Anti-Human IL-5R α Human CDR-Grafted Antibody KM8397

The reactivity of the anti-human IL-5R α human CDR-grafted antibody KM8397 with human IL-5R α decreased to about one half the reactivity of the anti-human IL-5R α human chimeric antibody KM1399.

Therefore, the activity of KM8397 was increased by modifying the amino acid sequence for the V region thereof by the methods described below.

(1) Modification of the Amino Acid Sequence for VH of the Anti-Human IL-5R α Human CDR-Grafted Antibody KM8397

By mutating the amino acids of VH of the anti-human IL-5R α human CDR-grafted antibody KM8397 shown in SEQ ID NOS: 62 & 63, various modified versions of VH of the anti-human IL-5R α human CDR-grafted antibody were prepared. The amino acids to be mutated were selected at random with reference to a computerized three-dimensional structural model for the V region of the anti-human IL-5R α mouse antibody KM1259. As the method for transfecting a mutation, a plasmid comprising a cDNA coding for a modified version of VH of interest of the anti-human IL-5R α human CDR-grafted antibody was obtained by performing the procedures described in subsection (1) of section 5 of Example 2 using primers for mutation.

Actually, a plasmid, phKM1259HV1, comprising a cDNA coding for the modified version 1 of VH (hereinafter referred to as "HV.1") of the anti-human IL-5R α human CDR-grafted antibody shown in SEQ ID NOS: 73 & 74 was obtained by performing the procedures described in subsection (1) of section 5 of Example 2 using the sequence shown in SEQ ID NO: 72 as a primer for mutation and using synthetic DNAs having base sequences of SEQ ID NOS: 56,57,58,59,72 and 61, respectively. In the amino acid sequence of HV.1, tyrosine in position 95 and alanine in position 97 located in the FR of SEQ ID NOS:62 and 63 have been replaced with leucine and glycine, respectively, which are the amino acids found in the V region of the mouse antibody KM1259 H chain and this is in order to retain the reactivity with human IL-5R α recognized in the mouse antibody and the human chimeric antibody.

Further, a plasmid, phKM1259HV2, comprising a cDNA coding for the modified version 2 of VH (hereinafter referred to as "HV.2") of the anti-human IL-5R α human CDR-grafted antibody shown in SEQ ID NOS:77 & 78 was obtained by performing the procedures described in subsection (1) of section 5 of Example 2 using the sequences shown in SEQ ID NOS: 72, 75 and 76 as primers for mutation and using synthetic DNAs having base sequences of SEQ ID NOS: 56, 57, 75, 76, 72 and 61, respectively. In the amino acid sequence of HV.2, glutamic acid in position 46, threonine in position 74, tyrosine in position 95 and alanine in position 97 located in the FR of SEQ ID NO: 63 have been replaced with alanine, arginine, leucine and glycine, respectively, which are the amino acids found in the V region of the mouse antibody KM1259 H chain and this is in order to retain the reactivity with human IL-5R α recognized in the mouse antibody and the human chimeric antibody.

Further, a plasmid, phKM1259HV3, comprising a cDNA coding for the modified version 3 of VH (hereinafter referred to as "HV.3") of the anti-human IL-5R α human CDR-grafted antibody shown in SEQ ID NOS: 82 & 83 was obtained by performing the procedures described in subsection (1) of section 5 of Example 2 using the sequences shown in SEQ ID NOS: 79, 80 and 81 as primers for mutation and using synthetic DNAs having base sequences of SEQ ID NOS: 56, 57, 79, 80, 81 and 61, respectively. In the amino acid sequence of HV.3, alanine in position 40, glutamic acid in position 46, arginine in position 67, alanine in position 72, threonine in position 74, alanine in position 79, tyrosine in position 95 and alanine in position 97 located in the FR of SEQ ID NO: 63 have been replaced with arginine, alanine, lysine, serine, arginine, valine, leucine and glycine, respectively, which are the amino acids found in the V region of the mouse antibody KM1259 H chain and this is in order to retain the reactivity with human IL-5R α recognized in the mouse antibody and the human chimeric antibody.

As version advances from HV.0 to HV.4 one by one, the number of the monoclonal antibody-derived amino acids involved in the modification increases with increasing version number from HV.0 to HV.3.

(2) Modification of the Amino Acid Sequence for VL of the Anti-Human IL-5R α Human CDR-Grafted Antibody KM8397

By mutating the amino acids of VL of the anti-human IL-5R α human CDR-grafted antibody KM8397 shown in SEQ ID NO: 71, various modified versions of VL of the anti-human IL-5R α human CDR-grafted antibody were prepared. The amino acids to be mutated were selected at random with reference to a computerized 3D structural model for the V region of the anti-human IL-5R α antibody KM1259. As the method for transfecting a mutation, a plasmid comprising a cDNA coding for a modified version of VL of interest of the anti-human IL-5R α human CDR-grafted antibody was obtained by performing the procedures described in subsection (1) of section 5 of Example 2 using primers for mutation.

Actually, a plasmid, phKM1259LV1, comprising a cDNA coding for the modified version 1 of VL (hereinafter referred to as "LV.1") of the anti-human IL-5R α human CDR-grafted antibody shown in SEQ ID NOS: 87 & 88 was obtained by performing the procedures described in subsection (1) of section 5 of Example 2 using the sequences shown in SEQ ID NO: 84, 85 and 86 as primers for mutation and using synthetic DNAs having base sequences of SEQ ID NOS: 64, 65, 84, 85, 68 and 86, respectively. In the amino acid sequence of LV.1, glutamine in position 37, lysine in position 45 and phenylalanine in position 98 located in the FR of SEQ ID NO: 71 have been replaced with arginine, glutamic acid and valine, respectively, which are the amino acids found in the V region of the monoclonal antibody KM1259 L chain and this is in order to retain the reactivity with human IL-5R α recognized in the monoclonal antibody and the human chimeric antibody.

Further, a plasmid, phKM1259LV2, comprising a cDNA coding for the modified version 2 of VL (hereinafter referred to as "LV.2") of the anti-human IL-5R α human CDR-grafted antibody shown in SEQ ID NOS: 91 & 92 was obtained by performing the procedures described in subsection (1) of section 5 of Example 2 using the sequences shown in SEQ ID NOS: 85, 86, 89 and 90 as primers for mutation and using synthetic DNAs having base sequences of SEQ ID NOS: 64, 65, 89, 85, 90 and 86, respectively. In the amino acid sequence for LV.2, threonine in position 22, glutamine in position 37, lysine in position 45, serine in position 77 and phenylalanine in position 98 located in the FR of SEQ ID NO: 71 have been replaced with glycine, arginine, glutamic acid, aspartic acid and valine, respectively, which are the amino acids found in the V region of the monoclonal antibody KM1259 L chain and this is in order to retain the reactivity with human IL-5R α recognized in the monoclonal antibody and the human chimeric antibody.

Further, a plasmid, phKM1259LV3, comprising a cDNA coding for the modified version 3 of VL (hereinafter referred to as "LV.3") of the anti-human IL-5R α human CDR-grafted antibody shown in SEQ ID NOS: 97 & 98 was obtained by performing the procedures described in subsection (1) of section 5 of Example 2 using the sequences shown in SEQ ID NOS: 85, 93, 94, 95 and 96 as primers for mutation and using synthetic DNAs having base sequences of SEQ ID NOS: 64, 93, 94, 85, 95 and 96, respectively. In the amino acid sequence of LV.3, serine in position 7, proline in position 8, threonine in position 22, glutamine in position 37, glutamine in position 38, lysine in position 45, serine in position 77, tyrosine in position 87 and phenylalanine in position 98 located in the FR of SEQ ID NO: 71 have been replaced with alanine, threonine, glycine, arginine, lysine, glutamic acid, aspartic acid, phenylalanine and valine, respectively, which are the amino acids found in the V region of the monoclonal antibody KM1259 L chain and this is in order to retain the reactivity with human IL-5R α recognized in the monoclonal antibody and the human chimeric antibody.

Further, a plasmid, phKM1259LV4, comprising a cDNA coding for the modified version 4 of VL (hereinafter referred to as "LV.4") of the anti-human IL-5R α human CDR-grafted antibody shown in SEQ ID NOS: 102 and 103 was obtained by performing the procedures described in subsection (1) of section 5 of Example 2 using the sequences shown in SEQ ID NOS: 93, 96, 99, 100 and 101 as primers for mutation and using synthetic DNAs having base sequences of SEQ ID NOS: 64, 93, 99, 100, 101 and 96, respectively. In the amino acid sequence of LV.4, serine in position 7, proline in position 8, threonine in position 22, glutamine in position 37, glutamine in position 38, proline in position 44, lysine in position 45, phenylalanine in position 71, serine in position 77, tyrosine in position 87 and phenylalanine in position 98 located in the FR of SEQ ID NO: 71 have been replaced with alanine, threonine, glycine, arginine, lysine, valine, glutamic acid, tyrosine, aspartic acid, phenylalanine and valine, respectively, which are the amino acids found in the V region of the monoclonal antibody KM 1259 L chain and this is in order to retain the reactivity with human IL-5R α recognized in the monoclonal antibody and the human chimeric antibody.

As a result, as version advances from LV.0 to HV.4 one by one, the number of the monoclonal antibody-derived amino acids involved in the modification increases with increasing version number from LV.0 to LV.4.

(3) Preparation of Anti-Human IL-5R α Human CDR-Grafted Antibodies having Various Modified Versions of V Region Using the humanized antibody expression vector pKANTEX93 constructed in section 1 of Example 2 and the various plasmids comprising cDNAs coding for various modified versions of the V region of the anti-human IL-5R α human CDR-grafted antibody obtained in subsections (1) and (2) of section 5 of Example 2, vectors for the expression of anti-human IL-5R α human CDR-grafted antibodies having various modified versions of the V region were constructed by the method described in subsection (3) of section 5 of Example 2. Table 3 shows combinations of various modified versions of the V region used in the expression vectors constructed and the designation of these expression vectors.

Figure 49:
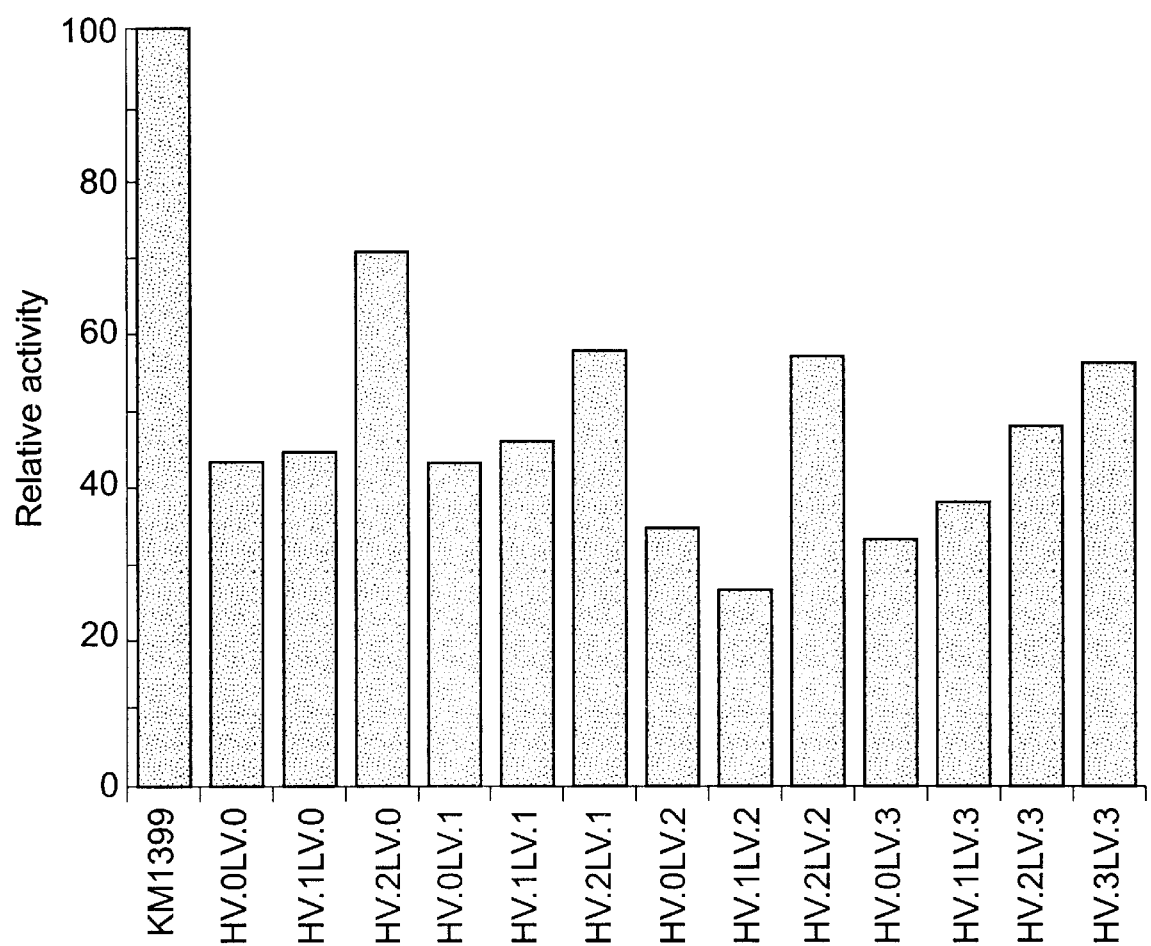
FIG. 49 shows the results of evaluation of the activities of various modified versions of anti-human IL-5R α chain human CDR-grafted antibodies in transient expression-culture supernatants in inhibiting binding of human IL-5 to a human IL-5 α chain. The vertical axis of the graph plots the inhibitory activity and the horizontal axis indicates the names of samples. The inhibitory activity is expressed in relative terms, with the activity of chimeric antibody KM1399 taken as 100.

Among these expression vectors, a total of 13 vectors pKANTEX1259HV0LV0, pKANTEX1259HV1LV0, pKANTEX1259HV2LV0, pKANTEX1259HV0LV1, pKANTEX1259HV1LV1, pKANTEX1259HV2LV1, pKANTEX1259HV0LV2, pKANTEX1259HV1LV2, pKANTEX1259HV2LV2, pKANTEX1259HV0LV3, pKANTEX1259HV2LV3, pKANTEX1259HV2LV3, and pKANTEX1259HV3LV3 were modified into transient expression vectors by the method described in subsection (1) of section 4 of Example 2. Using these transient expression vectors and in accordance with the method described in subsection (2) of section 4 of Example 2, the transient expression of anti-human IL-5R α human CDR-grafted antibodies having various modified versions of the V region was performed. As a control, the transient expression of the anti-human IL-5R α human chimeric antibody KM1399 was performed simultaneously. The binding activity for human IL-5R α of an antibody in the culture supernatant was determined by the ELISA method 1 described in subsection (2) of section 3 of Example 2, and the antibody concentration in the culture supernatant was determined by the ELISA method described in subsection (3) of section 4 of Example 2. Using two ELISA methods, the activities of anti-human IL-5R α human CDR-grafted antibodies having various modified versions of the V region are shown in FIG. 49 as relative values in which the activity of the human chimeric antibody KM1399 is taken as 100. In FIG. 49, various modified versions of anti-human IL-5R α human CDR-grafted antibodies are represented by a combination of VH and VL. From FIG. 49, a tendency is recognized with VH such that the activity increases as modification proceeds from HV.0 to HV.3. With respect to VL, a tendency is recognized such that the reactivity is high in LV.0 and LV.3 but low in LV.1 and LV.2. Then, a more accurate activity evaluation of anti-human IL-5R α human CDR-grafted antibodies comprising combinations of LV.0 and various modified VH; LV.3 and HV.0; LV.3 and HV.3; and LV.4 which is a further modified version of LV.3, and various modified VH was performed using purified antibodies as follows.

Briefly, using the 10 expression vectors for anti-human IL-5R α human CDR-grafted antibodies described above, i.e., pKANTEX1259HV0LV0, pKANTEX1259HV1LV0, pKANTEX1259HV2LV0, pKANTEX1259HV3LV0, pKANTEX1259HV0LV3, pKANTEX1259HV3LV3, pKANTEX1259HV0LV4, pKANTEX1259HV1LV4, pKANTEX1259HV2LV4, and pKANTEX1259HV3LV4 and according to the method described in subsection (2) of section 3 of Example 2, antibodies of interest were expressed in YB2/0 cells to thereby obtain transformant producing various anti-human IL-5R α human CDR-grafted antibodies at a productivity level of 2–4 μg/$10^6$ cells/24 hr. The transformants producing various anti-human IL-5R α human CDR-grafted antibodies were cultured and purified by the methods described in subsection (3) of section 3 of Example 2 to thereby obtain 1–2 mg each of various anti-human IL-5R α human CDR-grafted antibodies. About 4 μg each of the various purified anti-human IL-5R α human CDR-grafted antibodies were electrophoresed by the method described in subsection (3) of section 3 of Example 2 to measure their molecular weights. Under reducing conditions, the molecular weight of the antibody H chain is about 50 kDa and that of the antibody L chain about 25 kDa in each of the anti-human IL-5R α human CDR-grafted antibodies. Thus, the expression of H and L chains with the correct molecular weights was confirmed. Under non-reducing conditions, the molecular weight of the antibody is about 140 kDa in each of the anti-human IL-5R α human CDR-grafted antibodies. Thus, the expression of human CDR-grafted antibodies each composed of two H chains and two L chains of the correct size was confirmed. Further, the N terminal amino acid sequences for the H and L chains of the various purified anti-human IL-5R α human CDR-grafted antibodies were analyzed with a protein sequencer (470A, Applied Biosystems) by the automatic Edman method. As a result, the correct amino acid sequences as expected were obtained in each of those antibodies.

Figure 50A:
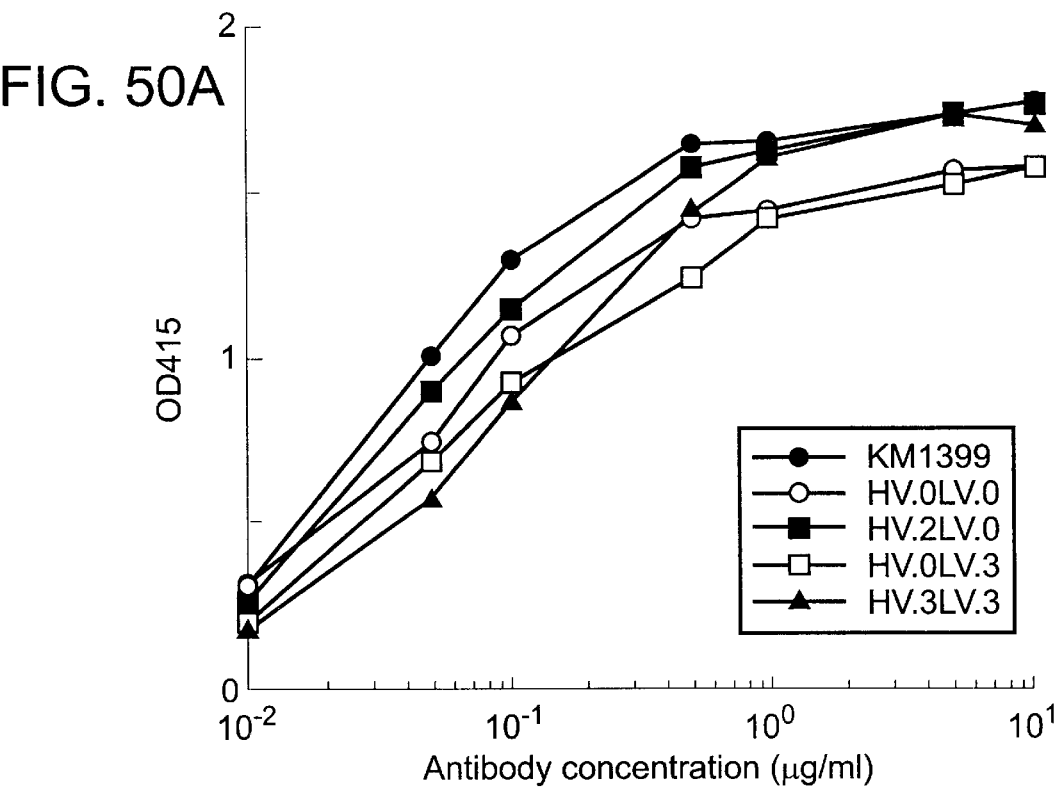
FIGS. 50A–B show the activities of various modified versions of anti-human IL-5R α chain human CDR-grafted antibodies in binding to a human IL-5 α chain. The vertical axis of each graph plots the activity in binding to the human IL-5 α chain and the horizontal axis, the antibody concentration. In the upper graph, ● refers to the activity of KM1399; ○, HV.0LV.0; ■, HV.2LV.0; □, HV.0LV.3; and ▼, HV.3LV.3. In the lower graph, ● refers to the activity of KM1399; ○, HV.0LV.0; ■, HV.3LV.0; □, HV.0LV.4; ▼, HV.1LV.4, △, HV.2LV.4; and x, H V.3LV.4.
Figure 50B:
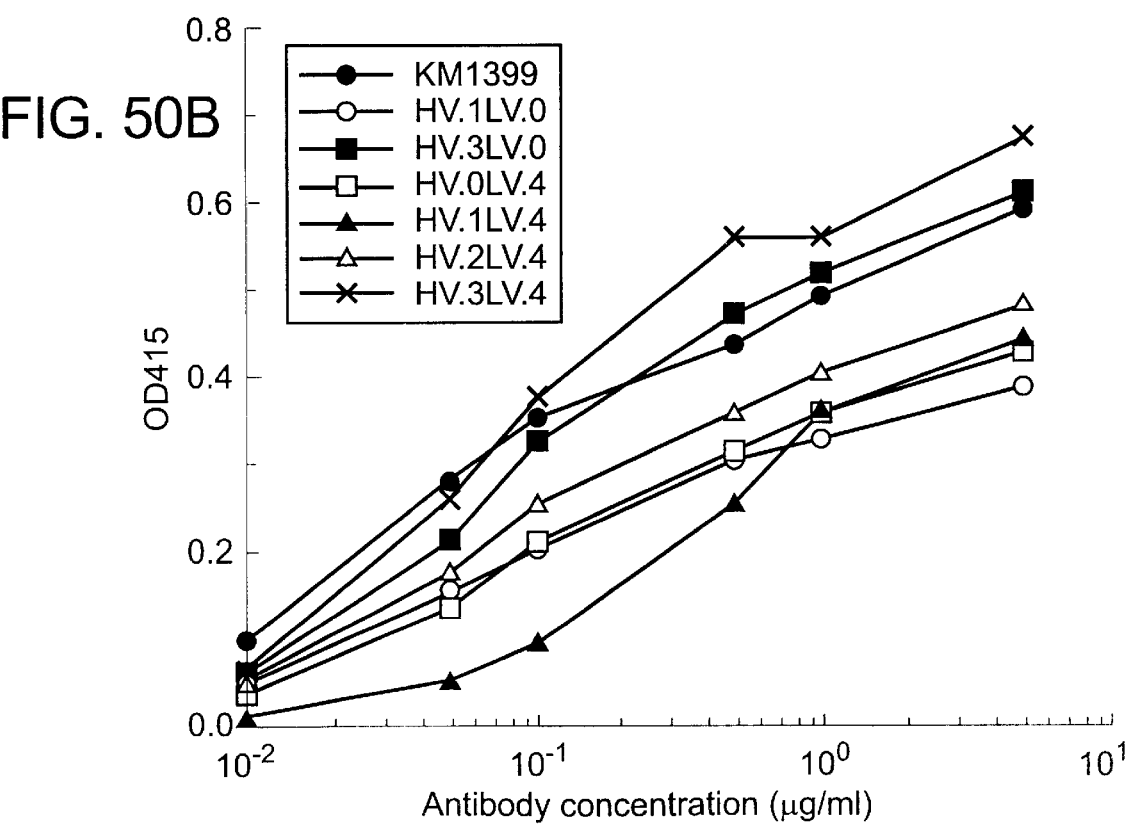

The reactivity with human IL-5R α in the various purified anti-human IL-5R α human CDR-grafted antibodies obtained above was determined by the ELISA method 2 described in subsection (2) of section 3 of Example 2 and the results are shown in FIG. 50. In FIG. 50, various modified versions of anti-human IL-5R α human CDR-grafted antibodies are represented by a combination of VH and VL. As shown in FIG. 50, of the 10 purified anti-human IL-5R α human CDR-grafted antibodies, HV.3LV.0 and HV.3LV.4 proved to have a reactivity with human IL-5R α as strong as the reactivity of the anti-human IL-5R α human chimeric antibody KM1399.

When the amino acid sequences for the anti-human IL-5R α human CDR-grafted antibodies HV.3LV.0 and HV.3LV.4 exhibiting a reactivity with human IL-5R α as strong as the reactivity of the anti-human IL-5R α human chimeric antibody KM1399 are compared, both have the same amino acid sequence which is shown as HV.3 for VH but they have different amino acid sequences for VL, i.e., shown as LV.0 and LV.4. While LV.0 is a sequence obtained by simply grafting the CDR to the FR of a human antibody, LV.4 is a sequence obtained by converting 11 amino acid residues within the FR of a human antibody to those amino acid residues found in the monoclonal antibody in order to increase activity. However, from the results shown in FIG. 50, the modification of amino acid residues makes little contributions to the increase of activity actually. Based on these facts, HV.3LV.0 which has a reactivity with human IL-5Rα as strong as the reactivity of the anti-human IL-5R α human chimeric antibody KM1399 and which is expected to be less antigenic against humans since the replacement of amino acids derived from the monoclonal antibody is less, has been selected as an anti-human IL-5R α human CDR-grafted antibody. HV.3LV.0 was designated as KM8399, and the transformant KM8399 producing the anti-human IL-5Rα human CDR-grafted antibody KM8399 was deposited with the National Institute of Bioscience and Human-Technology, Agency of Industrial Science and Technology on Sep. 3, 1996 under accession number FERM BP-5648.

In the preparation of the anti-human IL-5R α human CDR-grafted antibody KM8399, the following matters have been taken into consideration. As seen in the preparation of other human CDR-grafted antibodies, the activity in the anti-human IL-5R α human CDR-grafted antibody KM8397, which was obtained by simply grafting only the CDR of the anti-human IL-5R α monoclonal antibody KM1259 into the FR of a human antibody, decreased to about ½ of the activity of the monoclonal antibody KM1259. Hence, several amino acids within the FR of the V regions of H and L chains were modified into the amino acids found in the monoclonal antibody KM1259, and examined for an increase in activity. With respect to VH, the activity increased as the modification proceeded. On the other hand, with respect to VL, the modification of a small number of amino acids resulted in a decrease in activity; although the activity can be increased by increasing the number of amino acids modified, the activity only rose to the level of unmodified VL. Although the cause of this fact cannot be completely clarified without more detailed analysis (e.g., X-ray crystal analysis), the interaction between the VH and VL of an antibody is probably involved and the results of such interaction would vary depending on the antibody used. Because of such problems, no efficient method has yet been established for preparing a human CDR-grafted antibody of which is applicable to any antibody and trials and errors as made in the present Example are required. With such trials and errors being accumulated, a more efficient method for preparing human CDR-grafted antibodies could be established. The present Example shows the first case of successful preparation of an anti-human IL-5R α human CDR-grafted antibody and thus provides suggestions for efficient preparation of human CDR-grafted antibodies.

7. Preparation of Anti-Human IL-5R α Humanized Antibodies of Human Antibody IgG4 Subclass (1) Isolation and Analysis of a cDNA coding for the C Region (Cγ4) of Human Antibody IgG4 Subclass 1.1×10⁷ B cells were separated from 200 ml of peripheral blood from a healthy volunteer using anti-CD19 antibody coated Dynabeads (DYNABEADS M-450 Pan-B(CD19); Nippon Dyner) and DETACHaBEAD (Nippon Dyner) in accordance with the attached instructions. Then, MRNA was obtained from the separated cells using Quick Prep mRNA Purification Kit (Pharmacia Biotech) in accordance with the attached instructions. From all of the mRNA obtained, cDNA was synthesized using Time Saver cDNA Synthesis Kit (Pharmacia Biotech) in accordance with the attached instructions. Then PCR was performed as described in subsection (1) of section 5 of Example 2 using all of the cDNA obtained above and using, as primers, synthetic DNAs shown in SEQ ID NOS: 104 and 105 which are homologous to the 5' and 3' sides of a cDNA coding for human antibody Cγ4 [Nucleic Acid Research, 14, 1789 (1986)]. The 5' side and 3' side primers used in the PCR had been designed to have recognition sequences for the restriction enzymes ApaI and BamHI at their 5' terminals so that the cDNA to be obtained could be easily inserted into a humanized antibody expression vector. The reaction mixture after the PCR was purified with QIAquick PCR Purification Kit (Qiagen) and then added to 30 μl of a buffer containing 10 mM Tris-HCl (pH 7.5), 10 mM magnesium chloride and 1 mM DTT. To the resultant mixture, 10 units of the restriction enzyme ApaI (Takara Shuzo) were added and reacted at 37° C. for 1 hour. The reaction mixture was ethanol-precipitated and the precipitate was added to 10 μl of a buffer containing 20 mM Tris-HCl (pH 8.5), 100 mM potassium chloride, 10 mM magnesium chloride and 1 mM DTT, to which 10 units of the restriction enzyme BamHI (Takara Shuzo) were added and reacted at 30° C. for 1 hour. The reaction mixture was subjected to agarose gel electrophoresis to thereby recover about 0.5 μg of an approx. 1.0 kb ApaI-BamHI fragment.

Subsequently, 3 μg of plasmid pBluescriptSK(−) (Stratagene) were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the precipitate was added to 10 μl of a buffer containing 20 mM Tris-HCl (pH 8.5), 100 mM potassium chloride, 10 mM magnesium chloride and 1 mM DTT, to which 10 units of the restriction enzyme BamHI (Takara Shuzo) were added and reacted at 30° C. for 1 hour. The reaction mixture was subjected to agarose gel electrophoresis to thereby recover about 2 μg of an approx. 3.0 kb ApaI-BamHI fragment.

Figure 51:
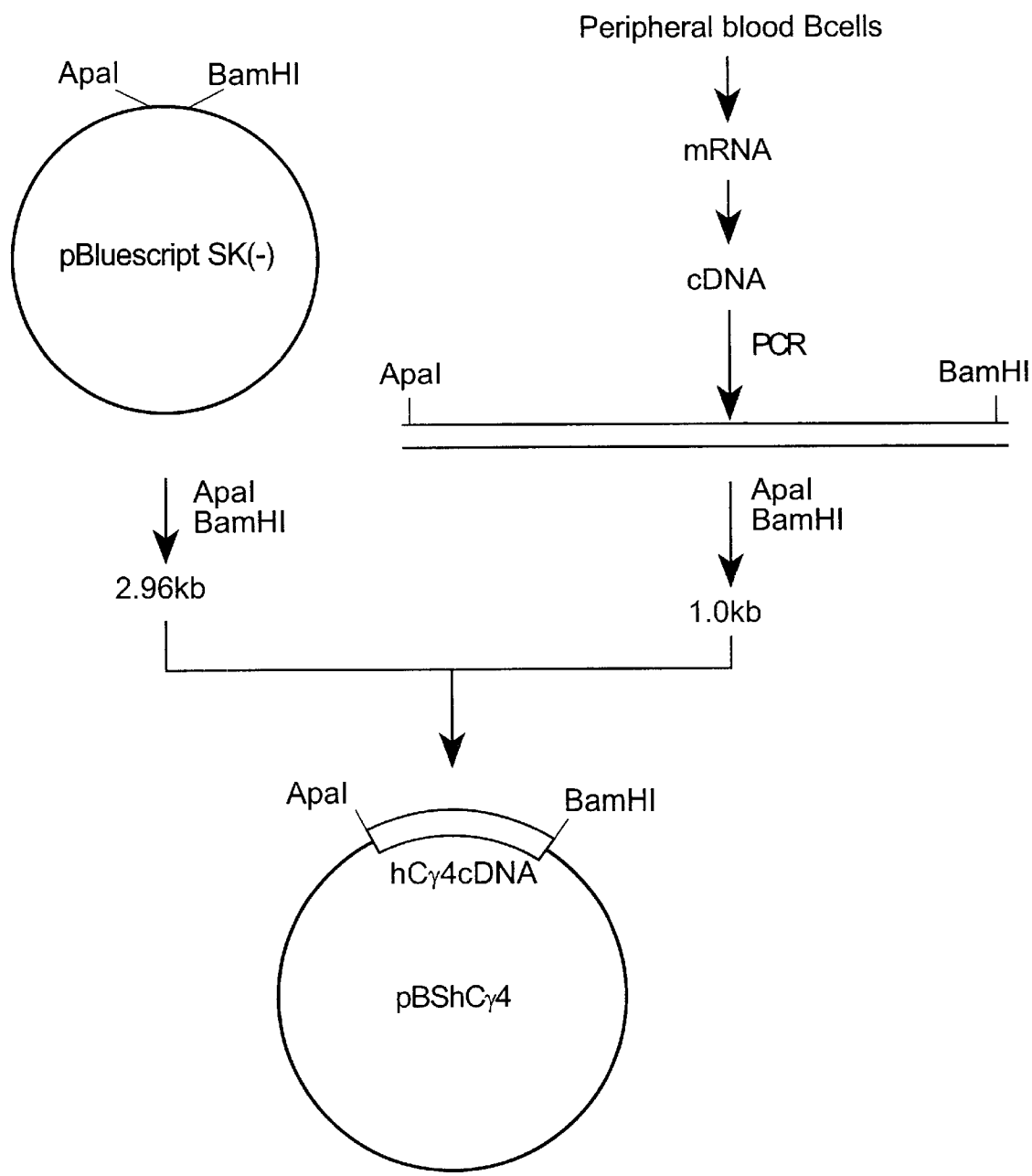
FIG. 51 shows steps for constructing plasmid pBShCγ4.

Then, 0.1 μg of the PCR-amplified ApaI-BamHI fragment obtained above and 0.1 μg of the ApaI-BamHI fragment from pBluescriptSK(−) obtained above were added to sterilized water to give a total volume of 20 μl and ligated using Ready-To-Go T4 DNA Ligase (Pharmacia Biotech). Using the thus obtained recombinant plasmid DNA solution, E. coli HB101 was transformed. From 10 transformant clones, each plasmid DNA was prepared and the base sequence thereof was determined. As a result, plasmid pBShCγ4 shown in FIG. 51 comprising a cDNA of interest coding for human antibody Cγ4 was obtained.

(2) Construction of an Expression Vector for Anti-Human IL-5R α Humanized Antibodies of Human Antibody IgG4 Subclass An expression vector for anti-human IL-5R α humanized antibodies of human antibody IgG4 subclass was constructed as described below using plasmid pBShCγ4 comprising a cDNA coding for human antibody Cγ4 obtained in subsection (1) of section 7 of Example 2, expression vector pKANTEX1259 for the anti-human IL-5R α human chimeric antibody KM1399 obtained in subsection (1) of section 3 of Example 2 and expression vector pKANTEX1259HV3LV0 for the anti-human IL-5R α human CDR-grafted antibody KM8399 obtained in subsection (3) of section 6 of Example 2.

Briefly, 4 μg of plasmid pBShCγ4 comprising a cDNA coding for human antibody Cγ4 were added to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. The reaction mixture was ethanol-precipitated, and the precipitate was added to 10 μl of a buffer containing 20 mM Tris-HCl (pH 8.5), 100 mM potassium chloride, 10 mM magnesium chloride and 1 mM DTT, to which 10 units of the restriction enzyme BamHI (Takara Shuzo) were added and reacted at 30° C. for 1 hour. The reaction mixture was subjected to agarose gel electrophoresis to thereby recover about 1 μg of an approx. 1.0 kb ApaI-BamHI fragment.

Subsequently, 3 μg each of expression vector pKANTEX1259 for the anti-human IL-5R α human type chimeric antibody KM1399 and expression vector pKANTEX1259HV3LV0 for the anti-human IL-5R α human CDR-grafted antibody KM8399 were added individually to 10 μl of a buffer containing 10 mM Tris-HCl (pH 7.5), 10 mM magnesium chloride and 1 mM DTT, to which 10 units of the restriction enzyme ApaI (Takara Shuzo) were added and reacted at 37° C. for 1 hour. Both reaction mixtures were ethanol-precipitated, and the precipitates were individually added to 10 μl of a buffer containing 20 mM Tris-HCl (pH 8.5), 100 mM potassium chloride, 10 mM magnesium chloride and 1 mM DTT, to which 10 units of the restriction enzyme BamHI (Takara Shuzo) were added and reacted at 30° C. for 1 hour. Both reaction mixtures were subjected to agarose gel electrophoresis to thereby recover about 2 μg of an approx. 12.59 kb ApaI-BamHI fragment from each reaction mixture.

Figure 52:
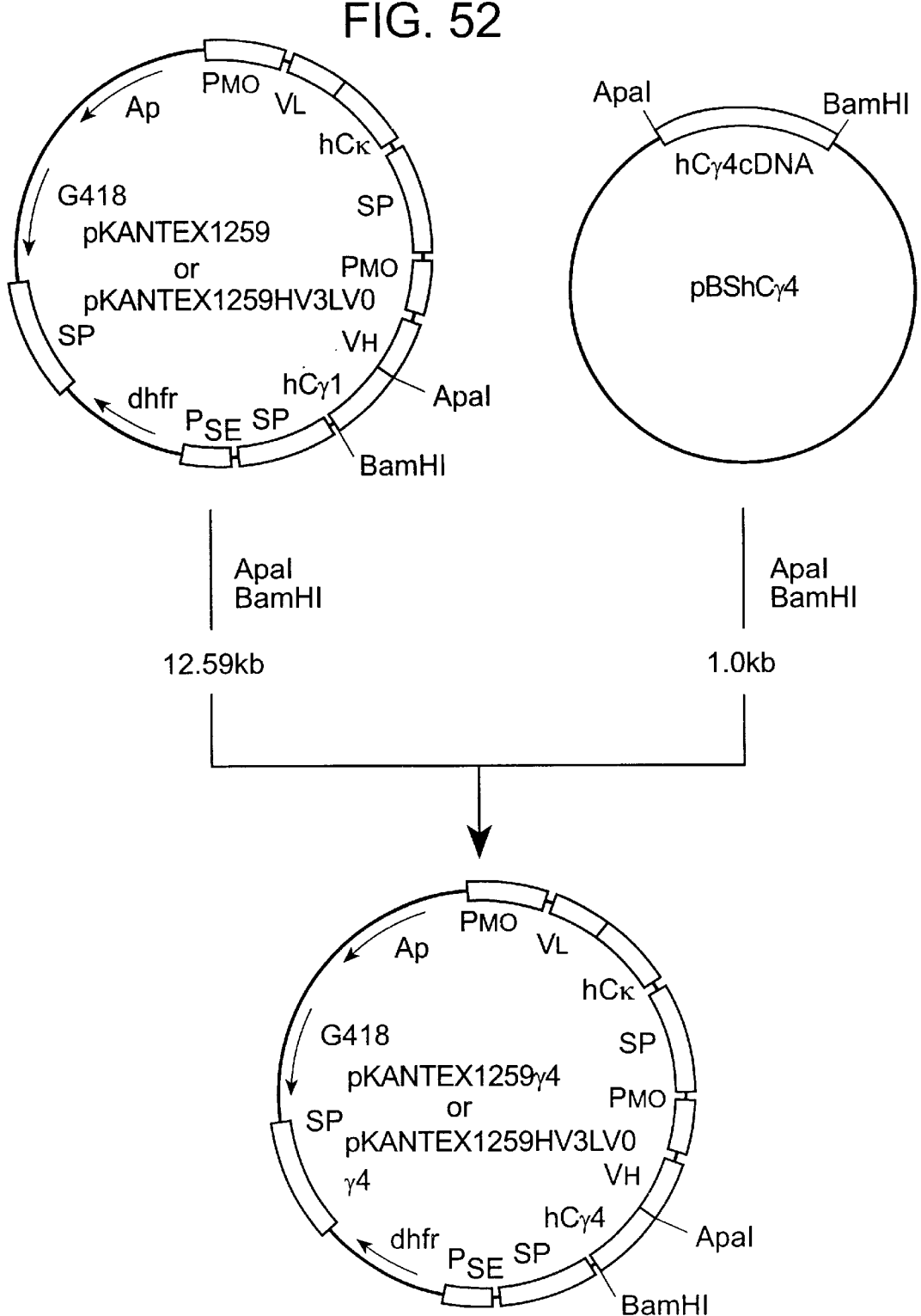
FIG. 52 shows steps for constructing plasmids pKANTEX1259γ4 and pKANTEX1259HV3LV0γ4.

A combination of 0.1 μg of the ApaI-BamHI fragment from plasmid pBShCγ4 and 0.1 μg of the ApaI-BamHI fragment from plasmid pKANTEX1259 and another combination of 0.1 μg of the ApaI-BamHI fragment from plasmid pBShCγ4 and 0.1 μg of the ApaI-BamHI fragment from plasmid pKANTEX1259HV3LV0 were added individually to sterilized water to give a total volume of 20 μl and ligated using Ready-To-Go T4 DNA Ligase (Pharmacia Biotech). Using each of the thus obtained recombinant plasmid DNA solutions, *E. coli* HB101 was transformed to thereby obtain expression vector pKANTEX1259γ4 for an anti-human IL-5R α human chimeric antibody of IgG4 subclass and expression vector pKANTEX1259HV3LV0γ4 for an anti-human IL-5R α human CDR-grafted antibody of IgG4 subclass shown in FIG. 52.

(3) Expression of Anti-Human IL-5R α Humanized Antibodies in Rat Myeloma YB2/0 Cells (ATCC CRL1581)

The expression of anti-human IL-5R α humanized antibodies in YB2/0 Cells was performed by the method described in subsection (2) of section 3 of Example 2 using the expression vector pKANTEX1259γ4 for an anti-human IL-5R α human chimeric antibody of IgG4 subclass and the expression vector pKANTEX1259HV3LV0γ4 for an anti-human IL-5R α human CDR-grafted antibody of IgG4 subclass obtained in subsection (2) of section 7 which were obtained in Example 2.

As a result, as a transformant producing an anti-human IL-5R α human chimeric antibody of IgG4 subclass, KM7399 (FERM BP-5649) was obtained and the anti-human IL-5R α human chimeric antibody of IgG4 subclass produced by this strain was designated as KM7399. The transformant KM7399 producing the anti-human IL-5R α human chimeric antibody KM7399 was deposited with the National Institute of Bioscience and Human-Technology, Agency of Industrial Science and Technology on Sep. 3, 1996 under accession number FERM BP-5649. The productivity of the anti-human IL-5R α human chimeric antibody KM7399 in the transformant KM7399 was about 3 μg/$10^6$ cells/24 hr.

Also, as a transformant producing an anti-human IL-5R α human CDR-grafted antibody of IgG4 subclass, KM9399 (FERM BP-5647) was obtained and the anti-human IL-5R α human CDR-grafted antibody of IgG4 subclass produced by this strain was designated as KM9399. The productivity of the anti-human IL-5R α human CDR-grafted antibody KM9399 in the transformant KM9399 was about 7 μg/$10^6$ cells/24 hr. The transformant KM9399 producing the anti-human IL-5R α human CDR-grafted antibody KM9399 was deposited with the National Institute of Bioscience and Human-Technology, Agency of Industrial Science and Technology on Sep. 3, 1996 under accession number FERM BP-5647.

(4) Purification of the Anti-Human IL-5R α Humanized Antibodies of Human Antibody IgG4 Subclass from Culture Supernatants The transformant KM7399 producing the anti-human IL-5R α human chimeric antibody of IgG4 subclass and the transformant KM9399 producing the anti-human IL-5R α human CDR-grafted antibody of IgG4 subclass which were obtained in subsection (3) of section 7 of Example 2 were cultured and purified according to the methods described in subsection (3) of section 3 of Example 2, to thereby obtain about 1 mg of KM7399 and about 5 mg of KM9399. About 4 μg each of the purified anti-human IL-5R α humanized antibodies of IgG4 subclass KM7399 and KM9399 were electrophoresed according to the method described in subsection (3) of section 3 of Example 2 to examine their molecular weights. The results are shown in FIG. 53. As shown in FIG. 53, the molecular weight of the H chain of each antibody is about 50 kDa and that of the L chain of each antibody about 25 kDa under reducing conditions. Thus, the expression of H chains and L chains of the correct molecular weight was confirmed. Under non-reducing conditions, the molecular weight of each anti-human IL-5R α humanized antibody is about 140 kDa. Thus, the expression of a human CDR-grafted antibody of the correct size composed of two H chains and two L chains was confirmed. Further, the N terminal amino acid sequences for the H and L chains of the purified anti-human IL-5R α humanized antibodies of IgG4 subclass KM7399 and KM9399 were analyzed with a protein sequencer (470A, Applied Biosystems) by the automatic Edman method. As a result, the correct amino acid sequences as expected were obtained.

(5) Reactivities of the Anti-Human IL-5R α Humanized Antibodies of Human Antibody IgG4 Subclass with Human IL-5R α (ELISA method 2)

Figure 54:
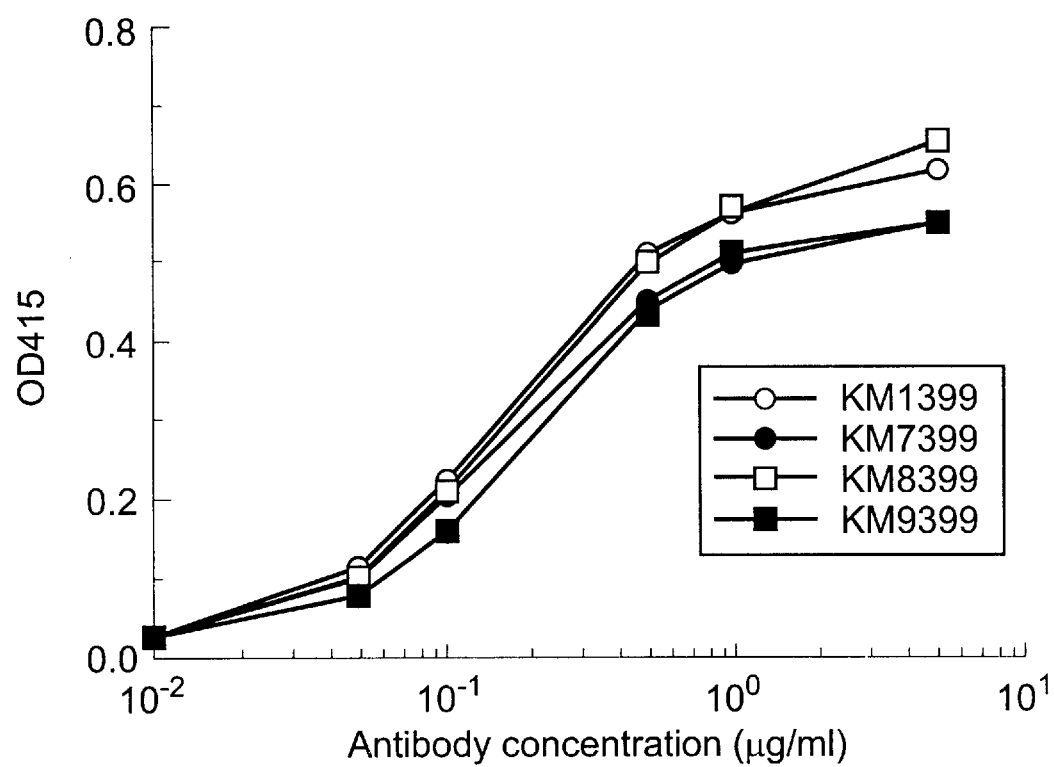
FIG. 54 shows the activity of anti-human IL-5R α chain human chimeric antibody KM1399 of a human antibody IgG1 subclass, human IL-5R α chain human chimeric antibody KM7399 of a human antibody IgG4 subclass, anti-human IL-5R α chain human CDR-grafted antibody KM8399 of a human antibody IgG1 subclass and anti-human IL-5R α chain human CDR-grafted antibody KM9399 of a human antibody IgG4 subclass in binding to a human IL-5 α chain. The vertical axis of the graph plots the activity of binding to the human IL-5 α chain and the horizontal axis, the antibody concentration. ○ refers to the activity of KM1399; ●, KM7399; □, KM8399; and ■, KM9399.

The reactivities of the anti-human IL-5R α human chimeric antibody of human antibody IgG1 subclass KM1399, the anti-human IL-5R α human CDR-grafted antibody of human antibody IgG1 subclass KM8399, the anti-human IL-5R α human chimeric antibody of IgG4 subclass KM7399 and the anti-human IL-5R α human CDR-grafted antibody of IgG4 subclass KM9399 with human IL-5R α were determined by the ELISA method 2 described in subsection (2) of section 3 of Example 2. The results are shown in FIG. 54. As shown in FIG. 54, the anti-human IL-5R α humanized antibodies of human antibody IgG4 subclass proved to have a reactivity with human IL-5R α as strong as the reactivity of the anti-human IL-5R α humanized antibodies of IgG1 subclass.

Example 3

1. Confirmation of the Specificity of Anti-hIL-5R α Antibodies

The specificity of anti-hIL-5R α monoclonal antibodies and anti-hIL-5R α humanized antibodies was confirmed by the following procedures using immunocyte staining.

Briefly, $5 \times 10^5$ cells obtained by transfecting a human IL-5R gene into CTLL-2 cells (ATCC TIB 214) [hereinafter referred to as "CTLL-2(h5R)"] [J. Exp. Med., 177, 1523 (1993)] or $5 \times 10^5$ CTLL-2 cells as a control were suspended in an immunocyte staining buffer (PBS containing 1% BSA, 0.02% EDTA and 0.05% sodium azide) and dispensed into a round bottom 96-well plate (100 μl/well). After centrifuging at 350×g for 1 minute at 4° C., the supernatant was discarded. Then, 50 μl of the immunocyte staining buffer containing 10 μg/ml of an hIL-5R α antibody were added to each well and reacted at 4° C. for 30 minutes. After the reaction, the immunocyte staining buffer was added (200 μl/well) and centrifuged at 350×g for 1 minute at 4° C. and then the supernatant was removed to wash the cells. The washing operation was further repeated twice. Thereafter, 50 μl of the immunocyte staining buffer containing FITC-labeled anti-mouse immunoglobulin antibody or FITC-labeled anti-human immunoglobulin antibody (both manufactured by Wako Pure Chemical Industries, Ltd.) diluted 30 folds with a staining buffer were added to each well and reacted at 4° C. for 30 minutes. After the reaction, a similar washing operation was repeated three times. Then, the cells were analyzed with a flow cytometer (Coulter).

Figure 55:
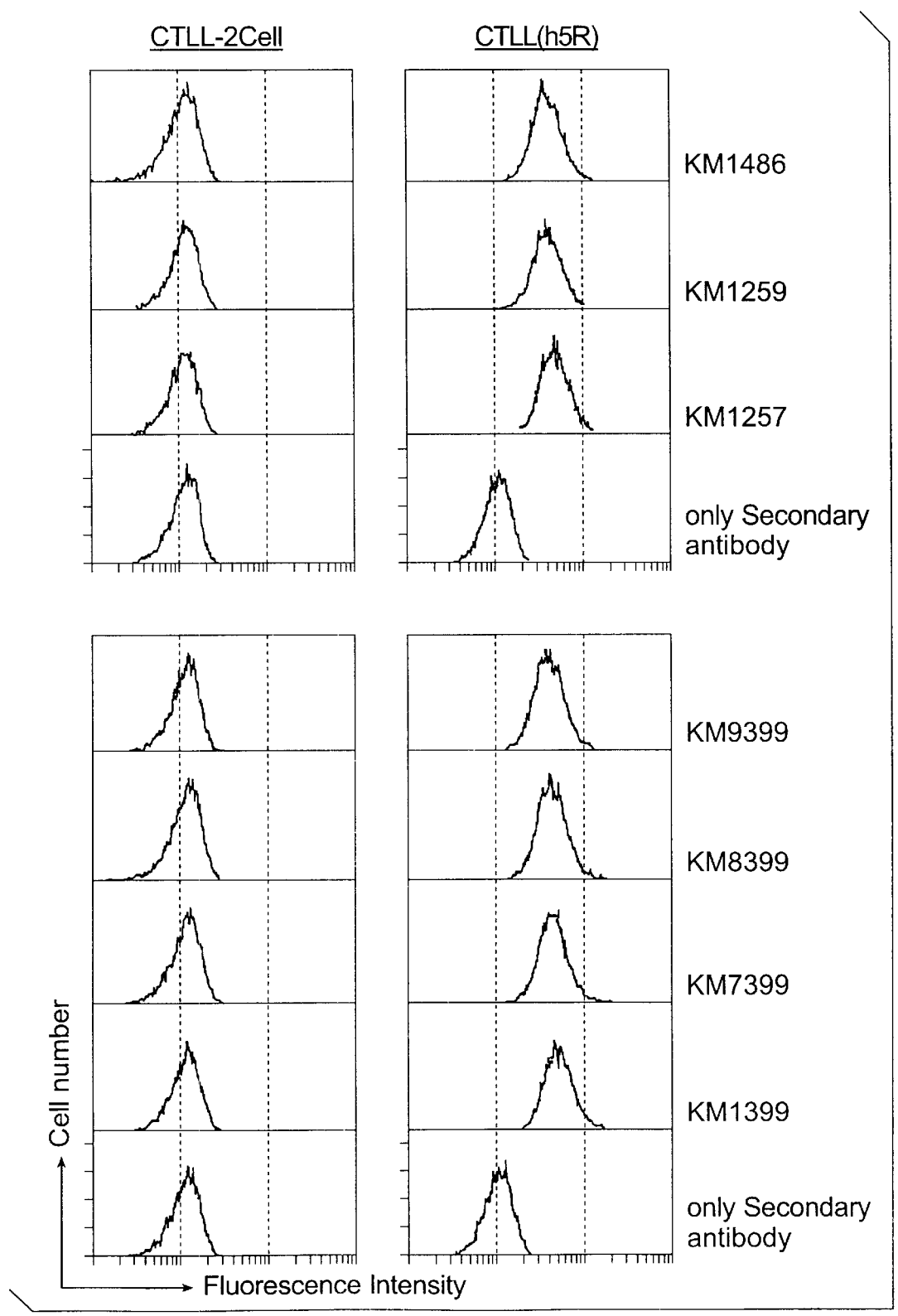
FIG. 55 shows the results of flowcytometric analysis of the reactivities of anti-human IL-5R α monoclonal antibodies KM1257, KM1259, KM1486, KM1399, KM7399, KM8399 and KM9399 with a human IL-5R gene-transfected CTLL-2 cell.

The results are shown in FIG. 55. Monoclonal antibodies KM1257, KM1259 and KM1486 and humanized antibodies KM1399, KM7399, KM8399 and KM9399 did not react with CTLL-2 cells, but specifically reacted with CTLL-2 (h5R). Thus, it has become clear that humanized antibodies KM1399, KM7399, KM8399 and KM9399 specifically recognize hIL-5R α.

2. Action of Anti-IL-5R α Antibodies to Inhibit the Biological Activity of IL-5

Since CTLL-2(h5R) cells exhibit a proliferation response depending on human IL-5 [J. Exp. Med., 177, 1523 (1993)], the effect of the anti-IL-5R α antibodies upon human IL-5 dependent cell proliferation in CTLL-2(h5R) cells was examined. Cell proliferation was evaluated by a color development method using Cell Counting Kit (Dojin Chemical Laboratory).

Briefly, $1 \times 10^4$ CTLL-2(h5R) cells were suspended in 50 μl of a normal medium and dispensed into a 96-well cell culture plate. These cells were mixed with 25 μl/well of various anti-IL-5R α antibodies diluted with a normal medium at 40 μg/ml and with 25 μl/well of a normal medium containing human IL-5 at 0.4 ng/ml as prepared by the method described in section 3 of Example 1 and cultured in a $CO_2$ incubator at 37° C. for 44 hours. Then, 10 μl/well of Cell Counting Kit solution were added to the plate and cells were cultured under 5% $CO_2$ incubator at 37° C. for another 4 hours. After completion of the cultivation, the absorbance at 450 nm was measured with Microwell Plate Reader Emax (Molecular Device). The CTLL-2(h5R) cell proliferation inhibiting activity of each antibody was calculated by the following formnula.

$$\text{Percent proliferation inhibition}(\%) = \frac{A-C}{100-B-C} \times 100$$

wherein

A: OD value in the presence of an antibody

B: OD value in the absence of an antibody

C: OD value in the absence of human IL-5.

Figure 56:
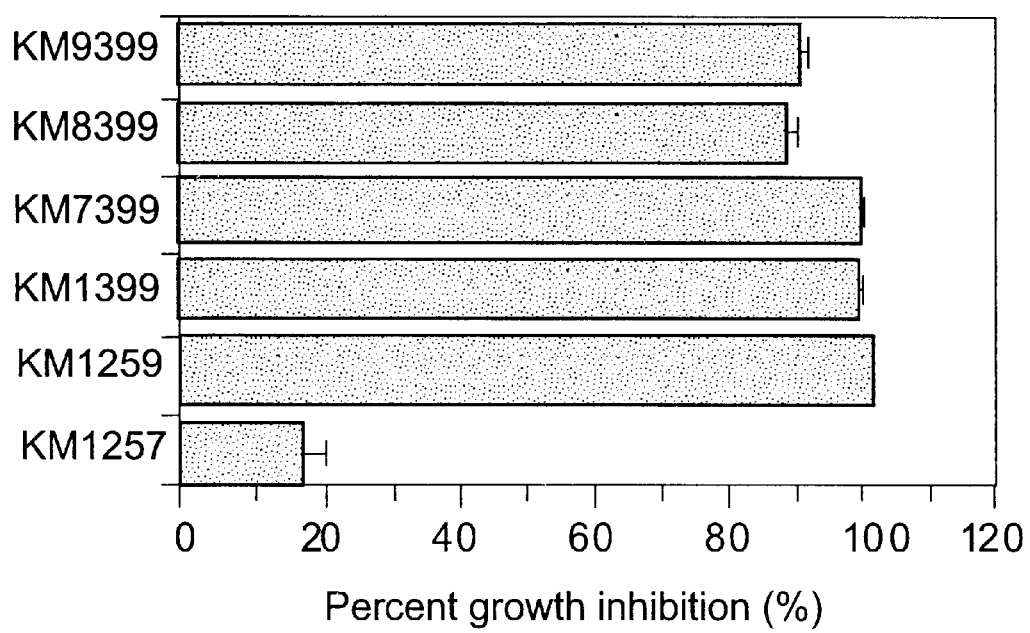
FIG. 56 shows the results of examination of the inhibitory action of anti-human IL-5R α monoclonal antibodies KM1257, KM1259, KM1486, KM1399, KM7399, KM8399 and KM9399 against IL-5-dependent growth of a human IL-5R gene-transfected CTLL-2 cell.

The results are shown in FIG. 56. Monoclonal antibodies KM1259 and KM1486 and humanized antibodies KM1399, KM7399, KM8399 and KM9399 inhibited the human IL-5 dependent proliferation of CTLL-2(h5R) cells. However, such activity was not recognized in monoclonal antibody KM1257.

3. Immunocyte Staining of Human Eosinophils

A polymorphonuclear leukocyte fraction was prepared from normal human blood and cultured for 3 days in the presence of human IL-5 to concentrate eosinophils. Then, the reactivity of anti-hIL-5R α monoclonal antibodies was examined with a flow cytometer.

Briefly, polymorphprep (Nicomed) was dispensed into eight 15-ml polypropylene centrifuge tubes (4 ml/tube) and each plated with 6 ml of heparinized normal human blood. Then, the tubes were centrifuged at 500×g for 30 minutes at room temperature to separate and recover polymorphonuclear leukocytes. The polymorphonuclear leukocytes were suspended in a normal medium to give a concentration of $1.25 \times 10^7$ cells/10 ml and dispensed into 4 cell culture dishes in 10 ml portions. Then, human IL-5 was added to the cell suspension at a final concentration of 2 ng/ml and the cells were cultured in a $CO_2$ incubator at 37° C. for 3 days. After completion of the cultivation, the cells were centrifuged (1,200 rpm, 5 min.) and suspended in the immunocyte staining buffer to give a concentration of $5 \times 10^6$ cells/ml.

Then, $5 \times 10^5$ cells were dispensed into a round bottom 96-well plate.

After the plate was centrifuged at 350×g for 1 minute at 4° C., the supernatant was removed. Then, 50 μl of 10% normal mouse serum-containing immunocyte staining buffer were added and reacted at 4° C. for 30 minutes. To the buffer, monoclonal antibody KM1259 labeled with biotin by conventional methods ["KOSO-KOTAI-HO" (Enzyme Antibody Method), Gakusai Kikaku Co., 1985] or, as a control, biotin-labeled anti-human granulocyte colony-stimulating factor monoclonal antibody KM341 [Agr. Biol. Chem., 53, 1095 (1989)] had been added at a concentration of 10 μg/ml. After the reaction, 200 μl of the immunocyte staining buffer were added to each well and centrifuged at 350×g for 1 minutes at 4° C. and then the supernatant was removed and the cells were washed. The washing operation was further repeated twice. Thereafter, phycoerythrin-labeled streptavidin (Becton Dickinson) diluted 10 folds with the immunocyte staining buffer was added (50 μl/well) and reacted at 4° C. for 30 minutes. After the reaction, a similar washing operation was repeated 3 times. Then, analysis was performed with a flow cytometer (Coulter) by forward scattering and 90-scattering for those cells which were recognized as polymorphonuclear leukocytes. Also, the same cells were stained by the May-Grunwald-Giemsa staining method ["SENSHOKUHOU NO SUBETE" (Review of Staining Methods), Ishiyaku Shuppan Co., 1988] and observed for polymorphonuclear leukocytes. As a result, it was confirmed that 75% of the cells were eosinophils.

Figure 57:
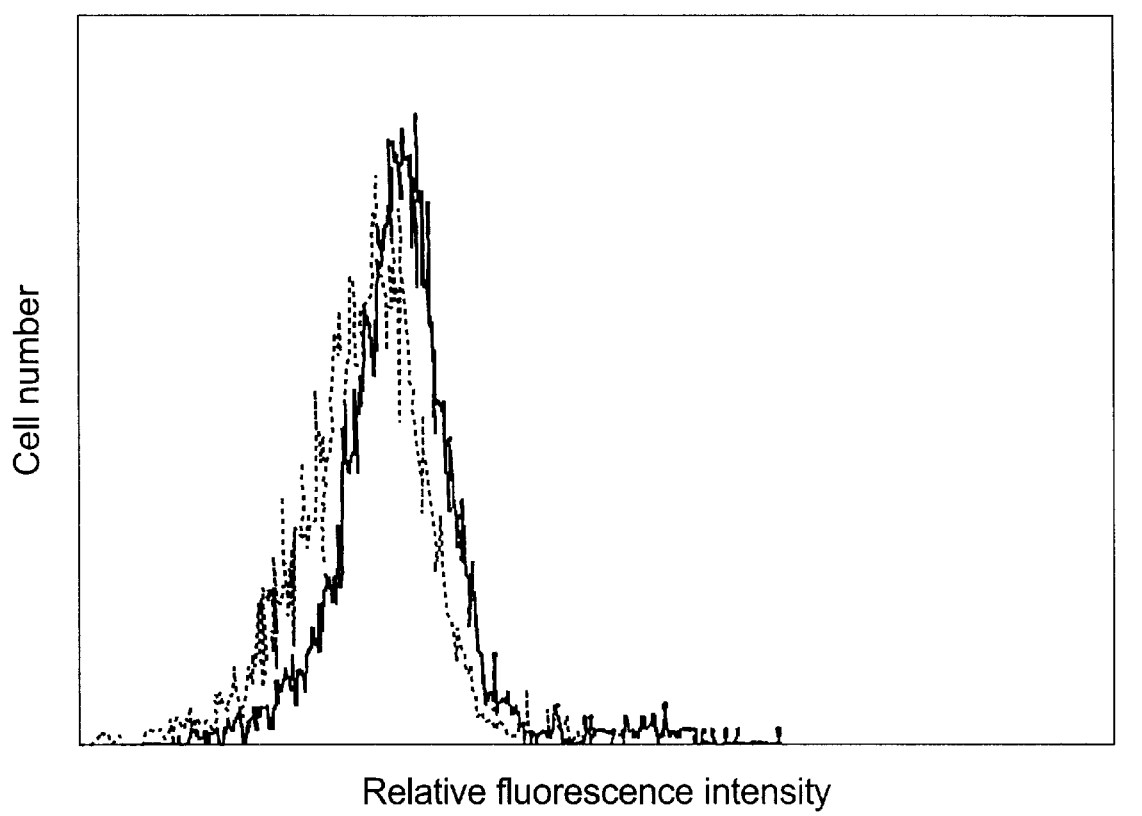
FIG. 57 shows the results of flowcytometric analysis of the reactivity of anti-human IL-5R α monoclonal antibody KM1259 with human eosinophils.

FIG. 57 shows the histogram obtained. Anti-human IL-5R α monoclonal antibody KM1259 exhibited a definite reactivity. Since 75% of the cells analyzed proved to be eosinophils, it was confirmed that anti-human IL-5R α monoclonal antibody KM1259 has a reactivity with human eosinophils.

4. Survival Inhibition of Human Eosinophils with Anti-IL-5R α Antibodies

Polymorphonuclear leukocyte fractions were prepared from normal human blood, and the action of anti-IL-5R α antibodies upon the survival of eosinophils in the presence of human IL-5 was examined.

Briefly, polymorphprep (Nicomed) was dispensed in 4 ml portions into fifteen 15-ml polypropylene centrifuge tubes and each plated with 8 ml of heparinized normal human blood. Then, the tubes were centrifuged at 500×g for 30 minutes at room temperature to separate and recover polymorphonuclear leukocytes.

Percoll stock solution was prepared by adding 1 volume of sterilized 1.5 M NaCl solution to 9 volumes of Percoll solution (Pharmacia). Then, 80% Percoll solution was prepared by adding 2 volumes of physiological saline to 8 volumes of Percoll stock solution, and 60% Percoll solution was prepared by adding 4 volumes of physiological saline to 6 volumes of Percoll stock solution. For the purpose of removing concomitant monocytes, 5 ml of 60% Percoll solution were dispensed into each of two 15 ml polypropylene centrifuge tubes, plated with the previously obtained polymorphonuclear leukocytes suspended in RPMI1640 medium and centrifuged at 500×g for 30 minutes at room temperature to separate and recover the precipitated polymorphonuclear leukocytes. Further, for the purpose of removing concomitant erythrocytes, 5 ml of 80% Percoll solution were dispensed into each of two 15-ml polypropylene centrifuge tubes, plated with the previously obtained polymorpho-nuclear leukocytes suspended in RPMI1640 medium and centrifuged at 500×g for 30 minutes at room temperature to separate and recover the polymorphonuclear leukocytes suspended in the Percoll layer.

Subsequently, cells were dispensed into a 48-well cell culture plate at $2\times10^6$ cells/well and human IL-5 was added at a final concentration of 0.1 ng/ml. Further, each of various anti-IL-5R α antibodies was added at a final concentration of 1 μg/ml. For each antibody, 2 wells were cultured and the solution in each well was adjusted to have a final volume of 1 ml. The cells were cultured in a $CO_2$ incubator at 37° C. for 3 days. After completion of the cultivation, the total volume of cell suspension was recovered from each well and centrifuged (3,000 rpm, 1 min.) to recover the cells. The thus obtained cells were suspended in 100 μl of PBS. Using 50 μl of this suspension, specimens were prepared with a cell specimen preparing device, Cytospin3 (Shandon). After specimens were stained by the May-Grunwald-Giemsa staining method, 200 cells were observed for each specimen and the number of eosinophils was counted.

Figure 58:
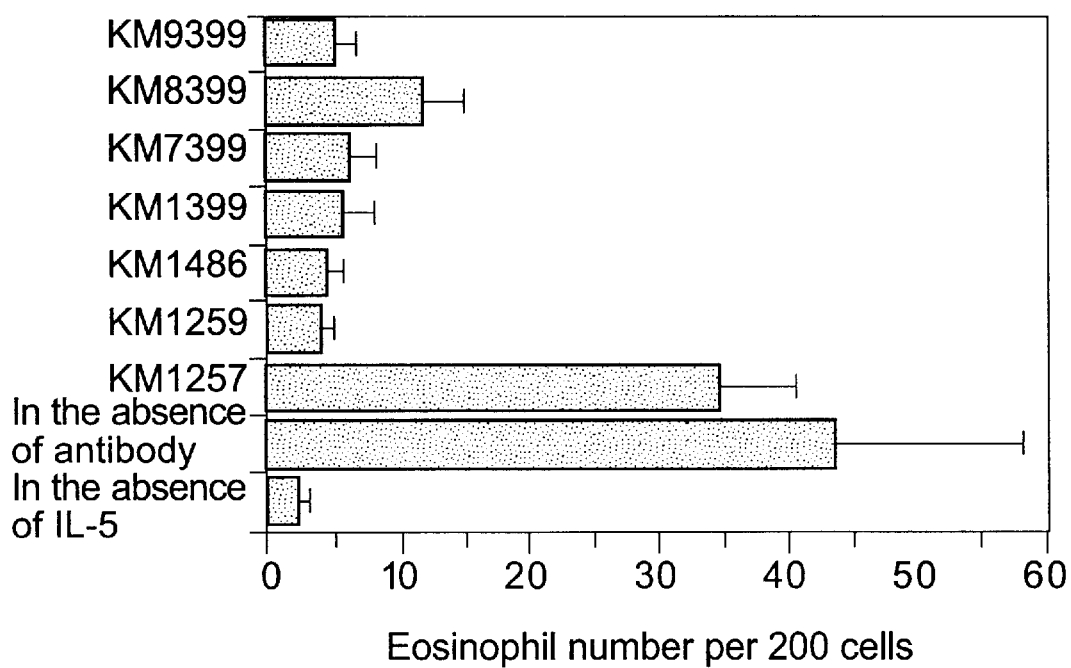
FIG. 58 shows the results of examination of inhibitory action of anti-human IL-5R α monoclonal antibodies KM1257, KM1259, KM1486, KM1399, KM7399, KM8399 and KM9399 for the survival of human eosinophils.

The results are shown in FIG. 58. Monoclonal antibodies KM1259 and KM1486 and humanized antibodies KM1399, KM7399, KM8399 and KM9399 were all found to have an activity to inhibit the eosinophil survival time prolongation by IL-5. However, such activity was not recognized in monoclonal antibody KM1257.

5. Detection of shIL-5R α with an Anti-hIL-5R α Antibodies

Anti-human IL-5R α monoclonal antibody KM1257 diluted with PBS to a concentration of 10 μg/ml was dispensed into a 96-well EIA plate (Greiner) (50 μl/well) and left at 4° C. overnight to allow the antibody to be adsorbed. After washing, 100 μl/well of PBS containing 1% bovine serum albumin (BSA)(1% BSA-PBS) were added and reaction was performed at room temperature for 1 hour to block the remaining active groups. After discarding 1% BSA-PBS, the purified shIL-5R α obtained in subsection (9) of section 1 of Example 1 that had been diluted with 1% BSA-PBS to a concentration of 1000–0.1 ng/ml was added and reacted at 4° C. overnight. After washing with Tween-PBS, anti-human IL-5R α monoclonal antibody KM1259 labeled with biotin by conventional methods ["KOSO-KOTAI-HO" (Enzyme Antibody Method), Gakusai Kikaku Co., 1985] and diluted with 1% BSA-PBS to a concentration of 1 μg/ml was added (50 μl/well) and reacted at room temperature for 2 hours. After washing with Tween-PBS, avidin-labeled peroxidase (Nippon Reizo) diluted 4000 folds with 1% BSA-PBS was added (50 μl/well) and reacted at room temperature for 1 hour. After washing with Tween-PBS, ABTS substrate solution [2,2-azinobis(3-ethylbenzothiazole-6-sulfonic acid)ammonium] was added to allow color development. Then, the absorbance at OD of 415 nm was measured (NJ2001; Japan Intermed).

Figure 59:
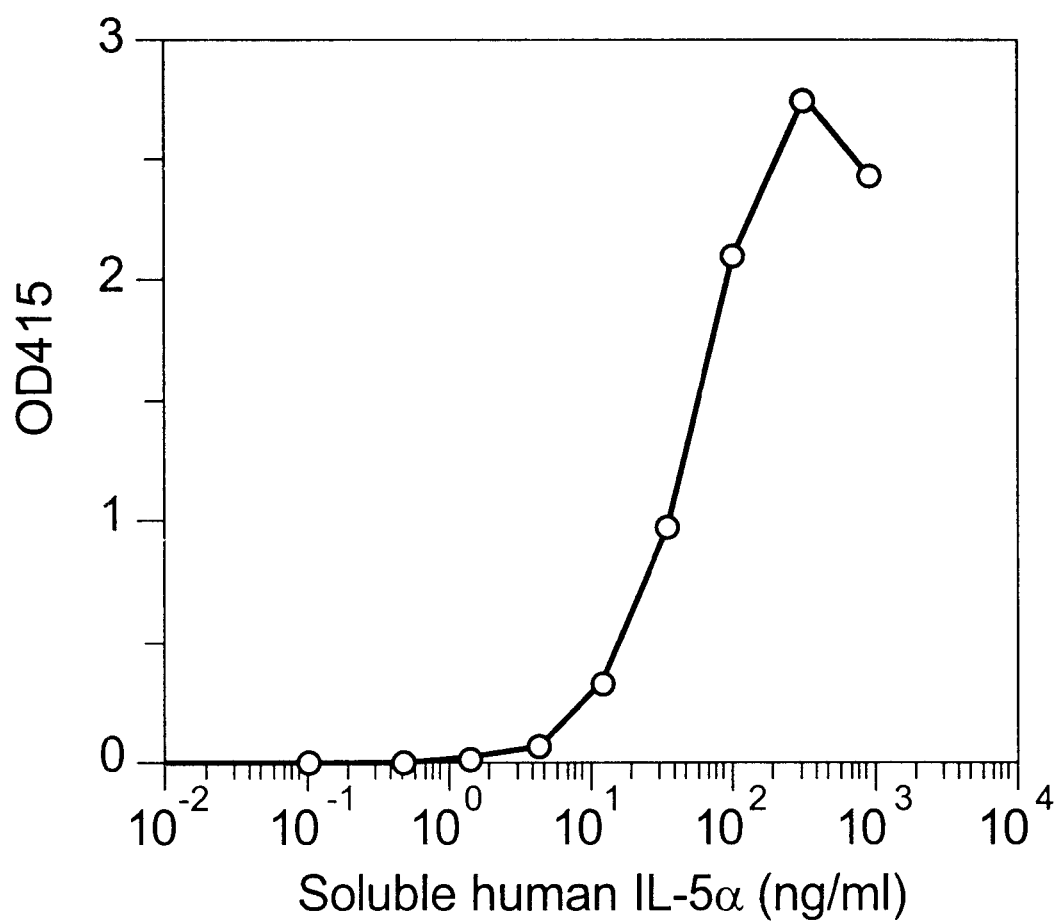
FIG. 59 shows the results of evaluation of a soluble human IL-5R α quantitative determination system using anti-human IL-5R α monoclonal antibody KM1257 and biotin-labeled KM1259.

The results are shown in FIG. 59. As a result, it has become clear that shIL-5R α can be measured by using anti-human IL-5R α monoclonal antibody KM1257 and biotin-labeled anti-human IL-5R α monoclonal antibody KM1259.

6. Detection of shIL-5R α by Western Blotting

The shIL-5R α described in subsection (9) of section 1 of Example 1 was thermally denatured in SDS-PAGE sample buffer containing 2-mercaptoethanol or SDS-PAGE sample buffer not containing 2-mercaptoethanol. The resultant mixture was electrophoresed on a commercial SDS-PAGE gradient gel (Atto), and then the protein was transferred to a PVDF membrane (Millipore). The PVDF membrane was soaked in PBS containing 10% BSA and left at 4° C. overnight for blocking. After completion of the blocking, the membrane was washed thoroughly with 0.05% Tween-containing PBS. Then, the membrane was soaked in a culture supernatant of the hybridoma obtained in section 5 of Example 1 at room temperature for 2 hours and washed thoroughly with 0.05% Tween-containing PBS. Further, the PVDF membrane was soaked at room temperature for 1 hour in a solution obtained by diluting peroxidase-labeled anti-mouse immunoglobulin antibody (Wako Pure Chemical Industries, Ltd.) with 1% BSA-PBS 1000 folds and then washed thoroughly with 0.05% Tween-containing PBS. After the washing solution was removed thoroughly, ECL reagent (Amersham) was applied to the PVFD membrane and reacted for 1 minute. After removing the excessive reagent, the membrane was sandwiched between two plastic films and placed in an X-ray film sensitizing cassette to thereby sensitize the ECL film. Thus, the reactivity of the antibodies were confirmed.

The results are shown in FIG. 60. KM1257 exhibited reactivity, but KM1259 and KM1486 did not.

7. Immunoprecipitation of shIL-5R α

An anti-mouse immunoglobulin antibody (DAKO) diluted with PBS 50 folds was dispensed into a 96-well EIA plastic plate (200 μl/well) and left at 4° C. overnight to allow the antibody to be adsorbed. After washing with PBS, 300 μl/well of 1% BSA-PBS were added and left at room temperature for 1 hour to perform blocking. After washing with PBS, 200 μl each of a culture supernatant of KM1257, KM1259 or KM1486 (they are anti-human IL-5R α monoclonal antibodies obtained in the preceding Examples) were added to each well and left at 4° C. overnight to allow the antibody to be adsorbed. After washing the plate, the shIL-5R α obtained in section 1 of Example 1 and diluted with PBS to a concentration of 10 μg/ml was dispensed into each well in an amount of 50 μl and reacted at 4° C. overnight. After the plate was washed with 0.05% Tween-containing PBS, 5×2-mercaptoethanol-free SDS-PAGE sample buffer [0.31 M Tris (pH 6.8), 10% SDS, 50% glycerol] or 5×2-mercaptoethanol-containing SDS-PAGE sample buffer [0.31 M Tris (pH 6.8), 10% SDS, 50% glycerol, 25% 2-mercaptoethanol] was added (50 μl/well) and left at room temperature for 2 hours while shaking. The reaction mixture was added to 200 μl of PBS and heated on a heat block. Then, using a commercial SDS-PAGE gradient gel (Atto), 25 μl of the reaction mixture were separated. After completion of the electrophoresis, the protein was transferred to a PVDF membrane (Millipore). The PVDF membrane was subjected to Western blotting analysis according to the method described in section 6 of Example 3 and using KM1257, to thereby detect shIL-5R α.

Figure 61:
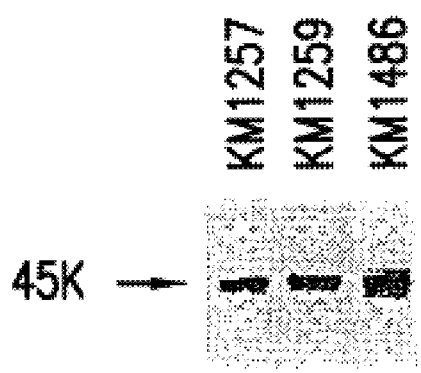
FIG. 61 shows the results of immunoprecipitation of shIL-5R α using anti-human IL-5R α monoclonal antibodies KM1257, KM1259 and KM1486.

The results are shown in FIG. 61. It has become clear that all of km1257, KM1259 and KM1486 immunoprecipitate shIL-5R α.

INDUSTRIAL APPLICABILITY

According to the present invention, monoclonal antibodies KM1257, KM1259 and KM1486 are provided which specifically bind to human IL-5 receptor α chain that is believed to be specifically expressed on human eosinophils. Also, humanized antibodies KM1399, KM8399, KM7399 and KM9399 are provided which specifically bind to human IL-5 receptor α chain that is believed to be specifically expressed on human eosinophils and which can inhibit the biological activity of human IL-5. The antibodies of the present invention are useful for immunological detection of human eosinophils in immunocyte staining and diagnosis or treatment of allergic diseases caused by the inhibition of the biological activity of IL-5. It should be particularly noted that the humanized antibodies of the invention are lower in antigenicity than the monoclonal antibodies and expected to maintain their effect for a long period.

Deposit of Microorganisms

The following microorganisms have been deposited in accordance with the terms of the Budapest Treaty with the National Institute of Bioscience and Human-Technology Agency of Industrial Science and Technology, International Depository Authority, 1–3, Higashi 1-chome, Tsukuba-shi, Ibaraki-ken, 305 Japan, on the dates indicated:

Deposit of Microorganisms
The following microorganisms have been deposited in accordance with the terms of the Budapest Treaty with the National Institute of Bioscience and Human-Technology Agency of Industrial Science and Technology, International Depository Authority, 1-3, Higashi 1-chome, Tsukuba-shi, Ibaraki-ken, 305 Japan, on the dates indicated:

| Microorganism | Accession Number | Date |
|---|---|---|
| Hybridoma KM1259 | FERM BP-5134 | June 13, 1995 |
| Hybridoma KM1399 | FERM BP-5650 | September 3, 1996 |
| Hybridoma KM1257 | FERM BP-5133 | June 13, 1995 |
| Hybridoma KM1486 | FERM BP-5651 | September 3, 1996 |
| Hybridoma KM7399 | FERM BP-5649 | September 3, 1996 |
| Hybridoma KM8399 | FERM BP-5648 | September 3, 1996 |
| Hybridoma KM9399 | FERM BP-5647 | September 3, 1996 |

What is claimed is:

1. An isolated antibody which reacts specifically with a human interleukin-5 receptor α chain and neutralizes activity of said interleukin-5 receptor α chain.

2. The antibody of claim 1, which is selected from monoclonal antibodies, humanized antibodies, single chain antibodies and disulfide-stabilized antibodies.

3. The antibody of claim 2, which is a monoclonal antibody.

4. The monoclonal antibody of claim 3, which binds to an epitope at 1–313 positions from the N-terminal amino acid of a human interleukin-5 receptor α chain and which specifically binds a human interleukin-5 receptor α chain on the surface of an immunocyte.

5. The monoclonal antibody of claim 3, which binds to an epitope at 1–313 positions from the N-terminal amino acid of the human interleukin-5 receptor α chain and which inhibits a biological activity of human interleukin-5.

6. The monoclonal antibody of claim 4, which belongs to IgG1 subclass, has CDR sequences in the variable region (V region) of the heavy chain (H chain) having the following amino acid sequences:

CDR1: Asp Tyr Gly Met Ala (SEQ ID NO:34),

CDR2: Ala Ile Ser Ser Gly Gly Ser Tyr Ile His Phe Pro Asp Ser Leu Lys Gly (SEQ ID NO:35),

CDR3: Arg Gly Phe Tyr Gly Asn Tyr Arg Ala Met Asp Tyr (SEQ ID NO:36), and has CDR sequences in the V region of the light chain (L chain) having the following amino acid sequences:

CDR1: Arg Ala Asn Glu Ser Val Asp His Asn Gly Val Asn Phe Met Asn (SEQ ID NO:37),

CDR2: Ala Ala Ser Asn Gln Gly Ser (SEQ ID NO:38),

CDR3: Gin Gln Ser Lys Asp Val Pro Trp Thr (SEQ ID NO:39).

7. The monoclonal antibody of claim 6, which is monoclonal antibody KM1257 produced by hybridoma KM1257 (FERM BP-5133).

8. The monoclonal antibody of claim 5, which belongs to IgG1 subclass, has CDR sequences in the V region of the H chain of the antibody having the following amino acid sequences:
   CDR1: Ser Tyr Val Ile His (SEQ ID NO:40),
   CDR2: Tyr Ile Asn Pro Tyr Asn Asp Gly Thr Lys Tyr Asn Glu Arg Phe Lys Gly (SEQ ID NO:41),
   CDR3: Glu Gly Ile Arg Tyr Tyr Gly Leu Leu Gly Asp Tyr (SEQ ID NO:42),
and has CDR sequences in the V region of the L chain having the following amino acid sequences:
   CDR1: Gly Thr Ser Glu Asp Ile Ile Asn Tyr Leu Asn (SEQ ID NO:43),
   CDR2: His Thr Ser Arg Leu Gln Ser (SEQ ID NO:44),
   CDR3: Gln Gln Gly Tyr Thr Leu Pro Tyr Thr (SEQ ID NO:45).

9. The monoclonal antibody of claim 5, which belongs to IgG1 subclass, has CDR sequences in the V region of the H chain of the antibody having the following amino acid sequences:
   CDR1: Asp Thr Tyr Met His (SEQ ID NO:46),
   CDR2: Arg Ile Asp Pro Ala Asn Gly Asn Thr Lys Ser Asp Pro Lys Phe Gln Ala (SEQ ID NO:47),
   CDR3: Gly Leu Arg Leu Arg Phe Phe Asp Tyr (SEQ ID NO:48),
and has CDR sequences in the V region of the L chain having the following amino acid sequences:
   CDR1: Ser Ala Ser Ser Ser Val Ser Tyr Met His (SEQ ID NO:49),
   CDR2: Asp Thr Ser Lys Leu Ala Ser (SEQ ID NO:50),
   CDR3: Gin Gin Trp Ser Ser Asn Pro Pro Ile Thr (SEQ ID NO:51).

10. The monoclonal antibody of claim 9, which is monoclonal antibody KM1486 produced by hybridoma KM1486 (FERM BP-5651).

11. Hybridoma KM1257 (FERM BP-5133) which produces the monoclonal antibody of claim 6.

12. Hybridoma KM1486 (FERM BP-5651) which produces the monoclonal antibody of claim 9.

13. The antibody of claim 2, which is a humanized antibody.

14. The humanized antibody of claim 13, which recognizes an epitope at 1–313 positions from the N-terminal amino acid of a human interleukin-5 receptor α chain and which reacts specifically with the human interleukin-5 receptor α chain by immunocyte staining.

15. The humanized antibody of claim 13, which recognizes an epitope at 1–313 positions from the N-terminal amino acid of a human interleukin-5 receptor α chain which inhibits a biological activity of human interleukin-5.

16. The antibody of claim 14 or 15, which belongs to human antibody IgG class.

17. The antibody of claim 13, 14 or 15, which is a human chimeric antibody.

18. The antibody of claim 17, wherein the human chimeric antibody is a chimeric antibody comprising the V region of the H chain and the V region of the L chain of a non-human animal antibody, and the constant region (C region) of the H chain and the C region of the L chain of a human antibody.

19. The antibody of claim 18, wherein the V region of the H chain of the antibody comprises the amino acid sequence of SEQ ID NO:27 and the V region of the L chain of the antibody comprises the amino acid sequence of SEQ ID NO:29.

20. The antibody of claim 18, wherein the V region of the H chain of the antibody comprises the amino acid sequence of SEQ ID NO:31 and the V region of the L chain of the antibody comprises the amino acid sequence of SEQ ID NO:33.

21. The antibody of claim 19 being antibody KM7399, wherein the C region of the H chain of the antibody is in a human antibody IgG4 subclass.

22. Transformant KM7399 (FERM BP-5649) which produces the antibody of claim 21.

23. The antibody of claim 13, wherein the humanized antibody is a human CDR-grafted antibody.

24. The antibody of claim 15, which is a human CDR-grafted antibody and has CDR sequences in the V region of the H chain and the V region of the L chain of a non-human animal antibody.

25. The antibody of claim 24, which has a CDR sequence in the V region of the H chain comprising
   CDR1: Ser Tyr Val Ile His (SEQ ID NO:40),
   CDR2: Tyr Ile Asn Pro Tyr Asn Asp Gly Thr Lys Tyr Asn Glu Arg Phe Lys Gly (SEQ ID NO:41), or
   CDR3: Glu Gly Ile Arg Tyr Tyr Gly Leu Leu Gly Asp Tyr (SEQ ID NO:42),
and has a CDR sequence in the V region of the L chain comprising
   CDR1: Gly Thr Ser Glu Asp Ile Ile Asn Tyr Leu Asn (SEQ ID NO:43),
   CDR2: His Thr Ser Arg Leu Gln Ser (SEQ ID NO:44), or
   CDR3: Gln Gln Gly Tyr Thr Leu Pro Tyr Thr (SEQ ID NO:45).

26. The antibody of claim 24, which has a CDR sequence in the V region of the H chain comprising
   CDR1: Asp Thr Tyr Met His (SEQ ID NO:46),
   CDR2: Arg Ile Asp Pro Ala Asn Gly Asn Thr Lys Ser Asp Pro Lys Phe Gln Ala (SEQ ID NO:47), or
   CDR3: Gly Leu Arg Leu Arg Phe Phe Asp Tyr (SEQ ID NO:48),
and has CDR sequence in the V region of the L chain comprising
   CDR1: Ser Ala Ser Ser Ser Val Ser Tyr Met His (SEQ ID NO:49),
   CDR2: Asp Thr Ser Lys Leu Ala Ser (SEQ ID NO:50), or
   CDR3: Gln Gln Trp Ser Ser Asn Pro Pro Ile Thr (SEQ ID NO:51).

27. The antibody of claim 25 being antibody KM8399, wherein the C region of the H chain of the antibody belongs to a human antibody IgG1 subclass.

28. The antibody of claim 25 being antibody KM9399, wherein the C region of the H chain of the antibody is in a human antibody IgG4 subclass.

29. Transformant KM8399 (FERM BP-5648) which produces the antibody of claim 27.

30. Transformant KM9399 (FERM BP-5647) which produces the antibody of claim 28.

31. The antibody of claim 2, wherein the antibody is a single chain antibody.

32. The single chain antibody of claim 31, which recognizes an epitope at 1–313 positions from the N-terminal amino acid of a human interleukin-5 receptor α chain and which inhibits a biological activity of human interleukin-5.

33. The antibody of claim 32, wherein the single chain antibody comprises the V region of the H chain and the V region of the L chain of a humanized antibody.

34. The single chain antibody of claim 32, which has CDR sequences in the V region of the H chain having the following amino acid sequences:

CDR1: Ser Tyr Val Ile His (SEQ ID NO:40),
CDR2: Tyr Ile Asn Pro Tyr Asn Asp Gly Thr Lys Tyr Asn Glu Arg Phe Lys Gly (SEQ ID NO:41),
CDR3: Glu Gly Ile Arg Tyr Tyr Gly Leu Leu Gly Asp Tyr (SEQ ID NO:42), and has CDR sequences in the V region of the L chain having the following amino acid sequences:

CDR1: Gly Thr Ser Giu Asp Ile Ile Asn Tyr Leu Asn (SEQ ID NO:43),
CDR2: His Thr Ser Arg Leu Gln Ser (SEQ ID NO:44),
CDR3: Gln Gln Gly Tyr Thr Leu Pro Tyr Thr (SEQ ID NO:45).

35. The single chain antibody of claim 32, which has CDR sequences in the V region of the H chain having the following amino acid sequences:

CDR1: Asp Thr Tyr Met His (SEQ ID NO:46),
CDR2: Arg Ile Asp Pro Ala Asn Gly Asn Thr Lys Ser Asp Pro Lys Phe Gln Ala (SEQ ID NO:47),
CDR3: Gly Leu Arg Leu Arg Phe Phe Asp Tyr (SEQ ID NO:48), and has CDR sequences in the V region of the L chain having the following amino acid sequences:

CDR1: Ser Ala Ser Ser Ser Val Ser Tyr Met His (SEQ ID NO:49),
CDR2: Asp Thr Ser Lys Leu Ala Ser (SEQ ID NO:50),
CDR3: Gln Gln Trp Ser Ser Asn Pro Pro Ile Thr (SEQ ID NO:51).

36. The antibody of claim 2, which is a disulfide-stabilized antibody.

37. The disulfide-stabilized antibody of claim 36, which recognizes an epitope at 1–313 positions from the N-terminal amino acid of a human interleukin-5 receptor α chain and which inhibits a biological activity of human interleukin-5.

38. The disulfide-stabilized antibody of claim 37, which comprises the V region of the H chain and the V region of the L chain of a humanized antibody.

39. The disulfide-stabilized antibody of claim 37, which has CDR sequences in the V region of the H chain having the following amino acid sequences:

CDR1: Ser Tyr Val Ile His (SEQ ID NO:40),
CDR2: Tyr Ile Asn Pro Tyr Asn Asp Gly Thr Lys Tyr Asn Glu Arg Phe Lys Gly (SEQ ID NO:41),
CDR3: Glu Gly Ile Arg Tyr Tyr Gly Leu Leu Gly Asp Tyr (SEQ ID NO:42), and has CDR sequences in the V region of the L chain having the following amino acid sequences:

CDR1: Gly Thr Ser Glu Asp Ile Ile Asn Tyr Leu Asn (SEQ ID NO:43),
CDR2: His Thr Ser Arg Leu Gln Ser (SEQ ID NO:44),
CDR3: Gln Gln Gly Tyr Thr Leu Pro Tyr Thr (SEQ ID NO:45).

40. The disulfide-stabilized antibody of claim 37, which has CDR sequences in the V region of the H chain having the following amino acid sequences:

CDR1: Asp Thr Tyr Met His (SEQ ID NO:46),
CDR2: Arg Ile Asp Pro Ala Asn Gly Asn Thr Lys Ser Asp Pro Lys Phe Gln Ala (SEQ ID NO:47),
CDR3: Gly Leu Arg Leu Arg Phe Phe Asp Tyr (SEQ ID NO:48), and has CDR sequences in the V region of the L chain having the following amino acid sequences:

CDR1: Ser Ala Ser Ser Ser Val Ser Tyr Met His (SEQ ID NO:49),
CDR2: Asp Thr Ser Lys Leu Ala Ser (SEQ ID NO:50),
CDR3: Gln Gln Trp Ser Ser Asn Pro Pro Ile Thr (SEQ ID NO:51).

41. A peptide comprising a CDR sequence in the V region of the H chain or the V region of the L chain of the monoclonal antibody of claim 6, 8 or 9, which specifically binds to a human interleukin-5 receptor α chain.

* * * * *